US008822535B2

(12) United States Patent
Roth et al.

(10) Patent No.: US 8,822,535 B2
(45) Date of Patent: Sep. 2, 2014

(54) METHODS, COMPOSITIONS AND ARTICLES OF MANUFACTURE FOR ENHANCING SURVIVABILITY OF CELLS, TISSUES, ORGANS, AND ORGANISMS

(75) Inventors: Mark B. Roth, Seattle, WA (US); Mike Morrison, Seattle, WA (US); Eric Blackstone, Seattle, WA (US); Dana Miller, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 1533 days.

(21) Appl. No.: 11/408,734

(22) Filed: Apr. 20, 2006

(65) Prior Publication Data

US 2007/0078113 A1    Apr. 5, 2007

Related U.S. Application Data

(60) Provisional application No. 60/673,037, filed on Apr. 20, 2005, provisional application No. 60/673,295, filed on Apr. 20, 2005, provisional application No. 60/713,073, filed on Aug. 31, 2005, provisional application No. 60/731,549, filed on Oct. 28, 2005, provisional application No. 60/762,462, filed on Jan. 26, 2006.

(51) Int. Cl.
*A61K 33/04* (2006.01)
(52) U.S. Cl.
CPC .............. *A61K 33/04* (2013.01); *Y10S 514/921* (2013.01)
USPC ............................ 514/553; 514/706; 514/921
(58) Field of Classification Search
None
See application file for complete search history.

(56) References Cited

U.S. PATENT DOCUMENTS

| | | | |
|---|---|---|---|
| 1,379,855 A | 5/1921 | Donner | 8/161 |
| 2,031,489 A | 2/1936 | Koenigsberger | 8/161 |
| 2,435,854 A | 2/1948 | Cecil | |
| 2,487,558 A | 11/1949 | Kamlet | 8/161 |
| 3,587,899 A | 6/1971 | Bender et al. | |
| 3,777,507 A | 12/1973 | Burton et al. | |
| 3,881,990 A | 5/1975 | Burton et al. | |
| 3,995,444 A | 12/1976 | Clark et al. | |
| 4,186,565 A | 2/1980 | Toledo-Pereyra | 62/306 |
| 4,292,817 A | 10/1981 | Loucks | |
| 4,473,637 A | 9/1984 | Guibert | |
| 4,502,295 A | 3/1985 | Toledo-Pereyra | 62/463 |
| 4,745,759 A | 5/1988 | Bauer et al. | |
| 4,798,824 A | 1/1989 | Belzer et al. | 514/60 |
| 4,807,442 A | 2/1989 | Linner et al. | 62/55.5 |
| 4,920,044 A | 4/1990 | Bretan, Jr. | |
| 4,923,442 A | 5/1990 | Segall et al. | |
| 4,938,961 A | 7/1990 | Collins et al. | 424/606 |
| 4,951,482 A | 8/1990 | Gilbert | 62/457.1 |
| 5,066,578 A | 11/1991 | Wikman-Coffelt | 435/1 |
| 5,157,930 A | 10/1992 | McGhee et al. | 62/78 |
| 5,173,088 A | 12/1992 | Maeda et al. | 23/295 |
| 5,231,025 A | 7/1993 | Gralnick | |
| 5,285,657 A | 2/1994 | Bacchi et al. | 62/457.9 |
| 5,326,706 A | 7/1994 | Yland et al. | 435/283 |
| 5,328,821 A | 7/1994 | Fisher et al. | |
| 5,370,989 A | 12/1994 | Stern et al. | 435/1 |
| 5,395,314 A | 3/1995 | Klatz et al. | 604/24 |
| 5,405,742 A | 4/1995 | Taylor | 435/1.2 |
| 5,434,045 A | 7/1995 | Jost | |
| 5,464,768 A | 11/1995 | Kiel et al. | |
| 5,470,738 A | 11/1995 | Frelinger et al. | |
| 5,476,763 A | 12/1995 | Bacchi et al. | |
| 5,476,764 A | 12/1995 | Bittensky | 435/2 |
| 5,552,267 A | 9/1996 | Stern et al. | 435/1.1 |
| 5,569,579 A | 10/1996 | Murphy | 435/2 |
| 5,571,801 A | 11/1996 | Segall et al. | |
| 5,580,781 A | 12/1996 | Naughton et al. | |
| 5,599,659 A | 2/1997 | Brasile et al. | |
| 5,681,278 A | 10/1997 | Igo et al. | |
| 5,693,462 A | 12/1997 | Raymond | 435/1.2 |
| 5,699,793 A | 12/1997 | Brasile | 128/630 |
| 5,719,174 A | 2/1998 | Sainsbury et al. | 514/410 |
| 5,736,397 A | 4/1998 | Garcia et al. | 435/374 |
| 5,739,169 A | 4/1998 | Gao et al. | |
| 5,752,929 A | 5/1998 | Klatz et al. | 604/51 |
| 5,770,583 A | 6/1998 | Haslwanter et al. | 514/57 |

(Continued)

FOREIGN PATENT DOCUMENTS

| | | |
|---|---|---|
| EP | 0061277 | 9/1982 |
| EP | 0073590 | 3/1983 |

(Continued)

OTHER PUBLICATIONS

JA Vick, MH Heiffer, CR Roberts, RW Caldwell, A Nies. "Treatment of Hemorrhagic Shock With a New Vasodilator." Military Medicine—Aug. 1973, pp. 490-494.*

W Zhao, R Wang. "H2S-induced vasorelaxation and underlying cellular and molecular mechanisms." Am J Physiol Heart Circ Physiol vol. 283, 2002, H474-H480.*

AF Almeida, TL Guidotti. "Differential Sensitivity of Lung and Brain to Sulfide Exposure: A Peripheral Mechanism for Apnea." Toxicological Sciences, vol. 50, 1999, pp. 287-293.*

Toxigenics' Study 420-0710C. "90 Day Vapor Inhalation Toxicity Study of Hydrogen Sulfide in B6C3F1 Mice." Feb. 25, 1983. 8 pages.*

(Continued)

*Primary Examiner* — Frederick Krass
*Assistant Examiner* — Isaac Shomer

(57) ABSTRACT

The present invention concerns the use of oxygen antagonists and other active compounds for inducing stasis or pre-stasis in cells, tissues, and/or organs in vivo or in an organism overall, in addition to enhancing their survivability. It includes compositions, methods, articles of manufacture and apparatuses for enhancing survivability and for achieving stasis or pre-stasis in any of these biological materials, so as to preserve and/or protect them. In specific embodiments, there are also therapeutic methods and apparatuses for organ transplantation, hyperthermia, wound healing, hemorrhagic shock, cardioplegia for bypass surgery, neurodegeneration, hypothermia, and cancer using the active compounds described.

3 Claims, 40 Drawing Sheets

(56) References Cited

U.S. PATENT DOCUMENTS

| | | | |
|---|---|---|---|
| 5,789,447 A | 8/1998 | Wink et al. | |
| 5,791,151 A | 8/1998 | Verhaag et al. | 62/78 |
| 5,801,005 A | 9/1998 | Cheever et al. | |
| 5,830,880 A | 11/1998 | Bosslet et al. | |
| 5,846,945 A | 12/1998 | McCormick | |
| 5,912,019 A | 6/1999 | Singh | 424/608 |
| 5,922,087 A | 7/1999 | Nishioka et al. | |
| 5,948,392 A | 9/1999 | Haslwanter et al. | 424/61 |
| 6,013,256 A | 1/2000 | Light et al. | 424/133.1 |
| 6,040,147 A | 3/2000 | Ridker et al. | |
| 6,046,046 A | 4/2000 | Hassanein | 435/284.1 |
| 6,054,261 A | 4/2000 | Masterson | 435/1.2 |
| 6,057,148 A | 5/2000 | Sugiyama et al. | |
| 6,100,082 A | 8/2000 | Hassanein | 435/284.1 |
| 6,109,260 A | 8/2000 | Bathe | 128/203.12 |
| 6,164,276 A | 12/2000 | Bathe et al. | 128/202.22 |
| 6,319,477 B1* | 11/2001 | Du Toit | 422/120 |
| 6,365,338 B1 | 4/2002 | Bull et al. | 435/1.1 |
| 6,490,880 B1 | 12/2002 | Walsh | 62/457.9 |
| 6,492,103 B1 | 12/2002 | Taylor | 435/1.2 |
| 6,524,785 B1 | 2/2003 | Cozzone et al. | 435/1.1 |
| 6,552,083 B1 | 4/2003 | Isobe et al. | 514/563 |
| 6,557,492 B1 | 5/2003 | Robohm | 119/203 |
| 6,602,277 B2 | 8/2003 | Grahn et al. | 607/108 |
| 6,857,443 B2 | 2/2005 | Volgyesi | 137/101.19 |
| 6,962,154 B2 | 11/2005 | Krebs | 128/203.12 |
| 7,045,140 B2 | 5/2006 | Motterlini et al. | 424/423 |
| 7,122,027 B2 | 10/2006 | Trescony et al. | |
| 7,214,398 B2 | 5/2007 | Roth et al. | |
| 7,923,037 B2 | 4/2011 | Tomaselli et al. | |
| 2002/0068265 A1 | 6/2002 | Lopez et al. | 435/1.1 |
| 2002/0155166 A1 | 10/2002 | Choi et al. | |
| 2003/0050227 A1 | 3/2003 | Kondo | 514/2 |
| 2003/0176317 A1 | 9/2003 | Guenzler-Pukall et al. | 514/1 |
| 2003/0185901 A1* | 10/2003 | Burrell et al. | 424/618 |
| 2003/0235571 A1 | 12/2003 | Gjon-Romanillos | 424/94.1 |
| 2004/0109903 A1 | 6/2004 | Shaklai et al. | 424/699 |
| 2004/0131703 A1 | 7/2004 | Bach et al. | |
| 2004/0157820 A1* | 8/2004 | Tsuchida et al. | 514/185 |
| 2004/0254215 A1 | 12/2004 | Arend et al. | 514/310 |
| 2005/0053912 A1 | 3/2005 | Roth | |
| 2005/0136125 A1* | 6/2005 | Roth | 424/600 |
| 2005/0147692 A1 | 7/2005 | Roth | 424/600 |
| 2005/0170019 A1 | 8/2005 | Roth | 424/705 |
| 2005/0217667 A1 | 10/2005 | Dhuper | 128/200.23 |
| 2005/0227948 A1 | 10/2005 | Schofield et al. | 514/114 |
| 2006/0003972 A1 | 1/2006 | Wallace et al. | 514/166 |
| 2006/0085944 A1 | 4/2006 | Roth et al. | |
| 2006/0270635 A1 | 11/2006 | Wallace et al. | 514/109 |
| 2007/0078113 A1 | 4/2007 | Roth et al. | |
| 2007/0265223 A1 | 11/2007 | Tomaselli et al. | |
| 2008/0085329 A1* | 4/2008 | Roth et al. | 424/701 |
| 2008/0171093 A1* | 7/2008 | Roth et al. | 424/600 |
| 2008/0171725 A1 | 7/2008 | Roth et al. | |
| 2008/0171726 A1 | 7/2008 | Roth et al. | |
| 2008/0187604 A1 | 8/2008 | Tomaselli et al. | |
| 2008/0199541 A1 | 8/2008 | Tomaselli et al. | |
| 2008/0226750 A1 | 9/2008 | Roth et al. | |
| 2008/0318864 A1 | 12/2008 | Roth et al. | |
| 2010/0021387 A1 | 1/2010 | Roth | |
| 2010/0143503 A1 | 6/2010 | Szabo | |
| 2010/0247680 A1 | 9/2010 | Szabo | |
| 2011/0195945 A1 | 8/2011 | Ruan et al. | |
| 2012/0040024 A1 | 2/2012 | Roth et al. | |
| 2012/0052479 A1 | 3/2012 | Roth et al. | |
| 2012/0244067 A1 | 9/2012 | Roth | |

FOREIGN PATENT DOCUMENTS

| | | |
|---|---|---|
| EP | 0153215 | 8/1985 |
| EP | 0158728 | 10/1985 |
| EP | 0203730 | 12/1986 |
| EP | 0681558 | 11/1993 |
| EP | 1323440 | 7/2003 |
| EP | 1395241 | 3/2004 |
| EP | 1879599 | 1/2008 |
| FR | 2816212 | 5/2002 |
| RU | 2177299 | 12/2001 |
| RU | 2177774 | 1/2002 |
| WO | WO 84/01292 | 4/1984 |
| WO | WO 91/01638 | 2/1991 |
| WO | WO 94/16991 | 8/1994 |
| WO | WO 94/17178 | 8/1994 |
| WO | WO 96/02461 | 2/1996 |
| WO | WO 01/80832 | 11/2001 |
| WO | WO 01/81546 | 11/2001 |
| WO | WO 01/92874 | 12/2001 |
| WO | WO 02/09514 | 2/2002 |
| WO | WO 02/101018 | 12/2002 |
| WO | WO 03011866 A1 * | 2/2003 |
| WO | WO 2004/043341 | 9/2003 |
| WO | WO 2004/060147 | 7/2004 |
| WO | WO 2005/039291 | 5/2005 |
| WO | WO 2005/041655 | 5/2005 |
| WO | WO 2005/041656 | 5/2005 |
| WO | WO 2005/046595 | 5/2005 |
| WO | WO 2005041655 A1 * | 5/2005 |
| WO | WO 2005/115075 | 12/2005 |
| WO | WO 2006/085127 | 8/2006 |
| WO | WO 2006/102536 | 9/2006 |
| WO | WO 2006/113914 | 10/2006 |
| WO | WO 2006/119258 | 11/2006 |
| WO | WO 2007/124447 | 7/2007 |
| WO | WO 2008/021550 | 2/2008 |
| WO | WO 2008/040002 | 4/2008 |
| WO | WO 2008/043081 | 4/2008 |
| WO | WO 2008/070741 | 4/2008 |
| WO | WO 2008/079993 | 7/2008 |
| WO | WO 2008/089439 | 7/2008 |
| WO | WO 2008/157393 | 12/2008 |
| WO | WO 2009/003061 | 12/2008 |
| WO | WO 2010/045582 | 4/2010 |

OTHER PUBLICATIONS

EE Bos, HGD Leuvenink, PM Snijder, NJ Kloosterhuis, J-L Hillebrands, JC Leemans, S Florquin, H van Goor. "Hydrogen Sulfide-Induced Hypometabolism Prevents Renal Ischemia/Reperfusion Injury." Journal of the American Society of Nephrology, vol. 20, 2009, pp. 1901-1905, full paper.*

Y-Y P Mok, MSBM Atan, CY Ping, WZ Jing, M Bhatia, S Moochhala, PK Moore. "Role of Hydrogen Sulfide in Haemorrhagic Shock in the Rat: Protective Effect of Inhibitors of Hydrogen Sulphide Biosynthesis." British Journal of Pharmacology, vol. 143, 2004, pp. 881-889.*

G Gutierrez, HD Reines, ME Wulf-Gutierrez. "Clinical Review: Hemorrhagic Shock." Critical Care, vol. 8 No. 5, 2004, pp. 373-381, Published Online Apr. 2, 2004.*

HW Davenport "The ABC of Acid-Base Chemistry, Sixth Edition, Revised." The University of Chicago Press, 1974. 3 total pages included.*

Eghbal et al., "H2S cytotoxicity mechanism involves reactive oxygen species formation and mitochondial depolarisation," *Toxicology*, 203:69-76, 2004.

PCT International Search Report and Written Opinion, issued in International Application No. PCT/US2006/015158, dated Jan. 31, 2007.

U.S. Appl. No. 60/673,295, filed Apr. 20, 2005, Roth.

Abe and Kimura, "The possible role of hydrogen sulfide as an endogenous neuromodulator," *J. Neuroscience*, 16:1066-1071, 1996.

Akamatsu et al., "Heme oxygenase-l-derived carbon monoxide protects hearts from transplant-associated ischemia reperfusion injury," *FASEB J*, Online Edition, Feb. 20, 2004.

Alam et al., "Heme oxygenase-1: past, present, and future," *Antioxid Redox Signal*, 4(4):559-562, 2002.

Ali et al., "Regulation of vascular nitric oxide in vitro and in vivo; a new role for endogenous hydrogen sulfide?" *Br. J. Pharmacol.*, 149:625-634, 2006.

Almeida and Guidotti, "Differential sensitivity of lung and brain to sulfide exposure: a peripheral mechanism for apnea," *Toxicol. Sci.*, 50:287-293, 1999.

(56) References Cited

OTHER PUBLICATIONS

Amersi et al., "Ex vivo exposure to carbon monoxide prevents hepatic ischemia/reperfusion injury through p38 MAP kinase pathway," *Hepatology*, 35(4):815-823, 2002.
Anderson and Azoulay, "Mechanisms and Kinetics of the Thermal Decomposition of Sodium Sulphide Pentahydrate under Controlled Water Vapour Pressure," *J. Chem. Soc. Dalton Trans.*, pp. 469-475, 1986.
Anthony et al., "Preservation of viable biological samples for experiments in space laboratories," *J. Biotech.*, 47:377-393, 1996.
Bak et al., "The role of heme oxygenase-related carbon monoxide and ventricular fibrillation in ischemic/reperfused hearts," *Free Radical Biol Med.*, 33:639-648, 2002.
Barbe et al., "Mechanisms underlying the coronary vasodilation in the isolated perfused hearts of rats submitted to one week of high carbon monoxide exposure in vivo," *Inhalation Toxicol.*, 14:273-285, 2002.
Baskar et al., "Hydrogen sulfide-induces DNA damage and changes in apoptotic gene expression in human lung fibroblast cells," *FASEB J.*, 21:247-255, 2007.
Beck et al., "Effects of tumbling trauma, scalding and hemorrhage on rat tissue non-protein sulfhydryl," *Proc. Soc. Exp. Biol. Med.* 86:823-827, 1954.
Behringer et al., "Survival without brain damage after clinical death of 60-120 mins in dogs using suspended animation by profound hypothermia," *Crit Care Med*, 31(5):1523-1531, 2003.
Bellamy et al., "Suspended animation for delayed resuscitation," *Crit Care Med*, 24(2 Suppl):S24-47, 1996.
Berglin and Carlsson, "Effect of hydrogen sulfide on the mutagenicity of hydrogen peroxide in *Salmonella typhimurium* strain TA102," *Mutation Res.*, 175:5-9, 1986.
Bernard et al., "Treatment of comatose survivors of out-of-hospital cardiac arrest with induced hypothermia," *N. Engl. J. Med.*, 346(8):557-563, 2002.
Bhambhani and Singh, "Physiological effects of hydrogen sulfide inhalation during exercise in healthy men," *J. Appl. Physiol.*, 71:1872-1877, 1991.
Bhatia et al., "Role of hydrogen sulfide in acute pancreatitis and associated lung injury," *FASEB J.*, pp. 1-17, Jan. 25, 2005.
Bhatia et al., "Role of Substance P in Hydrogen Sulfide-Induced Pulmonary Inflammation in Mice," *Am. J. Physiol. Lung Cell. Mol. Physiol.*, 291:L896-904, 2006.
Bhatia et al., "The role of hydrogen sulfide in lung inflammation," *Drug Discov. Today: Dis. Mechanism*, 3:71-75, 2006.
Bian et al., "Role of hydrogen sulphide in the cardioprotection caused by ischemic preconditioning in the rat heart and cardiac myocytes," *J. Pharmacol. Exp. Ther.*, 316:670-678, 2006.
Bickel et al., "Selective Inhibition of Hepatic Collagen Accumulation in Experimental Liver Fibrosis in Ratsw by a New Prolyl 4-Hydroxylase Inhibitor," *Hepatology*, 28:404-411, 1998.
Bishop et al., "Genetic Analysis of Pathways Regulated by the von Hippel-Lindau Tumor Suppressor in *Caenorhabditis elegans*," *PLoS Biol.*, 2:1549-1560, 2004.
Blackstone et al., "H2S Induces a Suspended Animation-Like State in Mice," *Science*, 308:518, 2005.
Brenneman et al., "Olfactory Mucosal Necrosis in Male CD Rats Following Acute Inhalation Exposure to Hydrogen Sulfide: Reversibility and the Possible Role of Regional Metabolism," *Toxicol. Pathol.*, 30:200-208, 2000.
Brouard et al., "Heme oxygenase-l-derived carbon monoxide requires the activation of transcription factor NK-κB to protect endothelial cells from tumor necrosis factor-α-mediated apoptosis," *J. Biol. Chem.*, 277(20):17950-17961, 2002.
Carlsson et al., "Catalase inhibition by sulfide and hydrogen peroxide-induced mutagenicity in *Salmonella typhimurium* strain TA102," *Mutation Res.*, 202:59-64, 1988.
Chauveau et al., "Gene transfer of heme oxygenase-1 and carbon monoxide delivery inhibit chronic rejection," *Am. J. Transplant.*, 2:581-592, 2002.

Chen and Morris, "Kinetics of Oxidation of Aqueous Sulfide by O2," *Environ. Sci. Technol.*, 6:529-537, 1972.
Chen et al., "Targeted Inactivation of Cystic Fibrosis Transmembrane Conductance Regulator Chloride Channel Gene Prevents Ischemic Preconditioning in Isolated Mouse Heart," *Circulation*, 110:700-704, 2004.
Cheng et al., "Hydrogen sulfide-induced relaxation of resistance mesenteric artery beds of rats," *Am. J. Physiol. Heart Circ. Physiol.*, 287-2316-2323, 2004.
CIIT (Chemical Industry Institute of Toxicology), In: *90 day vapor inhalation toxicity study of hydrogen sulfide in fischer 344 rats*, Toxigenics, 420-0710A, 1983.
CIIT (Chemical Industry Institute of Toxicology), In: *90 day vapor inhalation toxicity study of hydrogen sulfide in sprague-dawley rats*, Toxigenics, 420-0710B, 1983.
CIIT (Chemical Industry Institute of Toxicology), In: *90 day vapor inhalation toxicity study of hydrogen sulfide in B6C3F1 mice*, Toxigenics, 420-0710C, 1983.
Clark et al., "Cardioprotective Actions by a Water-Soluble Carbon Monoxide-Releasing Molecule," *Circ. Res.*, 93:2-8, 2003.
Clark et al., "Heme oxygenase-l-derived bilirubin ameliorates postischemic myocardial dysfunction," *Am. J. Physiol. Heart Circ. Physiol.*, 278:H643-H651, 2000.
Clegg, "Embryos of *Artemia franciscana* survive four years of continuous anoxia: the case for complete metabolic rate depression," *J. Exp. Biol.*, 200:467-475, 1997.
Clementi et al., "On the mechanism by which vascular endothelial cells regulate their oxygen consumption," *Proc. Natl. Acad. Sci. U.S.A,.* 96:1559-1562, 1999.
Cohen et al., "Adaptation to Hydrogen Sulfide of Oxygenic and Anoxygenic Photosynthesis among Cyanobacteria," *Applied Environ. Microbiol.*, 51:398-407, 1986.
Collin et al., "Inhibition of endogenous hydrogen sulfide formation reduces the organ injury caused by endotoxemia," *Br. J. Pharmacol.*, 146:498-505, 2005.
Database Caplus Chemical Abstract Service. Moser et al. "Octreotide promotes gallbladder absorption in prairie dogs: a potential cause of gallstones" XPO02319493, STN Accession No. 1995:594873.
Denis and Reed, "The action of blood on sulfides," *J. Biol. Chem.*, 72:385-394, 1927.
Distrutti et al., "5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity," *J. Pharmacol. Exp. Therapeutics*, 319:447-458, 2006.
Distrutti et al., "Evidence that hydrogen sulfide exerts antinociceptive effects in the gastrointestinal tract by activating Katp Channels," *J. Pharmacol. Exp. Therapeutics*, 316:325-335, 2006.
Doeller et al., "Polarographic measurment of hydrogen sulfide production and consumption by mammalian tissues," *Analytical Biochemistry*, 341:40-51, 2005.
Dorman et al., "Cytochrome oxidase inhibition induced by acute hydrogen sulfide inhalation: correlation with tissue sulfide concentrations in the rat brain, liver, lung, and nasal epithelium," *Toxicol. Sci.*, 65:18-25, 2002.
Dorman et al., "Fertility and developmental neurotoxicity effects of inhaled hydrogen sulfide in Sprague-Dawley rats," *Neurotoxicol Teratol*, 22(1):71-84, 2000.
Dorman et al., "Respiratory tract toxicity of inhaled hydrogen sulfide in Fischer-344 rats, Sprague-Dawley rats, and B6C3F1 mice following subchronic (90-day) exposure," *Toxicol. Appl. Pharmacol.*, 198:29-39, 2004.
Dulak et al., "Forum original research communication: heme oxygenase activity modulates vascular endothelial growth factor synthesis in vascular smooth muscle cells," *Antioxid Redox Signal*, 4(2):229-240, 2002.
Dziewiatkowski, "Fate of ingested sulfide sulfur labeled with radioactive sulfur in the rat," *J. Biol. Chem.*, 161:723-729, 1945.
Ebrahimkhani et al., "Hydrogen sulphide and the hyperdynamic circulation in cirrhosis: a hypothesis," *Gut*, 54:1668-1671, 2005.
Eto et al., "Brain hydrogen sulfide is severely decreased in Alzheimer's disease," *Biochem Biophys Res Commun*, 293:1485-1488, 2002.

(56) References Cited

OTHER PUBLICATIONS

Fiorucci et al., "Inhibition of Hydrogen Sulfide Generation Contributes to Gastric Injury Caused by Anti-Inflammatory Nonsteroidal Drugs," *Gastroentherology*, 129:1210-1224, 2005.
Fiorucci et al., "The Third Gas: H2S Regulates Perfusion Pressure in Both the Isolated and Perfused Normal Rat Liver in Cirrhosis," *Hepatology*, 42:539-548, 2005.
Foe and Alberts, "Reversible chromosome condensation induced in *Drosophila* embryos by anoxia: visualization of interphase nuclear organization," *J. Cell Biol.*, 100:1623-1636, 1985.
Franklin et al., "Inhibition of prolyl 4-hydroxylase in vitro and in vivo by members of a novel series of phenanthrolinones," *Biochem. J.*, 353:333-338, 2001.
Freeman et al., "SM-20, EGL-9, and the EGLN family of hypoxia-inducible factor prolyl hydroxylases," *Mol. Cells*, 16:1-12, 2003.
Friedman et al., "Prolyl 4-hydroxylase is required for viability and morphogenesis in *Caenorhabditis elegans*," *Proc. Natl. Acad. Sci. USA*, 97:4736-4741, 2000.
Fujimoto et al., "Carbon monoxide protects against cardiac ischemia—reperfusion injury in vivo via MAPK and Akt-eNOS pathways," *Arterioscler. Thromb. Vasc. Biol.*, 24:1848-1853, 2004.
Furne et al., "Oxidation of hydrogen sulfide and methanethiol to thiosulfate by rat tissues: a specialized function of the colonic mucosa," *Biochem. Pharmacol.*, 62:255-259, 2001.
Geng et al., "H2S generated by heart in rat and its effects on cardiac function," *Biochem. Biophys. Res. Commun.*, 313:362-368, 2004.
Gilbert et al., "Resuscitation from accidental hypothermia of 13.7° C with circulatory arrest," *The Lancet*, 355:375-376, 2000.
Giulivi, "Functional implications of nitric oxide produced by mitochondria in mitochondrial metabolism," *Biochem. J.*, 332:673-679, 1998.
Gorman et al., "The clinical toxicology of carbon monoxide," *Toxicology*, 187(1):25-38, 2003.
Grahn and Keller, "Heat Transfer in Humans : Lessons from Large Hibernators," In: *Life Ain the Cold: Evolution, Mechanisms, Adaptation, and Application. Twelfth International Hibernation Symposium*, Biological Papers of the University of Alaska, (Barnes and Carey, eds.) pp. 81-92, 2004.
Grahn et al., "Heat extraction through the palm of one hand improves aerobic exercise endurance in a hot environment," *J. Appl. Physiol.*, 99:972-978, 2005.
Guillemin and Krasnow, "The hypoxic response: huffing and HIF-ing," *Cell*, 89(1):9-12, 1997.
Guo et al., "Administration of a CO-releasing molecule at the time of reperfusion reduces infarct size in vivo," *Am. J. Physiol. Heart Circ. Physiol.*, 286:1649-1653, 2004.
Haase et al., "Resuscitation with 100% oxygen causes intestinal glutathione oxidation and reoxygenation injury in asphyxiated newborn piglets," *Ann Surg.*, 240(2):364-373, 2004.
Hand, "Induction of quiescence and diapause during life cycles of aquatic invertebrates: mechanisms and implications," *American Zoologist*, 40:1044-1045, 2000 (Abstract).
Hand, "Quiescence in *Artemia franciscana* embryos: reversible arrest of metabolism and gene expression at low oxygen levels," *J Experimental Biology*, 201:1233-1242, 1998 (Abstract).
Hand, In: *Surviving hypoxia mechanisms of control and adaptation*, ed. Hochachka, et al., CRC Press, Inc., Boca Raton, pp. 171-185, 1993.
Hays, In: *Studies of the Effects of Atmospheric Hydrogen Sulfide in Animals*, thesis dissertation, University of Missouri-Columbia, 1972.
Higuchi and Fukamachi, *Folia Pharmacoligica Japonica*, 73(3):307-319, 1997( in Japanese with English explanations of figures).
Hochachka et al., "Mechanism, origin, and evolution of anoxia tolerance in animals," *Comp. Biochem. Physiol. B Biochem. Mol. Biol.*, 130(4):435-459, 2001.
Hochachka et al., "Unifying theory of hypoxia tolerance: molecular/metabolic defense and rescue mechanisms for surviving oxygen lack," *Proc. Natl. Acad. Sci., USA*, 93(18):9493-9438, 1996.
Hochachka, "Defense strategies against hypoxia and hypothermia," *Science*, 231:234-241, 1986.
Hogman, "How can we improve platelet preparation and storage," *Transfus. Sci.*, 17:545-551, 1996.
Hyspler et al., "A simple, optimized method for the determination of sulphide in whole blood by GC-MS as a marker of bowel fermentation processes," *J Chrom.*, 770:255-259, 2002.
Ivan et al., "Biochemical purification and pharmacological inhibition of a mammalian prolyl hydroxylase acting on hypoxia-inducible factor," *Proc. Natl. Acad. Sci. USA*, 99:13459-13464, 2002.
Jiang et al., "Changes of the new gaseous transmitter H2S in patients with coronary heart disease," *J. First Mil. Med. Univ.*, 25:951-954, 2005.
Jiang et al., "Intracellular Ca2+ signaling in endothelial cells by the angiogenesis inhibitors endostatin and angiostatin," *Am. J. Physiol. Cell Physiol.*, 280:1140-1150, 2001.
Johansen et al., "Exogenous hydrogen sulfide (H2S) protects against regional myocardial ischemia-reperfusion injury: Evidence for a role of KATP channels," *Brain Res. Cardiol.*, 101:53-60, 2006.
Kage et al., "A fatal case of hydrogen sulfide poisoning in a geothermal power plant," *J. Forensic Sci.*, 43:908-910, 1998.
Kage et al., "Fatal and nonfatal poisoning by hydrogen sulfide at an industrial waste site," *J. Forensic Sci.*, 47:652-655, 2002.
Kage et al., "The usefulness of thiosulfate as an indicator of hydrogen sulfide poisoning: three cases, *Int. J. Legal Med.*," 110:220-222, 1997.
Kage et al., "Usefulness of thiosulfate as an indicator of hydrogen sulfide poisoning in forensic toxicological examination: A study with animal experiments," *Jpn. J. Forensic Toxicol.*, 10:223-227, 1992.
Kaillo et al., "Signal transduction in hypoxic cells: inducible nuclear translocation and recruitment of the CBP/p300 coactivator by the hypoxia-inducible factor-1alpha," *EMBO J.*, 17:6573-6586, 1998.
Kangas and Savolainen, "Urinary thiosulphate as an indicator of exposure to hydrogen sulphide vapour," *Clinica Chimica Acta*, 164:7-10, 1987.
Khan et al., "Effects of hydrogen sulfide exposure on lung mitochondrial respiratory chain enzymes in rats," *Toxicol Applied Pharmacol*, 103:482-490, 1990.
Kilburn and Warshaw, "Hydrogen sulfide and reduced-sulfur gases adversely affect neurophysiological functions," *Toxicology Indust Health*, 11(2):185-197, 1995.
Kilburn, "Measuring the effects of chemicals on the brain," *Environ Health*, 54(3):150, 1999.
Kilburn, "Neurotoxicity from airborne chemicals around a superfund site," *Environ Res*, 81(2):92-99, 1999.
Kimura and Kimura, "Hydrogen sulfide protects neurons from oxidative stress," *FASEB J.*, 18:1165-1167, 2004.
Kimura et al., "Hydrogen sulfide protects HT22 neuronal cells from oxidative stress," *Antioxid. Redox Signal.*, 8:661-670, 2006.
Kirkby and Adin, "Products of heme oxygenase and their potential therapeutic applications," *Am. J. Physiol. Renal Physiol.*, 290:563-571, 2006.
Kivirikko and Myllyharju, "Prolyl 4-hydroxylases and their protein disulfide isomerase subunit," *Matrix Biol.*, 16:357-368, 1998.
Kleinjan et al., "Equilibrium of the reaction between dissolved sodium sulfide and biologically produced sulfur," *Colloids and Surface B: Biointerfaces*, 43:228-237, 2005.
Kleinjan et al., "Kinetics of the chemical oxidation of polysulfide anions in aqueous solution," Water Res., 39:4093-4100, 2005.
Kondo et al., "Circannual Control of Hibernation by HP Complex in the Brain," *Cell*, 125:161-172, 2006.
Krishnamachary et al., "Regulation of colon carcinoma cell invasion by hypoxia-inducible factor 1," *Cancer Res.*, 63:1138-1143, 2003.
Kubo et al., "Direct inhibition of endothelial nitric oxide synthase by hydrogen sulfide: Contribution to dual modulation of vascular tension," *Toxicology*, 232:138-146, 2007.
Kubulus et al., "Mechanism of the delay phenomenon: tissue protection is mediated by heme oxygenase-1," *Am J Physiol Heart Circ Physiol*, 287:H2332-H2340, 2004.
Lambert et al., "Hydrogen sulfide (H2S) and sour gas effects on the eye. A historical perspective," *Sci. Total Environ.*, 367:1-22, 2006.
Lewis and Cochrane, "Alteration of sulfate and hydrogen metabolism in the human colon by changing intestinal transit rate," *Am. J. Gastroenterol.*, 102:624-633, 2007.

(56) References Cited

OTHER PUBLICATIONS

Li et al., "Hydrogen sulfide is a novel mediator of lipopolysaccharide-induced inflammation in the mouse," *FASEB J.*, 19:1196-1198, 2005.
Li et al., "Hydrogen sulphide—a novel mediator of inflammation?" *Curr. Opin. Pharmacol.*, 6:125-129, 2006.
Lin et al., "Sulfur revisited," *J. American Acad. Dermatol.*, 18:553-558, 1988.
Lundgren-Eriksson et al., "Radio-and chemotoxicity in mice during hypothermia," *Anticancer Res.*, 21(5):3269-74, 2001.
Majamaa et al., "Differences between collagen hydroxylases and 2-oxoglutarate dehydrogenase in their inhibition by structural analogues of 2-oxoglutarate," *Biochem. J.*, 229:127-133, 1985.
Majamaa et al., "The 2-oxoglutarate binding site of prolyl 4-hydroxylase. Identification of distinct subsites and evidence for 2-oxoglutarate decarboxylation in a ligand reaction at the enzyme-bound ferrous ion," *Eur. J. Biochem.*, 138:239-245, 1984.
Mannaioni et al., "Carbon monoxide: the bad and the good side of the coin, from neuronal death to anti-inflammatory activity," *Inflamm. Res.*, 55:261-273, 2006.
Masini et al., "Heme Oxygenase-1 and the Ischemia-Reperfusion Injury in the Rat Heart," *Exp. Biol. Med.*, 228:546-549, 2003.
Milby and Baselt, "Hydrogen Sulfide Poisoning: Clarification of Some Controversial Issues," *Am. J. Industrial. Med.*, 35:192-195, 1999.
Mok et al., "Role of hydrogen sulphide in haemorrhagic shock in the rat: protective effect of inhibitors of hydrogen sulphide biosynthesis," *Br. J. Pharmacol.*, 143:881-889, 2004.
Morse and Choi, "Heme oxygenase-1: from bench to bedside," *Am. J. Respir. Crit. Care Med.*, 172:660-670, 2005.
Moses et al., "Sampling and Analysing Mixtures of Sulphate, Sulphite, Thiosulphate and Polythionate," *Talanta*, 31:331-339, 1984.
Moulin et al., "Predicted regional flux of hydrogen sulfide correlates with distribution of nasal olfactory lesions in rats," *Toxicol. Sci.*, 66:7-15, 2002.
Nakao et al., "Carbon monoxide inhalation protects rat intestinal grafts from ischemia/reperfusion injury," *Am. J. Pathol.*, 163:1587-1598, 2003.
Nakao et al., "Ex Vivo Application of Carbon Monoxide in University of Wisconsin Solution to Prevent Intestinal cold Ischemia/Reperfusion Injury," *Am. J. Transplantation*, 6:2243-2255, 2006.
Nakao et al., "Protection against ischemia/reperfusion injury in cardiac and renal transplantation with carbon monoxide, biliverdin and both," *Am. J. Transplant.*, 5:282-291, 2005.
Nashef et al., "Determination of Hydrogen Sulfide with 5,5'-Dithiobis-(2-Nitrobenzoic Acid), N-Ethylmaleimide, and Parachloromercuribenzoate," *Analytical Biochem.*, 79:394-405, 1977.
Nicholson et al., "Inhibition of respiratory and bioenergetic mechanisms by hydrogen sulfide in mammalian brain," *J. Toxicol. Environ. Health Part A*, 54:491-507, 1998.
Nolan et al., "Therapeutic Hypothermia After Cardiac Arrest: An Advisory Statement by the Advanced Life Support Task Force of the International Liaison Committee on Resuscitation," *Circulation*, 108:118-121, 2003.
Nystul and Roth, "Carbon monoxide-induced suspended animation protects against hypoxic damage in *Caenorhabditis elegans*," *Proc. Natl. Acad. Sci. USA*, 101:9133-9136, 2004.
Nystul et al., "Suspended animation in *C. elegans* requires the spindle checkpoint," *Science*, 302(5647):1038-1041, 2003.
Oh et al., "Hydrogen sulfide inhibits nitric oxide production and nuclear factor-kappaB via heme oxygenase-1 expression in RAW264.7 macrophage stimulated with lipopolysaccharide," *Free Radical Biol. Med.*, 41:106-119, 2006.
Ott et al., "Inhalation of carbon monoxide prevents liver injury and inflammation following hind limb ischemia/reperfusion," *FASEB J.*, 19:106-108, 2005.
Otterbein et al., "Heme oxygenase: colors of defense against cellular stress," *Am J Physiol Lung Cell Mol Physiol*, 279(6):L1029-L1037, 2000.
Otterbein et al., "Heme oxygenase-1: unleashing the protective properties of heme," *Trends Immunol*, 24(8):449-455, 2003.
Padilla and Roth, "Oxygen deprivation causes suspended animation in the zebrafish embryo," *Proc. Natl. Acad. Sci., USA*, 98(13):7331-7335, 2001.
Padilla et al., "Dephosphorylation of cell cycle-regulated proteins correlates with anoxia-induced suspended animation in *Caenorhabditis elegans*," *Molec Biology of the Cell*, 13:1473-1483, 2002.
Pan et al., "Endogenous hydrogen sulfide contributes to the cardioprotection by metabolic inhibition preconditioning in the rat ventricular myocytes," *J. Mol. Cell Cardiol.*, 40:119-130, 2006.
Partlo et al., "Effects of repeated hydrogen sulphide (H2S) exposure on learning and memory in the adult rat," *Neurotoxicology*, 22(2):177-189, 2001.
Pearson et al., "Endogenous hydrogen sulfide and the cardiovascular system-what's the smell all about?" *Clin. Invest. Med.*, 29:146-150, 2006.
Petersen, "The effect of inhibitors on the oxygen kinetics of cytochrome c oxidase," *Biochim Biophys Acta*, 460:299-307, 1977.
Qu et al., "Hydrogen sulfide is a mediator of cerebral ischemic damage," *Stroke*, 37:889-893, 2006.
Ramasamy et al., "Sulfide-detoxifying enzymes in the human colon are decreased in cancer and unregulated in differentiation," *Am J. Physiol. Gastrointest. Liver Physiol.*, 291:288-296, 2006.
Roberts et al., "Two sensor kinases contribute to the hypoxic response of mycobacterium tuberculosis," *J. Biol. Chem.*, 279:23082-23087, 2004.
Rogers et al., "Behavioral and functional analysis of mouse phenotype: SHIRPA, a proposed protocol for comprehensive phenotype assessment," *Genome*, 8:711-713, 1997.
Rose et al., "Hydrogen sulfide protects colon cancer cells from chemopreventative agent beta-phenylethyl isothiocyanate induced apoptosis," *World J. Gastroenterol.*, 11:3990-3997, 2005.
Roth et al., "Buying time in suspended animation," *Scientific American*, 292:48-55, 2005.
Ryter and Otterbein, "Carbon Monoxide in biology and medicine," *BioEssays*, 26:270-280, 2004.
Sabatier, "Recherches Thermiques Sur Les Sufures," *Ann. Chim. Phys.*, 22:17-98, 1881.
Safar et al., "Suspended animation for delayed resuscitation from prolonged cardiac arrest that is unresuscitable by standard cardiopulmonary cerebral resuscitation," *Crit Care Med*, 28(11 Suppl):N214-218, 2000.
Saitoh et al., "Heart preservation in HTK solution: role of coronary vasculature in recovery of cardiac function," *Ann. Thorac. Surg.*, 69:107-112, 2000.
Schroeter et al., "Incorporation of tissue reaction kinetics in a computational fluid dynamics model for nasal extraction of inhaled hydrogen sulfide in rats," *Toxicol. Sci.*, 90:198-207, 2006.
Schroeter et al., "Use of a Pharmacokinetic-Driven Computational Fluid Dynamics Model to Predict Nasal Extraction of Hydrogen Sulfide in Rats and Humans," *ToxSci Advance Access*, published Sep. 19, 2006.
Searcy and Peterson, "Hydrogen sulfide consumption measured at low steady state concentrations using a sulfidostat," *Analytical Biochem.*, 324:269-275, 2004.
Semenza, "Hypoxia-inducible factor 1: oxygen homeostasis and disease pathology," *Trends Mol Med*, 7(8):345-350, 2001.
Shea and Howell, "High-Performance Liquid Chromatographic Measurement of Exogenous Thiosulfate in Urine and Plasma," *Analytical Biochem.*, 140:589-594, 1984.
Shimoda et al., "HIF-1 regulates hypoxic induction of NHE1 expression and alkalinization of intracellular pH in pulmonary arterial myocytes," *Am. J. Physiol. Lung Cell Mol. Physiol.*, 291:941-949, 2006.
Siddiq et al., "Hypoxia-inducible Factor Prolyl 4-Hydroxylase Inhibiton: A target for neuroprotection in the central nervous system," *J Biol. Chem.*, 16:41732-43, 2005.

(56) References Cited

OTHER PUBLICATIONS

Sivarajah et al., "The production of hydrogen sulfide limits myocardial ischemia reperfusion injury and contributes to the cardioprotective effects of preconditioning with endotoxin, but not ischemia in the rats," *Shock*, 26:154-161, 2006.

Srilatha et al., "Possible role for the novel gasotransmitter hydrogen sulphide in erectile dysfunction- a pilot study," *Eur. J. Pharm.*, 535:280-282, 2006.

Struve et al., "Neurotoxicological effects associated with short-term exposure of Sprague-Dawley rats to hydrogen sulfide," *Neurotoxicology*, 22(3):375-385, 2001.

Suarez and Darveau, "Multi-level regulation and metabolic scaling," *J. Exp. Biol.*, 208:1627-1634, 2005.

Tamura et al., "Phase-specific central regulatory systems of hibernation in Syrian hamsters," *Brain Res.*, 1045:88-96, 2005.

Tan et al., "Identification of a novel small-molecule inhibitor of the hypoxia-inducible factor 1 pathway," *Cancer Res.*, 65:605-612, 2005.

Teodoro and O'Farrell, "Nitric oxide-induced suspended animation promotes survival during hypoxia," *EMBO J*, 22(3):580-587, 2003.

The Hypothermia After Cardiac Arrest Study Group, "Mild Therapeutic Hypothermia to Improve the Neurologic Outcome after Cardiac Arrest," *N. Engl. J. Med.*, 346:549-556, 2002.

Tisherman, "Suspended animation for resuscitation from exsanguinating hemorrhage," *Crit Care Med*, 32(2 Suppl):S46-S50, 2004.

Truong et al., "Molecular Mechanisms of Hydrogen Sulfide Toxicity," *Drug Metabolism Rev.*, 38:733-744, 2006.

Tsuei and Kearney, "Hypothermia in the trauma patient," *Injury, Int. J. Care Injured*, 35:7-15, 2004.

Vahlkamp et al., "Inhibition of mitochondrial electron transfer in rats by ethanethiol and methanethiol," *Clinical Science*, 56:147-156, 1979.

Van Voorhies et al., "Broad oxygen tolerance in the nematode *Caenorhabditis elegans*," *J Exp Biol*, 203(Pt 16):2467-2478, 2000.

Vanden Hoek et al., "Induced hypothermia by central venous infusion: Saline ice slurry versus chilled saline," *Crit. Care. Med.*, 32:S425-S431, 2004.

Wang, "Two's company, three's a crowd: can $H_2S$ be the third endogenous gaseous transmitter?" *FASEB J*, 16(13):1792-1798, 2002.

Welsh et al., "The Thioredoxin Redox Inhibitors 1-Methylpropyl 2-Imidazolyl Disulfide and Pleurotin Inhibit Hypoxia-induced Factor Ialpha and Vascular Endothelial Growth Factor Formation," *Mol Cancer Therapeutics*, 2:235-43, 2003.

Whiteman et al., "The novel neuromodulator hydrogen sulfide: an endogenous peroxynitrite 'scavenger'?" *J. Neurochem.*, 90:765-768, 2004.

Wilms et al., "Reactions of mercaptans with cytochrome c oxidase and cytochrome c," *Biochim. Biophys. Acta*, 589:324-335, 1980.

Wingrove et al., "Nitric oxide contributes to behavioral, cellular, and developmental responses to low oxygen in *Drosophila*," *Cell*, 98:105-114, 1999.

Wowk, "Is hydrogen sulfide the secret to suspended animation?" *Croynics*, Jul./Aug. 2005.

Wu et al., Hydrogen sulfide ameliorates vascular calcification induced by vitamin D3 plus nicotine in rats, *Acta Pharmacologica Sinica*, 27:299-306, 2006.

Wu et al., "Mild Hypothermia Improves Survival after Prolonged, Traumatic Hemorrhagic Shock in Pigs," *J. Trauma*, 59:291-301, 2005.

Wunder et al., "Carbon monoxide, but not endothelin-1, plays a major role for the hepatic microcirculation in a murine model of early systemic inflammation," *Crit. Care Med.*, 33:2323-2331, 2005.

Xiao et al., "Hydrogen sulfide facilitates carotid sinus baroreflex in anesthetized rats," *Acta Pharmacologica Sinica*, 27:294-298, 2006.

Yaffe et al., "Smart aortic arch catheter: moving suspended animation from the laboratory to the field," *Crit Care Med*, 32(2 Suppl,):S51-S55, 2004.

Yang et al., "Hydrogen sulfide-induced apoptosis of human aorta smooth muscle cells via the activation of mitogen-activated protein kinases and caspase-3," *FASEB J.*, 18:1782-1784, 2004.

Yusuf et al., "Streptozotocin-induced diabetes in the rat is associated with enhanced tissue hydrogen sulfide biosynthesis," *Biochem. Biophys. Res. Commun.*, 333:1146-1152, 2005.

Zagli et al., "Hydrogen sulfide inhibits human platelet aggregation," *Eur. J. Pharmacol.*, 559:65-68, 2007.

Zanardo et al., "Hydrogen sulfide is an endogenous modulator of leukocyte-mediated inflammation," *FASEB J.*, 20:E1-E8, 2006.

Zhang et al., "Whole-body hypoxic preconditioning protects mice against acute hypoxia improving lung function," *J Appl Physiol*, 96(1):392-397, 2004.

Zhao and Wang, "H2S-induced vasorelaxation and underlying cellular and molecular mechanisms," *Am. J. Physiol. Heart Circ. Physiol.*, 283:H474-H480, 2002.

Zhu et al., "Hydrogen sulfide and its cardioprotective effects in myocardial ischemia in experimental rats," *J. Appl. Physiol.*, Oct. 12, 2006 (article in press).

Zuckerbraun et al., "Carbon monoxide protects against the development of experimental necrotizing enterocolitis," *Am. J. Physiol. Heart Circ. Physiol.*, 289:607-613, 2005.

Chunyu, et al., "The Regulatory Effect of Hydrogen Sulfide on Hypoxic Pulmonary Hypertension in Rats," *Biochemical and Biophysical Research Communications* 302(21), Mar. 2003, pp. 810-816.

EP Application No. 06751023.0: Communication Pursuant to Article 94(3) EPC dated Jun. 28, 2010.

EP Application No. 06751023.0: Communication Pursuant to Article 94(3) EPC dated Sep. 3, 2009.

EP Application No. 06751023.0: Communication Pursuant to Article 94(3) EPC dated Dec. 15, 2008.

Elrod, et al., "Hydrogen Sulfide Attenuates Myocardial Ischemia-Reperfusion Injury By Preservation of Mitochondrial Function," *PNAS* 104(39), Sep. 25, 2007, pp. 15560-15565.

Geng, et al., "Endogenous Hydrogen Sulfide Regulation of Myocardial Injury Induced by Isoproterenol," *Biochemical and Biophysical Research Communications* 318, Jun. 4, 2004, pp. 756-763.

Gonon, et al., "Nitric Oxide Mediates Protective Effect of Endothelin Receptor Antagonism During Myocardial Ischemia and Reperfusion," *American Journal of Physiology, Heart and circulatory Physiology* 286, May 2004, pp. H1767-H1773.

Jha, et al., "Hydrogen Sulfide Attenuates Hepatic Ischemia-Reperfusion Injury: Role of Antioxidant and Antiapoptotic Signaling," *Am J Physiol Heart Circ Physiol* 295, Jun. 12, 2008, pp. H801-H806.

Mok Yin-Yuan, et al., "Role of Hydrogen Sulphide in Haemorrhagic Shock in the Rat: Protective Effect of Inhibitors of Hydrogen Sulphide Biosynthesis," *British Journal of Pharmacology* 143 (7), Dec. 2004, pp. 881-889.

Nystul, et al., "Carbon monoxide-induced suspended animation protects against hypoxic damage in *Caenorhabditis elegans*," Proceedings of The National Academy of Sciences of USA, National Academy of Science, Washington, DC, US, Jun. 15, 2004, vol. 101, No. 24, pp. 9133-9136.

Osipov, et al., "Effect of Hydrogen Sulfide in a Porcine Model of Myocardial Ischemia-Reperfusion: Comparison of Different Administration Regimens and characterizations of the Cellular Mechanisms of Protection," *J Cardiovasc Pharmacol* 54(4), Oct. 2009, pp. 287-297.

Roth, et al., "Buying time in suspended animation," *Scientific American*, Jun. 6, 2005, vol. 292, No. 6, pp. 48-55.

Simon, et al., "Hemodynamic and metabolic Effects of Hydrogen Sulfide During Porcine Ischemia/Reperfusion Injury," *Shock* 30(4), Jan. 2008, pp. 359-364.

Teodoro, et al., "Nitric Oxide-Induced Suspended Animation Promotes Survival During Hypoxia," *EMBO Journal*, Oxford University Press, Surrey, GB, Feb. 3, 2003, vol. 22, No. 3, pp. 580-587.

Air Liquide Specialty Gases. Materials Safety Data Sheet for Hydrogen Selenide. Mar. 9, 2001, 5 printed pages. http://www.scottecatalog.com/msds.nsf/PrintView/7783-07-5?OpenDocument, accessed Aug. 12, 2013.

Bagarinao, et al., *Journal of Fish Biology*, 1993, 42, 729-748.

Brown, *Biochimica et Biophysica Acta*, 2001, 1504, 46-57.

(56) References Cited

OTHER PUBLICATIONS

Drabek, et al., "Intravenous hydrogen sulfide does not induce hypothermia or improve survival from hemorrhagic shock in pigs," Shock, 35(1):67-73 (2011).
Dubeau, et al., Journal of Chemical and Engineering Data, vol. 16, No. 1, 1971, pp. 78-79.
EP Application No. 06751023.0: Communication Pursuant to Article 94(3) EPC mailing date May 10, 2011.
EP Application No. 06751023.0: Communication Pursuant to Article 94(3) EPC mailing date Dec. 6, 2011.
EP Application No. 06751023.0: Communication Pursuant to Article 94(3) EPC mailing date Jun. 21, 2012.
EP Application No. 06751023.0: Communication Pursuant to Article 94(3) EPC mailing date Oct. 18, 2012.
Goodman and Gilman's The Pharmacological Basis of Therapeutics, 1987, Chapter 1, 3-13.
Gordon, Emerg. Med. J., 2001, 18, 81-89.
Haouzi, Respiratory Physiology & Neurobiology, 2008, 160, 109-115.
International Preliminary Report on Patentability, issued in PCT/US2006/015158, mailing date Oct. 23, 2007.
Partial International Search Report, issued in PCT/US2006/015158, mailing date Oct. 12, 2006.
Leslie, Science, 2008, 320, 1155-1157.
Li, Pediatric Critical Care Medicine, 2008, 9(1) 1101-1102.
Meads, Chemical Primer:An Elementary Work, 1885, 40-41.
The Merk Manual, Hypothermia, www.merck.com/mmhe/print/sec24/ch291/ch291b.html, Jun. 9, 2008.
Merriam-Webster Online. obtained: Feb. 11, 2009: http://merriam-webster.com/dictionary/protect.
Remington'S Pharmaceutical Sciences, 1990, Chapter 85, 1570-1580.
Stedman'S Medical Dictionary, www.thomsonhc.com/pdre/librarian/PFDefulatlActionld/pdrcommon.stedmans, 2000.
U.S. Appl. No. 10/971,575: Non-Final Rejection, mailing date Jun. 19, 2008.
U.S. Appl. No. 10/971,575: Final Rejection, mailing date Feb. 24, 2009.
U.S. Appl. No. 10/971,575: Non-Final Rejection, mailing date Sep. 28, 2009.
U.S. Appl. No. 10/971,575: Final Rejection, mailing date Jul. 7, 2010.
U.S. Appl. No. 10/971,575: Non-Final Rejection, mailing date Mar. 2, 2011.
U.S. Appl. No. 10/971,575: Final Rejection, mailing date Sep. 30, 2011.
U.S. Appl. No. 10/971,575: Non-Final Rejection, mailing date Nov. 14, 2012.
U.S. Appl. No. 10/971,575: Non-Final Rejection, mailing date Jul. 1, 2013.
U.S. Appl. No. 13/194,635: Non-Final Rejection mailing date Sep. 12, 2013.
Verrier, Journal of Cardiovascular Pharmacology, 1996, 27 26-30 (pp. 1-7).
Wall, Theriogenology, 2008, 69, 2-9.
Yanamato, Stroke, 2001, 32, 232-239.
Zhao, The EMBO Journal, 2001, 20(21), 6008-6016.
Affonso, et al. "Blood parameters and metabolites in the teleost fish macropomum exposed to sulfide or hypoxia," Comp Biochem. Physiol. C, 133:375-382, 2002.
Brown, et al., "Rapid reduction of nitric oxide by mitochondria, and reversible inhibition of mitochondrial respiration by nitric oxide," Biochem. J., 315:295-299, 1996.
Finney, et al., "Protection of the Ischemic Heart wuth DMSO Alone or DMSO with Hydrogen Peroxidie*," Annals of New York Academy of Sciences, 141:231-24, 1967.
Gordon, E-letter responses to Science, "Toxicant-induced regulated hypothermia", available online at http:--www.sciencemag.org-content-308-5721-518-reply#sci_el_1431?sid=c9415725-831f-44e1-8264-b2cbb5e18398, p. 2, 2005, accessed Apr. 3, 2014.
Gunter, et al., "Physiologic Changes in Acute Anoxia with Anesthesia and Hypothermia," J. Appl. Physiol., 13:57-60, 1958.
Harvey, "Cooling of Embryonic Cells, Isolated Blastoderms, and Intact Embryos of the Zebra Fish Brachydanio rerio to -196 degrees C," Cryobiology, 20(4):440-447, 1983.
Hetastarch. Baltimore Washington Medical Center Webpage downloaded from http:--mybwmc.org-library-41-061100, 1 page, 2001, accessed Apr. 3, 2014.
Kaneko, et al., "L-cysteine inhibits insulin release from pancreatic β-cell: Possible involvement of metabolic production of hydrogen sulfide a novel gasotransmitter," Diabetes, 55(5):1391-1397, 2006.
Koshimoto, et al., "Effect of Osmolality and Oxygen Tension on the Survival of Mouse Sperm Frozen to Various temperatures in Various Concentrations of Glycerol and Raffinose," Cryobiology 41:204-231, 2000.
Kuroda, et al., "Pancreatic Secretory trypsin Inhibitor as a Marker for Early Detection of Rejection in Canine Pancreas Allotransplantation," Transplantation, 46(4): 493-495, 1988.
Mt. Everest Information, available online at: http:--web.archive.org-web-20030207054012-http:--www.teameverest03.org-everest_info-index.html, 2003, accessed Apr. 3, 2014.
Rosenthal, "Suspended Animation—Surgery's Frontier," Reprinted from the Science page of The New York Times of Nov. 13, 1990, available online at: http:--198.170.115.106-surgery.html, 4 pages, accessed Apr. 3, 2014.
Satterly, et al., "Hydrogen sulfide as a pharmacologic adjunct to resuscitation in a porcine model of severe hemorrhage and ischemia-reperfusion injury," Crit Care Med, 40(12) (abstract only).
Schurmann, et al., "Lethal Oxygen Levels at Different Temperatures and the Preferred Temperature During Hypoxia of the Atlantic Cod, Gadus morhua L.," J. Fish Biol., 41:927-934, 1992.
Sodha, et al., "Hydrogen Sulfide Therapy Attenuates the Inflammatory Response in a Porcine Model of Myocardial Ischemia—Reperfusion Injury," J Thorac Cardiovasc Surg., 138(4):977-984, 2009.
Sodha, et al., "The effects of therapeutic sulfide on myocardial apoptosis in response to ischemia-reperfusion injury," Eur J Cardo-Thoracic Surgery, 33(5):906-13, 2008.
United States Patent and Trademark Office: Final Office Action dated Jan. 8, 2009, U.S. Appl. No. 10/972,063.
United States Patent and Trademark Office: Final Office Action dated Mar. 16, 2010, U.S. Appl. No. 10/972,063.
United States Patent and Trademark Office: Final Office Action dated Nov. 26, 2007, U.S. Appl. No. 10/480,430.
United States Patent and Trademark Office: Non-Final Office Action dated Aug. 19, 2009, U.S. Appl. No. 10/972,063.
United States Patent and Trademark Office: Non-Final Office Action dated Mar. 20, 2009, U.S. Appl. No. 11/837,484.
United States Patent and Trademark Office: Non-Final Office Action dated May 12, 2008, U.S. Appl. No. 10/480,430.
United States Patent and Trademark Office: Non-Final Office Action dated May 18, 2007, U.S. Appl. No. 10/480,430.
United States Patent and Trademark Office: Non-Final Office Action dated May 2, 2008, U.S. Appl. No. 10/972,063.
U.S. Appl. No. 10/972,063: Non-Final Rejection dated Nov. 5, 2010, 20 pages.
U.S. Appl. No. 13/194,635: Non-Final Rejection dated Sep. 12, 2013, 10 pages.
West, "Climbing Mt. Everest Without Oxygen: An Analysis of Maximal Exercise During Extreme Hypoxia," Respiration Physiology, 52(3):265-279, 1983.
Whiteman, et al., "P073. Hydrogen sulfide regulates the availability of nitric oxide through the formation of a novel nitrosothiol: Implications for cardiovascular function and human disease," Posters, Nitric Oxide 14:A39-A44, 2006.

* cited by examiner

FIG. 8A-B

METHODS, COMPOSITIONS AND ARTICLES OF MANUFACTURE FOR ENHANCING SURVIVABILITY OF CELLS, TISSUES, ORGANS, AND ORGANISMS

This application is related to U.S. Provisional Patent Application 60/673,037 and 60/673,295 both filed on Apr. 20, 2005, as well as U.S. Provisional Patent Application 60/713,073, filed Aug. 31, 2005, U.S. Provisional Patent Application 60/731,549, filed Oct. 28, 2005, and U.S. Provisional Patent Application 60/762,462, filed on Jan. 26, 2006, all of which are hereby incorporated by reference in their entirety.

The government may own rights in the present invention pursuant to grant number GM048435 from the National Institute of General Medical Sciences (NIGMS).

BACKGROUND OF THE INVENTION

1. Field of the Invention

The present invention relates generally to the field of cell biology and physiology. More particularly, it concerns methods, compositions and apparatuses for enhancing survivability of and/or reducing damage to cells, tissues, organs, and organisms, particularly under adverse conditions, including but not limited to hypoxic or anoxic states, using one or more substances, including those that compete with oxygen. In certain embodiments, the present invention includes methods, compositions and apparatuses for treating, preventing, and diagnosing diseases and conditions by exposing a subject to an oxygen antagonist, protective metabolic agent, or other chemical compound discussed herein, or a precursor thereof, that can achieve its stated goal (collectively referred to as "active compounds").

2. Description of Related Art

Stasis is a Latin term meaning "standstill." In the context of stasis in living tissues, the most common forms of stasis relate to the preservation of tissues for transplant or reattachment. Typically, such tissues are immersed in a physiologic fluid, such as saline, and placed in the cold to reduce biochemical processes leading to cellular damage. This stasis is incomplete and cannot be relied upon for extended periods. In fact, the success of organ transplant and limb reattachment is inversely related to the time the organ or limb is out of contact with the intact organism.

A more extreme version of stasis involves placing an entire organism into what is known colloquially as "suspended animation." Though still considered largely within the realm of science fiction, some notoriety has been achieved when wealthy individuals have sought to be cryopreserved after death, in the hope that future medical breakthroughs will permit their revival and cure of their fatal ailments. Allegedly, more than one hundred people have been cryopreserved since the first attempt in 1967, and more than one thousand people have made legal and financial arrangements for cryonics with one of several organizations, for example, Alcor Life Extension Foundation. Such methods involve the administration of anti-ischemic drugs, low temperature preservation, and methods to perfuse whole organisms with cryosuspension fluids. It has not yet been substantiated that this form of organismal stasis is reversible.

The utility of inducing stasis in biological matter as contemplated by the compositions, methods, or articles of manufacture described herein, is characterized by induction or onset of stasis followed by a period of time in which the stasis is maintained, followed then by reversion to a normal or near normal physiological state, or a state that one skilled in the art would recognize as a state that is better than the state of the biological matter had it never undergone stasis, in whole or in part. Stasis can also be defined as what it is not. Organismal stasis is not any of the following states: sleep, comatose, death, anesthetized, or grand mal seizure.

There are numerous reports of individuals who have survived apparent cessation of pulse and respiration after exposure to hypothermic conditions, usually in cold-water immersion. Though not fully understood by scientists, the ability to survive such situations likely derives from what is called the "mammalian diving reflex." This reflex is believed to stimulate the vagal nervous system, which controls the lungs, heart, larynx and esophagus, in order to protect vital organs. Presumably, cold-water stimulation of nerve receptors on the skin causes shunting of blood to the brain and to the heart, and away from the skin, the gastro-intestinal tract and extremities. At the same time, a protective reflex bradycardia, or slowing of the heart beat, conserves the dwindling oxygen supplies within the body. Unfortunately, the expression of this reflex is not the same in all people, and is believed to be a factor in only 10-20% percent of cold-water immersion cases.

Compositions and methods that do not rely fully or at all on hypothermia and/or oxygen may be useful in the context of organ preservation, as well as for tissue or cell preservation. Cells and tissue are currently preserved using hypothermia, frequently at temperatures substantially below freezing, such as in liquid nitrogen. However, dependence on temperature can be problematic, as apparatuses and agents for producing such low temperatures may not be readily available when needed or they may require replacement. For example, tissue culture cells are often stored for periods of time in tanks that hold liquid nitrogen; however, these tanks frequently require that the liquid nitrogen in the unit be periodically replaced, otherwise it becomes depleted and the temperature is not maintained. Furthermore, damage to cells and tissue occurs as a result of the freeze/thaw process. Thus, improved techniques are needed.

Moreover, the lack of ability to control cellular and physiologic metabolism in whole organisms subjected to traumas such as amputation and hypothermia is a key shortcoming in the medical field. On the other hand, the anecdotal evidence discussed above strongly suggests that if properly understood and regulated, it is possible to induce stasis in cells, tissues and whole organisms. Thus, there is a great need for improved methods for controlling metabolic processes particularly under traumatic conditions.

SUMMARY OF THE INVENTION

Therefore, the present invention provides methods, compositions, articles of manufacture, and apparatuses to induce stasis in cells, tissues and organs located within or derived from an organism, as well as in the organism itself. Such methods, compositions, articles of manufacture, and apparatuses can be employed to protect biological matter, as well as to prevent, treat, or diagnose diseases and conditions in the organism. In addition, such methods may directly induce stasis themselves, or they may act indirectly by not inducing stasis themselves, but by enhancing the ability of biological matter to enter stasis in response to an injury or disease condition, e.g., by reducing the time or level of injury or disease required to achieve stasis. Such a condition may be referred to as pre-stasis. Details of such applications and other uses are described below.

The invention is based, in part, on studies with compounds that were determined to have a protective function, and thus, serve as protective agents. Moreover, the overall results of studies involving different compounds indicate that compounds with an available electron donor center are particularly effective in inducing stasis or pre-stasis. In addition, these compounds induce reversible stasis, meaning they are not so toxic to the particular biologic matter that the matter dies or decomposes. It is further contemplated that the present invention can be used to enhance survivability of and/or to prevent or reduce damage to biological matter, which may be subject to or under adverse conditions.

In particular embodiments, methods of the present invention are used to induce stasis or pre-stasis in biological matter, e.g., cells, tissues, organs, and/or organisms, after an injury (e.g., a traumatic injury) or after the onset or progression of a disease, in order to protect the biological matter from damage associated with the injury or disease prior to, during, or following treatment of the injury or disease. In other embodiments, methods of the present invention are used to induce or promotes stasis or pre-stasis in biological matter prior to subjection to an injurious event (e.g., an elective surgery) or prior to the onset or progression of a disease, in order to protect the biological matter from damage associated with adverse conditions such as injury or disease. Such methods are generally referred to as "pre-treatment" with an active compound. Pre-treatment includes methods wherein biological matter is provided with an active compound both before and during, and before, during and after biological matter is subjected to adverse conditions (e.g., an injury or onset or the progression of a disease), and methods wherein biological matter is provided with an active compound only before biological matter is subjected to adverse conditions.

According to various embodiments of the methods of the present invention, stasis may be induced by treating biological matter with an active compound that induces stasis directly itself or, alternatively, by treating biological matter with an active compound that does not itself induce stasis, but instead, promotes or enhances the ability of or decreases the time required for the biological matter to achieve stasis in response to another stimuli, such as, but not limited to, an injury, a disease, hypoxia, excessive bleeding, or treatment with another active compound.

In particular embodiments, treatment with an active compound induces "pre-stasis," which refers to a hypometabolic state through which biological matter must transition to reach stasis. Pre-stasis is characterized by a reduction in metabolism within the biological material of a magnitude that is less than that defined as stasis. In order to achieve stasis using an active compound, the biological matter necessarily must transition through a graded hypometabolic state in which oxygen consumption and $CO_2$ production are reduced less than two-fold in the biological matter. Such a continuum, in which metabolism or cellular respiration is reduced by an active compound to a degree less than two-fold, can be described as a state of "pre-stasis".

To the extent that stasis comprises a two-fold reduction (i.e., a reduction to 50% or less) in either $CO_2$ production or $O_2$ consumption, direct measurement of these parameters in the biological matter using methods known to those in the art in which a reduction of less than two-fold is detected is indicative of pre-stasis. Accordingly, certain measurements of carbon dioxide and oxygen levels in the blood as well as other markers of metabolic rate familiar to those skilled in the art including, but not limited to, blood $pO_2$, $VO_2$, $pCO_2$, pH, and lactate levels, may be used in the instant invention to monitor the onset or progression of pre-stasis. While indicators of metabolic activity, e.g., $CO_2$ production via cellular respiration and $O_2$ consumption, are reduced less than two-fold as compared to normal conditions, pre-stasis may be associated with an at least 10%, 15%, 20%, 25%, 30%, 35%, 40%, 45%, or 50% reduction in $CO_2$ evolution, which refers to the amount of $CO_2$ released from the lungs. In addition, in various embodiments, pre-stasis is characterized by a reduction in one or more indicators of metabolic activity that is less than or equal to 1%, 2%, 5%, 10%, 15%, 20%, 25%, 30%, 35%, 40%, 45%, or 49% as compared to normal physiological conditions. In other embodiments, pre-stasis is characterized by its ability to enhance or promote entry into stasis in response to another stimuli (wherein the another stimuli may include prolonged treatment with the same active agent), or its ability to enhance survival of or protect biological matter from damage resulting from an injury, the onset or progression of the disease, or bleeding, particularly bleeding that can lead to irreversible tissue damage, hemorrhagic shock, or lethality.

While methods of the present invention explicitly exemplified herein may refer to inducing "stasis," it is understood that these methods may be readily adapted to induce "pre-stasis," and that such methods of inducing pre-stasis are contemplated by the present invention. In addition, the same active compounds used to induce stasis may also be used to induce pre-stasis, by providing them to biological matter at a lower dosage and/or for a shorter time than used to induce stasis.

In certain embodiments, the present invention involves exposing biological matter to an amount of an agent, so as to achieve stasis of the biological matter. In some embodiments, the present invention concerns methods for inducing stasis in in vivo biological matter comprising: a) identifying an organism in which stasis is desired; and, b) exposing the organism to an effective amount of an oxygen antagonist or other active compound to induce stasis in the in vivo biological matter. Inducing "stasis" in biological matter means that the matter is alive but is characterized by one or more of the following: at least a two-fold reduction in the rate or amount of carbon dioxide production by the biological matter; at least a two-fold (i.e., 50%) reduction in the rate or amount of oxygen consumption by the biological matter; and at least a 10% decrease in movement or motility (applies only to cells or tissue that move, such as sperm cells or a heart or a limb, or when stasis is induced in the entire organism) (collectively referred to as "cellular respiration indicators"). In certain embodiments of the invention, it is contemplated that there is about, at least about, or at most about a 2-, 3-, 4-, 5-, 6-, 7-, 8-, 9-, 10-, 15-, 20-, 25-, 30-, 35-, 40-, 45-, 50-, 60-, 70-, 80-, 90-, 100-, 150-, 200-, 250-, 300-, 350-, 400-, 450-, 500-, 600-, 700-, 800-, 900-, 1000-, 1100-, 1200-, 1300-, 1400-, 1500-, 1600-, 1700-, 1800-, 1900-, 2000-, 2100-, 2200-, 2300-, 2400-, 2500-, 2600-, 2700-, 2800-, 2900-, 3000-, 3100-, 3200-, 3300, 3400-, 3500-, 3600-, 3700-, 3800-, 3900-, 4000-, 4100-, 4200-, 4300-, 4400-, 4500-, 5000-, 6000-, 7000-, 8000-, 9000-, or 10000-fold or more reduction in the rate of oxygen consumption by the biological matter, or any range derivable therein. Alternatively, it is contemplated that embodiments of the invention may be discussed in terms of a reduction in the rate of oxygen consumption by the biological matter as about, at least about, or at most about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein. It is contemplated that any assay to measure oxygen consumption may be employed, and a typical assay will involve utilizing a closed environment and measuring the difference between the oxygen put into the environment and oxygen that is left in the environment after a period of time. It is further contemplated that carbon dioxide production can be measured to determine the amount of oxygen consumption by biological matter. Thus, there may be decreases in carbon dioxide production, which would correspond to the decreases in oxygen consumption discussed above.

In methods of the invention, stasis or pre-stasis is temporary and/or reversible, meaning that the biological matter no longer exhibits the characteristics of stasis at some later point in time. In some embodiments of the invention, instead of an oxygen antagonist, a compound that is not does not qualify as an oxygen antagonist is administered. It is contemplated that methods discussed with respect to oxygen antagonists may be applied with respect to any compound that is an oxygen antagonist, protective metabolic agent, compound with the structure of Formula I, II, III, or IV, any other compound discussed herein, or a salt or precursor thereof. A compound that achieves any method of the invention and qualifies as an oxygen antagonist, protective metabolic agent, compound with the structure of Formula I, II, III, or IV, or a salt or precursor thereof, will be considered an "active compound." In particular embodiments, induction of stasis is desired in which case the compound may be referred to as an "active stasis compound." It is contemplated that in some embodiments of the invention, a method is achieved by inducing stasis. For example, therapeutic methods may involve inducing stasis, in which case the active compound is an active stasis compound. It is specifically contemplated that in embodiments in which active compounds are discussed, the invention includes, and may be limited to, oxygen antagonists.

In certain embodiments of the present invention, biological matter is treated with an active compound that does not induce stasis by itself (at least not at the level and/or duration of time provided), but rather induces biological matter to enter a pre-stasis state that has therapeutic benefits and that enhances the ability of the biological matter to achieve stasis in response to another stimuli, such as, e.g., an injury, disease state, or treatment with another active compound or the same active compound if used for a longer duration or greater dosage.

The term "biological matter" refers to any living biological material (mammalian biological material in preferred embodiments) including cells, tissues, organs, and/or organisms, and any combination thereof. It is contemplated that stasis may be induced in a part of an organism (such as in cells, in tissue, and/or in one or more organs), whether that part remains within the organism or is removed from the organism, or the whole organism will be placed in a state of stasis. Moreover, it is contemplated in the context of cells and tissues that homogenous and heterogeneous cell populations may be the subject of embodiments of the invention. The term "in vivo biological matter" refers to biological matter that is in vivo, i.e., still within or attached to an organism. Moreover, the term "biological matter" will be understood as synonymous with the term "biological material." In certain embodiments, it is contemplated that one or more cells, tissues, or organs is separate from an organism. The term "isolated" can be used to describe such biological matter. It is contemplated that stasis may be induced in isolated biological matter.

An organism or other biological matter in need of stasis is an organism or biological matter in which stasis of all or part of the organism may yield direct or indirect physiological benefits. For example, a patient at risk for hemorrhagic shock may be considered in need of stasis, or a patient who will undergo coronary artery bypass surgery may benefit from protecting the heart from ischemia/reperfusion injury. Other applications are discussed throughout the application. In some cases, an organism or other biological matter is identified or determined to be in need of stasis based on one or more tests, screens, or evaluations that indicate a condition or disease, or the risk of a condition or disease that can be prevented or treated by undergoing stasis. Alternatively, the taking of a patient medical or family medical history (patient interview) may yield information that an organism or other biological matter is in need of stasis. As would be evident to one skilled in the art, one application of the present invention would be to reduce the overall energy demands of a biological material by inducing stasis.

Alternatively, an organism or other biological matter may be in need of an active compound to enhance survivability. For instance, a patient may need treatment for an injury or disease or any other application discussed herein. They may be determined to be in need of enhanced survivability or treatment based on methods discussed in the previous paragraph, such as by taking a patient medical or family medical history.

The term "oxygen antagonist" refers to a substance that competes with oxygen insofar as it is used by a biological matter that requires oxygen for it to be alive ("oxygen-utilizing biological matter"). Oxygen is typically used or needed for various cellular processes that create the biological matter's primary source of readily utilizable energy. An oxygen antagonist effectively reduces or eliminates the amount of oxygen that is available to the oxygen-utilizing biological matter, and/or the amount of oxygen that can be used by the oxygen-utilizing biological matter. In one embodiment, an oxygen antagonist may achieve its oxygen antagonism directly. In another embodiment, an oxygen antagonist may achieve its oxygen antagonism indirectly.

A direct oxygen antagonist competes with molecular oxygen for the binding to a molecule (e.g., a protein) that has an oxygen binding site or oxygen binding capacity. Antagonism may be competitive, non-competitive, or uncompetitive as known in the art of pharmacology or biochemistry. Examples of direct oxygen antagonists include, but are not limited to, carbon monoxide (CO), which competes for oxygen binding to hemoglobin and to cytochrome c oxidase.

An indirect oxygen antagonist influences the availability or delivery of oxygen to cells that use oxygen for energy production (e.g., in cellular respiration) in the absence of directly competing for the binding of oxygen to an oxygen-binding molecule. Examples of indirect oxygen antagonists include, but are not limited to, (i) carbon dioxide, which, through a process known as the Bohr effect, reduces the capacity of hemoglobin (or other globins, like myoglobin) to bind to oxygen in the blood or hemolymph of oxygen-utilizing animals, thereby reducing the amount of oxygen that is delivered to oxygen-utilizing cells, tissues, and organs of the organism, thereby reducing the availability of oxygen to cells that use oxygen; (ii) inhibitors of carbonic anhydrase (Supuran et al., 2003, incorporated by reference in its entirety) which, by virtue of inhibiting the hydration of carbon dioxide in the lungs or other respiratory organs, increase the concentration of carbon dioxide, thereby reducing the capacity of hemoglobin (or other globins, like myoglobin) to bind to oxygen in the blood or hemolymph of oxygen-utilizing animals, thereby reducing the amount of oxygen that is delivered to oxygen-utilizing cells, tissues, and organs of the organism, thereby reducing the availability of oxygen to cells that use oxygen; and, (iii) molecules that bind to oxygen and sequester it from or rendering it unavailable to bind to oxygen-binding molecules, including, but not limited to oxygen chelators, antibodies, and the like.

In some embodiments, an oxygen antagonist is both a direct and an indirect oxygen antagonist. Examples include, but are not limited to, compounds, drugs, or agents that directly compete for oxygen binding to cytochrome c oxidase and are also capable of binding to and inhibiting the enzymatic activity of carbonic anhydrase. Thus, in some embodiments an oxygen antagonist inhibits or reduces the amount of cellular respiration occurring in the cells, for instance, by binding sites on cytochrome c oxidase that would otherwise bind to oxygen. Cytochrome c oxidase specifically binds oxygen and then converts it to water. In some embodiments, such binding to cytochrome c oxidase is preferably releasable and reversible binding (e.g., has an in vitro dissociation constant, $K_d$, of at least $10^{-2}$, $10^{-3}$, or $10^{-4}$ M, and has an in vitro dissociation constant, $K_d$, not greater than $10^{-6}$, $10^{-7}$, $10^{-8}$, $10^{-9}$, $10^{-10}$, or $10^{-11}$ M). In some embodiments, an oxygen antagonist is evaluated by measuring ATP and/or carbon dioxide output.

The term "effective amount" means an amount that can achieve the stated result. In certain methods of the invention, an "effective amount" is, for example, an amount that induces stasis in the biological matter in need of stasis. In other methods, an "effective amount" is, for example, an amount that induces pre-stasis in biological matter in need of stasis or in need of enhanced survival. In additional embodiments, an "effective amount" may refer to an amount that increases the survivability of an organism or other biological matter. This can be determined (or assumed) based on comparison or previous comparison to untreated biological matter or biological matter treated with a different dosage or regimen that does not experience a difference in survivability.

It will be understood that when inducing stasis in a tissue or organ, an effective amount is one that induces stasis in the tissue or organ as determined by the collective amount of cellular respiration of the tissue or organ. Accordingly, for example, if the level of oxygen consumption by a heart (collectively with respect to cells of the heart) is decreased at least about 2-fold (i.e., 50%) after exposure to a particular amount of a certain oxygen antagonist or other active stasis compound, it will be understood that that was an effective amount to induce stasis in the heart. Similarly, an effective amount of an agent that induces stasis in an organism is one that is evaluated with respect to the collective or aggregate level of a particular parameter of stasis. It will be also understood that when inducing stasis in an organism, an effective amount is one that induces stasis generally of the whole organism, unless a particular part of the organism was targeted. In addition, it is understood that an effective amount may be an amount sufficient to induce stasis by itself, or it may be an amount sufficient to induce stasis in combination with another agent or stimuli, e.g., another active compound, an injury, or a disease state.

The concept of an effective amount of a particular compound is related, in some embodiments, to how much utilizable oxygen there is available to the biological matter. Generally, stasis can be induced when there is about 100,000 ppm or less of oxygen in the absence of any oxygen antagonist (room air has about 210,000 ppm oxygen). The oxygen antagonist serves to alter how much oxygen is effectively available. At concentration of 10 ppm of oxygen, suspended animation is induced. Thus, while the actual concentration of oxygen that biological matter is exposed to may be higher, even much higher, than 10 ppm, stasis can be induced because of the competitive effect of an oxygen antagonist with oxygen for binding to essential oxygen metabolizing proteins in the biological matter. In other words, an effective amount of an oxygen antagonist reduces the effective oxygen concentration to a point where the oxygen that is present cannot be used. This will happen when the amount of an oxygen antagonist reduces the effective oxygen concentration below the $K_m$ of oxygen binding to essential oxygen metabolizing proteins (i.e., comparable to 10 ppm of oxygen). Accordingly, in some embodiments, an oxygen antagonist reduces the effective concentration of oxygen by about or at least about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 150-, 200-, 250-, 300-, 350-, 400-, 450-, 500-, 600-, 700-, 800-, 900-, 1000-, 1100-, 1200-, 1300-, 1400-, 1500-, 1600-, 1700-, 1800-, 1900-, 2000-, 2100-, 2200-, 2300-, 2400-, 2500-, 2600-, 2700-, 2800-, 2900-, 3000-, 3100-, 3200-, 3300, 3400-, 3500-, 3600-, 3700-, 3800-, 3900-, 4000-, 4100-, 4200-, 4300-, 4400-, 4500-, 5000-, 6000-, 7000-, 8000-, 9000-, or 10000-fold or more, or any range derivable therein. Alternatively, it is contemplated that embodiments of the invention may be discussed in terms of a reduction in effective oxygen concentration as about, at least about, or at most about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein. It is understood that this is another way of indicating a decrease in cellular respiration.

Furthermore, in some embodiments, stasis can be measured indirectly by a drop in core body temperature of an organism. It is contemplated that a reduction in core body temperature of about, at least about, or at most about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50° F. or more, or any range derivable therein may be observed in methods of the invention. In some embodiments of the invention, hypothermia can be induced, such as moderate hypothermia (at least 10° F. reduction) or severe hypothermia (at least 20° F. reduction).

Moreover, the effective amount can be expressed as a concentration with or without a qualification on length of time of exposure. In some embodiments, it is generally contemplated that to induce stasis or achieve other stated goals of the invention, the biological matter is exposed to an oxygen antagonist or other active compound for about, at least about, or at most about 5, 10, 15, 20, 25, 30, 35, 40, 45, 50, 55, 60 seconds, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. It is further contemplated that the amount of time may be indefinite, depending on the reason or purpose for administering the oxygen antagonist or other active compound. Thereafter, biological matter may continue to be exposed to an oxygen antagonist or other active compound, or, in other embodiments of the invention, the biological matter may no longer be exposed to the oxygen antagonist or other active compound. This latter step can be achieved either by removing or effectively removing the oxygen antagonist or other active compound from the presence of the biological matter in which stasis was desired, or the biological matter may be removed from an environment containing the oxygen antagonist or other active compound. Additionally, matter may be exposed to or provided with any active compound continuously (a period of time without a break in exposure), intermittently (exposure on multiple occasions), or on a periodic basis (exposure on multiple occasions on a regular basis). The dosages of the active compound on these different bases may the same or they may vary. In certain embodiments, an active compound is provided periodically by providing or exposing biological matter to an active compound 1, 2, 3, 4, 5, 6, 7, 8, 9, or 10 times every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, or any range derivable therein.

Furthermore, in some embodiments of the invention, biological matter is exposed to or provided with an active compound for a sustained period of time, where "sustained" means a period of time of at least about 2 hours. In other embodiments, biological matter may be exposed to or provided with an active compound on a sustained basis for more than a single day. In such circumstances, the biological matter is provided with an active compound on a continuously sustained basis. In certain embodiments, biological matter may be exposed to or provided with an active compound for about 2, 3, 4, 5, 6, 7, 8, 9, 10, 11, 12 or more hours (or any range derivable therein) for 2, 3, 4, 5, 6, 7 days, and/or 1, 2, 3, 4, 5 weeks, and/or 1, 2, 3, 4, 5, 6, 7, 8, 9, 10, 11, 12 months, and/or 1, 2, 3, 4, 5, 6, 7, 8, 9, 10, 11, 12, 13, 14, 15, 16, 17, 18, 19, 20 or more years (or any range derivable therein) continuously, intermittently (exposure on multiple occasions), or on a periodic basis (exposure on a recurring regular basis).

In some embodiments, biological matter may be exposed to or provided with an active compound at least before and during; before, during, and after; during and after; or solely after a particular injury, trauma, or treatment (for instance, surgery), adverse condition or other relevant event or situation. This exposure may or may not be sustained.

The dosages of the active compound on these different bases may the same or they may vary.

Moreover, in certain embodiments, an active compound may be provided on a continuously sustained basis at level that is considered "low," meaning a level that is less than the amount that causes metabolic flexibility such as seen with drop in CBT, heart rate, or $CO_2$ or $O_2$ consumption or production.

In certain embodiments, biological matter is exposed or provided an active compound, such as a metabolic agent, in an amount that exceeds what was previously understood to be the maximum tolerated dose before adverse physiological ramifications such as apnea ("period of time during which breathing is markedly reduced such that the subject takes 10% or fewer number of breaths"), lack of observable skeletal muscle movement, dystonia, and/or hyperactivity. Such an amount may be particularly relevant to increasing survivability in some embodiments of the invention, for instance, to increase the chances of surviving adverse conditions, such as those that would induce death from hemorrhagic shock.

A physiological state can be induced by active compounds of the present invention which enhances survivability in an organism in need of survivability enhancement and comprises a set of observable physiological changes in response to an effective dose of an active compound, said changes may comprise one, more or all of hyperpnea, apnea and the concomitant or subsequent loss of neuromuscular tone or voluntary control of movement with continued heartbeat. A transient and measurable change in arterial blood color may also be observed. Hyperpnea refers to rapid, shallow breathing. Apnea refers to a cessation of breathing or the reduction as described above.

In certain embodiments, the subject becomes apneic, which is marked by a cessation in breathing and then an apnic breath after a short period of time. In rats, this occurs after approximately 20 seconds. Thus, it is contemplated that a subject induced into apnea may exhibit 0, 1, 2, 3, 4, 5, 6, 7, 8, 9, 10% the number of breaths subsequent to exposure to an active compound. The subject may have an occasional breath, which may be considered an apnic breath, thereafter. In certain embodiments of the invention, apnea continues until the subject is no longer exposed to the active compound.

In some embodiments of the invention, an effective amount may be expressed as $LD_{50}$, which refers to the "median lethal dose," which means the dose that is administered that kills half the population of animals (causes 50% mortality). Moreover, in further embodiments, an effective amount may be independent of the weight of the biological matter ("weight independent"). In rodents and humans, for example, the $LD_{50}$ of $H_2S$ gas is approximately 700 ppm before adverse physiological effects occur. Moreover, in some embodiments of the invention, increasing survivability refers generally to living longer, which is an embodiment of the invention.

The present invention also concerns methods for inducing apnea in an organism comprising administering to the organism an effective amount of an active compound. In certain embodiments, the organism also does not exhibit any skeletal muscle movement as a result of the active compound. It is specifically contemplated that the organism may be mammal, including a human. In other embodiments, an effective amount exceeds what is considered a lethal concentration. In further embodiments, the concentration may be a lethal amount though the exposure time may be about, at least about, or at most about 10, 15, 20, 25, 30, 35, 40, 45, 50, 55, 60 seconds, 1, 2, 3, 4, 5 minutes or more (or any range derivable therein or any other time period specified in this disclosure). In particular embodiments, a mammal is exposed to at least about 600 ppm of an active gas compound, such as $H_2S$.

Additionally, in certain embodiments, there is a step of identifying an animal in need of treatment. In other embodiments, there is a step of observing apnea in the organism. In even further embodiments, methods involving obtaining a blood sample from the organism and/or evaluating the color of the organism's blood. It has been observed that exposure to $H_2S$ changes the color of blood from a mammal; it goes from bright red to a darker, red wine color and then to brick red. Evaluating the color may be done visually without any instruments or machines, while in other embodiments, an instrument may be used, such as a spectrophotometer. Furthermore, a blood sample may be obtained from an organism and other types of analysis may be done on it. Alternatively, a blood sample may not be needed and instead, blood may be evaluated without the sample. For instance, a modified pulse-oximeter that shines IR or visible light through the finger may be employed to monitor color changes in the blood.

In certain embodiments, biological matter is exposed to an effective amount of an active compound that does not lead to stasis or pre-stasis. In some embodiments, there may be no evidence of a reduction in oxygen consumption or carbon dioxide production while the active compound is present.

In additional embodiments, an organism may be exposed to the active compound while sleeping. Moreover, as discussed above, the exposure may be regular, such as daily (meaning exposure at least once a day).

It is specifically contemplated that in some embodiments an active compound is provided to a subject by nebulizer. This may be applied with any embodiment of the invention. In certain cases, the nebulizer is used for the treatment of hemorrhagic shock. In further embodiments, the active compound is provided as a single dose to the subject. In specific cases, a single dose or multiple doses is one that would induce apnea in a subject. In some embodiments, a subject is given at least about 1,000, 2,000, 3,000, 4,000, 5,000, 6,000, 7,000, 8,000, 9,000, 10,000, 11,000, 12,000 or more ppm $H_2S$ gas. The exposure time may be any of the times discussed herein, including about or about at most 10, 9, 8, 7, 6, 5, 4, 3, 2, 1, 0.5, 0.1 minutes or less (or any range derivable therein).

In further embodiments, after exposure to an active compound the metabolic rate of biologic matter may change. In certain embodiments, the RQ ratio ($CO_2$ production/$O_2$ consumption) of the biological matter changes after exposure to an active compound. This may occur after an initial exposure or repeated exposure or after an acute exposure. In some embodiments, the RQ ratio decreases after exposure. The decrease may be a decrease of about, at least about or at most about 5, 10, 15, 20, 25, 30, 35, 40, 45, 50, 55, 60, 65, 70, 75, 80% or more, or any range derivable therein. The decrease may be a result of $O_2$ consumption increasing of $CO_2$ production decreasing in relation to $O_2$ consumption.

In some embodiments, no other physiological change is observed in biological matter exposed to the active compound except that its RQ ratio changes after the exposure. Therefore, in some embodiments of the invention, methods involve measuring an RQ ratio in a subject. This may occur before and/or after exposure to the active compound.

Therefore, in some embodiments of the invention, stasis is induced, and a further step in methods of the invention is to maintain the relevant biological matter in a state of stasis. This can be accomplished by continuing to expose the biological matter to an oxygen antagonist or other active compound and/or exposing the biological matter to a nonphysiological temperature or another oxygen antagonist or other active compound. Alternatively, the biological matter may be placed in a preservation agent or solution, or be exposed to normoxic or hypoxic conditions. It is contemplated that biological matter may be maintained in stasis for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. Moreover, it is contemplated that in addition to or instead of changing the temperature, other changes in the environment may be implemented such as a change in pressure or to effect a cryoprotectant or cryopreservation environment (e.g., one containing glycerol).

It will be appreciated that "stasis" with respect to a whole animal and "stasis" with respect to cells or tissues may require different lengths of time in stasis. Thus, with respect to human subjects, e.g., subjects undergoing a surgical treatment, treatment for malignant hyperthermia, or trauma victim, a time of stasis of up to 12, 18, or 24 hours is generally contemplated. With respect to non-human animal subjects, e.g. non-human animals shipped or stored for commercial purposes, stasis for a period of 2 or 4 days, 2 or 4 weeks, or longer is contemplated.

The term "expose" is used according to its ordinary meaning to indicate that biological matter is subjected to an oxygen antagonist or other active compound. This can be achieved in some embodiments by contacting biological matter with an oxygen antagonist or active compound. In other embodiments, this is achieved by contacting the biological matter with an active compound, which may or may not be an oxygen antagonist. In the case of in vivo cells, tissues, or organs, "expose" may further mean "to lay open" these materials so that it can be contacted with an oxygen antagonist or other active compound. This can be done, for example, surgically. Exposing biological matter to an oxygen antagonist or other active compound can be by incubation in or with (includes immersion) the antagonist, perfusion or infusion with the antagonist, injection of biological matter with an oxygen antagonist or other active compound, or applying an oxygen antagonist or other active compound to the biological matter. In addition, if stasis of the entire organism is desirable, inhalation or ingestion of the oxygen antagonist or other active compound, or any other route of pharmaceutical administration is contemplated for use with oxygen antagonists or other active compound. Furthermore, the term "provide" is used according to its ordinary and plain meaning to mean "to supply." It is contemplated that a compound may be provided to biological matter in one form and be converted by chemical reaction to its form as an active compound. The term "provide" encompasses the term "expose" in the context of the term "effective amount," according to the present invention.

In some embodiments, an effective amount is characterized as a sublethal dose of the oxygen antagonist or other active compound. In the context of inducing stasis of cells, tissues, or organs (not the whole organism), a "sublethal dose" means a single administration of the oxygen antagonist or active compound that is less than half of the amount of the oxygen antagonist or active compound that would cause at least a majority of cells in a biological matter to die within 24 hours of the administration. If stasis of the entire organism is desired, then a "sublethal dose" means a single administration of the oxygen antagonist or active compound that is less than half of the amount of the oxygen antagonist that would cause the organism to die within 24 hours of the administration. In other embodiments, an effective amount is characterized as a near-lethal dose of the oxygen antagonist or active compound. Similarly, in the context of inducing stasis of cells, tissues, or organs (not the whole organism), a "near lethal dose" means a single administration of the oxygen antagonist or active compound that is within 25% of the amount of the inhibitor that would cause at least a majority of cell(s) to die within 24 hours of the administration. If stasis of the entire organism is desired, then a "near lethal dose" means a single administration of the oxygen antagonist or active compound that is within 25% of the amount of the inhibitor that would cause the organism to die within 24 hours of the administration. In some embodiments a sublethal dose is administered by administering a predetermined amount of the oxygen antagonist or active compound to the biological material. It is specifically contemplated that this may be implemented with respect to any active compound.

Furthermore, it is contemplated that in some embodiments an effective amount is characterized as a supralethal dose of the oxygen antagonist or other active compound. In the context of inducing stasis of cells, tissues, or organs (not the whole organism), a "supra-lethal dose" means a single administration of an active compound that is at least 1.5 times (1.5×) the amount of the active compound that would cause at least a majority of cells in a biological matter to die within 24 hours of the administration. If stasis of the entire organism is desired, then a "supra-lethal dose" means a single administration of the active compound that is at least 1.5 times the amount of the active compound that would cause the organism to die within 24 hours of the administration. It is specifically contemplated that the supra-lethal dose can be about, at least about, or at most about 1.5×, 2×, 3×, 4×, 5×, 10×, 20×, 30×, 40×, 50×, 60×, 70×, 80×, 90×, 100×, 150×, 200×, 250×, 300×, 400×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, the amount of the active compound that would cause at least a majority of cells in a biological matter (or the entire organism) to die within 24 hours of the administration.

The amount of the active compound that is provided to biological matter can be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg, mg/kg, or mg/m2, or any range derivable therein. Alternatively, the amount may be expressed as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mM or M, or any range derivable therein.

In some embodiments an effective amount is administered by monitoring, alone or in combination, the amount of oxygen antagonist or other active compound administered, monitoring the duration of administration of the oxygen antagonist or other active compound, monitoring a physiological response (e.g., pulse, respiration, pain response, movement or motility, metabolic parameters such as cellular energy production or redox state, etc.) of the biological material to the administration of the oxygen antagonist or other active compound and reducing, interrupting or ceasing administration of the compound(s) when a predetermined floor or ceiling for a change in that response is measured, etc. Moreover, these steps can be employed additionally in any method of the invention.

Tissue in a state of stasis or that has undergone stasis can be used in a number of applications. They can be used, for example, for transfusion or transplantation (therapeutic applications, including organ transplants); for research purposes; for screening assays to identify, characterize, or manufacture other compounds that induce stasis; for testing a sample from which the tissue was obtained (diagnostic applications); for preserving or preventing damage to the tissue that will be placed back into the organism from which they were derived (preventative applications); and for preserving or preventing damage to them during transport or storage. Details of such applications and other uses are described below. The term "isolated tissue" means that the tissue is not located within an organism. In some embodiments, the tissue is all or part of an organ. The terms "tissue" and "organ" are used according to their ordinary and plain meanings. Though tissue is composed of cells, it will be understood that the term "tissue" refers to an aggregate of similar cells forming a definite kind of structural material. Moreover, an organ is a particular type of tissue.

The present invention concerns methods for inducing stasis in isolated tissue comprising: a) identifying the tissue in which stasis is desired; and, b) exposing the tissue to an effective amount of an oxygen antagonist to induce stasis.

Compositions, methods, and articles of manufacture of the invention can be used on biological matter that will be transferred back into the donor organism from which it was derived (autologous) or a different recipient (heterologous) subject. In some embodiments, biological matter is obtained directly from a donor organism. In others, the biological matter is placed in culture prior to exposure to an oxygen antagonist or other active compound. In some situations, the biological matter is obtained from a donor organism administered extracorporeal membrane oxygenation prior to retrieval of the biological matter, which is a technique implemented to aid in the preservation of biological matter. Moreover, methods include administering or implanting the biological matter in which stasis was induced to a live recipient organism.

In some embodiments, an organ or tissue to be retrieved and then transplanted is exposed to the oxygen antagonist or other active compound while still in the donor subject. It is contemplated that in some cases, the vasculature of the donor is used to expose the organ or tissue to the oxygen antagonist or other active compound. This can be done if the heart is still pumping or a pump, catheter, or syringe can be used to administer the oxygen antagonist or other active compound into the vasculature for delivery to the organ or tissue Methods of the invention also concern inducing stasis in isolated tissue comprising incubating the tissue with an oxygen antagonist or active stasis compound that creates hypoxic conditions for an effective amount of time for the tissue to enter stasis.

Cells in a state of stasis or that have undergone stasis can be used in a number of applications. They can be used, for example, for transfusion or transplantation (therapeutic applications); for research purposes; for screening assays to identify, characterize, or manufacture other compounds that induce stasis; for testing a sample from which the cells were obtained (diagnostic applications); for preserving or preventing damage to the cells that will be placed back into the organism from which they were derived (preventative applications); and for preserving or preventing damage to cells during transport or storage. Details of such applications and other uses are described below.

The present invention concerns methods for inducing stasis in one or more cells separate from an organism comprising: a) identifying the cell(s) in which stasis is desired; and, b) exposing the cell(s) to an effective amount of an oxygen antagonist or other active stasis compound to induce stasis.

It is contemplated that the cell may be any oxygen-utilizing cell. The cell may be eukaryotic or prokaryotic. In certain embodiments, the cell is eukaryotic. More particularly, in some embodiments, the cell is a mammalian cell. Mammalian cells contemplated for use with the invention include, but are not limited to those that are from a: human, monkey, mouse, rat, rabbit, hamster, goat, pig, dog, cat, ferret, cow, sheep, and horse.

Moreover, cells of the invention may be diploid but in some cases, the cells are haploid (sex cells). Additionally, cells may be polyploid, aneuploid, or anucleate. The cell can be from a particular tissue or organ, such as one from the group consisting of: heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord. Moreover, the cell can also be characterized as one of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

The present invention also provides methods, compositions, and apparati for enhancing survivability of and/or reducing damage to biological matter under adverse conditions by reducing metabolic demand, oxygen requirements, temperature, or any combination thereof in the biological matter of interest. In some embodiments of the invention, survivability of biological matter is enhanced by providing it with an effective amount of a protective metabolic agent. The agent enhances survivability by preventing or reducing damage to the biological matter, preventing all or part of the matter from dying or senescing, and/or extending the lifespan of all or part of the biological matter, relative to biological matter not exposed to the agent. Alternatively, in some embodiments the agent prolongs survival of tissue and/or an organism that would otherwise not survive without the agent.

It is contemplated that a "protective metabolic agent" is a substance or compound capable of reversibly altering the metabolism of biological matter that is exposed to or contacted with it and that promotes or enhances the survivability of the biological matter.

In certain embodiments, the protective metabolic agent induces stasis in the treated biological matter; while, in other embodiments, the protective metabolic agent does not directly itself induce stasis in the treated biological matter. Protective metabolic agents, and other active compounds, may enhance survivability and/or reduce damage to biological matter without inducing stasis in the biological matter per se, but rather by reducing cellular respiration and corresponding metabolic activity to a degree that is less than about a fifty percent decrease in oxygen consumption or carbon dioxide production. Additionally, such compounds may cause the biological matter to more quickly, easily, or effectively enter into or achieve stasis in response to an injury or disease state, e.g., by inducing the biological matter to achieve a state of pre-stasis.

Survivability includes survivability when the matter is under adverse conditions—that is, conditions under which there can be adverse and nonreversible damage or injury to biological matter. Adverse conditions can include, but are not limited to, when oxygen concentrations are reduced in the environment (hypoxia or anoxia, such as at high altitudes or under water); when the biological matter is incapable of receiving that oxygen (such as during ischemia), which can be caused by i) reduced blood flow to organs (e.g., heart, brain, and/or kidneys) as a result of blood vessel occlusion (e.g., myocardial infarction, and/or stroke), ii) extracorporeal blood shunting as occurs during heart/lung bypass surgery (e.g., "pumphead syndrome" in which heart or brain tissue is damaged as a result of cardiopulmonary bypass), or iii) as a result of blood loss due to trauma (e.g., hemorrhagic shock or surgery); hypothermia, where the biological material is subjected to sub-physiological temperatures, due to exposure to cold environment or a state of low temperature of the biological material, such that it is unable to maintain adequate oxygenation of the biological materials; hyperthermia, whereby temperatures where the biological material is subjected to supra-physiological temperatures, due to exposure to hot environment or a state of high temperature of the biological material such as by a malignant fever; conditions of excess heavy metals, such as iron disorders (genetic as well as environmental) such as hemochromatosis, acquired iron overload, sickle-cell anemia, juvenile hemochromatosis African siderosis, thalassemia, porphyria cutanea tarda, sideroblastic anemia, iron-deficiency anemia and anemia of chronic disease. It is contemplated that a protective metabolic agent is an oxygen antagonist in certain embodiments of the invention. It is also contemplated that in certain other embodiments, an oxygen antagonist is not a protective metabolic agent. In other embodiments of the invention, one or more compounds may be used to increase or enhance survivability of biological matter; reversibly inhibit the metabolism and/or activity of biological matter; reduce the oxygen requirement of biological matter; reduce or prevent damage to biological matter under adverse conditions; prevent or reduce damage or injury to biological matter; prevent aging or senescence of biological matter; and, provide a therapeutic benefit as described throughout the application with respect to oxygen antagonists. It is contemplated that embodiments relating to inducing stasis are applicable to these other embodiments as well. Therefore, any embodiment discussed with respect to stasis may be implemented with respect to these other embodiments.

An active compound used for inducing stasis or any of these other embodiments may lead or provide their desired effect(s), in some embodiments, only when they are in the context of the biological matter (i.e., have no lasting effect) and/or they may provide for these effect(s) for more than 24 hours after the biological matter is no longer exposed to it. Moreover, this can also be the case when a combination of active compounds is used.

In certain embodiments, biological matter is exposed to an amount of an oxygen antagonist or other active compound that reduces the rate or amount of carbon dioxide production by the biological matter at least 2-fold, but also by about, at least about, or at most about 3-, 4-, 5-, 6-, 7-, 8-, 9-, 10-, 15-, 20-, 25-, 30-, 35-, 40-, 45-, 50-, 100-, 200-, 300-, 400-, 500-fold of more, or any range derivable therein. Alternatively, it is contemplated that embodiments of the invention may be discussed in terms of a reduction in the rate or amount of carbon dioxide production by the biological matter as about, at least about, or at most about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein. In still further embodiments, biological matter is exposed to an amount of an oxygen antagonist or other active compound that reduces the rate or amount of oxygen consumption by the biological matter at least 2-fold, but also by about, at least about, or at most about 3-, 4-, 5-, 6-, 7-, 8-, 9-, 10-, 15-, 20-, 25-, 30-, 35-, 40-, 45-, 50-, 100-, 200-, 300-, 400-, 500-fold of more, or any range derivable therein. Alternatively, it is contemplated that embodiments of the invention may be discussed in terms of a reduction in the rate or amount of oxygen consumption by the biological matter as about, at least about, or at most about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein. In still further embodiments, biological matter is exposed to an amount of an oxygen antagonist or other active compound that decreases movement or motility by at least 10%, but also by about, at least about, or at most about 15, 20, 25, 30, 35, 40, 45, 50, 55, 60, 65, 70, 75, 80, 85, 90, 95, 99, or 100%, or any range derivable therein. As with other embodiments, these characteristics and parameters are in the context of whichever biological matter is induced into a state of stasis. Thus, if stasis is induced in an organism's heart, these parameters would be evaluated for the heart, and not the whole organism. In the context of organisms, a reduction in oxygen consumption on the order of roughly 8-fold is a kind of stasis referred to as "hibernation." Moreover, it will be understood in this application that a reduction in oxygen consumption on the order of around 1000-fold can be considered "suspended animation." It will be understood that embodiments of the invention concerning stasis can be achieved at the level of hibernation or suspended animation, if appropriate. It is understood that a "-fold reduction" is relative to the reduced amount; for example, if a non-hibernating animal consumes 800 units of oxygen, the hibernating animal consumes 100 units of oxygen.

Additionally, in some embodiments of the invention, methods are provided for reducing cellular respiration, which may or may not be as high as that needed to reach stasis. A reduction in oxygen consumption by about, at least about, or at most about 1, 2, 5, 10, 15, 20, 25, 30, 35, 40, 45, 50, 55, 60, 65, 70, 75, 80, 85, 90, 95, or 100% is provided in methods of the invention. This can also be expressed and assessed in terms of any cellular respiration indicator.

It is contemplated that biological matter may be exposed to one or more oxygen antagonists or other active compounds more than one time. It is contemplated that biological matter may be exposed to one or more active compounds 1, 2, 3, 4, 5, 6, 7, 8, 9, 10 or more times, meaning when a biological matter is exposed multiple times that there are periods of respite (with respect to exposure to the active compound) in between.

It is also contemplated that an active compound may be administered before, during, after, or any combination thereof, in relation to the onset or progression of an injurious insult or disease condition. In certain embodiments, pre-treatment of biological matter to an active compound is sufficient to enhance survivability and/or reduce damage from an injurious or disease insult. Pre-treatment is defined as exposure of the biological matter to the active compound before the onset or detection of the injurious or disease insult. Pre-treatment can be followed by termination of exposure at or near the onset of the insult or continued exposure after the onset of insult.

In certain embodiments, methods including pre-exposure to an active compound (i.e., pre-treatment) are used to treat conditions in which an injurious or disease insult is 1) scheduled or elected in advance, or 2) predicted in advance to likely occur. Examples meeting condition 1 include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient in need of an organ transplant. Examples meeting condition 2 include, but are not limited to, medical conditions in which a risk of injury or disease progression is inherent (e.g., in the context of unstable angina, following angioplasty, bleeding aneurysms, hemorrhagic strokes, following major trauma or blood loss), or in which the risk can be diagnosed using a medical diagnostic test.

Exposure to the active compound may enhance survivability or reduce damage when exposure occurs after the onset or detection of the injurious or disease insult to achieve a therapeutic effect. Exposure to the active compound may be brief or extended. The exposure duration may be only for as long as needed to reach an indicator of stasis activity or pre-stasis (e.g., blood $pCO_2$, $pO_2$, pH, lactate, or sulfhemoglobin levels, or body temperature), or it may be longer. In certain embodiments, exposure occurs following traumatic injury (including iatrogenic and/or non-iatrogenic injuries) to an organism and is used to induce stasis or pre-stasis in the entire organism or injured tissue therein, so as to prevent or minimize damage, e.g., ischemic and reperfusion injury prior to, during, and/or following treatment.

In one embodiment, the present invention includes a method of protecting a mammal from suffering cellular damage from a surgery, comprising providing to the mammal an amount of hydrogen sulfide or other active compound sufficient to induce the mammal to enter pre-stasis prior to the surgery. The surgery may be elective, planned, or emergency surgery, such as, e.g., cardiopulmonary surgery. The hydrogen sulfide may be administered by any means available in the art, including, e.g., intravenously or by inhalation.

In another embodiment, the present invention includes a method of protecting a mammal from suffering cellular damage from a disease or adverse medical condition, comprising providing to the mammal an amount of hydrogen sulfide or other active compound sufficient to induce the mammal to enter pre-stasis or stasis prior to the onset or progression of the disease or adverse medical condition. This embodiment may be used in the context of a variety of different diseases and adverse medical conditions, including, e.g., unstable angina, post-angioplasty, aneurism, hemorrhagic stroke or shock, trauma, and blood loss.

In specific embodiments, the invention concerns methods of preventing an organism, such as a mammal, from bleeding to death or suffering irreversible tissue damage as a result of bleeding by providing to the mammal an amount of hydrogen sulfide or other active compound sufficient to prevent the animal from bleeding to death. In certain additional embodiments, the organism may go into hemorrhagic shock but not die from excessive bleeding. The terms "bleeding" and "hemorrhaging" are used interchangeably to refer to any discharge of blood from a blood vessel. It includes, but is not limited to, internal and external bleeding, bleeding from an injury (which may be from an internal source, or from an external physical source such as from a gunshot, stabbing, physical trauma, etc.).

Moreover, additional embodiments of the invention concern prevention of death or irreversible tissue damage from blood loss or other lack of oxygenation to cells or tissue, such as from lack of an adequate blood supply. This may be the result of, for example, actual blood loss, or it may be from conditions or diseases that prevent cells or tissue from being perfused (e.g., reperfusion injury), that cause blockage of blood to cells or tissue, that reduce blood pressure locally or overall in an organism, that reduce the amount of oxygen is carried in the blood, or that reduces the number of oxygen carrying cells in the blood. Conditions and diseases that may be involved include, but are not limited to, blood clots and embolisms, cysts, growths, tumors, anemia (including sickle cell anemia), hemophilia, other blood clotting diseases (e.g., von Willebrand, ITP), and atherosclerosis. Such conditions and diseases also include those that create essentially hypoxic or anoxic conditions for cells or tissue in an organism because of an injury, disease, or condition.

In some cases, a sublethal collective dose or a nonlethal collective dose is administered to the biological matter. As discussed above, with respect to inducing stasis in biological matter that is not an entire organism, a "sublethal collective dose" means an amount of multiple administrations of the active compound that collectively is less than half of the amount of the active compound that would cause at least a majority of cell(s) to die within 24 hours of one of the administrations. In other embodiments, an effective amount is characterized as a near-lethal dose of the oxygen antagonist or other active compound. Likewise, a "near lethal collective dose" means an amount of multiple administrations of the oxygen antagonist or other active compound that is within 25% of the amount of the active compound that would cause at least a majority of cell(s) to die within 24 hours of the one of the administrations. Also, a "supra-lethal collective dose" means an amount of multiple administrations of the active compound that is at least 1.5 times the amount of the active compound that would cause at least a majority of cell(s) (or the entire organism) to die within 24 hours of the one of the administrations. It is contemplated that multiple doses can be administered so as to induce stasis in the whole organism. The definition for "sub-lethal collective dose," "near-lethal collective dose" and "supra-lethal collective dose" can be extrapolated based on the individual doses discussed earlier for stasis in whole organisms.

Biological matter may be exposed to or contacted with more than one oxygen antagonist or other active compound. Biological matter may be exposed to at least one active compound, including 2, 3, 4, 5, 6, 7, 8, 9, 10 or more oxygen antagonists or other active compound, or any range derivable therein. With multiple active compounds, the term "effective amount" refers to the collective amount of active compounds. For example, the biological matter may be exposed to a first active compound and then exposed to a second active compound. Alternatively, biological matter may be exposed to more than one active compound at the same time or in an overlapping manner. Furthermore, it is contemplated that more than one active compounds may be comprised or mixed together, such as in a single composition to which biological matter is exposed. Therefore, it is contemplated that, in some embodiments, a combination of active compounds is employed in compositions, methods, and articles of manufacture of the invention.

Biological matter may be provided with or exposed to an active compound through inhalation, injection, catheterization, immersion, lavage, perfusion, topical application, absorption, adsorption, or oral administration. Moreover, biological matter may be provided with or exposed to an active compound by administration to the biological matter intravenously, intradermally, intraarterially, intraperitoneally, intralesionally, intracranially, intraarticularly, intraprostaticaly, intrapleurally, intratracheally, intranasally, intrathecally, intravitreally, intravaginally, intrarectally, topically, intratumorally, intramuscularly, intraperitoneally, intraocularly, subcutaneously, subconjunctival, intravesicularlly, mucosally, intrapericardially, intraumbilically, intraocularally, orally, topically, locally, by inhalation, by injection, by infusion, by continuous infusion, by localized perfusion, via a catheter, or via a lavage.

Methods and apparatuses of the invention involve a protective agent that in some embodiments is an oxygen antagonist. In still further embodiments, the oxygen antagonist is a reducing agent. Additionally, the oxygen antagonist can be characterized as a chalcogenide compound. It will be understood that active compounds may also be protective agents. Moreover, any chalcogenide compound can be considered an active compound so long as it achieves a goal of the invention, regardless of whether it is an oxygen antagonist.

In certain embodiments, the chalcogenide compound comprises sulfur, while in others, it comprises selenium, tellurium, or polonium. In certain embodiments, a chalcogenide compound contains one or more exposed sulfide groups. It is contemplated that this chalcogenide compounds contains 1, 2, 3, 4, 5, 6 or more exposed sulfide groups, or any range derivable therein. In particular embodiments, such a sulfide-containing compound is $CS_2$ (carbon disulfide).

Moreover, in some methods of the invention, stasis is induced in cell(s) by exposing the cell(s) to a reducing agent that has a chemical structure of (referred to as Formula I):

wherein X is N, O, Po, S, Se, or Te;
wherein Y is N or O;
wherein $R_1$ is H, C, lower alkyl, a lower alcohol, or CN;
wherein $R_2$ is H, C, lower alkyl, or a lower alcohol, or CN;
wherein n is 0 or 1;
wherein m is 0 or 1;
wherein k is 0, 1, 2, 3, or 4; and,
wherein p is 1 or 2.

The terms "lower alkyl" and "lower alcohol" are used according to their ordinary meanings and the symbols are the ones used to refer to chemical elements. This chemical structure will be referred to as the "reducing agent structure" and any compound having this structure will be referred to as a reducing agent structure compound. In additional embodiments, k is 0 in the reducing agent structure. Moreover, in other embodiments, the $R_1$ and/or $R_2$ groups can be an amine or lower alkyl amine. In others, $R_1$ and/or $R_2$ could be a short chain alcohol or a short chain ketone. Additionally, $R_1$ and $R_2$ may be a linear of branched chain bridge and/or the compound may be a cyclic compound. In still further embodiments, X may also be a halogen. The term "lower" is meant to refer to 1, 2, 3, 4, 5, or 6 carbon atoms, or any range derivable therein. Moreover, $R_1$ and/or $R_2$ may be other small organic groups, including, $C_2$-$C_5$ esters, amides, aldehydes, ketones, carboxylic acids, ethers, nitrites, anhydrides, halides, acyl halides, sulfides, sulfones, sulfonic acids, sulfoxides, and/or thiols. Such substitutions are clearly contemplated with respect to $R_1$ and/or $R_2$. In certain other embodiments, $R_1$ and/or $R_2$ may be short chain versions of the small organic groups discussed above. "Short chain" means 1, 2, 3, 4, 5, 6, 7, 8, 9, 10, 11, or 12 carbon molecules, or any range derivable therein.

It is contemplated that the reducing agent structure compound can be a chalcogenide compound in some cases. In certain embodiments, the chalcogenide compound has an alkyl chain with an exposed chalcogenide. In others, the chalcogenide compound has a chalcogenide that becomes exposed once it is taken up by the biological matter. In this respect, the chalcogenide compound is similar to a prodrug as an oxygen antagonist. Therefore, one or more sulfur, selenium, oxygen, tellurium, polonium, or ununhexium molecules on the compound becomes available subsequent to exposure of the biological matter to the chalcogenide compound. In this context, "available" means that the sulfur, selenide, oxygen, tellurium, polonium, or ununhexium will retain a negative charge.

In certain embodiments, the chalcogenide is a salt, preferably salts wherein the chalcogen is in a −2 oxidation state. Sulfide salts encompassed by embodiments of the invention include, but are not limited to, sodium sulfide ($Na_2S$), sodium hydrogen sulfide (NaHS), potassium sulfide ($K_2S$), potassium hydrogen sulfide (KHS), lithium sulfide ($Li_2S$), rubidium sulfide ($Rb_2S$), cesium sulfide ($Cs_2S$), ammonium sulfide (($NH_4)_2S$), ammonium hydrogen sulfide ($NH_4$)HS, beryllium sulfide (BeS), magnesium sulfide (MgS), calcium sulfide (CaS), strontium sulfide (SrS), barium sulfide (BaS), and the like. In like fashion, embodiments of the present invention encompass, but are not limited to, corresponding selenide and telluride salts. It is specifically contemplated that the invention includes compositions containing a chalcogenide salt (chalcogenide compound that is a salt) with a pharmaceutically acceptable carrier or prepared as a pharmaceutically acceptable formulation. In still further embodiments, the reducing agent structure compound is selected from the group consisting of $H_2S$, $H_2Se$, $H_2Te$, and $H_2Po$. In some cases, the reducing agent structure of Formula (I) has an X that is an S. In others, X is Se, or X is Te, or X is Po, or X is O. Furthermore, k in the reducing agent structure is 0 or 1 in some embodiments. In certain embodiments, the reducing agent structure compound is dimethylsulfoxide (DMSO), dimethylsulfide (DMS), carbon monoxide, methylmercaptan ($CH_3SH$), mercaptoethanol, thiocyanate, hydrogen cyanide, methanethiol (MeSH), or $CS_2$. In particular embodiments, the oxygen antagonist is $H_2S$, $H_2Se$, $CS_2$, MeSH, or DMS. Compounds on the order of the size of these molecules are particularly contemplated (that is, within 50% of the average of their molecular weights).

In certain embodiments, a selenium-containing compound such as $H_2Se$ is employed. The amount of $H_2Se$ may be in the range of 1 to 1000 parts per billion in some embodiments of the invention. It is further contemplated that any embodiment discussed in the context of a sulfur-containing compound may be implemented with a selenium-containing compound. This includes substituting one of more sulfur atoms in a sulfur-containing molecule with a corresponding selenium atom.

A further aspect of the invention encompasses compounds represented by Formula IV:

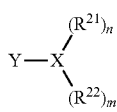

(IV)

wherein:
X is N, O, P, Po, S, Se, Te, O—O, Po—Po, S—S, Se—Se, or Te—Te;
n and m are independently 0 or 1; and
wherein $R^{21}$ and $R^{22}$ are independently hydrogen, halo, cyano, phosphate, thio, alkyl, alkenyl, alkynyl, alkoxy, aminoalkyl, cyanoalkyl, hydroxyalkyl, haloalkyl, hydroxyhaloalkyl, alkylsulfonic acid, thiosulfonic acid, alkylthiosulfonic acid, thioalkyl, alkylthio, alkylthioalkyl, alkylaryl, carbonyl, alkylcarbonyl, haloalkylcarbonyl, alkylthiocarbonyl, aminocarbonyl, aminothiocarbonyl, alkylaminothiocarbonyl, haloalkylcarbonyl, alkoxycarbonyl, aminoalkylthio, hydroxyalkylthio, cycloalkyl, cycloalkenyl, aryl, aryloxy, heteroaryloxy, heterocyclyl, heterocyclyloxy, sulfonic acid, sulfonic alkyl ester, thiosulfate, or sulfonamido; and
Y is cyano, isocyano, amino, alkyl amino, aminocarbonyl, aminocarbonyl alkyl, alkylcarbonylamino, amidino, guanidine, hydrazino, hydrazide, hydroxyl, alkoxy, aryloxy, hetroaryloxy, cyloalkyloxy, carbonyloxy, alkylcarbonyloxy, haloakylcarbonyloxy, arylcarbonyloxy, carbonylperoxy, alkylcarbonylperoxy, arylcarbonylperoxy, phosphate, alkylphosphate esters, sulfonic acid, sulfonic alkyl ester, thiosulfate, thiosulfenyl, sulfonamide, —$R^{23}R^{24}$, wherein $R^{23}$ is S, SS, Po, Po—Po, Se, Se—Se, Te, or Te—Te, and $R^{24}$ is defined as for $R^{21}$ herein, or Y is

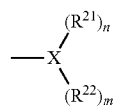

wherein X, $R^{21}$ and $R^{22}$, are as defined herein.

Moreover, it is contemplated that in some embodiments of the invention, biological matter is provided with a precursor compound that becomes the active version of the Formula I or IV compound by exposure to biological matter, such as by chemical or enzymatic means. In addition, the compound may be provided to the biological matter as a salt of the compound, in the form of a free radical, or a negatively charged, positively charged or multiply charged species. Some compounds qualify as both a Formula I and a Formula IV compound and in such cases, the use of the phrase "Formula I or Formula IV" is not intended to connote the exclusion of such compounds.

A compound identified by the structure of Formula I or Formula IV may also, in certain embodiments, be characterized as an oxygen antagonist, protective metabolic agent, or a precursor, prodrug, or salt thereof. It is further contemplated that the compound need not be characterized as such or qualify as such to be a compound used in the invention, so long as it achieves a particular method of the invention. In some other embodiments, the compound may be considered a chalcogenide compound. It is specifically contemplated that any compound identified by the structure of Formula I or Formula IV or set forth in this disclosure may be used instead of or in addition to an oxygen antagonist in methods, compositions, and apparatuses of the invention; similarly, any embodiments discussed with respect to any of structure having Formula I or Formula IV or otherwise set forth in this disclosure may be may be used instead of or in addition to an oxygen antagonist. Moreover, any compound identified by the structure of Formulas I or IV or set forth in this disclosure may be combined with any oxygen antagonist or any other active compound described herein. It is also contemplated that any combination of such compounds may be provided or formulated together, sequentially (overlapping or nonoverlapping), and/or in an overlapping sequential manner (the administration of one compound is initiated and before that is complete, administration of another compound is initiated) in methods, compositions, and other articles of manufacture of the invention to achieve the desired effects set forth herein. In certain embodiments, more than one compound with the structure of Formula I or Formula IV is provided. In certain embodiments, multiple different compounds with a structure from the same formula (i.e., Formula I or Formula IV) are employed, while in other embodiments, when multiple different compounds are employed, they are from different formulas.

In specific embodiments, it is contemplated that multiple active compounds are used, wherein one of the compounds is carbon dioxide ($CO_2$). It is contemplated that at least one other compound is also a Formula I and/or Formula IV compound in some embodiments. In certain cases, carbon dioxide is provided to biological matter in combination with $H_2S$ or an $H_2S$ precursor (together, sequentially, or in an overlapping sequential manner).

The amount of carbon dioxide to which the biological matter may be exposed are about, at least about, or at most about, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more, or any range derivable therein. In certain embodiments, the amount is expressed in terms of ppm, such as about, at least about, or at most about 350, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 60000, 70000, 80000, 90000, 100000, 110000, 120000, 130000, 140000, 150000, 160000, 170000, 180000, 190000, 200000, 210000, 220000, 230000, 240000, 250000, 260000, 270000, 280000, 290000, 300000 or more ppm, or any range derivable therein, as well as an molar equivalents. It is contemplated that these concentrations could apply to any other active compound in gaseous form.

In other embodiments, it is specifically contemplated that the active compound is sodium sulfide, sodium thiomethoxide, cysteamine, sodium thiocyanate, cysteamine-S-phosphate sodium salt, or tetrahydrothiopryan-4-ol. In additional embodiments, the active compound is dimethylsulfoxide, thioacetic acid, selenourea, 2-(3-Aminopropyl)-aminoethanethiol-dihydrogen-phosphate-ester, 2-mercapto-ethanol, thioglycolicether, sodium selenide, sodium methane sulfinate, thiourea, or dimethylsulfide. It is specifically contemplated that these compounds, or any others discussed herein including any compound with Formula I, II, III, or IV, may be provided or administered to biological matter in an amount that is about, at least about, or at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 mM or mmol/kg (of biological matter), or any range derivable therein.

It is specifically contemplated that any subset of active compounds identified by name or structure may be used in methods, compositions and articles of manufacture. It is also specifically contemplated that any subset of these compounds may be disclaimed as not constituting embodiments of the invention. The present invention also concerns pharmaceutical compositions comprising a therapeutically effective amount of one or more active compounds. It is understood that such pharmaceutical compositions are formulated in pharmaceutically acceptable compositions. For example, the composition may include a pharmaceutically acceptable diluent.

In certain embodiments, the pharmaceutical composition contains an effective dose of an active to provide when administered to a patient a Cmax or a steady state plasma concentration of the active compound to produce a therapeutically effective benefit. In certain embodiments, the Cmax or steady state plasma concentration to be achieved is about, at least about, or at most about 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 3000, 4000, 5000, 6000, 7000, 8000, 9000, 10000 µM or more, or any range derivable therein. In certain embodiments, such as with $H_2S$, the desired Cmax or steady state plasma concentration is about between 10 µM to about 10 mM, or between about 100 µM to about 1 mM, or between about 200 µM to about 800 µM. Appropriate measures may be taken to consider and evaluate levels of the compound already in the blood, such as sulfur.

In certain embodiments, the pharmaceutical composition provides an effective dose of $H_2S$ to provide when administered to a patient a $C_{max}$ or a steady state plasma concentration of between 10 µM to 10 mM, between about 100 µM to about 1 mM, or between about 200 µM to about 800 µM. In relating dosing of hydrogen sulfide to dosing with sulfide salts, in typical embodiments, the dosing of the salt is based on administering approximately the same sulfur equivalents as the dosing of the $H_2S$. Appropriate measures will be taken to consider and evaluate levels of sulfur already in the blood.

In certain embodiments, the composition comprises a gaseous form of one or more of the active compounds specified above. In another embodiment, the composition comprises a salt of one or more of these compounds. In one particular embodiment, a pharmaceutical composition comprises a gaseous form of Formula I or IV or a salt of Formula I or IV. A gaseous form or salt of $H_2S$ is specifically contemplated in some aspects of the invention. It is contemplated that the amount of gas to which biological matter is provided is about, at least about, or at most about 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 60000, 70000, 80000, 90000, 100000, 110000, 120000, 130000, 140000, 150000, 160000, 170000, 180000, 190000, 200000, 210000, 220000, 230000, 240000, 250000, 260000, 270000, 280000, 290000, 300000, 310000, 320000, 330000, 340000, 350000, 360000, 370000, 380000, 390000, 400000 or more ppm, or any range derivable therein. Alternatively, the effective amount of gas(es) may be expressed as about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein, with respect to the concentration in the air to which the biological matter is exposed. Moreover, it is contemplated that with some embodiments, the amount of gas to which biological matter is provided is about, at least about, or at most about 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 parts per billion (ppb) or any range derivable therein. In particular embodiments, the amount of hydrogen selenide provided to biological matter is on this order of magnitude.

In some embodiments of the invention, the pharmaceutical composition is a liquid. As discussed elsewhere, the composition may be a liquid with the relevant compound(s) dissolved or bubbled into the composition. In some cases, the pharmaceutical composition is a medical gas. According to the United States Food and Drug Administration, "medical gases" are those gases that are drugs within the meaning of §201(g)(1) of the Federal Food, Drug and Cosmetic Act ("the Act") (21 U.S.C. §321(g) and pursuant to §503(b)(1)(A) of the Act (21 U.S.C. §353(b)(1)(A) are required to be dispensed by prescription. As such, such medical gases require an appropriate FDA label. A medical gas includes at least one active compound.

The present invention further comprises apparatuses and articles of manufacture comprising packaging material and, contained within the packaging material, an active stasis compound, wherein the packaging material comprises a label that indicates that it can be used for inducing stasis in in vivo biological matter.

In some embodiments, the apparatus or article of manufacture further includes a pharmaceutically acceptable diluent. In particular other embodiments, the apparatus or article of manufacture has a buffering agent. The active compound is provided in a first sealed container and the pharmaceutically acceptable diluent is provided in a second sealed container. In other embodiments, the device or article further has instructions for mixing the active compound and the diluent. Additionally, the active compound can be reconstituted for achieving any method of the invention, such as for inducing stasis in in vivo biological matter. It is contemplated that any label would specify the result to be achieved and the use of the compound for patients in need of that result.

The present invention also concerns an article of manufacture comprising packed together: an active compound, instructions for use of the active stasis compound, comprising: (a) identifying in vivo tissue in need of stasis treatment; and (b) administering an effective amount of the active compound to the in vivo biological matter.

In further embodiments of the invention, there is an article of manufacture comprising a medical gas including an active compound and a label comprising details or use and administration for inducing stasis in a biological matter or any other method of the invention.

The present invention also concerns kits and methods of using these kits. In some embodiments, there are kits for the delivery of an active compound to a tissue site in need of stasis treatment, or any other treatment of the claimed invention, comprising: a drape adapted for forming a sealed envelope against a tissue site; a container comprising an oxygen antagonist; and an inlet in the drape, wherein the container comprising the active compound is in communication with the inlet. In certain embodiments, the kit includes an outlet in the drape wherein the outlet is in communication with a negative pressure source. In some cases, the drape comprises elastomeric material and/or has a pressure sensitive adhesive covering the periphery of the drape. The outlet may be placed in fluid communication with the negative pressure source, which may or may not be a vacuum pump. There may also be a flexible conduit communicating between the outlet and the negative pressure source. In some embodiments, the kit includes a canister, which may or may not be removable, in fluid communication between the outlet and the negative pressure source. It is contemplated that the container includes an active compound that is in gaseous communication with the inlet. In certain embodiments, the container includes an active compound that is a gas or a liquid gas. The kit may also include a vaporizer in communication between the container comprising an oxygen antagonist and the inlet. In addition, it may have a return outlet in communication with the container comprising the active compound.

In particular embodiments, the active compound in the kits is carbon monoxide, carbon dioxide, $H_2Se$, and/or $H_2S$. In certain embodiments, the tissue site for which the kit or method is applied is wounded.

Moreover, it will be generally understood that any compound discussed herein as an oxygen antagonist can be provided in prodrug form to the biological matter, meaning that the biological matter or other substance(s) in the environment of the biological matter alters the prodrug into its active form, that is, into an oxygen antagonist. It is contemplated that the term "precursor" covers compounds that are considered "prodrugs."

The oxygen antagonist or other active compound may be or may be provided as a gas, semi-solid liquid (such as a gel or paste), liquid, or solid. It is contemplated that biological matter may be exposed to more than one such active compound and/or to that active compound in more than one state. Moreover, the active compound may be formulated for a particular mode of administration, as is discussed herein. In certain embodiments, the active compound is in pharmaceutical acceptable formulation for intravenous delivery.

In certain embodiments, the active compound is a gas. In particular embodiments, the gaseous active compound includes carbon monoxide, carbon dioxide, nitrogen, sulfur, selenium, tellurium, or polonium, or a mixture thereof. Moreover, it is specifically contemplated that the active compound is a chalcogenide compound as a gas. In some embodiments, the active compound is in a gas mixture comprising more than one gas. The other gas(es) is a non-toxic and/or a non-reactive gas in some embodiments. In some embodiments, the other gas is a noble gas (helium, neon, argon, krypton, xenon, radon, or ununoctium), nitrogen, nitrous oxide, hydrogen, or a mixture thereof. For instance, the non-reactive gas may simply be a mixture that constitutes "room air," which is a mixture of nitrogen, oxygen, argon and carbon dioxide, as well as trace amounts of other molecules such as neon, helium, methane, krypton, and hydrogen. The precise amounts of each varies, though a typical sample might contain about 78% nitrogen, 21% oxygen, 0.9% argon, and 0.04% carbon dioxide. It is contemplated that in the context of the present invention, "room air" is a mixture containing about 75 to about 81% nitrogen, about 18 to about 24% oxygen, about 0.7 to about 1.1% argon, and about 0.02% to about 0.06% carbon dioxide. A gaseous active compound may be first diluted with a non-toxic and/or non-reactive gas prior to administration or exposure to biological matter. Additionally or alternatively, any gaseous active compound may be mixed with room air prior to administration or exposure to biological matter or the compound may be administered or exposed to the biological matter in room air.

In some instances, the gas mixture also contains oxygen. An active compound gas is mixed with oxygen to form an oxygen gas ($O_2$) mixture in other embodiments of the invention. Specifically contemplated is an oxygen gas mixture in which the amount of oxygen in the oxygen gas mixture is less than the total amount of all other gas or gases in the mixture.

In some embodiments, the active compound gas is carbon monoxide and the amount of carbon monoxide is about the same or exceeds any amount of oxygen in the oxygen gas mixture. In particular embodiments, carbon monoxide is employed with blood-free biological matter. The term "blood-free biological matter" refers to cells and organs whose oxygenation is not dependent, or no longer dependent, on the vasculature, such as an organ for transplant. Preferably, the atmosphere will be 100% CO, but as will be evident to one skilled in the art, the amount of CO may be balanced with gases other than oxygen providing that the amount of usable oxygen is reduced to a level that prevents cellular respiration. In this context, the ratio of carbon monoxide-to-oxygen is preferably 85:15 or greater, 199:1 or greater or 399:1 or greater. In certain embodiments, the ratio is about, at least about, or at most about 1:1, 2:1, 2.5:1, 3:1, 4:1, 5:1, 6:1, 7:1, 8:1, 9:1, 10:1, 15:1, 20:1, 25:1, 30:1. 35:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1, 400:1, 410:1, 420:1, 430:1, 440:1, 450:1, 460:1, 470:1, 480:1, 490:1, 500:1 or more, or any range derivable therein.

In still further embodiments, the above numbers pertain to the ratio of carbon monoxide to a mixture of oxygen and one or more other gases. In some cases, it is contemplated that the other gas is a nonreactive gas such as nitrogen ($N_2$). Thus, in other embodiments of the invention, the above numbers apply to ratios of carbon monoxide to a combination of oxygen and nitrogen ($O_2/N_2$) that can be used in methods and apparatuses of the invention. Accordingly, it will be understood that other gases may or may not be present. In some embodiments, the CO:oxygen ratio is balanced with one or more other gases (non-carbon monoxide and non-oxygen gases). In particular embodiments, the CO:oxygen ratio is balanced with nitrogen. In still further embodiments, the amount of CO is a ratio of CO compared to room air, as is described by the numbers above.

In some cases, the amount of carbon monoxide is relative to the amount of oxygen, while in others, it is an absolute amount. For example, in some embodiments of the invention, the amount of oxygen is in terms of "parts per million (ppm)" which is a measure of the parts in volume of oxygen in a million parts of air at standard temperature and pressure of 20° C. and one atmosphere pressure and the balance of the gas volume is made up with carbon monoxide. In this context, the amount of carbon monoxide to oxygen is related in terms of parts per million of oxygen balanced with carbon monoxide. It is contemplated that the atmosphere to which the biological material is exposed or incubated may be at least 0, 50, 100, 200, 300, 400, 500, 1000, or 2000 parts per million (ppm) of oxygen balanced with carbon monoxide and in some cases carbon monoxide mixed with a non-toxic and/or non-reactive gas The term "environment" refers to the immediate environment of the biological matter, that is, the environment with which it is in direct contact. Thus, the biological material must be directly exposed to carbon monoxide, and it is insufficient that a sealed tank of carbon monoxide be in the same room as the biological matter and be considered to be incubated an "environment" according to the invention. Alternatively, the atmosphere may be expressed in terms of kPa. It is generally understood that 1 million parts=101 kPa at 1 atmosphere. In embodiments of the invention, the environment in which a biological material is incubated or exposed to is about, at least about, or at most about 0.001, 0.005, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20. 0.21, 0.22, 0.23, 0.24, 0.25, 0.26, 0.27, 0.28, 0.29, 0.30, 0.35, 0.40, 0.45, 0.50, 0.55, 0.60, 0.65, 0.70, 0.75, 0.80, 0.5, 0.90, 0.95, 1.0 kPa or more $O_2$, or any range derivable therein. As described above, such levels can be balanced with carbon monoxide and/or other non-toxic and/or non-reactive gas(es) Also, the atmosphere may be defined in terms of CO levels in kPa units. In certain embodiments, the atmosphere is about, at least about, or at most about 1, 5, 10, 15, 20, 25, 30, 35, 40, 45, 50, 55, 60, 65, 70, 75, 80, 85, 90, 95, 101, 101.3 kPa CO, or any range derivable therein. In particular embodiments, the partial pressure is about or at least about 85, 90, 95, 101, 101.3 kPa CO, or any range derivable therein.

The amount of time the sample is incubated or exposed to carbon monoxide can also vary in embodiments of the invention. In some embodiments, the sample is incubated or exposed to carbon monoxide for about, for at least about, or for at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more minutes and/or, 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7, 8, 9, 10 or more days.

In some embodiments, the invention concerns compositions and articles of manufacture that contain one or more active compounds. In certain embodiments, a composition has one or more of these active compounds as a gas that is bubbled in it so that the composition provides the compound to the biological matter when it is exposed to the composition. Such compounds may be gels, liquids, or other semi-solid material. In certain embodiments, a solution has an oxygen antagonist as a gas bubbled through it. It is contemplated that the amount bubbled in the gas will provide the appropriate amount of the compound to biological material exposed to the solution. In certain embodiments, the amount of gas bubbled into the solution is about, at least about, or at most about 0.5, 1.0, 1.5, 2.0. 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100 times or more, or any range derivable therein, than the amount to which the biological matter is effectively provided.

Biological matter is exposed to the gas in a closed container in some embodiments of the invention. In some cases, the closed container can maintain a particular environment or modulate the environment as is desired. The environment refers to the amount of oxygen antagonist that the biological matter is exposed and/or the temperature, gas composition, or pressure of the environment. In some cases, the biological matter is placed under a vacuum before, during, or after exposure to an oxygen antagonist or other active compound. Moreover, in other cases, the biological matter is exposed to a normoxic environment after being exposed to an oxygen antagonist or other active compound. In certain embodiments, the present invention includes methods for inducing stasis or protecting biological matter from injury or disease that include providing an active compound to the biological matter in combination with providing another stasis-inducing active compound or environmental condition to the biological matter. Such combination treatment may occur in any order, e.g., simultaneously or sequentially. In certain embodiments, an active compound is provided to biological matter, and the biological matter is subsequently placed under hypoxic conditions, such as 5% $O_2$, or sequentially exposed to increasingly hypoxic conditions, such as 5% $O_2$ followed by 4% $O_2$, 3% $O_2$, 2% $O_2$, 1% $O_2$, or $O_2$-free conditions, or any sequential combination of such conditions.

Moreover, in other embodiments, the environment containing the biological matter cycles at least once to a different amount or concentration of the oxygen antagonist or other active compound, wherein the difference in amount or concentration is by at least one percentage difference. The environment may cycle back and forth between one or more amounts or concentrations of the oxygen antagonist or other active compound, or it may gradually increase or decrease the amount or concentrations of an that compound. In some cases, the different amount or concentration is between about 0 and 99.9% of the amount or concentration of the oxygen antagonist or other active compound to which the biological matter was initially exposed. It is contemplated that the difference in amount and/or concentration is about, at least about, or at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

Methods of the invention can also include a step of subjecting biological matter to a controlled temperature environment. In certain embodiments, the biological matter is exposed to a temperature that is a "nonphysiological temperature environment," which refers to a temperature in which the biological matter cannot live in for more than 96 hours. The controlled temperature environment can have a temperature of about, at least about, or at most about −210, −200, −190, −180, −170, −160, −150, −140, −130, −120, −110, −100, −90, −80, −70, −60, −50, −40, −30, −20, −10, −5, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200° C. or more, or any range derivable therein. Biological matter may also be exposed to an oxygen antagonist or other active compound at room temperature, which means a temperature between about 20° C. and about 25° C. Furthermore, it is contemplated the biological matter achieves a core temperature of any amount or range of amounts discussed.

It is contemplated that the biological matter can be subjected to a nonphysiological temperature environment or a controlled temperature environment before, during or after exposure to the oxygen antagonist(s) or other active compound(s). Furthermore, in some embodiments, the biological matter is subjected to a nonphysiological temperature environment or a controlled temperature environment for a period of time between about one minute and about one year. The amount of time may be about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. Moreover, there may also be a step of increasing the ambient temperature relative to the reduced temperature.

Moreover, it is contemplated that the temperature may be altered or cycled during the process in which temperature is controlled. In some embodiments, the temperature of the biological matter may first be reduced before it is placed in the environment that has the oxygen antagonist or other active compound, while in others, the biological matter may be cooled by placing it in the environment with the active compound, that is below the temperature of the biological matter. The biological matter and/or environment may be cooled or heated gradually, such that the temperature of the biological matter or environment starts at one temperature but then reaches another temperature.

Methods of the invention can also include a step of subjecting biological matter to a controlled pressure environment. In certain embodiments, the biological matter is exposed to pressure that is lower than the pressure under which the organism is typically under. In certain embodiments, the biological matter is subjected to a "nonphysiological pressure environment," which refers to a pressure under which the biological matter cannot live under for more than 96 hours. The controlled pressure environment can have a pressure of about, at least about, or at most $10^{-14}$, $10^{-13}$, $10^{-12}$, $10^{-11}$, $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 0.2, 0.3, 0.4 or 0.5 atm or more, or any range derivable therein.

It is contemplated that the biological matter can be subjected to a nonphysiological pressure environment or a controlled pressure environment before, during or after exposure to the active compound(s). Furthermore, in some embodiments, the biological matter is subjected to a nonphysiological pressure environment or a controlled pressure environment for a period of time between about one minute and about one year. The amount of time may be about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein.

Moreover, it is contemplated that the pressure may be altered or cycled during the process in which pressure is controlled. In some embodiments, the pressure to which the biological matter is exposed may first be reduced before it is placed in the environment that has the active compound, while in others, the biological matter placed under pressure after exposure to an active compound. The pressure may be reduced gradually, such that the pressure of the environment starts at one pressure but then reaches another pressure within 10, 20, 30, 40, 50, 60 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days or more, and any combination or range derivable therein. In certain embodiments, methods include modulating environmental oxygen levels or removing the biological material from an environment having oxygen. Operationally, exposing biological material to an environment in which oxygen is diminished or absent may mimic exposure of the biological material to an oxygen antagonist. It is contemplated that in some embodiments of the invention, biological matter is exposed to or provided with an active compound under conditions in which the environment of the biological matter is hypoxic or anoxic, as described in further detail below. This may be intentional or nonintentional. Thus, in some embodiments of the invention, biological matter is intentionally placed in an environment that is anoxic or hypoxic or in an environment that is made anoxic or hypoxic. In other embodiments, the biological matter is under such conditions as a result of an unintended situation, for example, if the biological matter is under ischemic or potentially ischemic conditions. Therefore, it is contemplated in some cases that the hypoxic or anoxic conditions would damage the matter in the absence of the active compound.

In certain methods of the invention, there also is a step of assessing the level of the oxygen antagonist and/or oxidative phosphorylation in the biological matter in which stasis was induced. Moreover, in some embodiments of the invention, there is a step of assessing the level of cellular metabolism that is generally occurring in the biological matter. In some cases, the amount of the active compound in the biological matter is measured and/or a reduction in the temperature of the biological matter is assessed. Moreover, in some methods of the invention, the extent of one or more therapeutic effects is evaluated.

In certain other embodiments, any toxicity effect on the biological matter from an active compound and/or environmental change (temperature, pressure) is monitored or controlled for. It is contemplated that toxicity can be controlled for by altering the level, amount, duration, or frequency of an active compound and/or environmental change to which the biological matter is exposed. In certain embodiments the alteration is a reduction, while in certain other embodiments, the alteration is an increase. It is contemplated that the skilled artisan is aware of a number of ways of evaluating toxicity effects in biological matter.

Other optional steps for methods of the invention include identifying an appropriate active compound; diagnosing the patient; taking a patient history and/or having one or more tests done on the patient prior to administering or prescribing an active compound to the patient.

Compositions, methods, and articles of manufacture of the invention can be used on biological matter that will be transferred back into the donor organism from which it was derived (autologous) or a different recipient (heterologous) subject. In some embodiments, biological matter is obtained directly from a donor organism. In others, the biological matter is placed in culture prior to exposure to an oxygen antagonist or other active compound. In some situations, the biological matter is obtained from a donor organism administered extracorporeal membrane oxygenation prior to retrieval of the biological matter, which is a technique implemented to aid in the preservation of biological matter. Moreover, methods include administering or implanting the biological matter in which stasis was induced to a live recipient organism.

Methods of the invention also concern inducing stasis in in vivo biological matter comprising incubating the biological matter with an oxygen antagonist or other active compound that creates hypoxic conditions for an effective amount of time for the biological matter to enter stasis.

Furthermore, other embodiments of the invention include methods of reducing oxygen demand in in vivo biological matter comprising contacting the biological matter with an effective amount of an oxygen antagonist or other active compound to reduce their oxygen demand. It is contemplated that oxygen demand is reduced about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein, with respect to the amount of oxygen demand in cells of the biological matter or a representative sample of cells from the biological matter not exposed or no longer exposed to the oxygen antagonist or other active compound.

Other aspects of the invention concern methods for preserving in vivo biological matter comprising exposing the in vivo biological matter to an effective amount of an oxygen antagonist or other active compound to preserve the biological matter in vivo.

The present invention also concerns a method of delaying or reducing the effects of trauma on or in an organism comprising exposing biological matter at risk for trauma to an effective amount of an oxygen antagonist or other active compound.

In other aspects of the invention, there are methods for treating or preventing hemorrhagic shock in a patient comprising exposing the patient to an effective amount of an oxygen antagonist or other active compound. Alternatively, in some embodiments methods prevents lethality in the patient as a result of the bleeding and/or hemorrhagic shock. In such methods of preventing a patient from bleeding to death or prevent lethality in a bleeding patient, steps include exposing the patient to an effective amount of an oxygen antagonist or other active compound. In certain embodiments, the oxygen antagonist is specifically contemplated to be a chalcogenide compound such as $H_2S$.

Methods for reducing heart rate in an organism are also included as part of the invention. Such methods involve contacting the biological sample or organism with an effective amount of an oxygen antagonist or other active compound.

One embodiment of the invention relates to a method of inducing hibernation in a mammal comprising contacting the mammal with an effective amount of an oxygen antagonist or other active compound.

In another embodiment, there is a method of anesthetizing an organism comprising exposing biological matter in which anesthesia is desired to an effective amount of an oxygen antagonist or other active compound. It is contemplated that the anesthesia may be similar to local or general anesthesia.

The present invention further includes methods of protecting a mammal from radiation therapy or chemotherapy comprising contacting the mammal with an effective amount of an oxygen antagonist or other active compound prior to or during radiation therapy or chemotherapy. With local administration of the cancer therapy, it is specifically contemplated that the oxygen antagonist or other active compound may also be administered locally to the affected organ, tissue, and/or cells. In certain embodiments, methods can be used for preventing or reducing hair loss in a chemotherapy patient. It is contemplated that such a patient may have already received chemotherapy or be a candidate for chemotherapy. In particular cases, it is contemplated that an active compound is provided to the patient as a topical gel to be applied where the hair loss is anticipated or present.

The present invention also covers reducing the oxygen requirement of biological matter, meaning that the amount of oxygen required by the biological matter to survive is reduced. This can be achieved by providing an effective amount of one or more active compounds. It is generally known how much oxygen particular biological matter require to survive, which can also be dependent on time, pressure, and temperature. In certain embodiments of the invention, the oxygen requirement of the biological matter is reduced by about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein, as compared to the requirement of the biological matter in the absence of the effective amount of the active compound(s).

In additional embodiments, there are methods of treating a hyperproliferative disease (e.g., cancer) in a mammal comprising contacting the mammal with an effective amount of an oxygen antagonist or other active compound and subjecting the mammal to hyperthermia therapy.

While methods of the invention may be applied to preserving organs for transplant, other aspects of the invention concern the recipient organism. In some embodiments, there are methods of inhibiting rejection of an organ transplant in a mammal comprising providing the mammal with an effective amount of an oxygen antagonist or other active compound.

Temperature regulation can be achieved in organisms by employing oxygen antagonists or other active compounds. In some embodiments, there is a method of treating a subject with hypothermia comprising (a) contacting the subject with an effective amount of an oxygen antagonist, and then (b) subjecting the subject to an environmental temperature above that of the subject. In other embodiments, the present invention includes a method of treating a subject with hyperthermia comprising (a) contacting the subject with an effective amount of an oxygen antagonist or other active compound. In some cases, treatment of hyperthermia also includes (b) subjecting the subject to an environmental temperature that is at least about 20° C. below that of the subject. As discussed above, exposing the subject to nonphysiological or a controlled temperature environment can be used in additional embodiments. It is contemplated that this method may be achieved with active compounds generally.

In some cases, the invention concerns a method for inducing cardioplegia in a patient undergoing bypass surgery comprising administering to the patient an effective amount of an oxygen antagonist or other active compound. It is contemplated that administration may be local to the heart so as to protect it.

Other aspects of the invention relate to a method for preventing hematologic shock in a patient comprising administering to the patient an effective amount of an oxygen antagonist or other active compound.

Moreover, there are methods for promoting wound healing in an organism comprising administering to the organism or wound an effective amount of an oxygen antagonist or other active compound.

In addition, the present invention covers a method for preventing or treating neurodegeneration in a mammal comprising administering to the mammal an effective amount of an oxygen antagonist or other active compound.

The present invention also covers reducing the oxygen requirement of biological matter, meaning that the amount of oxygen required by the biological matter to survive is reduced. This can be achieved by providing an effective amount of one or more active compounds. It is generally known how much oxygen particular biological matter require to survive, which can also be dependent on time, pressure, and temperature. In certain embodiments of the invention, the oxygen requirement of the biological matter is reduced by about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein, as compared to the requirement of the biological matter in the absence of the effective amount of the active compound(s).

Additional embodiments of the invention concern methods for preventing hair loss, such as from chemotherapy, by administering to a patient who has or will undergo chemotherapy an effective amount of at least one active compound.

In cases in which biological matter is being protected from damage or further damage, it is contemplated that the biological matter may be exposed to an oxygen antagonist within about, within at least about, or within at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein, after initial damage (trauma or wound or degeneration) occurs. Thus in additional embodiments of the invention, methods include an initial assessment of any damage, trauma, a wound, or degeneration.

In certain embodiments of the invention there are methods for treating a patient affected with a hematological disorder, which means a disease, disorder or condition that affects any hematopoietic cells or tissue. Examples include sickle cell disease and thalassemia. Thus, in some embodiments, there are methods of treating a patient with sickle cell disease or thalassemia with an effective amount of an active compound. In other embodiments, there are methods for enhancing survivability in a patient with cystic fibrosis (CF) by administering or providing an effective amount of an active compound. In other methods of the invention, there are methods for treating cyanide poisoning in a subject comprising administering an effective amount of an active compound. In certain embodiments, the compound is $H_2S$.

Other aspects of the invention concern methods for preserving one or more cells that are separate from an organism comprising contacting the cell(s) with an effective amount of an oxygen antagonist or other active compound to preserve the one or more cells. In addition to the cells and cell types discussed above and elsewhere in this application, it is contemplated that shrimp embryos are specifically contemplated for use with the present invention.

Moreover, in some embodiments of the invention, there are methods for preserving platelets. Shortcomings of the prior art are reduced or eliminated using techniques of this disclosure. Embodiments concerning platelets and oxygen reduction find wide application including but not limited to any application that would benefit from longer-lasting storage of platelets.

In one embodiment, oxygen reduction techniques can be embodied in a kit. For example, the kit currently sold under product number 261215, available from Becton Dickinson, makes use of select techniques described here. That kit includes an anaerobic generator (e.g., a hydrogen gas generator), Palladium Catalysts, an anaerobic indicator, and a gas impermeable, sealable, "BioBag" into which the above components (together with platelets in a gas-permeable bag) are placed and sealed.

In other embodiments of the invention, there are methods for reversibly inhibiting metabolism of a cell and/or organism by providing an effective amount of an active compound. It is specifically contemplated that rotenone is not the compound employed in this method, or possibly other methods of the invention. Moreover, it is also contemplated that in some embodiments, rotenone is excluded as an active compound. Similarly, it is contemplated that nitric oxide may be excluded as an active compound.

In other embodiments of the invention, methods are provided for enhancing the ability of biological matter to enter stasis in response to an injury or disease by providing an effective amount of an active compound, thereby protecting the biological matter from damage or injury, thereby enhancing survival of biological matter. Related embodiments include methods of preparing or priming biological matter for entry into stasis in response to an injury or disease by providing an effective amount of an active compound. Other related embodiments include method of inducing biological matter into pre-stasis, thereby protecting the biological matter from damage or injury. For example, treatment with an active compound at a dosage or for a time less than required to induce stasis enables the biological matter to more readily or more completely achieve a beneficial state of stasis in response to an injury or disease, while in the absence of treatment with the active compound, the biological matter would die or suffer damage or injury before it reached a protective level of stasis, e.g., a level sufficient to render the biological matter resistant to lethal hypoxia.

Certain injuries and disease states cause biological matter to reduce its metabolism and/or temperature to degrees that may not achieve stasis. For example, hypoxia, ischemia, and blood loss all reduce the amount of oxygen available and supplied to oxygen utilizing biological matter, thereby reducing oxygen utilization in cells of the biological matter, reducing energy production derived from oxidative phosphorylation, and thereby decreasing thermogenesis, leading to hypothermia. Depending on the severity or time elapsed following the onset or progression of the injurious or disease insult, "stasis" may or may not have been achieved. Treatment with an active compound lowers the threshold (i.e., the severity or duration of the insult that is needed to achieve stasis) for induction of stasis, or it may add to or synergize with the injurious or disease stimuli to induce stasis in biological matter under injurious conditions that would not have resulted in stasis were it not for the active compound treatment. Such activity of active compounds is determined by comparing the stasis-inducing effects (magnitude, kinetics) of injurious or disease stimuli alone with those in which the biological matter was pre-exposed, exposed concomitantly, exposed after, or any combination thereof, to the active compound. For example, as described in Example 11 of the instant patent application, pre-exposure of mice to 150 ppm $H_2S$ in air caused an approximately two-fold drop in $CO_2$ production prior to exposure to hypoxia (5% $O_2$). Subsequently, $CO_2$ production in pre-treated mice fell approximately 50-fold during hypoxia. In contrast, while $CO_2$ production in control, $H_2S$ untreated mice also fell, the hypoxia survivability of the mice was not achieved, presumably since the mice died before stasis was achieved.

In other aspects of the invention, there are methods for inducing sleep in an organism comprising exposing the organism to an effective amount of an active compound, wherein the effective amount is less than an amount that can induce stasis in the organism. The term "sleep" is used according to its ordinary and plain meaning in a medical context. Sleep is distinguishable from other states of unconsciousness, which are also contemplated as states that can be achieved using methods of the invention.

The present invention also concerns methods for anesthetizing biological matter comprising exposing the matter to an effective amount of an active compound, wherein the effective amount is less than an amount that can induce stasis in the organism.

In the methods discussed above, an effective amount that is less than an amount that can induce stasis in an organism may be reduced with respect to duration and/or amount. That reduction may be a reduction in amount by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent, or any range derivable therein, of the amount to induce stasis. A reduction may be a reduction in duration (length of exposure time) by 1, 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7, days, 1, 2, 3, 4, 5 weeks, and/or 1, 2, 3, 4, 5, 6, 7, 8, 9, 10, 11, 12 months, or any range derivable therein. Alternatively, the reduction may be in terms of the overall effective amount provided to the biological matter, which may be a reduction of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent, or any range derivable therein, relative to the overall effective amount to induce stasis in an organism of that species and/or size.

It is specifically contemplated that the present invention can be used for preserving organisms that are used for consumption or laboratory research, such as flies, frogs, fish, mice, rats, dogs, shrimp, and embryos thereof.

Methods of the invention can involve employing an apparatus or system that maintains the environment in which biological matter is placed or exposed to. The invention includes an apparatus in which an oxygen antagonist or other active compound, particularly as a gas, is supplied. In some embodiments, the apparatus includes a container with a sample chamber for holding the biological matter, wherein the container is connected to a supply of gas comprising the oxygen antagonist(s). It is specifically contemplated that the container may be a solid container or it may flexible, such as a bag.

In some embodiments, the invention is an apparatus for preserving cell(s), the apparatus comprising: a container having a sample chamber with a volume of no greater than 775 liters; and a first gas supply in fluid communication with the sample chamber, the first gas supply including carbon monoxide. In further embodiments, the apparatus also includes a cooling unit that regulates the temperature inside the sample chamber and/or a gas regulator that regulates the amount of oxygen antagonist or other active compound in the chamber or the amount of oxygen antagonist or other active compound in a solution that is in the chamber.

It is contemplated that there may be a gas supply for a second or additional gas or a second or additional gas supply for the oxygen antagonist or other active compound. The second gas supply may be connected with the sample chamber or it may be connected with the first gas supply. The additional gas, as discussed above, may be a non-toxic and/or non-reactive gas.

A gas regulator is part of the apparatus in some embodiments of the invention. One, two, three, or more gas regulators may be employed. In some cases, the gas regulator regulates the gas supplied to the sample chamber from the first gas supply. Alternatively, it regulates the gas supplied to the sample chamber or first gas supply from the second gas supply, or there may be a regulator for both the first and second gas supplies. It is further contemplated that any gas regulator can be programmed to control the amount of gas supplied to the sample chamber and/or to another gas supply. The regulation may or may not be for a specified period of time. There may be a gas regulator, which may or may not be programmable, for any gas supply directly or indirectly connected to the sample chamber. In some cases, the gas regulator is electronically programmable.

In some cases, the pressure and/or the temperature inside the chamber can be regulated with either a pressure regulator or temperature regulator, respectively. As with the gas regulator, these regulators may be electronically programmable. The apparatus of the invention may also have a cooling and/or heating unit to achieve the temperatures discussed above. The unit may or may not be electronically programmable.

In additional embodiments, the apparatus includes a wheeled cart on which the container rests or it may have one or more handles.

It is specifically contemplated that the invention includes an apparatus for cell(s), tissues, organs, and even whole organisms, in which the apparatus has: a container having a sample chamber; a first gas supply in fluid communication with the sample chamber, the first gas supply including the oxygen antagonist(s) or other active compound(s); and an electronically-programmable gas regulator that regulates gas supplied to the sample chamber from the first gas supply.

In some embodiments, the apparatus also has a structure configured to provide a vacuum within the sample chamber.

Moreover, any oxygen antagonist or other active compound described in this application is contemplated for use with apparatuses of the invention. In specific embodiments, carbon monoxide can be administered using this apparatus. In other cases, a chalcogenide compound can be administered or a compound having the reducing agent structure. In still further embodiments, an active compound is administered using the apparatus. In specific embodiments, the invention covers a device or its use. In certain embodiments, the device is single dose delivery device. In other embodiments, the device is an inhaler or nebulizer. In even further embodiments, other devices include, but are not limited to, an injection device such as a pen, a pump such as an infusion pump, or a patch. Moreover, it is contemplated that these devices may or may not be single dose delivery devices.

Additionally, the present invention concerns screening assays. In some embodiments, a candidate substance is screened for the ability to act as an oxygen antagonist or active compound, specifically including a protective metabolic agent. This can be done using any assay described herein, such as by measuring carbon dioxide output. Any substance identified as having exhibiting characteristics of an oxygen antagonist or other active compound can be further characterized or tested. Moreover, it is contemplated that such a substance can be administered to biological matter to induce stasis or manufactured thereafter.

In certain embodiments, there are screening methods for active compounds, including active stasis compounds. Furthermore, the methods of screening may be for oxygen antagonists or for any other compounds that can effect the methods discussed herein. In some embodiments, there are screening methods involving a) exposing a zebrafish embryo to a substance; b) measuring the heart rate of the embryo; c) comparing the heart rate of the embryo in the presence of the substance to the heart rate in the absence of the substance, wherein a reduction of heart rate, such as by 50% or more, identifies the substance as a candidate active compound. Instead of zebrafish embryos, it is contemplated that other non-human organisms may be used as well, such as fish, frogs, flies, shrimp, or their embryos. In further embodiments, the heart rate of the embryo is measured by counting the number of heartbeats. This can be done, in some cases, by viewing the embryo under a dissecting microscope.

Other screening embodiments involve: a) exposing a nematode to a substance; b) assaying one or more of the following cellular respiration factors: i) core body temperature; ii) oxygen consumption; iii) motility; or, iv) carbon dioxide production; c) comparing the cellular respiration factor of the nematode in the presence of the substance to the cellular respiration factor in the absence of the substance, wherein a reduction of the characteristic identifies the substance as a candidate active compound. It is specifically contemplated that motility of the nematodes is assayed in some methods of the invention.

In some embodiments, the methods first involve identifying an appropriate substance to screen. In certain embodiments, the substance will be a chalcogenide, reducing agent, or have the structure of Formula I or Formula IV, or any other compound discussed herein.

It is further contemplated that subsequent screens can be done in organisms considered higher or more complex than those used in preliminary or initial screens. Thus, it is contemplated that one or more cellular respiration factors will be assayed in these other organisms to further evaluate a candidate compound. In certain embodiments, subsequent screens involve the use of mice, rats, dogs, etc.

It is contemplated that a number of different organisms or biological matter (other cells or tissues) could be used and a number of different cellular respiration factors could be assayed in screening methods of the invention. In addition, it is contemplated that multiple such screens are performed at the same time in some embodiments of the invention.

It will of course be understood that in order for the substance to be considered a candidate active compound (or oxygen antagonist, or stasis inducer or protective metabolic agent, etc.) the substance must not kill the organism or cells in the assay and the effect must be reversible (that is, the characteristic that is altered needs to resume to its level before the exposure to the substance).

It is of course understood that any method of treatment can be used in the context of a preparation of a medicament for the treatment of or protection against the specified disease or condition. This includes, but is not limited to, the preparation of a medicament for the treatment of hemorrhagic or hematologic shock, wounds and tissue damage, hyperthermia, hypothermia, neurodegeneration, sepsis, cancer, and trauma. Moreover, the invention includes, but is not limited to, the preparation of a medicament for a treatment to prevent death, shock, trauma, organ or tissue rejection, damage from cancer therapy, neurodegeneration, and wound or tissue damage.

As discussed above, organismal stasis is not any of the following states: sleep, comatose, death, anesthetized, or grand mal seizure. However, it is contemplated in some embodiments of the invention, that such states are the desired goal of employing methods, compositions and articles of manufacture of the invention. Any embodiment discussed with respect to one aspect of the invention applies to other aspects of the invention as well. Moreover, embodiments may be combined.

Any embodiment involving "exposing" biological matter to an active compound may also be implemented so that biological matter is provided with the active compound or administered the active compound. The term "provide" is used according to its ordinary and plain meaning: "to supply or furnish for use" (Oxford English Dictionary), which, in the case of patients, may refer to the action performed by a doctor or other medical personnel who prescribes a particular active compound or administers it directly to the patient.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 18 50 ppm $H_2S$ added to CO increases fraction of flies that survive anoxia. Adult flies were made anoxic in low-flow experiments, either directly from room air (no pretreatment) or after being exposed to 50 ppm $H_2S$ balanced with CO.

DESCRIPTION OF ILLUSTRATIVE EMBODIMENTS

I. Stasis

Figure 1:
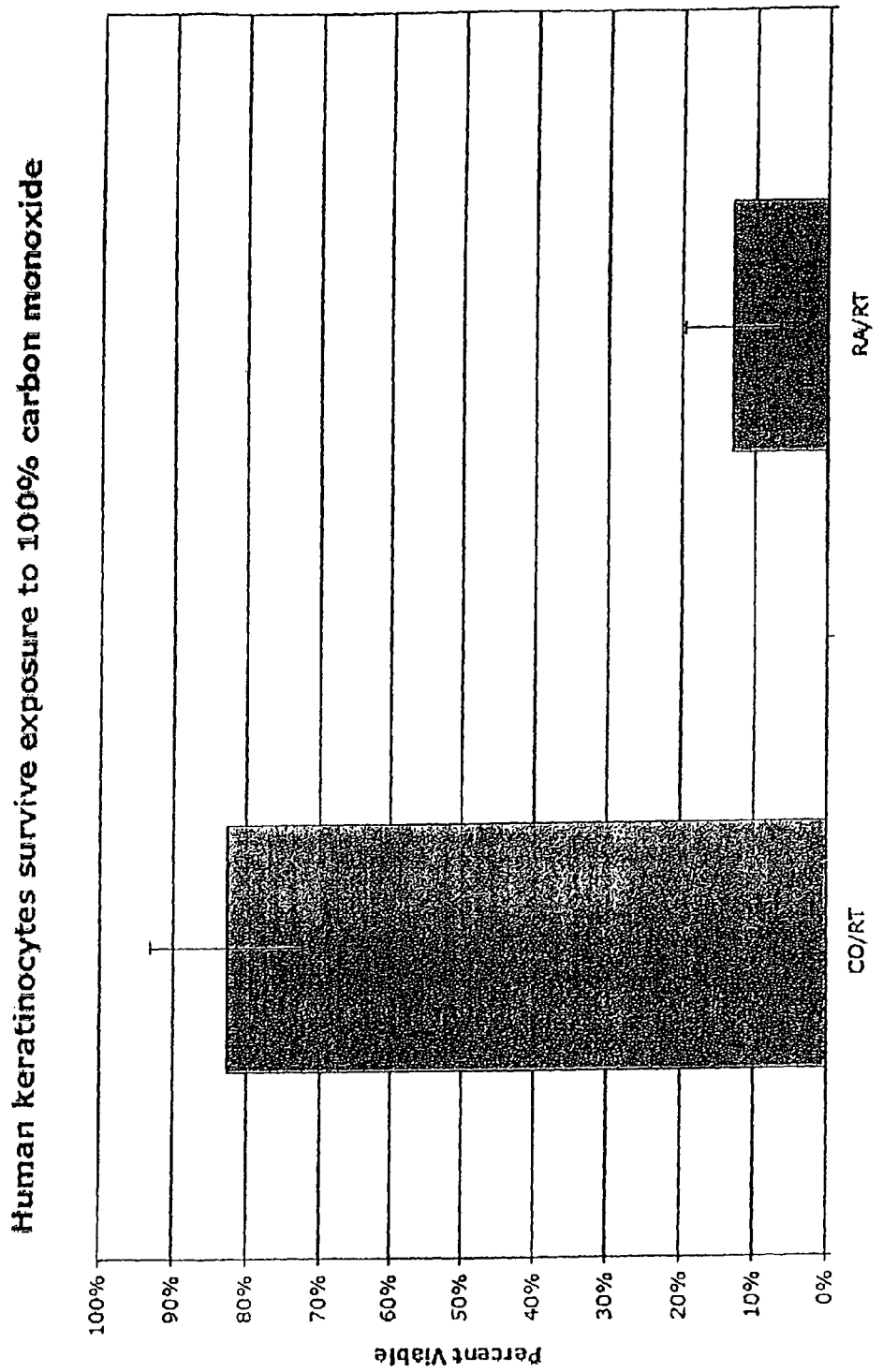
FIG. 1 Human keratinocytes survive exposure to 100% CO. Cells were inspected visually using an inverted phase contrast microscope. Quantitation of the number of viable keratinocytes as judged by trypan blue staining, which is an indicator of cell death.

In "stasis" or "suspended animation," a cell, tissue or organ, or organism (collectively referred to as "biological material") is living, but cellular functions necessary for cell division, developmental progression, and/or metabolic state are slowed or even stopped. This state is desirable in a number of contexts. Stasis can be used as a method of preservation by itself, or it may be induced as part of a cryopreservation regimen. Biological materials may be preserved for research use, for transportation, for transplantation, for therapeutic treatment (such as ex vivo therapy), and to prevent the onset of trauma, for example. Stasis with respect to entire organisms has similar uses. For instance, transportation of organisms could be facilitated if they had entered stasis. This might reduce physical and physiological damage to the organism by reducing or eliminating stress or physical injury. These embodiments are discussed in further detail below. Stasis may be beneficial by decreasing the need of the biological material for oxygen and, therefore, bloodflow. It may extend the period of time that biological material can be isolated from a life-sustaining environment and exposed to a death-inducing environment.

While recovery has been reported from accidental hypothermia for a relatively prolonged period of time (Gilbert et al., 2000), there has been recent interest in intentionally inducing suspended animation in organisms. (The discussion of any reference is not to be construed as an admission that the reference constitutes prior art. In fact, some references discussed herein would not be prior art with respect to the priority applications.) Controlled hyperthermia has been explored, as well as the administration of a cold flush of a solution into the aorta (Tisherman, 2004), induction of cardiac arrest (Behringer et al., 2003), or nitric oxide-induced suspended animation (Teodoro et al., 2004).

An organism in stasis is distinguishable from an organism under general anesthesia. For example, an organism in mild stasis (between about 2- and about 5-fold decrease in cellular respiration) that is exposed to room air will begin to shiver, while an organism under anesthesia will not. Also, an organism in mild stasis is anticipated to respond to a toe squeeze, while an organism under anesthesia usually does not. Consequently, stasis is not the same thing as being under anesthesia as it is commonly practiced.

$CO_2$ production is a direct marker of cellular respiration related to metabolism of an organism. This may be distinguished from "$CO_2$ evolution," which refers to the amount of $CO_2$ blown out of the lungs. Certain active compounds, e.g., hydrogen sulfide, can inhibit carbonic anhydrase activity in the lungs, this inhibiting conversion of carbonate to $CO_2$ and its liberation from the pulmonary blood, thereby exhibiting an associated reduction in $CO_2$ evolution, without a corresponding decrease in cellular $CO_2$ production.

The present invention is based on the observation that certain types of compounds effectively induce reversible stasis in biological matter. Other patent applications discuss induction of stasis, including the following: U.S. patent application Ser. Nos. 10/971,576, 10/972,063, and 10/971,575; U.S. patent application Ser. No. 10/971,576; U.S. patent application Ser. No. 10/972,063; and U.S. patent application Ser. No. 10/971,575, all of which are hereby incorporated by reference.

A. Thermoregulation

Stasis in a warm-blooded animal will affect thermoregulation. Thermoregulation is a characteristic of so-called "warm-blooded" animals, which permits the organism to maintain a relatively constant core body temperature even when exposed to significantly altered (cold or hot) environmental temperatures. The ability to control thermoregulation by induction of stasis is one aspect of the invention, and permits uses similar to those discussed above.

Thermal regulation may be facilitated by placing of organisms, limbs or isolated organs or tissues into chambers/devices, the temperature of which can be controlled. For example, warm rooms or chamber-like devices similar to hyperbaric chambers may encompass an entire organism and be connected to thermo-regulatory apparti. Smaller devices such as blankets, sleeves, cuffs or gloves (e.g., CORE CONTROL cooling system by AVAcore Technologies, Palo Alto, Calif., U.S. Pat. No. 6,602,277) are also contemplated. Such chambers/devices may be used both to increase or reduce ambient temperatures.

B. Biological Matter

Biological matter contemplated for use with the present invention include material derived from invertebrates and vertebrates, including mammals; biological materials includes organisms. In addition to humans, the invention can be employed with respect to mammals of veterinary or agricultural importance including those from the following classes: canine, feline, equine, bovine, ovine, murine, porcine, caprine, rodent, lagomorph, lupine, and ursine. The invention also extends to fish and birds. Other examples are disclosed below.

Moreover, the type of biological matter varies. It can be cells, tissues and organs, as well as organisms for which different compositions, methods, and apparatuses have relevance. The nonprovisional U.S. patent application Ser. Nos. 10/971,576, 10/972,063, and 10/971,575 are hereby incorporated by reference in their entireties.

In some embodiments, the biological material is or comprises cells. It is contemplated that the cell may be any oxygen-utilizing cell. The cell may be eukaryotic or prokaryotic. In certain embodiments, the cell is eukaryotic. More particularly, in some embodiments, the cell is a mammalian cell. Mammalian cells contemplated for use with the invention include, but are not limited to those that are from a: human, monkey, mouse, rat, rabbit, hamster, goat, pig, dog, cat, ferret, cow, sheep, and horse.

Moreover, cells of the invention may be diploid, but in some cases, the cells are haploid (sex cells). Additionally, cells may be polyploid, aneuploid, or anucleate. The cell can be from a particular tissue or organ, such as one from the group consisting of: heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord. Moreover, the cell can also be characterized as one of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

1. Different Sources

The following are examples of sources from which biological matter may be obtained. Embodiments of the invention include, but are not limited to, these examples.

a. Mammals

In certain aspects of the invention, the mammal is of the Order Monotremata, Marsupialia, Insectivora, Macroscelidia, Dermoptera, Chiroptera, Scandentia, Primates, Xenarthra, Pholidota, Tubulidentata, Lagomorpha, Rodentia, Cetacea, Carnivora, Proboscidea, Hyracoidea, Sirenia, Perissodactyla, or Artiodactyla.

Examples of Monotremata include the Families Tachyglossidae (e.g., Echidnas) and Ornithorhynchidae (e.g., Platypus). Examples of Marsupialia include the Families Didelphidae (e.g., Opossums), Microbiotheriidae (e.g., Monito del Monte), Caenolestidae (e.g., Rat Oppossums), Dasyuridae (e.g., Marsupial mice), Myrmecobiidae (e.g., Numbat), Thylacinidae (e.g., Thylacine), Peramelidae (e.g., Bandicoots), Thylacomyidae (e.g., Rabbit Bandicoots), Notoryctidae (e.g., Marsupial Moles), Phalangeridae (e.g., Cuscuses), Petauridae (e.g., Ringtails, Gliders), Burramyidae (e.g., Pygmy Possums), Macropodidae (e.g., Kangaroos, Wallabies), Tarsipedidae (e.g., Honey Possum), Vombatidae (e.g., Wombats), and Phascolarctidae (e.g., Koalas).

Insectivora includes, for example, the Families Solenodontidae (e.g., Solenodons), Tenrecidae (e.g., Tenrecs, Otter Shrews), Chrysochloridae (e.g., Golden Moles), Erinaceidae (e.g., Hedgehogs, Moonrats), Soricidae (e.g., Shrews), and Talpidae (e.g., Moles, Desmans). The Order Macroscelidia includes the Family Macroscelidia (e.g., Elephant Shrews). The Order Scandentia includes Tupaiidae (e.g., Tree Shrews). The Order Dermoptera includes the Family Cynocephalidea (e.g., Flying Lemurs). Chiroptera includes the Families Pteropodidae (e.g., Fruit Bats, Flying Foxes), Rhinopomatidae (e.g., Mouse-Tailed Bats), Craseonycteridae (e.g., Hog-Nosed or Bumblebee Bat), Emballonuridae (e.g., Sheath- Tailed Bats), Nycteridae (e.g., Slit-Faced Bats), Megadermatidae (e.g., False Vampire Bats), Rhinolophidae (e.g., Horshoe Bats), Noctilionidae (e.g., Bulldog Bats, Fisherman Bats), Mormoopidae, Phyllostomidae (e.g., New World Leaf-Nosed Bats), Natalidae, Furipteridae, Thyropteridae, Myzapodidae, Vespertilionidae (e.g., Common Bats), Mystacinidae (e.g., Short-Tailed Bats), and Molossjdae (e.g., Free-Tailed Bats).

The Order Primates includes the Families Lemuridae (e.g., Lemurs), Chemogaleidae (e.g., Mouse Lemurs), Indriidae (e.g., Indri, Woolly Lemur), Daubentoniidae (e.g., Aye-Aye), Lorisidae (e.g., Lorises, Bushbabies, Galagos), Tarsiidae (e.g., Tarsiers), Cebidae (e.g., New World Monkeys, Marmosets, Tamarins), Hylobatidae (e.g., Gibbons), Pongidae (e.g., Apes), and Hominidae (e.g., Man).

Examples of Xenarthra include Myrmecophagidae (e.g., Anteaters), Bradypodidae (e.g., Three-Toed Sloths), Megalonychidae (e.g., Two-Toed Sloths), and Dasypodidae (e.g., Armadillos). Examples of Pholidota include Manidae (e.g., Pangolins). Examples of Tubulidentata include Orycteropodidae (e.g., Aardvarks). Examples of Lagomorpha include Ochotonidae (e.g., Pikas) and Leporidae (e.g., Hares and Rabbits).

The Order Rodentia includes the Families Aplodontidae (e.g., Mountain Beavers), Sciuridae (e.g., Squirrels, Marmots, Chipmunks), Geomyidae (e.g., Pocket Gophers), Heteromyidae (e.g., Pocket Mice, Kangaroo Rats), Castoridae (e.g., Beaver), Anomaluridae (e.g., Scaly-Tailed Squirrels), Pedetidae (e.g., Springhare), Muridae (e.g., Rats and Mice), Gliridae (e.g., Dormice), Seleviniidae (e.g., Desert Dormouse), Zapodidae (e.g., Jumping Mice), Dipodidae (e.g., Jerboas), Hystricidae (e.g., Old World Porcupines), Erethizontidae (e.g., New World Porcupines), Caviidae (e.g., Guinea Pigs, Maras), Hydrochaeridae (e.g., Capybara), Dinomyidae (e.g., Pacarana), Agoutidae (e.g., Pacas), Dasyproctidae (e.g., Agoutis), Chinchillidae (e.g., Chinchillas, Viscachas), Capromyidae (e.g., Hutias), Myocastoridae (e.g., Nutria), Ctenomyidae (e.g., Tuco-Tucos), Octodontidae (e.g., Octodonts, Degus), Abrocomidae (e.g., Chichilla Rats), Echimyidae (e.g., Spiny Rats), Thryonomyidae (e.g., Cane Rats), Petromyidae (e.g., African Rock Rat), Bathyergidae (e.g., Mole Rat), and Ctenodactylidae (e.g., Gundis).

The Order Cetacea includes the Families Iniidae (e.g., Amazon Popoise), Lipotidae, Platanistidae, Pontoporiidae, Ziphiidae (e.g., Beaked Whales), Physeteridae (e.g., Sperm Whales), Monodontidae (e.g., Beluga Whale, Narwhal), Delphinidae (e.g., Marine Dolphins, Killer Whales), Phocoenidae (e.g., Porpoises), Balaenopteridae (e.g., Rorquals), Balaenidae (e.g., Right Whales), and Eschrichtiidae (e.g., Gray Whales).

The Order Carnivora includes the Families Canidae (e.g., Dogs, Foxes, Wolves, Jackals, Coyotes), Ursidae (e.g., Bears), Procyonidae (e.g., Raccoons, Coatis, Kinkajous, Lesser Pandas), Ailuropodidae (e.g., Giant Pandas), Mustelidae (e.g., Weasels, Skunks, Badgers, Otters), Viverridae (e.g., Civets, Genets), Herpestidae (e.g., Mongooses), Protelidae (e.g., Aardwolf), Hyaenidae (e.g., Hyenas), Felidae (e.g., Cats), Otariidae (e.g., Eared Seals, Sea Lions), Odobenidae (e.g., Walrus), and Phocidae (e.g., Earless Seals).

The Order Proboscidea includes the Family Elephantidae (e.g., Elephants). Hyracoidea includes the Family Procaviidae (e.g., Hyraxes). Sirenia includes the Families Dugongidae (e.g., Dugong) and Trichechidae (e.g., Manatees). The Order Perissodactyla includes the Families Equidae (e.g., Horses, Asses, Zebras), Tapiridae (e.g., Tapirs), and Rhinocerotidae (e.g., Rhinoceroses). The Order Artiodactyla includes the Families Suidae (e.g., Pigs, Babirusa), Tayassuidae (e.g., Peccaries), Hippopotamidae (e.g., Hippopotamuses), Camelidae (e.g., Camels, Llamas, Vicunas), Tragulidae (e.g., Chevrotains), Moschidae (e.g., Musk Deer), Cervidae (e.g., Deer, Elk, Moose), Giraffidae (e.g., Giraffe, Okapi), Antilocapridae (e.g., Pronghorn), and Bovidae (e.g., Cattle, Sheep, Antelope, Goats).

b. Reptiles

In certain embodiments, the biological material is a reptile or is derived from a reptile. The reptile may be of the Order Chelonia, Pleurodira, Squamata, Rhynchocephalia, or Crocodylia. A reptile of the Order Chelonia may be, for example, a Carettochelyidae, Chelydridae (e.g., Snapping Turtles), Cheloniidae (e.g., Loggerhead Turtles, Green Turtles), Dermatemydidae (e.g., Leatherback Turtles), Emydidae (e.g., Painted Turtles, Pond Sliders, Pond Turtles, Snail-Eating Turtles, Box Turtles), Kinostemidae (e.g., Stinkpot Turtles), Saurotypidae, Testudinidae (e.g., Galapagos Tortoises, Desert Tortoises, Aldabra Turtles, Spu-Thighed Tortoises, Hermann's Tortoise), Trionychidae (e.g., Chinese Softshells, Spiny Softshells), or a Platystemidae. A reptile of the Order Pleurodira may be, for example, a Chelidae (e.g., Snake-Necked Turtles) or Pelomedusidae (e.g., Helmeted Turtles).

A reptile of the Order Squamata may be, for example, an Agamidae (e.g., Rainbow Lizards, Bearded Dragons, Indian Bloodsuckers, Spiny-Tailed Lizards), Chamaeleontdidae (e.g., Chameleons), Iguanidae (e.g., Anoles, Basilisks, Collared Lizards, Iguanas, Homed Lizards, Chuckwallas, Sagebrush Lizards, Side-Blotched Lizards), Gekkonidae (e.g., Geckos), Pygopodidae, Teiidae (e.g., Race Runners, Tegus), Lacertidae (e.g., Sand Lizards, Ocellated Lizards, Viviparous Lizards, Wall Lizards, Long-Tailed Lizards), Xantuslidae, Scincidae (e.g., Skinks), Cordylidae (e.g., Sungazers), Dibamidae, Xenosauridae, Anguidae (e.g., Slow Worm, Alligator Lizards, Sheltopusik, Glass Lizards), Helodermatidae (e.g., Gila Monster), Lanthanotidae, Varanidae (e.g., Monitors), Leptotyphlopidae, Typhlopidae, Anomalepididae, Aniliidae (e.g., Pipe Snakes), Uropeitidae, Xenopeltidae, Boidae (e.g., Boas, Anacondas, Rock Pythons), Acrochordidae (e.g., Wart Snakes), Colubridae (e.g., Mangrove Snakes, Whip Snakes, Smooth Snakes, Egg-Eating Snakes, Boomslangs, Rat Snakes, Aesculapian Snakes, Four-Lined Snakes, Oriental Beauty Snake, Tentacled Snakes, Hognose Snakes, Kingsnakes, Montpelier Snakes, Grass Snakes, Water Snakes, Garter Snakes, Twig Snakes, Keelback Snakes), Elapidae (e.g., Death Adders, Kraits, Mambas, Coral Snakes, Cobras, Copperhead, Puff Adder), Viperidae (e.g., Vipers, Right Adders, Rattlesnakes, Massasaugas, Adder), Hydrophiidae (e.g., Sea Brait), Amphisbaenidae (e.g., Worm Lizard), Bipedidae, or a Trogonophidae (e.g., Burrowing Lizard).

A reptile of the Order Rhynchocephalia may be, for example, a Sphenodontidae (e.g., Tuataras). A reptile of the Order Crocodylia may be, for example, an Alligatoridae (e.g., Alligators, Caiman), Crocodylidae (e.g., Crocodiles), or a Gavialidae (e.g., Gharials).

c. Amphibians

The biological material of the present invention may be an amphibian or may be derived from an amphibian. The amphibian may be, for example, a frog or a toad. The frog or toad may be, for example, an Arthroleptidae (e.g., screeching frogs), Ascaphidae (e.g., tailed frogs), Brachycephalidae (e.g., gold frogs and shield toads), Bufonidae (e.g., true toads), Centrolenidae (e.g., glass frogs and leaf frogs), Dendrobatidae (e.g., poison-dart frogs), Discoglossidae (e.g., fire-bellied toads), Heleophrynidae (e.g., ghost frogs), Hemisotidae (e.g., shovel-nosed frogs), Hylidae (e.g., New World tree frogs), Hyperoliidae (e.g., African tree frogs), Leiopelmatidae (e.g., New Zealand frogs), Leptodactylidae (e.g., neotropical frogs), Megophryidae (e.g., South Asian frogs), Microhylidae (e.g., microhylid frogs), Myobatrachidae (e.g., Australian frogs), Pelobatidae (e.g., spadefoot toads), Pelodytidae (e.g., parsley frogs), Pipidae (e.g., tongueless frogs), Pseudidae (e.g., paradox frogs), Ranidae (e.g., riparian frogs and true frogs), Rhacophoridae (e.g., Old World tree frogs), Rhinodermatidae (e.g., Darwin's frogs), Rhinophrynidae (e.g., burrowing toad), Sooglossidae (e.g., Seychelle frogs), Caudata (e.g., salamanders), or a Gymnophiona (e.g., caecilians).

The amphibian may be a salamander. The salamander may be, for example, an Ambystomatidae (e.g., mole salamanders), Amphiumidae (e.g., amphiumas), Cryptobranchidae (e.g., giant salamanders and hellbenders), Dicamptodontidae (e.g., Pacific giant salamanders), Hynobiidae (e.g., Asiatic salamanders), Plethodontidae (e.g., lungless salamanders), Proteidae (e.g., mudpuppies and waterdogs), Rhyacotritonidae (e.g., torrent salamanders), Salamandridae (e.g., newts and salamanders), or a Sirenidae (e.g., sirens). Alternatively, the amphibian may be a Caecilian. The Caecilian may be, for example, a Caeciliidae (e.g., caecilians), Ichthyophiidae (e.g., Asiatic tailed caecilians), Rhinatrematidae (e.g., neotropical tailed caecilians), Scolecomorphidae (e.g., African caecilians), Typhlonectidae (e.g., aquatic caecilians), or an Uraeotyphlidae (e.g., Indian caecilians).

d. Birds

The biological material of the present invention may be a bird or may be derived from a bird. The bird may be, for example, an Anseriforme (e.g., waterfowl), Apodiforme (e.g., hummingbirds and swifts), Caprimulgiforme (e.g., nightbirds), Charadriiforme (e.g., shorebirds), Ciconiiforme (e.g., storks), Coliiforme (e.g., mousebirds), Columbiforme (e.g., doves and pigeons), Coraciiforme (e.g., kingfishers), Craciforme (e.g., chacalacas, curassows, guans, megapodes), Cuculiforme (e.g., cuckoos, hoatzin, turacos), Falconiforme (e.g., diurnal birds of prey), Galliforme (e.g., chicken-like birds), Gaviiforme (e.g., loons), Gruiforme (e.g., coots, cranes, rails), Passeriforme (e.g., perching birds), Pelecaniforme (e.g., pelicans), Phoenicopteriforme (e.g., flamingos), Piciforme (e.g., woodpeckers), Podicipediforme (e.g., grebes), Procellariiforme (e.g., tube-nosed seabirds), Psittaciforme (e.g., parrots), Sphenisciforme (e.g., penguins), Strigiforme (e.g., owls), Struthioniforme (e.g., cassowaires, emus, kiwis, ostriches, rheas), Tinamiforme (e.g., tinamous), Trogoniforme (e.g., trogons), or a Turniciforme (e.g., buttonquail).

e. Fish

The biological material of the present invention may be a fish or may be derived from a fish. The fish may be, for example, an Acipenseriforme (e.g., paddlefishes, spoonfishes, and sturgeons), Polypteriforme (e.g., bichirs, birchers, lobed-finned pike, and reed fishes), Atheriniforme (e.g., rainbow fishes and silversides), Beloniforme (e.g., halfbeeks and needlefishes), Beryciforme, Channiforme, Cyprinodontiforme (e.g., killifishes), Dactylopteriforme (e.g., flying gurnards), Gasterosteiforme (e.g., pipefishes and sticklebacks), Mugiliforme (e.g., mullets), Pegasiforme (e.g., dragonfishes and sea moths), Perciforme (e.g., perch-like fishes), Pleuronectiforme (e.g., flatfishes, flounders, and soles), Scorpaeniforme (e.g., scorpion fishes and sculpins), Stephanoberyciforme, Synbranchiforme (e.g., swamp eels), Tetraodontiforme (e.g., cowfishes, filefishes, leatherjackets, puffers, triggerfishes, and trunkfishes), Zeiforme (e.g., boarfishes, dories, and john dories), Atherinomorpha, Clupeiforme (e.g., anchovies and herrings), Aulopiforme, Albuliforme, Anguilliforme (e.g., eels), Elopiforme (e.g., tarpons), Notacanthiformes (e.g., spiny eels and tapirfishes), Sacopharyngiformes, Lampridiforme (e.g., opahs and ribbonfishes), Characiforme (e.g., leporins and piranhas), Cypriniforme (e.g., minnows, suckers, zebra fish), Gonorhynchiforme (e.g., milkfish and shellears), Gymnotiforme, Siluriforme (e.g., catfishes), Aphredoderiforme (e.g., cavefishes and pirate perches), Batrachoidiforme, Gadiforme (e.g., cods and hakes), Gobiesociforme, Lophiiforme (e.g., anglerfishes), Ophidiiforme, Percopsiforme (e.g., troutperches), Polymixiiforme (e.g., beardfishes), Cetomimiforme, Ctenothrissiforme, Esociforme (e.g., mudminnows and pikes), Osmeriforme (e.g., Argentines and smelts), Salmoniforme (e.g., salmons), Myctophiforme (e.g., Latern Fishes), Ateleopodiforme, Stomiiforme, Amiiforme (e.g., bowfins), Semionotiforme (e.g., gars), Syngnathiforme (e.g., pipefishes and seahorses), Ceratodontiforme (e.g., Australian lungfishes), Lepidosireniforme (e.g., South American lungfishes and African lungfishes), or a Coelacanthiforme (e.g., coelacanths).

f. Invertebrates

The biological material maybe an invertebrate or derived from an invertebrate. The invertebrate may be, for example, a Porifera (e.g., sponges), Cnidaria (e.g., jellyfish, hydras, sea anemones, Portuguese man-of-wars, and corals), Platyhelminthe (e.g., flatworms, including planaria, flukes, and tapeworms), Nematoda (e.g., roundworms, including rotifers and nematodes), Mollusca (e.g., mollusks, snails, slugs, octopuses, squids), Annelida (e.g., segmented worms, including earthworms, leeches, and marine worms), Echinodermata (e.g., sea stars, sea cucumbers, sand dollars, sea urchins), Phoronida (e.g., Horseshoe Worms), Tardigrada (e.g., Water Bears), Acanthocephala (e.g., Spiny Headed Worms), Ctenophora (e.g., Comb Jellies), or an Arthropod (e.g., arachnids, crustaceans, millipedes, centipedes, insects).

An Arthropod may be, for example, a Coleoptera (e.g., beetles), Diptera (e.g., true flies), Hymenoptera (e.g., ants, bees, wasps), Lepidoptera (e.g., butterflies, moths), Mecoptera (e.g., scorpion flies), Megaloptera, Neuroptera (e.g., lacewings and relatives), Siphonaptera (e.g., fleas), Strepsiptera (e.g., parasitic insects and twisted-winged parasites), Trichoptera (e.g., caddisflies), Anoplura (e.g., sucking lice), Hemiptera (e.g., true bugs and their relatives), Mallophaga (e.g., biting lice), Psocoptera (e.g., psocids), Thysanoptera (e.g., thrips), Orthoptera (e.g., grasshoppers, locusts), Dermaptera (e.g., earwigs), Dictyoptera, Embioptera (e.g., webspinners), Grylloblattodea, Mantophasmatodea (e.g., gladiators), Plecoptera (e.g., stoneflies), Zoraptera (e.g., zorapterans), Ephemeroptera (e.g., mayflies), Odonata (e.g., dragonflies and damselflies), Phasmatoptera (e.g., walkingsticks), Thysanura (e.g., bristletails), Archaeognatha, Collembola (e.g., snow flies and springtails), Chilopoda (e.g., centipedes), Diplopoda (e.g., millipedes), Pauropoda (e.g., pauropods, pauropodans, and progoneates), Symphyla (e.g., pseudocentipedes and symphylans), Malacostraca (e.g., crabs, krill, pill bugs, shrimp), Maxillopoda, Branchiopoda (e.g., branchiopods), Cephalocarida, Ostracoda (e.g., ostracods), Remipedia, Branchiura, Cirripedia (e.g., barnacles), Arachnida (e.g., arachnids, including amblypygids, spiders, daddy longlegs, harvestmen, microscorpions, book scorpions, false scorpions, pseudoscorpions, scorpions, solpugids, sun spiders, and uropygids), Merostomata (e.g., horseshoe crabs), or a Pycnogonida (e.g., sea spiders).

g. Fungi

The biological material of the present invention may be a fungi or may be derived from a fungi. The fungi may be, for example, an Ascomycota (sac fungi), Basidiomycota (club fungi), Chytridiomycota (chytrids), Deuteromycota, or a Zygomycota. The fungi may be a *Rhizopus, Pilobolus,*

*Arthrobotrys, Aspergillus, Allomyces, Chytridium, Agaricus, Amanita, Cortinarius, Neurospora, Morchella, Saccharomyces, Pichia, Candida, Schizosaccharomyces,* or *Ergot.* In particular embodiments the fungi may be *Saccharomyces cerevisiae, Schizosaccharomyces pombe, Candida albicans,* or *Pichia pastoris.* h. Plants

The biological material of the present invention may be a plant or may be derived from a plant. The plant may be a Bryophyte (e.g., mosses, liverworts, hornworts), Lycophyte (e.g., club mosses, ground pine), Sphenophyte (e.g., horsetails), Pterophyte (e.g., ferns), Cycadophyte (e.g., cycads), Gnetophyte (e.g., gnetum, ephedra, welwitschia), Coniferophyte (e.g., conifers), Ginkophyte (e.g., ginko), or Anthophyte (e.g., flowering plants). The Anthophyte may be a monocot or a dicot. Non-limiting examples of monocotyledonous plants include wheat, maize, rye, rice, turfgrass, sorghum, millet, sugarcane, lily, iris, agave, aloe, orchids, bromeliads, and palms. Non-limiting examples of dicotyledonous plants include tobacco, tomato, potato, soybean, sunflower, alfalfa, canola, rose, *Arabidopsis,* coffee, citrus fruits, beans, alfalfa, and cotton.

i. Protists

The biological material of the present invention may be a Protist or may be derived from a Protist. The Protist may be a Rhodophyte (e.g., red algae), Phaeophyte (e.g., brown algae, kelp), Chlorophyte (e.g., green algae), Euglenophyte (e.g., euglenoids) Myxomycot (e.g., slime molds), Oomycot (e.g., water molds, downy mildews, potato blight), or Bacillariophyte (e.g., diatoms).

j. Prokaryotes

In certain aspects of the invention, the biological material is a prokaryote or is derived from a prokaryote. In certain embodiments the prokaryote is an Archaea (archaebacteria). The archaebacteria may be, for example, a Crenarchaeota, Euryarchaeota, Korarchaeota or Nanoarchaeota. In certain aspects the Euryarchaeota is a Halobacteria, Methanobacteria, Methanococci, Methanomicrobia, Methanosarcinae, Methanopyri, Archeoglobi, Thermoplasmata, or a Thermococci. Specific, non-limiting examples of archaebacteria include: *Aeropyrum pernix, Methanococcus jannaschii, Halobacterium marismortui,* and *Thermoplasma acidophilum.*

In certain embodiments the prokaryote is an Eubacteria. The Eubacteria may be, for example, an Actinobacteria, Aquificae, Bacteroidetes, Green sulfur bacteria, Chlaamydiae, Verrucomicrobia, Chloroflexi, Chrysiogenetes, Cyanobacteria, Deferribacteres, *Deinococcus-Thermus,* Dictyoglomi, Fibrobacteres/Acidobacteria, Firmicutes, Fusobacteria, Gemmatimonadetes, Nitrospirae, Omnibacteria, Planctomycetes, Proteobacteria, Spirochaetes, Thermodesulfobacteria, or Thermotogae. Non-limiting examples of Actinobacteria include bacteria of the genera *Actinomyces, Arthrobacter, Corynebacterium, Frankia, Micrococcus, Micromonospora, Mycobacterium, Propionibacterium,* and *Streptomyces.* Specific examples of Actinobacteria include *Mycobacterium leprae, Mycobacterium tuberculosis, Mycobacterium avium, Corynebacterium glutamicum, Propionibacterium acnes,* and *Rhodococcus equi.*

Non-limiting examples of Aquificae include bacteria of the genera *Aquifex, Hydrogenivirga, Hydrogenobacter, Hydrogenobaculum, Thermocrinis, Hydrogenothermus, Persephonella, Sulfurihydrogenibium, Balnearium, Desulfurobacterium,* and *Thermovibrio.* Non-limiting examples of Firmicutes include bacteria of the genera Bacilli, Clostridia, and Molecutes. Specific examples of Firmicutes include: *Listeria innocua, Listeria monocytogenes, Bacillus subtilis, Bacillus anthracis, Bacillus thuringiensis, Staphylococcus aureus, Clostridium acetobutylicum, Clostridium difficile, Clostridium perfringens, Mycoplasma genitalium, Mycoplasma pneumoniae, Mycoplasma pulmonis, Streptococcus pneumoniae, Streptococcus pyogenes, Streptococcus mutans, Lactococcus lactis,* and *Enterococcus faecalis.*

Non-limiting examples of Chlamydiae/Verrucomicrobia include bacteria such as *Chlamydia trachomatis, Chlamydia pneumoniae,* I *Chlamydia psittaci.* Non-limiting examples of *Deinococcus-Thermus* include bacteria of the genera *Deinococcus* and *Thermus.*

Proteobacteria are gram-negative bacteria. Non-limiting examples of Proteobacteria include bacteria of the genera *Escherichia, Salmonella, Vibrio, Rickettsia, Agrobacterium, Brucella, Rhizobium, Neisseria, Bordetella, Burkholderi, Buchnera, Yersinia, Klebsiella, Proteus, Shigella, Haemophilus, Pasteurella, Actinobacillus, Legionella, Mannheimia, Coxiella, Aeromonas, Francisella, Moraxella, Pseudomonas, Campylobacter,* and *Helicobacter.* Specific examples of Proteobacteria include: *Rickettsia conorii, Rickettsia prowazekii, Rickettsia typhi, Ehrlichia bovis, Agrobacterium tumefaciens, Brucella melitensis, Rhizobium rhizogenes, Neisseria meningitides, Bordetella parapertussis, Bordetella pertussis, Burkholderi mallei, Burkholderi pseudomallei, Neisseria gonorrhoeae, Escherichia coli, Salmonella enterica, Salmonella typhimurium, Yersinia pestis, Klebsiella pneumoniae, Yersinia enterocolitica, Proteus vulgaris, Shigella flexneri, Shigella sonnei, Shigella dysenterica, Haemophilus influenzae, Pasteurella multocida, Actinobacillus actinomycetemcomitans, Actinobacillus pleuropneumoniae, Haemophilus somnus, Legionella pneumophila, Mannheimia haemolytica, Vibrio cholerae, Vibrio parahaemolyticus, Coxiella burnetii, Aeromonas hydrophila, Aeromonas salmonicida, Francisella tularesis, Moraxella catarrhalis, Pseudomonas aeruginosa, Pseudomonas putida, Campylobacter jejuni,* and *Helicobacter pylori.*

Non-limiting examples of Spirochaetes include bacteria of the families Brachyspiraceae, Leptospiraceae, and Spirochaetaceae. Specific examples of Spirochaetes include *Borrelia burgdorferi,* and *Treponema pallidum.*

2. Different Types of Biological Matter

Methods and apparatuses of the invention can be applied to organisms. Stasis of the organism can be induced or stasis within cells, tissues, and/or organs of the organism can be induced. Biological matter in which stasis can be induced that are contemplated for use with methods and apparatuses of the invention are limited only insofar as the comprise cells utilizing oxygen to produce energy.

Stasis can be induced in cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, stasis can be induced in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, stasis can be induced in plants or parts of plants, including fruit, flowers, leaves, stems, seeds, cuttings. Plants can be agricultural, medicinal, or decorative. Induction of stasis in plants may enhance the shelf life or pathogen resistance of the whole or part of the plant.

Methods and apparatuses of the invention can be used to induce stasis in in vivo biological matter. This can serve to protect and/or preserve the biological matter or the organism itself or to prevent damage or injury (or further damage or injury) to them or the organism overall.

3. Assays

Stasis can be measured by a number of ways, including by quantifying the amount of oxygen consumed by a biological sample, the amount of carbon dioxide produced by the sample (indirect measurement of cellular respiration), or characterizing motility.

To determine the rate of consumption of oxygen or the rate of production of carbon dioxide the biological matter is placed into a chamber that is sealed with two openings; for gas import and export. Gas (room air or other gases) is passed into the chamber at a given flow rate and out of the exit port to maintain approximately 1 atmosphere of pressure in the chamber. Before and after exposure to the chamber the gas is passed through a carbon dioxide detector and or an oxygen detector to measure (every second) the amount of each compound in the gas mixture. Comparison of these values over time gives the rate of oxygen consumption or carbon dioxide production.

II. Oxygen Antagonists and Other Active Compounds

The present invention concerns methods, compositions and articles of manufacture involving one or more agents that can act on biological matter so as to produce a number of effects, including, but not limited to, inducing stasis, enhancing or increasing survivability, reversibly inhibiting metabolism, reducing cellular or organismal metabolism and activity, reducing the oxygen requirement, reducing or preventing damage, preventing ischemic damage, preventing aging or senescence, and/or a achieve a variety of therapeutic applications discussed herein. It certain embodiments, the agents are qualified as "active compounds."

In some embodiments, the agent is an oxygen antagonist, which may act directly or indirectly. Oxygen metabolism is a fundamental requirement for life in aerobic metazoans. Aerobic respiration accounts for the vast majority of energy production in most animals and also serves to maintain the redox potential necessary to carry out important cellular reactions. In hypoxia, decreased oxygen availability results in inefficient transfer of electrons to molecular oxygen in the final step of the electron transport chain. This inefficiency results in both a decrease in aerobic energy production and an increase in the production of damaging free radicals, mainly due to the premature release of electrons at complex III and the formation of $O_2^-$ by cytochrome oxidase (Semenza, 1999). Limited energy supplies and free radical damage can interfere with essential cellular processes such as protein synthesis and maintenance of membrane polarities (Hochachka et al., 1996), and will ultimately lead to cell death.

In other embodiments, the agent is a protective metabolic agent. Metabolism is generally understood as referring to chemical processes (in a cell or organism) that are required for life; they involve a variety of reactions to sustain energy production and synthesize (anabolism) and break down (catabolism) complex molecules.

In certain embodiments of the invention, an active compound has a chemical structure as set forth as Formula I or IV described herein, or is a precursor of Formula I or IV.

A variety of chemical structures and compounds are described herein. The following definitions apply to terms used to described these structures and compounds discussed herein:

"Alkyl," where used, either alone or within other terms such as "arylalkyl", "aminoalkyl", "thioalkyl" "cyanoalkyl" and "hydroxyalkyl", refers to linear or branched radicals having one to about twenty carbon atoms. The term "lower alkyl" refers to $C_1$-$C_6$ alkyl radicals. As used herein the term alkyl includes those radicals that are substituted with groups such as hydroxy, halo (such as F, Cl, Br, I), haloalkyl, alkoxy, haloalkoxy, alkylthio, cyano, isocyano, carboxy (—COOH), alkoxycarbonyl, (—COOR), acyl, acyloxy, amino, alykamino, urea (—NHCONHR), thiol, alkylthio, sulfoxy, sulfonyl, arylsulfonyl, alkylsulfonyl, sulfonamido, arylsulfonamido, heteroaryl, heterocyclyl, heterocycloalkyl, amidyl, alkylimino carbonyl, amidino, guanidono, hydrazino, hydrazide, sodium sulfonyl (—$SO_3Na$), sodium sulfonylalkyl (—$RSO_3Na$). Examples of such radicals include, but are not limited to, methyl, ethyl, n-propyl, isopropyl, n-butyl, isobutyl, sec-butyl, tert-butyl, pentyl, iso-amyl, hexyl and the like.

"Hydroxyalkyl" refers to an alkyl radical, as defined herein, substituted with one or more hydroxyl radicals. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Arylalkyl" refers to the radical R'R— wherein an alkyl radical, "R" is substituted with an aryl radical "R'." Examples of arylalkyl radicals include, but are not limited to, benzyl, phenylethyl, 3-phenylpropyl, and the like.

"Aminoalkyl" refers to the radical $H_2NR'$—, wherein an alkyl radical is substituted with am amino radical. Examples of such radicals include aminomethyl, amino ethyl, and the like. "Alkylaminoalkyl" refers to an alkyl radical substituted with an alkylamino radical.

"Alkylsulfonamido" refers to a sulfonamido group (—S(O)$_2$—NRR') appended to an alkyl group, as defined herein.

"Thioalkyl" refers to wherein an alkyl radical is substituted with one or more thiol radicals. "Alkylthioalkyl" refers to wherein an alkyl radical is substituted with one or more alkylthio radicals. Examples include, but are not limited to, methylthiomethyl, ethylthioisopropyl, and the like. Arylthioalkyl" refers to wherein an alkyl radical, as herein defined, is substituted with one or more arylthio radicals.

"Carboxyalkyl" refers to the radicals —$RCO_2H$, wherein an alkyl radical is substituted with a carboxyl radical. Example include, but are not limited to, carboxymethyl, carboxyethyl, carboxypropyl, and the like.

"Alkylene" refers to bridging alkyl radicals.

The term "alkenyl" refers to an unsaturated, acyclic hydrocarbon radical in so much as it contains at least one double bond. Such alkenyl radicals contain from about 2 to about 20 carbon atoms. The term "lower alkenyl" refers to $C_1$-$C_6$ alkenyl radicals. As used herein, the term alkenyl radicals includes those radicals substituted as for alkyl radicals. Examples of suitable alkenyl radicals include propenyl, 2-chloropropenyl, buten-1-yl, isobutenyl, pent-1-en-1-yl, 2-2-methy-1-buten-1-yl, 3-methyl-1-buten-1-yl, hex-2-en-1-yl, 3-hydroxyhex-1-en-1-yl, hept-1-en-1-yl, and oct-1-en-1-yl, and the like.

The term "alkynyl" refers to an unsaturated, acyclic hydrocarbon radical in so much as it contains one or more triple bonds, such radicals containing about 2 to about 20 carbon atoms. The term "lower alkynyl" refers to $C_1$-$C_6$ alkynyl radicals. As used herein, the term alkynyl radicals includes those radicals substituted as for alkyl radicals. Examples of suitable alkynyl radicals include ethynyl, propynyl, hydroxypropynyl, but-1-yn-1-yl, but-1-yn-2-yl, pent-1-yn-1-yl, pent-1-yn-2-yl, 4-methoxypent-1-yn-2-yl, 3-methylbut-1-yn-1-yl, hex-1-yn-1-yl, hex-1-yn-2-yl, hex-1-yn-3-yl, 3,3-dimethyl-1-butyn-1-yl radicals and the like "Alkoxy," refers to the radical R'O—, wherein R' is an alkyl radical as defined herein. Examples include, but are not limited to, methoxy, ethoxy, propoxy, butoxy, isopropoxy, tert-butoxy alkyls, and the like. Alkoxyalkyl" refers to alkyl radicals substituted by one or more alkoxy radicals. Examples include, but are not limited to, methoxymethyl, ethoxyethyl, methoxyethyl, isopropoxyethyl, and the like.

"Alkoxycarbonyl" refers to the radical R—O—C(O)—, wherein R is an alkyl radical as defined herein. Examples of alkoxycarbonyl radicals include, but are not limited to, methoxycarbonyl, ethoxycarbonyl, sec-butoxycarbonyl, isoprpoxycarbonyl, and the like. Alkoxythiocarbonyl refers to R—O—C(S)—.

"Aryl" refers to the monovalent aromatic carbocyclic radical consisting of one individual ring, or one or more fused rings in which at least one ring is aromatic in nature, which can optionally be substituted with one or more, preferably one or two, substituents such as hydroxy, halo (such as F, Cl, Br, I), haloalkyl, alkoxy, haloalkoxy, alkylthio, cyano, carboxy (—COOH), alkoxycarbonyl, (—COOR), acyl, acyloxy, amino, alykamino, urea (—NHCONHR), thiol, alkylthio, sulfoxy, sulfonyl, arylsulfonyl, alkylsulfonyl, sulfonamido, arylsulfonamido, heteroaryl, heterocyclyl, heterocycloalkyl, amidyl, alkylimino carbonyl, amidino, guanidono, hydrazino, hydrazide, sodium sulfonyl (—$SO_3Na$), sodium sulfonylalkyl (—$RSO_3Na$), unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, indanyl, anthraquinolyl, tert-butyl-phenyl, 1,3-benzodioxolyl, and the like.

"Arylsulfonamido" refers to a sulfonamido group, as defined herein, appended to an aryl group, as defined herein.

"Thioaryl" refers to an aryl group substituted with one or more thiol radicals.

"Alkylamino" refers to amino groups that are substituted with one or two alkyl radicals. Examples include monosubstituted N-alkylamino radicals and N,N-dialkylamino radicals. Examples include N-methylamino, N-ethylamino, N,N-dimeythylamino N,N-diethylamino, N-methyl, N-ethyl-amino, and the like.

"Aminocarbonyl" refers to the radical $H_2NCO$—. "Aminocarbonylalkyl" refers to the substitution of an alkyl radical, as herein defined, by one or more aminocarbonyl radicals.

"Amidyl" refers to RCO—NH—, wherein R is a H or alkyl, aryl, or heteroaryl, as defined herein.

"Imino carbonyl" refers to a carbon radical having two of the four covalent bond sites shared with an imino group. Examples of such imino carbonyl radicals include, for example, C=NH, C=$NCH_3$, C=NOH, and C=$NOCH_3$. The term "alkylimino carbonyl" refers to an imino radical substituted with an alkyl group, The term "amidino" refers to a substituted or unsubstituted amino group bonded to one of two available bonds of an iminocarbonyl radical. Examples of such amidino radicals include, for example, $NH_2$—C=NH, $NH_2$—C=$NCH_3$, NH—C=$NOCH_3$ and $NH(CH_3)$—C=NOH. The term "guanidino" refers to an amidino group bonded to an amino group as defined above where said amino group can be bonded to a third group. Examples of such guanidino radicals include, for example, $NH_2$—C(NH)—NH—, $NH_2$—C($NCH_3$)—NH—, $NH_2$—C($NOCH_3$)—NH—, and $CH_3NH$—C(NOH)—NH—. The term "hydrazino" refers to —NH—NRR', where R and R' are independently hydrogen, alkyl and the like. "Hydrazide" refers to —C(=O)—NH—NRR'.

The term "heterocyclyl" refers to saturated and partially saturated heteroatom-containing ring-shaped radicals having from 4 through 15 ring members, herein referred to as "$C_4$-$C_{15}$ heterocyclyl" selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like. Such heterocyclyl groups may be optionally substituted with groups such as substituents such as hydroxy, halo (such as F, Cl, Br, I), haloalkyl, alkoxy, haloalkoxy, alkylthio, cyano, carboxy (—COOH), alkoxycarbonyl, (—COOR), acyl, acyloxy, amino, alykamino, urea (—NHCONHR), thiol, alkylthio, sulfoxy, sulfonyl, arylsulfonyl, alkylsulfonyl, sulfonamido, arylsulfonamido, heteroaryl, heterocyclyl, heterocycloalkyl, amidyl, alkylimino carbonyl, amidino, guanidono, hydrazino, hydrazide, sodium sulfonyl (—$SO_3Na$), sodium sulfonylalkyl (—$RSO_3Na$).

"Heteroaryl" refers to monovalent aromatic cyclic radicals having one or more rings, preferably one to three rings, of four to eight atoms per ring, incorporating one or more heteroatoms, preferably one or two, within the ring (chosen from nitrogen, oxygen, or sulfur), which can optionally be substituted with one or more, preferably one or two substituents selected from substituents such as hydroxy, halo (such as F, Cl, Br, I), haloalkyl, alkoxy, haloalkoxy, alkylthio, cyano, carboxy (—COOH), alkoxycarbonyl, (—COOR), acyl, acyloxy, amino, alykamino, urea (—NHCONHR), thiol, alkylthio, sulfoxy, sulfonyl, arylsulfonyl, alkylsulfonyl, sulfonamido, arylsulfonamido, heteroaryl, heterocyclyl, heterocycloalkyl, amidyl, alkylimino carbonyl, amidino, guanidono, hydrazino, hydrazide, sodium sulfonyl (—$SO_3Na$), sodium sulfonylalkyl (—$RSO_3Na$), unless otherwise indicated. Examples of heteroaryl radicals include, but are not limited to, imidazolyl, oxazolyl, thiazolyl, pyrazinyl, thienyl, furanyl, pyridinyl, quinolinyl, isoquinolinyl, benzofuryl, benzothiophenyl, benzothiopyranyl, benzimidazolyl, benzoxazolyl, benzothiazolyl, benzopyranyl, indazolyl, indolyl, isoindolyl, quinolinyl, isoquinolinyl, naphthyridinyl, benezenesulfonyl-thiophenyl, and the like.

"Heteroaryloxy" refers to heteroaryl radicals attached to an oxy radical. Examples of such radicals include, but are not limited to, 2-thiophenyloxy, 2-pyrimidyloxy, 2-pyridyloxy, 3-pyridyloxy, 4-pyridyloxy, and the like "Heteroaryloxyalkyl" refers to alkyl radicals substituted with one or more heteroaryloxy radicals. Examples of such radicals include 2-pyridyloxymethyl, 3-pyridyloxyethyl, 4-pyridyloxymethyl, and the like.

"Cycloalkyl" refers to monovalent saturated carbocyclic radicals consisting of one or more rings, typically one or two rings, of three to eight carbons per ring, which can typically be substituted with one or more, substitutents hydroxy, halo (such as F, Cl, Br, I), haloalkyl, alkoxy, haloalkoxy, alkylthio, cyano, carboxy (—COOH), alkoxycarbonyl, (—COOR), acyl, acyloxy, amino, alykamino, urea (—NHCONHR), thiol, alkylthio, sulfoxy, sulfonyl, arylsulfonyl, alkylsulfonyl, sulfonamido, arylsulfonamido, heteroaryl, heterocyclyl, heterocycloalkyl, amidyl, alkylimino carbonyl, amidino, guanidono, hydrazino, hydrazide, sodium sulfonyl (—$SO_3Na$), sodium sulfonylalkyl (—$RSO_3Na$), unless otherwise indicated. Examples of cycloalkyl radicals include, but are not limited to, cyclopropyl, cyclobutyl, 3-ethylcyclobutyl, cyclopentyl, cycloheptyl, and the like. "Cycloalkenyl" refers to radicals having three to ten carbon atoms and one or more carbon-carbon double bonds. Typical cycloalkenyl radicals have three to seven carbon atoms. Examples include cyclobutenyl, cyclopentenyl, cyclohexenyl, cycloheptenyl, and the like "Cycloalkenylalkyl" refers to radicals wherein an alkyl radical, as defined herein, is substituted by one or more cycloalkenyl radicals.

"Cylcoalkoxy" refers to cycloalkyl radicals attached to an oxy radical. Examples include, but are not limited to, cyclohexoxy, cyclopentoxy and the like.

"Cylcoalkoxyalkyl" refers to alkyl radicals substituted one or more cycloalkoxy radicals. Examples include cyclohexoxyethyl, cyclopentoxymethyl, and the like. Sulfinyl" refers to —S(O)—.

"Sulfonyl" refers to —$S(O)_2$—, wherein "alkylsulfonyl" refers to a sulfonyl radical substituted with an alkyl radical, $RSO_2$—, arylsulfonyl refers to aryl radicals attached to a sulfonyl radical. "Sulfonamido" refers to —$S(O)_2$—NRR'.

"Sulfonic acid" refers to —$S(O)_2OH$. "Sulfonic ester" refers to —$S(O)_2OR$, wherein R is a group such as an alkyl as in sulfonic alkyl ester.

"Thio" refers to —S—. "Alkylthio" refers to RS— wherein a thiol radical is substituted with an alkyl radical R. Examples include methylthio, ethylthio, butylthio, and the like. "Arylthio" refers to R'S—, wherein a thio radical is substituted with an aryl radical, as herein defined. "Examples include, but are not limited to, phenylthio, and the like. Examples include, but are not limited to, phenylthiomethyl and the like. "Alkylthiosulfonic acid" refers to the radical $HO_3SR'S$—, wherein an alkylthioradical is substituted with a sulfonic acid radical.

"Thiosulfenyl" refers to —S—SH.

"Acyl", alone or in combination, refers to a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like.

The term "acylthiol" and "acyldisulfide" refers to the radicals RCOS— and RCOSS— respectively.

The term "thiocarbonyl" refers to the compounds and moieties which contain a carbon connected with a double bond to a sulfur atom —C(═S)—. "Alkylthiocarbonyl" refers to wherein a thiocarbonyl group is substituted with an alkyl radical, R. as defined herein, to form the monovalent radical RC(═S)—. "Aminothiocarbonyl" refers to a thiocarbonyl group substituted with an amino group, $NH_2C$(═S)—.

"Carbonyloxy" refers to —OCOR.
"Alkoxycarbonyl" refers to —COOR.
"Carboxyl" refers to —COOH.

For those compounds with stereoisomers, all stereoisomers thereof, including cis/trans geometric isomers, diastereomers and the individual enantiomers are contemplated A. Carbon Monoxide Carbon monoxide (CO) is a colorless, odorless, and tasteless gas that can be toxic to animals, including humans. According to the Center for Disease Control, more than 450 people unintentionally die from carbon monoxide each year.

It can be toxic to organisms whose blood carries oxygen to sustain its survival. It may be poisonous by entering the lungs through normal breathing and displacing oxygen from the bloodstream. Interruption of the normal supply of oxygen jeopardizes the functions of the heart, brain and other vital functions of the body. However, the use of carbon monoxide for medical applications is being explored (Ryter et al., 2004).

At amounts of 50 parts per million (ppm), carbon monoxide presents no symptoms to humans exposed to it. However, at 200 ppm, within two-three hours the carbon monoxide can cause a slight headache; at 400 ppm, within one to two hours it can cause a frontal headache that may become widespread within three hours; and, at 800 ppm it can cause dizziness, nausea, and/or convulsions within 45 minutes, and render the subject insensible within two hours. At levels of around 1000 ppm, an organism can expire after exposure for more than around 1-2 minutes.

Because of the well-known and well-documented toxic effects of carbon monoxide to an organism, it is thus surprising and unexpected that carbon monoxide can be used to induce stasis of and/or help preserve live biological samples. It is thus contemplated that carbon monoxide can be used for inducing stasis in isolated biological matter, such as blood-free biological matter (because of the effects that carbon monoxide has with respect to hemoglobin, which is a separate pathway than the one involved in inducing stasis).

In addition to exposure to carbon monoxide either to induce stasis or to limit or prevent any damage caused by a stasis-inducing agent, the invention contemplates that carbon monoxide may be used in combination with agents or methods that assist in the preservation and/or transplantation/grafting process of biological materials.

B. Chalcogenide Compounds

Compounds containing a chalcogen element; those in Group 6 of the periodic table, but excluding oxides, are commonly termed "chalcogenides" or "chalcogenide compounds (used interchangeably herein). These elements are sulfur (S), selenium (Se), tellurium (Te) and polonium (Po). Common chalcogenides contain one or more of S, Se and Te, in addition to other elements. Chalcogenides include elemental forms such as micronized and/or nanomilled particles of S and Se. Chalcogenide compounds can be employed as reducing agents.

The present inventor, though not bound by the following theory, believes that the ability of chalcogenides to induce stasis in cells, and to permit modulation of core body temperature in animals, stems from the binding of these molecules to cytochrome oxidase. In so doing, chalcogenides inhibit or reduce the activity of oxidative phosphorylation. The ability of chalcogenides to block autonomous thermoregulation, i.e., to permit core body temperatures of "warm-blooded" animals to be manipulated through control of environmental temperatures, is believed to stem from the same mechanism as set forth above—binding to cytochrome oxidase, and blocking or reducing the activity of oxidative phosphorylation. Chalcogenides may be provided in liquid as well as gaseous forms.

Chalcogenides can be toxic, and at some levels lethal, to mammals. In accordance with the present invention, it is anticipated that the levels of chalcogenide should not exceed lethal levels in the appropriate environment. Lethal levels of chalcogenides may be found, for example in Material Safety Data Sheets for each chalcogenide or from information sheets available from the Occupational Safety and Health Administration (OSHA) of the US Government.

While carbon monoxide and chalcogenide compounds can both induce stasis by acting as an oxygen antagonist, they have different toxic effects that are separate from their abilities to induce stasis. Moreover, the concentrations needed to mediate a stasis effect are different because of the different affinities of cytochrome oxidase. While the affinity of cytochrome oxidase for oxygen is about 1:1 as compared to carbon monoxide, the affinity for $H_2S$ appears on the order of about 300:1 as compared to oxygen. This impacts what toxic effects are observed with a stasis-inducing concentration. Thus, it is contemplated that chalcogenide compounds are particularly suited for inducing stasis of biological matter in whole organisms and of whole organisms.

It also may prove useful to provide additional stimuli to a biological matter before withdrawing the chalcogenide. In particular, it is envisioned that one may subject an animal to increased ambient temperature prior to removing the source of chalcogenide.

1. $H_2S$ and Other Sulfur Containing Compounds

Hydrogen sulfide ($H_2S$) is a potentially toxic gas that is often associated with petrochemical and natural gas, sewage, paper pulp, leather tanning, and food processing. The primary effect, at the cellular level, appears to be inhibition of cytochrome oxidase and other oxidative enzymes, resulting in cellular hypoxia. Exposure to extreme levels (500 ppm) results in sudden collapse and unconsciousness, a so-called "knockdown" effect, followed by recovery. Post-exposure effects may persist for years, and include loss of coordination, memory loss, motor dysfunction, personality changes, hallucination and insomnia.

Most contact with $H_2S$, however, occurs well below such acute toxicity levels. Nonetheless, there is general concern over longterm contact at sub-acute levels. Some reports exist indicating persistent impairments in balance and memory, as well as altered sensory motor functions may occur in humans following chronic low-level $H_2S$ exposure. Kilburn and Warshaw (1995); Kilburn (1999). Others have reported that perinatal exposure of rats to low (20 or 50 ppm) $H_2S$ for 7 hours per day from gestation through post-natal day 21 resulted in longer dendritic branches with reduced aborization of cerebellar Purkinje cells. Other neurologic defects associated with relatively low levels of $H_2S$ include altered brain neurotransmitter concentrations and altered neurologic responses, such as increased hippocampal theta EEG activity.

Behavioral toxicity was studied in rats exposed to moderate levels of $H_2S$. The results showed that $H_2S$ inhibits discriminated avoidance responses immediately after the end of the exposure (Higuchi and Fukamachi, 1997), and also interferes with the ability of rats to learn a baited radial arm maze task (Partlo et al., 2001). In another perinatal study using 80 ppm $H_2S$, no neuropathological effects or altered motor activity, passive avoidance, or acoustic startle response in exposed rat pups was seen. Dorman et al. (2000). Finally, Struve et al. (2001) exposed rats to $H_2S$ by gas at various levels for 3 hours per day on five consecutive days. Significant reductions in motor activity, water maze performance and body temperature following exposure to 80 ppm or greater $H_2S$ were observed. Taken together, these reports indicate that $H_2S$ can have a variety of effects on the biochemistry of mammalian tissues, but there is no clear pattern of response in terms of behavior.

Once dissolved in plasma, $H_2S$ will be involved in a series of chemical reactions. The chemical reactions are: (1) the dissociation of the molecular $H_2S$ to form the bisulfide ion, (2) the dissociation of the bisulfide ion to the sulfide ion, and (3) the self ionization of water. The reactions are given below:

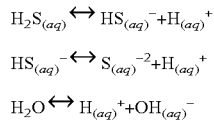

Using the equilibrium constants $K_1=1.039\ E^{-07}$, $K_2=6.43\ E^{-16}$ and $K_w=1.019\ E^{-14}$, at pH 7.4 the calculated amount of the different species relative to the total S concentration are approximately 23% $H_2S$ and 77% $HS^-$, while the amount of $S^{2-}$ tends to zero.

The inventor uses an extractive alkylation technique coupled with gas chromatography and mass specific detection to quantify hydrogen sulfide (adapted from Hyspler et al., 2002). This method involves firstly adding a 50 μL sample of blood, serum or tissue extract that has been diluted in nitrogen purged deoxygenated water to a concentration of 1 mg/mL, together with 150 μL of a reaction buffer consisting of 5 mM benzalkonium chloride (BZK) in a saturated borate buffer. Added to this is first, 100 μL of a 15 μM solution of 4-chlorobenzyl methyl sulfide (4CBMS) in ethyl acetate and then 100 μL of a 20 mM solution of pentafluorobenzylbromide (PFBBr) in toluene. This solution is then sealed and incubated at 55° C. with rotation or shaking for 2 hr. After this incubation period, 200 μL of a saturated solution of $KH_2PO_4$ is then added, and the organic phase is removed and analyzed by gas chromatography and mass specific detection according to the methods described in Hyspler et al., 2002. These measurements are then compared to a standard curve generated using the same method described above, beginning with known standard concentrations ranging from 1 μM to 1 mM of $Na_2S$ prepared in nitrogen purged deoxygenated $H_2O$, in order to determine the concentration of endogenous hydrogen sulfide levels. In order to analyze bound and/or oxidized sulfide levels, the same method is applied, except that a denaturing/reducing reaction buffer is used, which consists of 5 mM BZK with 1% tetraethylammonium hydroxide (TEAH) and 1 mM tris(2-carboxyethyl)-phosphine hydrochloride (TCEP) in saturated borate buffer, instead of the reaction buffer described above.

Typical levels of hydrogen sulfide contemplated for use in accordance with the present invention include values of about 1 to about 150 ppm, about 10 to about 140 ppm, about 20 to about 130 ppm, and about 40 to about 120 ppm, or the equivalent oral, intravenous or transdermal dosage thereof. Other relevant ranges include about 10 to about 80 ppm, about 20 to about 80 ppm, about 10 to about 70 ppm, about 20 to about 70 ppm, about 20 to about 60 ppm, and about 30 to about 60 ppm, or the equivalent oral, intravenous or transdermal thereof. It also is contemplated that, for a given animal in a given time period, the chalcogenide atmosphere should be reduced to avoid a potentially lethal build up of chalcogenide in the subject. For example, an initial environmental concentration of 80 ppm may be reduced after 30 min to 60 ppm, followed by further reductions at 1 hr (40 ppm) and 2 hrs (20 ppm).

a. $H_2S$ Precursors

The present invention also concerns the use of compounds and agents that can yield $H_2S$ under certain conditions, such as upon exposure, or soon thereafter, to biological matter. It is contemplated that such precursors yield $H_2S$ upon one or more enzymatic or chemical reactions.

3. Other Chalcogenides

In certain embodiments, the reducing agent structure compound is dimethylsulfoxide (DMSO), dimethylsulfide (DMS), methylmercaptan ($CH_3SH$), mercaptoethanol, thiocyanate, hydrogen cyanide, methanethiol (MeSH), or $CS_2$. In particular embodiments, the oxygen antagonist is $CS_2$, MeSH, or DMS. Compounds on the order of the size of these molecules are particularly contemplated (that is, within about 50% of their molecular weights).

Additional compounds that are envisioned as useful for inducing stasis include, but are not limited to, the following structures, many of which are readily available and known to those of skill in the art (identified by CAS number): 104376-79-6 (Ceftriaxone Sodium Salt); 105879-42-3; 1094-08-2 (Ethopropatine HCl); 1098-60-8 (Triflupromazine HCl); 111974-72-2; 113-59-7; 113-98-4 (Penicillin G $K^+$); 115-55-9; 1179-69-7; 118292-40-3; 119478-56-7; 120138-50-3; 121123-17-9; 121249-14-7; 1229-35-2; 1240-15-9; 1257-78-9 (Prochlorperazine Edisylate Salt); 128345-62-0; 130-61-0 (Thioridazine HCl) 132-98-9 (Penicillin V $K^+$); 13412-64-1 (Dicloxacillin $Na^+$ Hydrate); 134678-17-4; 144604-00-2; 146-54-3; 146-54-5 (Fluphenazine 2HCl); 151767-02-1; 159989-65-8; 16960-16-0 (Adrenocorticotropic Hormone Fragment 1-24); 1982-37-2; 21462-39-5 (Clindamycin HCl); 22189-31-7; 22202-75-1; 23288-49-5 (Probucol); 23325-78-2; 24356-60-3 (Cephapirin); 24729-96-2 (Clindamycin); 25507-04-4; 26605-69-6; 27164-46-1 (Cefazolin $Na^+$); 2746-81-8; 29560-58-8; 2975-34-0; 32672-69-8 (Mesoridazine Benzene Sulfonate); 32887-01-7; 33286-22-5 (($^+$)-cis-Diltiazem HCl); 33564-30-6 (Cefoxitin $Na^+$); 346-18-9; 3485-14-1; 3511-16-8; 37091-65-9 (Azlocillin $Na^+$); 37661-08-8; 3819-00-9; 38821-53-3 (Cephradine); 41372-02-5; 42540-40-9 (Cefamandole Nafate); 4330-99-8 (Trimeprazine hemi-($^+$)-tartrate Salt); 440-17-5 Trifluoperazine 2HCl; 4697-14-7 (Ticarcillin $2Na^+$); 4800-94-6 (Carbenicillin $2Na^+$); 50-52-2; 50-53-3; 5002-47-1; 51481-61-9 (Cimetidine); 52239-63-1 (6-propyl-2-thiouracil); 53-60-1 (Promazine HCl); 5321-32-4; 54965-21-8 (Albendazole); 5591-45-7 (Thiothixene); 56238-63-2 (Cefuroxime $Na^+$); 56796-39-5 (Cefinetazole $Na^+$); 5714-00-1; 58-33-3 (Promethazine HCl); 58-38-8; 58-39-9 (Perphenazine); 58-71-9 Cephalothin $Na^+$); 59703-84-3 (Piperacillin $Na^+$); 60-99-1 (Methotrimeprazine Maleate Salt); 60925-61-3; 61270-78-8; 6130-64-9 (Penicillin G Procaine Salt Hydrate); 61318-91-0 Sulconazole Nitrate Salt); 61336-70-7 Amoxicillin Trihydrate); 62893-20-3 Cefoperazone $Na^+$); 64485-93-4 (Cefotaxime $Na^+$); 64544-07-6; 64872-77-1; 64953-12-4 Moxalactam $Na^+$); 66104-23-2 (Pergolide Mesylate Salt); 66309-69-1; 66357-59-3 (Ranitidine HCl); 66592-87-8 (Cefodroxil); 68401-82-1; 69-09-0 (Chlorpromazine HCl); 69-52-3 (Ampicillin $Na^+$); 69-53-4 (Ampicillin); 69-57-8 Penicillin G $Na^+$); 70059-30-2; 70356-03-5; 7081-40-5; 7081-44-9 (Cloxacillin $Na^+$ $H_2O$); 7177-50-6 Nafcillin Na+ $H_2O$); 7179-49-9; 7240-38-2 (Oxacillin Na $H_2O$); 7246-14-2; 74356-00-6; 74431-23-5; 74849-93-7; 75738-58-8; 76824-35-6 (Famotidine); 76963-41-2; 79350-37-1; 81129-83-1; 84-02-6 (Prochlorperazine Dimaleate Salt); 87-08-1 (Phenoxymethylpenicillinic Acid); 87239-81-4; 91-33-8 (Benzthiazide); 91832-40-5; 94841-17-5; 99294-94-7; 154-42-7 (6-Thioguanine); 36735-22-5; 536-33-4 (Ethionamide); 52-67-5 (D-Penicillamine); 304-55-2 (Meso-2,3-Dimercaptosuccinic Acid); 59-52-9 2,3-Dimercapto $^+$ propanol 6112-76-1 (6-mercaptopurine); 616-91-1 (N-acetyl-L-cysteine); 62571-86-2 (Captopril); 52-01-7 (spironolactone); and, 80474-14-2 (fluticasone propionate). Further compounds that are contemplated as possibly useful for stasis include those with the chemical structure of Formulas I or IV.

C. Other Antagonists or Active Compounds and Related Environmental Conditions

1. Hypoxia and Anoxia

Hypoxia is a common natural stress and several well conserved responses exist that facilitate cellular adaptation to hypoxic environments. To compensate for the decrease in the capacity for aerobic energy production in hypoxia, the cell must either increase anaerobic energy production or decrease energy demand (Hochachka et al., 1996). Examples of both of these responses are common in metazoans and the particular response used depends, in general, on the amount of oxygen available to the cell.

In mild hypoxia, oxidative phosphorylation is still partially active, so some aerobic energy production is possible. The cellular response to this situation, which is mediated in part by the hypoxia-inducible transcription factor, HIF-1, is to supplement the reduced aerobic energy production by upregulating genes involved in anaerobic energy production, such as glycolytic enzymes and glucose transporters (Semenza, 2001; Guillemin et al., 1997). This response also promotes the upregulation of antioxidants such as catylase and superoxide dismutase, which guard against free radical-induced damage. As a result, the cell is able to maintain near normoxic levels of activity in mild hypoxia.

In an extreme form of hypoxia, referred to as "anoxia"—defined here as <0.001 kPa $O_2$—oxidative phosphorylation ceases and thus the capacity to generate energy is drastically reduced. In order to survive in this environment, the cell must decrease energy demand by reducing cellular activity (Hochachka et al., 2001). For example, in turtle hepatocytes deprived of oxygen, a directed effort by the cell to limit activities such as protein synthesis, ion channel activity, and anabolic pathways results in a 94% reduction in demand for ATP (Hochachka et al., 1996). In zebrafish (*Danio rerio*) embryos, exposure to anoxia leads to a complete arrest of the heartbeat, movement, cell cycle progression, and developmental progression (Padilla et al., 2001). Similarly, *C. elegans* respond to anoxia by entering into suspended animation, in which all observable movement, including cell division and developmental progression, ceases (Padilla et al., 2002; Van Voorhies et al., 2000). *C. elegans* can remain suspended for 24 hours or more and, upon return to normoxia, will recover with high viability. This response allows *C. elegans* to survive the hypoxic stress by reducing the rate of energetically expensive processes and preventing the occurrence of damaging, irrevocable events such as aneuploidy (Padilla et al., 2002; Nystul et al., 2003).

One recently discovered response is the hypoxia-induced generation of carbon monoxide by heme oxygenase-1 (Dulak et al., 2003). Endogenously produced carbon monoxide can activate signaling cascades that mitigate hypoxic damage through anti-apoptotic (Brouard et al., 2003) and anti-inflammatory (Otterbein et al., 2000) activity, and similar cytoprotective effects can be achieved in transplant models by perfusion with exogenous carbon monoxide (Otterbein et al, 2003; Amersi et al., 2002). At higher concentrations, carbon monoxide competes with oxygen for binding to iron-containing proteins, such as mitochondrial cytochromes and hemoglobin (Gorman et al., 2003), though the cytoprotective effect that this activity may have in hypoxia has not been investigated.

Despite the existence of these sophisticated defense mechanisms against hypoxic damage, hypoxia is still often a damaging stress. For example, mammals have both heme oxygenase-1 and HIF-1, and some evidence suggests that suspended animation is possible in mammals as well (Bellamy et al., 1996; Alam et al., 2002). Yet, hypoxic damage due to trauma such as heart attack, stroke or blood loss is a major cause of death. The understanding of the limitations of the two fundamental strategies for surviving hypoxic stress, remaining animated or suspending animation, is hampered by the fact that it has been based on studies in a variety of systems under a variety of conditions.

"Hypoxia" occurs when the normal physiologic levels of oxygen are not supplied to a cell or tissue. "Normoxia" refers to normal physiologic levels of oxygen for the particular cell type, cell state or tissue in question. "Anoxia" is the absence of oxygen. "Hypoxic conditions" are those leading to cellular hypoxia. These conditions depend on cell type, and on the specific architecture or position of a cell within a tissue or organ, as well as the metabolic status of the cell. For purposes of the present invention, hypoxic conditions include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%; alternatively, these numbers could represent the percent of atmosphere at 1 atmosphere of pressure (101.3 kPa). An oxygen concentration of zero percent defines anoxic conditions. Thus, hypoxic conditions include anoxic conditions, although in some embodiments, hypoxic conditions of not less than 0.5% are implemented. As used herein, "normoxic conditions" constitute oxygen concentrations of around 20.8% or higher.

Standard methods of achieving hypoxia or anoxia are well established and include using environmental chambers that rely on chemical catalysts to remove oxygen from the chamber. Such chambers are available commercially from, for example, BD Diagnostic Systems (Sparks, Md.) as GASPAK Disposable Hydrogen+Carbon Dioxide Envelopes or BIO-BAG Environmental Chambers. Alternatively, oxygen may be depleted by exchanging the air in a chamber with a non-oxygen gas, such as nitrogen. Oxygen concentration may be determined, for example using a FYRITE Oxygen Analyzer (Bacharach, Pittsburgh Pa.).

It is contemplated that methods of the invention can use a combination of exposure to oxygen antagonist or other active compound and alteration of oxygen concentrations compared to room air. Moreover, the oxygen concentration of the environment containing biological matter can be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein. Moreover, it is contemplated that a change in concentration can be any of the above percentages or ranges, in terms of a decrease or increase compared to room air or to a controlled environment.

D. Mitochondrial Targeting Agents

Selectively targeting mitochondria is considered an embodiment of the invention in some aspects so as to enhance activity. Such selective mitochondrial targeting has been accomplished by conjugating agents to a lipophilic triphenylphosphonium cation, which readily cross lipid bilayers and accumulate approximately a 1000 fold within the mitochondrial matrix drive by the large potential (150 to −180 mv) across the mitochondrial inner membrane. Analogs of both vitamin E and ubiquinone have been prepared and used to successfully target mitochondria. (Smith et al., 1999; Kelso et al., 2001; Dhanasekaran et al., 2004). A thiol, thibutyltriphosphonium bromide (shown below), has been prepared and used to target mitochondria wherein it accumulated several hundred-fold (Burns et al., 1995; Burns & Murphey), 1997).

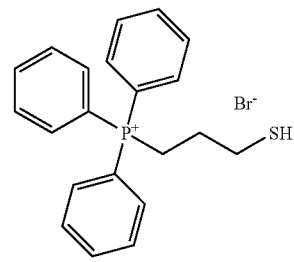 [SMILES: SCCC[P+](c1ccccc1)(c1ccccc1)c1ccccc1 ; [Br-]]

Such conjugates would appear to be suitable candidates for active compounds. In addition to free thiol agents, thiosulfenyl substituted compounds, (H—S—S—R) may be useful. It is contemplated that in some embodiments the agents have the structure:

where Z is P or N;

$R^1$, $R^2$ and $R^3$ are aryl, heteroaryl, alkylaryl, cycloalkyl, or alkyl (suitably phenyl, benzyl, tolyl, pyridyl, cyclohexyl, $C_3$-$C_{10}$ alkyl, optionally halogenated);

$R^4$ is —$R^5SR^6$, wherein $R^5$ is $C_1$-$C_{10}$ alkyl, $R^6$ is H or SH, $SO_3H$, or $PO_3H$.

III. Testing for Stasis

Various compounds useful for inducing stasis may be initially evaluated using a variety of different tests. Stasis can be measured by a number of ways, including by quantifying the amount of oxygen consumed by a biological sample, the amount of carbon dioxide produced by the sample (indirect measurement of cellular respiration), or characterizing motility.

To determine the rate of consumption of oxygen or the rate of production of carbon dioxide the biological matter is placed into a chamber that is sealed with two openings; for gas import and export. Gas (room air or other gases) is passed into the chamber at a given flow rate and out of the exit port to maintain approximately 1 atmosphere of pressure in the chamber. Before and after exposure to the chamber the gas is passed through a carbon dioxide detector and or an oxygen detector to measure (every second) the amount of each compound in the gas mixture. Comparison of these values over time gives the rate of oxygen consumption or carbon dioxide production.

Other screens to identify candidate active stasis compounds have been established. These screens and variations of thereof may be employed as part of the invention or to implement aspects of the invention.

A. Assays with Zebrafish

A screening assay for stasis inducers was established using 48 hour old zebrafish (*D. rerio*) embryos. These embryos are transparent, allowing one to view, using a dissecting microscope with a 4-20 times power lense, the heart beat and resultant blood flow into the main vessel along the back and into the tail. Heart rate in these animals is an indicator of the metabolic activity of the organism, such that a reduction in the heart rate signifies a reduction in metabolism. Embryos were dissected from their egg casings and distributed five per well in flat bottomed polystyrene tissue culture plates and incubated in 1 mL of standard fish water. The fishwater is composed of 1 teaspoon Instant Ocean (artificial sea water mixture, Aquarium Systems, Inc.) per 5 gallons. Calcium chloride is adjusted to 150 ppm and sodium bicarbonate to ~100 ppm. Conductivity of the water is at 900 microsiemens and the pH is about 6.5-7.4. A solution of hydrogen sulfide was prepared by bubbling a mixture of hydrogen sulfide (100 ppm) balanced with room air into a flask containing 150 mL of fishwater at a rate of 100 cubic centimeters per minute for 60-90 minutes. It was estimated that this was sufficient to achieve a saturated or nearly saturated or mostly saturated solution of hydrogen sulfide. Based on the known solubility of hydrogen sulfide in Ringer's solution at pH 7 at 1 atmosphere and room temperature, it was estimated that the fish water contained approximately 0.1 molar hydrogen sulfide. Fish were exposed to the hydrogen sulfide solution and their heart rates were monitored over the ensuing 24 hours by counting the number of beats per minute. Control fish (exposed to fishwater alone) had heart beats of approximately 160-200 beats per minute that did not change significantly over the 24 hour observation period. By 2-3 hours following exposure to the hydrogen sulfide-containing fishwater, heart beats were reduced by about half to 60-80 beats per minute. By four hours, heart beats were reduced further, including some examples where the heart beat was zero or only a few beats per minute. After five hours of exposure, the hydrogen sulfide solution was replaced with normal fishwater and the embryos were allowed to recover overnight at 28 degrees Celsius. By 24 hours after initial exposure to hydrogen sulfide, treated and rinsed animals displayed a normal heart rate of 160-200 beats per minute. Because hydrogen sulfide caused the quiescence of the heart beat, in some cases to a standstill, followed by a return to normalcy, hydrogen sulfide was deemed to have been identified as a stasis inducer or other active compound by the criteria of this screening assay.

B. Assays with Nematodes

A screening assay was established using nematodes (*C. elegans*). Nematodes do not survive well at 4 degrees Celsius, such that at 24 hours at that temperature, they are all dead. Worms were exposed for X minutes at room temperature to an atmosphere containing Y % carbon monoxide, prior to exposing them to 4 degrees C. for 16 hrs. Compared to control worms pre-exposed to room air which were all dead, carbon monoxide treated worms survived with high viability after exposure to cold. Since carbon monoxide is a known stasis inducer in nematodes and neonatal human foreskin keratinocytes, the nematode assay is capable of identifying stasis inducing compounds as such by their ability to increase the survivability of worms exposed to lethal hypothermia when the worms are pre-equilibrated in the stasis inducer or other active compound.

IV. Therapeutic or Preventative Applications

A. Trauma

In certain embodiments, the present invention may find use in the treatment of patients who are undergoing, or who are susceptible to trauma. Trauma may be caused by external insults, such as burns, wounds, amputations, gunshot wounds, or surgical trauma, internal insults, such as stroke or heart attack that result in the acute reduction in circulation, or reductions in circulation due to non-invasive stress, such as exposure to cold or radiation. On a cellular level, trauma often results in exposure of cells, tissues and/or organs to hypoxia, thereby resulting in induction of programmed cell death, or "apoptosis." Systemically, trauma leads to the induction of a series of biochemical processes, such as clotting, inflammation, hypotension, and may give rise to shock, which if it persists may lead to organ dysfunction, irreversible cell damage and death. Biological processes are designed to defend the body against traumatic insult; however they may lead to a sequence of events that proves harmful and, in some instances, fatal.

Therefore, the present invention contemplates the placement of tissues, organs, limbs and even whole organisms into stasis as a way of protecting them from the detrimental effects of trauma. In a specific scenario, where medical attention is not readily available, induction of stasis in vivo or ex vivo, alternatively in conjunction with reduction in the temperature of the tissue, organ or organism, can "buy time" for the subject, either by bringing medical attention to the subject, or by transporting the subject to the medical attention. The present invention also contemplates methods for inducing tissue regeneration and wound healing by prevention/delay of biological processes that may result in delayed wound healing and tissue regeneration. In this context, in scenarios in which there is a substantial wound to the limb or organism, the induction of stasis induction of stasis in vivo or ex vivo, alternatively in conjunction with reduction in the temperature of the tissue, organ or organism, can aid in the wound healing and tissue regeneration process by managing the biological processes that inhibit healing and regeneration.

In addition to wound healing and hemorrhagic shock discussed below, methods of the invention can be implemented to prevent or treat trauma such as cardiac arrest or stroke. The invention has particular importance with respect to the risk of trauma from emergency surgical procedures, such as thoracotomy, laparotomy, and splenic transection.

1. Wound Healing

In many instances, wounds and tissue damage are intractable or take excessive periods of time to heal. Examples are chronic open wounds (diabetic foot ulcers and stage 3 & 4 pressure ulcers), acute and traumatic wounds, flaps and grafts, and subacute wounds (i.e., dehisced incisions). This may also apply to other tissue damage, for example burns and lung damage from smoke/hot air inhalation.

Previous experiments show hibernation to be protective against injury (e.g., pin's in brains), therefore it may have healing effects. Consequently, this technology may be useful in the control of wound healing processes, by bringing the tissue into a more metabolically controlled environment. More particularly, the length of time that cells or tissue are kept in stasis can vary depending on the injury. In some embodiments of the invention, biological matter is exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months or more.

2. Hematologic Shock (Hemorrhagic Shock)

Shock is a life-threatening condition that progresses rapidly when interventions are delayed. Shock is a state in which adequate perfusion to sustain the physiologic needs of organ tissues is not present. This is a condition of profound haemodynamic and metabolic disturbance characterized by failure of the circulatory system to maintain adequate perfusion of vital organs. It may result from inadequate blood volume (hypovolaemic shock), inadequate cardiac function (cardiogenic shock) or inadequate vasomotor tone, also referred to as distributive shock (neurogenic shock, septic shock, anaphylactic shock). This often results in rapid mortality of the patient. Many conditions, including sepsis, blood loss, impaired autoregulation, and loss of autonomic tone, may produce shock or shocklike states. The present invention is anticipated to prevent detrimental effects of all the above states of shock, and sustain the life of the biological matter undergoing such shock.

In hemorrhagic shock, blood loss exceeds the body's ability to compensate and provide adequate tissue perfusion and oxygenation. This is frequently due to trauma, but may also be caused by spontaneous hemorrhage (e.g., gastrointestinal bleeding, childbirth), surgery, and other causes. Most frequently, clinical hemorrhagic shock is caused by an acute bleeding episode with a discrete precipitating event. Less commonly, hemorrhagic shock may be seen in chronic conditions with subacute blood loss.

Physiologic compensation mechanisms for hemorrhage include initial peripheral and mesenteric vasoconstriction to shunt blood to the central circulation. This is then augmented by a progressive tachycardia. Invasive monitoring may reveal an increased cardiac index, increased oxygen delivery (i.e., $DO_2$), and increased oxygen consumption (i.e., $VO_2$) by tissues. Lactate levels, the acid-base status, and other markers also may provide useful indicators of physiologic status. Age, medications, and comorbid factors all may affect a patient's response to hemorrhagic shock.

Failure of compensatory mechanisms in hemorrhagic shock can lead to death. Without intervention, a classic trimodal distribution of deaths is seen in severe hemorrhagic shock. An initial peak of mortality occurs within minutes of hemorrhage due to immediate exsanguination. Another peak occurs after 1 to several hours due to progressive decompensation. A third peak occurs days to weeks later due to sepsis and organ failure.

In the United States, accidental injury is the leading cause of morbidity and mortality in persons between the ages of 1 and 44 years. In 2001, 157,078 resident deaths occurred as the result of injuries. Of these, 64.6 percent were classified as unintentional, 19.5 percent were suicides, 12.9 percent were homicides, 2.7 percent were of undetermined intent, and 0.3 percent involved legal intervention or operations of war. The leading causes of injury death were motor vehicle traffic, firearm, and falls. A large proportion of these fatalities result from massive blood loss due to the trauma, leading to hemorrhagic shock.

In the majority of trauma injury cases, patients who come to a hospital's emergency department are treated by emergency physicians and discharged without requiring surgery or care by a trauma service. However, patients with serious injuries require stabilization within the "Golden Hour" after the injury occurred, to improve the chances of survival and to minimize disability.

As most shock cases are due to injury caused by an accident, pre-hospital care is critical to the survival of the patient. This involves rapid assessment, stabilization, and expeditious transport to an appropriate center for evaluation and definitive care. In all patients with shock syndrome, the maintenance of a patent airway, adequate breathing and adequate circulation are the primary focus of emergency treatment. Assessment is essential, as changes in client condition indicate progression of the shock syndrome. Early intervention is vital to minimize damage to tissues and organs and minimize permanent disability and early identification of the primary clinical cause is critical. Treatments are directed toward correcting the cause of the shock syndrome and slowing progression. Intravenous access and fluid resuscitation (typically IV saline) are standard, however, there is some debate over this. Rapid reversal of hypovolemia may increase hemorrhage, dislodge partially formed clots, and dilute clotting factors.

Once at the emergency department, the focus is on optimizing perfusion and oxygenation of vital organs. Diagnosis and management of the underlying hemorrhage must be performed rapidly and concurrently with management of shock. There are two major stages of shock: early compensation stage and progressive stage. It is contemplated that embodiments of the invention may be applied to patients in either or both stages.

When hypovolemic shock results from massive hemorrage, the replacement fluid of choice is whole blood or packed red blood cells. Crystalloid solutions will temporarily improve circulating volume, but the patient also needs replacement of red blood cells to carry oxygen to the tissues. Management of shock focuses on fluid management, acid-base balance, and improving myocardial contraction. Treating the underlying cause of shock should also be treated in order to diminish the progression of the shock syndrome. Whole body hibernation was induced in mice, and there was an immediate drop in overall metabolic state (as measured by $CO_2$ evolution). This was reversible, and the mice seem to function normally, even after repeated exposures. Accordingly, the invention concerns inducing a whole body hibernetic state using $H_2S$ (or other oxygen antagonist or other active compound), to preserve the patient's vital organs and life. This will allow for transport to a controlled environment (e.g., surgery), where the initial cause of the shock can be addressed, and then the patient brought back to normal function in a controlled manner. For this indication, the first hour after injury, referred to as the "golden hour," is crucial to a successful outcome. Stabilizing the patient in this time period is the major goal, and transport to a critical care facility (e.g., emergency room, surgery, etc.) where the injury can be properly addressed. Thus, it would be ideal to maintain the patient in stasis to allow for this and to address immediate concerns such as source of shock, replenish blood loss, and reestablish homeostasis. While this will vary significantly, in most cases, the amount of time stasis will be maintained is between about 6 and about 72 hours after injury. In some embodiments of the invention, biological matter is exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, and any range or combination therein.

The biology of lethal hemorrhage and the physiological events that lead to shock and ultimately death are not fully understood. However, there are mechanisms through which $H_2S$ could reduce the lethal effects of ischemic hypoxia. Hydrogen sulfide inhibits cytochrome C oxidase and could reduce oxygen demand by inhibiting this enzyme[3]. Decreased oxygen demand may reduce the deleterious effects of low oxygen levels including a reduction of metabolic acidosis. Furthermore, tissue sulfhydryl levels decrease during shock (Beck et al., 1954). Exogenous $H_2S$ may prevent this hyposulfidic state and maintain sulfur homeostasis.

Hydrogen sulfide is naturally produced in animals and exhibits potent biological activities (Kamoun, 2004). Most proteins contain disulfide linked cysteine residues, and the reversible conversion from free thiol to disulfide can regulate specific enzyme activities (Ziegler, 1985). Furthermore, sulfide is electronegative and exhibits high affinity for transition metals. Proteins containing transition metal atoms, such as cytochrome oxidase, can be profoundly affected by $H_2S$. And finally, metabolism of $H_2S$ into other molecules containing reduced sulfur increases the number of thiols that may exhibit specific biological activity. In addition to (or perhaps because of) these potential modes of action, $H_2S$ may exert effects on cardiopulmonary, neuroendocrine, immune, and/or hemostatic systems that ultimately prove beneficial in injury and disease.

A U.S. provisional patent application entitled "Methods, compositions and articles of manufacture for treating shock" filed on Apr. 20, 2006 in the names of Mark B. Roth, Mike Morrison, and Eric Blackstone describes the treatment of shock and is hereby incorporated by reference.

B. Hypothermia

In yet another embodiment, the present inventor proposes use of the present invention to treat people with extreme hypothermia. The methods and compositions of the present invention are useful for inducing hypothermia in a mammal in need of hypothermia. Hypothermia can be mild, moderate or profound. Mild hypothermia comprises achievement of a core body temperature of approximately between 0.1 and 5 degrees Celsius below the normal core body temperature of the mammal. The normal core body temperature of a mammal is usually between 35 and 38 degrees Celsius. Moderate hypothermia comprises achievement of a core body temperature of approximately between 5 and 15 degrees Celsius below the normal core body temperature of the mammal. Profound hypothermia comprises achievement of a core body temperature of approximately between 15 and 37 degrees Celsius below the normal core body temperature of the mammal.

Mild hypothermia is known in the art to be therapeutically useful and effective in both non-human mammals and in humans. The therapeutic benefit of mild hypothermia has been observed in human clinical trials in the context of out-of-hospital cardiac arrest. Exposure of humans to mild hypothermia in the context of cardiac arrest results in a survival advantage and an improved neurological outcome compared to standard of care with normothermia, or absence of mild hypothermia (Bernard et al., 2002; The Hypothermia After Cardiac Arrest Study Group et al. 2002).

Methods and compositions of the present invention may have advantages over other methods known in the art, including, but not limited to, packing the subject in ice, or surrounding the subject with a "cooling tent" that circulates cool air or liquid, for inducing mild, moderate, or profound hypothermia in mammals or humans. In these cases, the subject resists the reduction of core body temperature below normothermia and tries to generate heat by shivering. Shivering, and the body heat engendered therein, can have a negative impact on the achievement of mild hypothermia by, for example, slowing the rate of decrease in the core body temperature that is achieved using the standard methods of hypothermia induction. Consequently, humans subjected to therapeutic levels of hypothermia are also treated with a drug that inhibits shivering (by blocking neurotransmission at the neuromuscular junctions) (Bernard et al., 2002).

In a preferred embodiment, methods and compositions of the present invention are combined with invasive methods or medical devices known in the art to induce therapeutic hypothermia in mammals or humans. Such invasive methods and devices include, but are not limited to, flexible probes or catheters that can be inserted into the vasculature of the subject in need of hypothermia, wherein the temperature of the catheter is adjusted to below the normal body temperature of the subject, resulting in the cooling of blood which is in contact with the catheter. The cooled blood subsequently engenders a decrease in the core body temperature of the mammal. By incorporating feedback from a thermocouple monitoring the core body temperature of the mammal, the temperature of the catheter can be modulated so as to maintain a pre-specified core body temperature. Such medical devices for achieving and maintaining mild or moderate hypothermia, referred to in the art as endovascular temperature therapy, are known in the art and are described for example on the World Wide Web at innercool.com and radiantmedical.com.

The method provides that patients with extreme hypothermia are administered or exposed to an oxygen antagonist or other active compound and then gradually restored to normal temperature while withdrawing, in a controlled fashion, the oxygen antagonist or other active compound. In this way, the oxygen antagonist or other active compound buffers the biological systems within the subject so that they may be initiated gradually without shock (or harm) to the subject.

In one embodiment, a subject suffering from hypothermia with be given an oral or intravenous dose of an oxygen antagonist or other active compound. Intravenous provision may be preferred because of the potential non-responsiveness of the subject and the ability to provide a controlled dosage over a period of time. Alternatively, if available, the oxygen antagonist or other active compound may be provide in a gaseous state, for example, using a mask for inhalation or even a sealed chamber that can house the entire subject.

Ideally, the patient will be stabilized in terms of heart rate, respiration and temperature prior to effecting any change. Once stable, the ambient environmental temperature will be increased, again gradually. This may be accomplished simply by removing the subject from the hypothermic conditions. A more regulated increase in temperature may be effected by adding successive layers of clothing or blankets, by use of a thermal wrap with gradual increase in heat, or if possible, by placing the subject in chamber whose temperature may be gradually increased.

It is preferred that the vital signs of the subject are monitored over the course of the temperature increase. Also, in conjunction with increasing the temperature, the oxygen antagonist or other active compound is removed from the subject's environment. Both heat and oxygen antagonist (or other active compound) treatment are ceased at the appropriate endpoint, judged by the medical personnel monitoring the situation, but in any event at the time the subject's temperature and other vital signs return to a normal range. Continued monitoring following cessation of treatment is recommended for a period of at least 24 hrs.

C. Hyperthermia

Under certain conditions, which can result from genetic, infectious, drug, or environmental causes, patients can loose homeostatic temperature regulation resulting in severe uncontrollable fever (hyperthermia). This can result in mortality or long-term morbidity, especially brain damage, if it is not controlled properly.

Mice inhaled $H_2S$ at 80 ppm immediately underwent hibernation. This included an inability to regulate their body temperature when ambient temperatures were dropped below room temperature. Accordingly, this technology could be used to control whole body temperature in certain states of hyperthermia. This would likely involve administration of $H_2S$ (or other oxygen antagonist or active compound) through inhalation or perfused into the blood supply to induce a hibernation state. It would be useful to have the patient to be in stasis for between about 6 and about 24 hours, during which time the source of the fever can be addressed. In some embodiments of the invention, a patient is exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, and any range or combination therein.

This can be combined with some whole-body temperature regulation (ice bath/blanket/cooling system).

D. Cardioplegia and Coronary Heart Disease

In certain embodiments, the present invention may find use as solutions for the treatment of coronary heart disease (CHD) including a use for cardioplegia for cardiac bypass surgery (CABG).

CHD results from athlerosclerosis, a narrowing and hardening of the arteries that supply oxygen rich blood to the heart muscle. The arteries harden and become narrow due to the buildup of plaque on the inner walls or linings of the arteries. Blood flow to the heart is reduced as plaque narrows the coronary arteries. This decreases the oxygen supply to the heart muscle. This may manifest in 1) angina, which is chest pain or discomfort that happens when the heart is not getting enough blood; 2) heart attack, which can occur when a blood clot suddenly cuts off most or all blood supply to part of the heart and cells in the heart muscle that do not receive enough oxygen-carrying blood begin to die, potentially causing permanent damage to the heart muscle; 3) heart failure, which is when the heart is unable to pump blood effectively to the rest of the body; arrhythmias, which are changes in the normal rhythm of the heartbeats.

Since 1990, more people have died from CHD than any other cause. 3.8 million men and 3.4 million women die each year from CHD. In 2002, over 500,000 people in the United States alone died as a direct result of heart disease. Despite improvements in survival rates, 1 in 4 men, and 1 in 3 women in the U.S. still die within a year of a recognized first heart attack.

Medical treatment of CHD includes medications to reduce the risk of heart attack, heart failure and stroke, together with important lifestyle changes to prevent the further build-up of fatty deposits in the coronary arteries. Nonetheless, some type of surgical intervention is also frequently indicated.

About one-third of CHD patients will undergo coronary angioplasty and stenting. During balloon angioplasty, a balloon-tipped catheter is employed to push plaque back against the arterial wall to allow for improved blood flow in the artery. Coronary stenting often accompanies the angioplasty procedure. Stents are small wire-mesh metal tubes that provide scaffolding to support the damaged arterial wall, reducing the chance that the vessel will close again (restenosis) after angioplasty. In the United States, nearly one million balloon angioplasty procedures are performed each year. Not all patients are able to be treated by this technique; such patients must undergo heart surgery. Michaels et al., 2002.

About 10% of CHD patients will undergo coronary artery bypass graft (CABG) surgery. Patients with severe narrowing or blockage of the left main coronary artery or those with disease involving two or three coronary arteries are generally considered candidates for bypass surgery. In CABG, the surgeon uses a portion of a healthy vessel (either an artery or a vein) from another part of the body to create a detour (or bypass) around the blocked portion of the coronary artery. Patients typically receive from 1 to 5 bypasses in a given operation. During the procedure, generally the heart is placed in a state of paralysis, known as cardioplegia (CP), during which a heart-lung machine artificially maintains circulation. Patients are under general anesthesia during the operation, which usually lasts between 3 to 6 hours.

Approximately 13% of all patients will be re-admitted to the hospital within 30 days due to reasons related to the CABG. Hannan et al., 2003; Mehlhom et al., 2001. One of the main reasons for re-admission is heart failure, presumably due to ischemic damage during the surgery. Thus, much work is being done to improve the protection of the myocardium during the period when the heart is not being perfused normally.

Recent advances in cardiac surgery have centered upon optimization of cardioplegic parameters in the hope of preventing postoperative ventricular dysfunction and improving overall outcome. Cohen et al., 1999.

Cardioplegic solutions are perfused through the vessels and chambers of the heart and cause its intrinsic beating to cease, while maintaining the viability of the organ. Cardioplegia (paralysis of the heart) is desirable during open-heart surgery and during the procurement, transportation, and storage of donor hearts for use in heart transplantation procedures.

Early cardioplegic techniques employed cold crystalloid solutions to initiate and maintain intraoperative cardiac arrest. However, it has become clear that blood cardioplegia facilitated aerobic myocardial metabolism during the cross-clamp period and reduced anaerobic lactate production. Furthermore, blood cardioplegia improves oxygen carrying capacity, enhanced myocardial oxygen consumption and preserved myocardial high-energy phosphate stores. Several different cardioplegic solutions are available and different techniques for using cardioplegia solutions are known in the art. For example, cardioplegic solutions often have varying amounts of potassium, magnesium, and several other minor components. Sometimes drugs are added to the cardioplegic solution to aid in muscle relaxation and protection from ischemia. Current approaches also include blood-only formulations with appropriate electrolyte supplementation, such as glutamate-aspartate. Specific examples of frequently used solutions are the St Thomas Hospital solution, University of Wisconsin Solution, Stanford Solution, and the Bretschneider Solution. Examples of other emerging solutions involve adenosine, insulin or L-arginine containing solutions mentioned earlier. Varying the temperature at which the cardioplegic solution is used may also have beneficial effects.

A combination of continuous retrograde along with intermittent antegrade cardioplegia reduces myocardial lactate production, preserved ATP stores, and improved metabolic recovery after cross-clamp release. Tepid (29° C.) cardioplegia reduces lactate and acid production during cardioplegic arrest, and improves post-operative ventricular function. Cardioplegic flows of at least 200 mL/min are required to washout detrimental metabolic end-products and improve ventricular function. It is abundantly clear now that future directions in cardioplegic management will involve the use of cardioplegic additives to further improve protective effects. For example, attempts have been made to harness the beneficial effects of ischemic pre-conditioning using adenosine. Similarly, insulin cardiopolegia has been employed in order to enhance ventricular performance by stimulating early post-operative aerobic metabolism. Finally, L-arginine, a nitric oxide donor has been demonstrated to be beneficial in experimental studies and may represent a further option for the enhancement of intraoperative myocardial protection. Future benefit of cardioplegic supplementation is likely to be observed in high-risk with poor ventricular function, for which current protective techniques are inadequate. There is a steady increase in the incidence of high-risk patients presenting, and these cases, and consequent complications, place a disproportionate burden on the health care system. Thus, improvements in this area hold great promise for the advancement of care in this field.

Despite the protective effects provided by the current methods for inducing cardioplegia, there is still some degree of ischemic-reperfusion injury to the myocardium. Ischemic-reperfusion injury during cardiac bypass surgery results in poor outcomes (both morbidity and mortality), especially due to an already weakened state of the heart. Myocardial ischemia results in anaerobic myocardial metabolism. The end products of anaerobic metabolism rapidly lead to acidosis, mitochondrial dysfunction, and myocyte necrosis. High-energy phosphate depletion occurs almost immediately, with a 50 percent loss of ATP stores within 10 minutes. Reduced contractility occurs within 1 to 2 minutes, with development of ischemic contracture and irreversible injury after 30 to 40 minutes of normothermic (37° C.) ischemia.

Reperfusion injury is a well-known phenomenon following restoration of coronary circulation. Reperfusion injury is characterized by abnormal myocardial oxidative metabolism. In addition to structural changes created during ischemia, reperfusion may produce cytotoxic oxygen free radicals. These oxygen free radicals play a significant role in the pathogenesis of reperfusion injury by oxidizing sarcolemmal phospholipids and thus disrupting membrane integrity. Oxidized free fatty acids are released into the coronary venous blood and are a marker of myocardial membrane phospholipid peroxidation. Protamine induces complement activation, which activates neutrophils. Activated neutrophils and other leukocytes are an additional source of oxygen free radicals and other cytotoxic substances.

The present invention provides methods and compositions for inducing cardioplegia that will provide greater protection to the heart during bypass surgery. In certain embodiments, the present invention provides a cardioplegic solution comprising $H_2S$ (or another active compound) dissolved in solution or bubbled as a gas in the solution. In some embodiments, the invention further comprises at least a first device, such as a catheter or cannula, for introducing an appropriate dose of the cardioplegic solution to the heart. In certain aspects, the invention further comprises at least a second device, such as a catheter or cannula, for removing the cardioplegic solution from the heart.

Bypass surgery typically last for 3-6 hours, however, complications and multiple vessel CABG can extend the duration to 12 hours or longer. It is contemplated that the heart would be kept in stasis during the surgery. Thus, in some embodiments of the invention, the heart is exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18 hours or more, and any range or combination therein.

E. Reducing Damage from Cancer Therapy

Cancer is a leading cause of mortality in industrialized countries around the world. The most conventional approach to the treatment of cancer is by administering a cytotoxic agent to the cancer patient (or treatment ex vivo of a tissue) such that the agent has a more lethal effect on the cancer cells than normal cells. The higher the dose or the more lethal the agent, the more effective it will be; however, by the same token, such agents are all that more toxic (and sometimes lethal) to normal cells. Hence, chemo- and radiotherapy are often characterized by severe side effects, some of which are life threatening, e.g., sores in the mouth, difficulty swallowing, dry mouth, nausea, diarrhea, vomiting, fatigue, bleeding, hair loss and infection, skin irritation and loss of energy (Curran, 1998; Brizel, 1998).

Recent studies suggest that transient and reversible lowering of the core body temperature, or "hypothermia," may lead to improvements in the fight against cancer. Hypothermia of 28° C. was recently found to reduce radiation, doxorubicin- and cisplatin-induced toxicity in mice. The cancer fighting activity of these drugs/treatments was not compromised when administered to cooled animals; rather, it was enhanced, particularly for cisplatin (Lundgren-Eriksson et al., 2001). Based on this and other published work, the inventor proposes a further reduction in core temperature will provide benefit to cancer patients. Thus, the present invention contemplates the use of oxygen antagonists or other active stasis compound to induce stasis in normal tissues of a cancer patient, thereby reducing the potential impact of chemo- or radiotherapy on those tissues. It also permits the use of higher doses of chemo- and radiotherapy, thereby increasing the anti-cancer effects of these treatments.

Treatment of virtually any hyperproliferative disorder, including benign and malignant neoplasias, non-neoplastic hyperproliferative conditions, pre-neoplastic conditions, and precancerous lesions, is contemplated. Such disorders include restenosis, cancer, multi-drug resistant cancer, primary psoriasis and metastatic tumors, angiogenesis, rheumatoid arthritis, inflammatory bowel disease, psoriasis, eczema, and secondary cataracts, as well as oral hairy leukoplasia, bronchial dysplasia, carcinomas in situ, and intraepithelial hyperplasia. In particular, the present invention is directed at the treatment of human cancers including cancers of the prostate, lung, brain, skin, liver, breast, lymphoid system, stomach, testicles, ovaries, pancreas, bone, bone marrow, gastrointestine, head and neck, cervix, esophagus, eye, gall bladder, kidney, adrenal glands, heart, colon and blood. Cancers involving epithelial and endothelial cells are also contemplated for treatment.

Generally, chemo- and radiotherapy are designed to reduce tumor size, reduce tumor cell growth, induce apoptosis in tumor cells, reduce tumor vasculature, reduce or prevent metastasis, reduce tumor growth rate, accelerate tumor cell death, and kill tumor cells. The goals of the present invention are no different. Thus, it is contemplated that one will combine oxygen antagonist (or other active compound) compositions of the present invention with secondary anti-cancer agents (secondary agents) effective in the treatment of hyperproliferative disease. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

Secondary anti-cancer agents include biological agents (biotherapy), chemotherapy agents, and radiotherapy agents. More generally, these other compositions are provided in a combined amount effective to kill or inhibit proliferation of the cancer or tumor cells, while at the same time reducing or minimizing the impact of the secondary agents on normal cells. This process may involve contacting or exposing the cells with an oxygen antagonist (or other active compound) and the secondary agent(s) at the same time. This may be achieved by contacting the cell with a single composition or pharmacological formulation that includes both agents, or by contacting or exposing the cell with two distinct compositions or formulations, at the same time, wherein one composition includes an oxygen antagonist and the other includes the second agent(s).

Alternatively, the oxygen antagonist (or other active compound) therapy may precede or follow the secondary agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In certain embodiments, it is envisioned that biological matter will be kept in stasis for between about 2 and about 4 hours while the cancer treatment is being administered. In some embodiments of the invention, biological matter is exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6 hours or more, and any range or combination therein.

Various combinations may be employed; the active compound is "A" and the secondary anti-cancer agent, such as radio- or chemotherapy, is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the oxygen antagonists or other active compounds of the present invention to a patient will follow general protocols for the administration of chemotherapeutics, taking into account the toxicity, if any, of the compound. It is expected that the treatment cycles would be repeated as necessary. It also is contemplated that various standard therapies, as well as surgical intervention, may be applied in combination with the above-described anti-cancer therapy. It is further contemplated that any combination treatment contemplated for use with an active compound and a non-active compound (such as chemotherapy), may be applied with respect to multiple active compounds.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a composition of the invention (for example, a hypoxic antitumor compound) or a chemotherapeutic or radiotherapeutic agent is delivered to a target cell or are placed in direct juxtaposition with the target cell. In combination therapy, to achieve cell killing or stasis, both agents may be delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000)

As discussed earlier, examples of immunotherapies currently under investigation or in use are immune adjuvants (e.g., Mycobacterium bovis, Plasmodium falciparum, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin- Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hanibuchi et al., 1998). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the anti-tumor therapies described herein.

F. Neurodegeneration

The present invention may be used to treat neurodegenerative diseases. Neurodegenerative diseases are characterized by degeneration of neuronal tissue, and are often accompanied by loss of memory, loss of motor function, and dementia. With dementing diseases, intellectual and higher integrative cognitive faculties become more and more impaired over time. It is estimated that approximately 15% of people 65 years or older are mildly to moderately demented. Neurodegenerative diseases include Parkinson's disease; primary neurodegenerative disease; Huntington's Chorea; stroke and other hypoxic or ischemic processes; neurotrauma; metabolically induced neurological damage; sequelae from cerebral seizures; hemorrhagic shock; secondary neurodegenerative disease (metabolic or toxic); Alzheimer's disease, other memory disorders; or vascular dementia, multi-infarct dementia, Lewy body dementia, or neurodegenerative dementia.

Evidence shows that the health of an organism, and especially the nervous system, is dependent upon cycling between oxidative and reductive states, which are intimately linked to circadian rhythms. That is, oxidative stress placed upon the body during consciousness is cycled to a reductive environment during sleep. This is thought to be a large part of why sleep is so important to health. Certain neurodegenerative disease states, such as Huntington's disease and Alzheimer's disease, as well as the normal processes of aging have been linked to a discord in this cycling pattern. There is also some evidence that brain $H_2S$ levels are reduced in these conditions (Eto et al., 2002).

The present invention can be used to regulate and control the cycling between the oxidative and reduced states, for example, to prevent or reverse the effects of neurodegenerative diseases and processes. Controlling circadian rhythms can have other applications, for example, to adjust these cycling patterns after traveling from one time zone to another, so as to adjust to the new time zone. Furthermore, reduced metabolic activity overall has been shown to correlate with health in aged animals and humans. Therefore, the present invention would also be useful to suppress overall metabolic function to increase longevity and health in old age. It is contemplated that this type of treatment would likely be administered at night, during sleep for period of approximately 6 to 10 hours each day. This could require daily treatment for extended periods of time from months to years.

G. Aging

Furthermore, in certain states of stasis, including but not limited to states where the biological matter is in a state of suspended animation, aging itself may be thoroughly or completely inhibited for the period of time when the biological matter is in that state. Thus the present invention may inhibit aging of biological material, with respect to extending the amount of time the biological material would normally survive and/or with respect to progression from one developmental stage of life to another.

H. Blood Disease

A number of blood diseases and conditions may be addressed using compositions and methods of the invention. These diseases include, but are not limited to, thalassemia and sickle cell anemia.

1. Thalassemia

Normal hemoglobin contains two alpha and two beta globin polypeptide (protein) chains, each bound to an iron containing heme ring. Thalassemia is a group of conditions in which there is an imbalance of alpha and beta chains leading to the unpaired chains precipitating on the normally fragile red blood cell membrane, leading to cell destruction. This leads to severe anemia that the marrow tries to compensate for by trying to make more red cells. Unfortunately due to toxicity from unpaired chains this process is very inefficient leading to massive expansion of the marrow space and spread of blood making to other parts of the body. This and the anemia lead to major toxicities. Several models exist as to why unpaired globin chains are so damaging but many entail that increased free radicals generated by the iron attached to the unpaired globin chains are central to the early destruction of the red cells. Thus any intervention that might decrease the oxidative damage from these free radicals could increase red cell lifespan, improve the anemia, lead to decreased need for making red cells, and less damage from marrow expansion and spread.

It is estimated that over 30,000 children are born with severe thalassemia each year, of which it is estimated that most living in developed countries live into their twenties, while in third world countries (where the majority of patients live) most die as young children. Based on the current results in other model systems presented here, it expected that exposing animals with thalassemia to sulfides will increase their red cells' ability to withstand oxidative damage, leading to prolonged red cell survival.

2. Sickle Cell Disease

Normal hemoglobin (HbA) contains two alpha and two beta globin polypeptide (protein) chains, each bound to an iron containing heme ring. In sickle cell disease (SCD; also called sickle cell anemia) is a group of conditions in which a mutant beta chain leads to an altered hemoglobin (HbS). Upon deoxygention HbS can polymerize (crystallize) and precipitate damaging the normally fragile red blood cell membrane, leading to cell destruction and anemia low red blood cells (RBC). In addition cells with polymerized HbS change shape (sickle) and become sticky and activate mechanisms leading to coagulation and blockage of blood flow. This can lead to hypoxic damage of the surrounding tissue resulting in pain, organ dysfunction and eventually premature death. Decreased stores of sulfur containing antioxidants are noted in patients. In addition oxidative damage and increased reactive oxygen species (ROS) have been implicated in crystallization, RBC membrane damage and tissue damage related to inadequate blood flow. Sulfides have been implicated in "re-charging" antioxidant stores, and potentially minimizing oxidative damage. There are reasons to think sulfides could prevent problems at several stages of sickle cell pathology. Furthermore, given the ability of oxygen antagonists to protect from hypoxia in other systems, suggests that it should also protect animals and humans subjected to the adverse conditions posed by this disease state.

Over 120,000 children are born with SCD each year. Patients in developed countries now live into their 40's and 50's however with tremendous problems with pain and organ damage including stroke, lung, heart and skin problems. In third world countries (where the majority of patients live) most die as young children. Our hypothesis is that exposing animals and eventually humans with SCD to sulfides will result in health improvements.

IV. Preservation Applications

The present invention can be used to preserve or store a variety of biological matter, including cells, tissues, organs, and whole organisms for transport and/or storage purposes. In certain embodiments, the biological matter is preserved so as to prevent damage from adverse conditions.

In embodiments of the invention, biological matter can be exposed to an active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. It is contemplated that active compounds may be used to induce stasis and that other agents may be used to maintain stasis and preserve them for any significant period of time. Alternatively, it is contemplated that an active compound may be used to induce and/or maintain stasis. This may be in combination with other agents, such environmental changes in pressure and/or temperature.

1. Cells

As discussed above, a variety of cells are contemplated for use with the present invention. It is contemplated that such cells can be preserved in methods, apparatuses, and compositions of the invention.

a. Platelets

In certain embodiments, the present invention may find use in the preservation of platelets. Platelets are small cell fragments (~⅓ size of erythrocytes) that play a vital role in the formation of blood clots at the site of bleeding. Hemostasis is achieved by adherence to the walls of blood vessels, release of coagulating chemicals, forming blood clots to plug the rupture in the vascular wall and/or narrowed blood vessels. Normal platelet counts are between 150,000-400,000 counts/µL. Platelet concentrates are transfused for a variety of indications, for example: 1) to prevent bleeding due to thrombocytopenia; 2) in a bleeding patient to maintain a platelet count above 50,000; 3) to address abnormal platelet function that is congenital or due to medications, sepsis, malignancy, tissue trauma, obstetrical complications, extra corporeal circulation, or organ failure such as liver or kidney disease.

Each unit of platelets contains an average of $0.8$-$0.85 \times 10^{11}$ platelets. Platelet concentrates also contain about 60 mL of plasma (coagulation factors) and small numbers of red blood cells and leukocytes. Platelet units must be maintained at room temperature (20° C.-24° C.) and agitated during storage. They can be stored at the Blood Center for up to 5 days. Longer storage is not possible at present due to deterioration of the platelets, and the risk of microbial contamination. Two sources of platelets currently exist:

1) Pooled random donor platelet concentrates are prepared from platelets that have been harvested by centrifuging units of whole blood. Up to 8 units of platelets, each from a separate donor, can be pooled into a single bag for transfusion. Platelets expire 4 hours after pooling. All units are from the same ABO type. If ABO compatible platelets are unavailable, ABO incompatible platelets can be substituted with very little risk. The usual adult dose is 4-6 units of pooled random donor platelets.

2) Apheresis platelets, collected from a single donor, are prepared in standard (equivalent to ~4 pooled units) and "large" (equivalent to ~6 pooled units) sizes. An apheresis platelet concentrate contains 200-400 mL of plasma. They may be collected as a random unit (random apheresis platelets) or be obtained for a specific recipient from a family member or a volunteer HLA compatible "directed" donor. Apheresis platelets expire 4 hours after processing for release from the blood center.

Platelet storage poses problems that are not found with the storage of whole blood or other components. While whole blood, red and white cells may be stored at 4° C. for weeks, platelets will aggregate in cold storage and when allowed to settle. Therefore, the standard method of storing platelets is at room temperature, approximately 20 to 24° C., with gentle agitation. Even under these conditions, platelets can only be stored for 5 days before they need to be discarded. This problem of outdating results in approximately $500 million annually in lost revenue for US hospitals. If even a moderate increase in shelf life could be attained, approximately 90% of this loss could be avoided.

An additional problem with platelet storage is bacterial contamination. Contamination is primarily due to staphylococci from the skin during the phlebotomy, or else donor bacteremia. The bacterial contamination of platelets represents the largest infectious risk with any blood transfusion procedure.

A significant factor affecting the viability of platelets is regulation of pH. Virtually all units of platelets stored according to the currently accepted methods show a decrease in pH from their initial value of approximately 7.0. This decrease is primarily due to the production of lactic acid by platelet glycolysis and to a lesser extent to accumulation of $CO_2$ from oxidative phosphorylation. As the pH falls, the platelets change shape from discs to spheres. If the pH falls below 6.0, irreversible changes in platelet morphology and physiology render them non-viable after transfusion. An important goal in platelet preservation, therefore, is to prevent this decrease in pH. It was previously thought that platelets must be stored in a container permeable to oxygen since glycolysis is stimulated when oxygen availability is limited (see e.g., U.S. Pat. No. 5,569,579). The present invention, however, demonstrates that the viability of stored platelets can be extended by storing them in an anoxic environment.

The present invention provides methods and compositions that increase the survival time of stored platelets and reduce bacterial contamination. In one embodiment, the present invention provides a sealable, oxygen-impermeable container into which the platelets are placed. After sealing, an anaerobic generator (e.g., a sodium borohydride tablet with a palladium catalyst) converts the atmospheric oxygen in the container to water. The container can also contain an indicator, which indicates the level of oxygen tension. Once in anoxic conditions, the platelets can also be stored at lower temperatures.

The platelets may be suspended and stored in plasma or any platelet storage solution known in the art. For example, U.S. Pat. Nos. 4,828,976 and 4,447,415 disclose several commonly used solutions suitable for the storage of platelets.

Typically, platelets are stored in plasma from the donor and administered in that form.

Generally, the invention consists of a sealed environment (container, jar, impermeable bag, or chamber) in which the oxygen tension can be reduced to less than 1% (10,000 ppm) and more specifically in the range of 10-100 ppm, or less. The reduction in atmospheric oxygen in this environment can be achieved by a number of methods known in the art. For example, the reduction in atmospheric oxygen can be achieved with the generation of hydrogen gas, with or without a catalyst, to combine with the oxygen to produce water.

Other reactions could be catalyzed to combine the oxygen with other compounds, such as carbon to produce carbon dioxide, and so on. Also, the oxygen could be replaced by exchanging all the air in the chamber with gas containing any combination of gases that do not include oxygen. Also, the oxygen could be removed by placing the chamber under vacuum, to remove all gases. Alternatively, the oxygen could be competed by using another gas or compound that competes for oxygen, such as CO. A combination of removal of oxygen and competition of remaining oxygen could also be used. The device may also comprise a way to measure the concentration of oxygen to ensure the appropriate anaerobic state has been achieved. For example, oxygen concentration can be measured using an anaerobic indicator based on methlyene blue that changes from blue color to colorless in the absence of oxygen. Alternatively, an oxygen meter or other oxygen measuring device could be used.

The device also comprises some way to contain the platelets in the sealed environment such that the oxygen can be removed from the solution containing the platelets, as well as from the platelets themselves. An example of this is to have the platelets in a gas-permeable bag placed inside the sealed environment. The platelets could also be held in an open container inside the sealed environment. Alternatively, the platelets could be placed directly in the impermeable, sealed container/bag.

The Bio-Bag™ from Becton Dickinson (product number 261215) is one example of a sealable, oxygen-impermeable container that can be used to create an anoxic environment for the storage of platelets. The Bio-Bag, which is a kit sold for the isolation of anaerobic bacteria, includes a sealable, gas-impermeable bag; an anaerobic indicator; an anaerobic generator (hydrogen gas generator); and palladium catalysts. The platelets in a gas-permeable bag, would be sealed inside of the Bio-Bag for storage.

The anaerobic generator in the Bio-Bag is a device activated by the addition of water, which passes through a series of channels to a filter paper wick. The wick delays and regulates the introduction of water into the tablet chamber, providing a controlled release of the hydrogen gas. The gas-generating tablet consists of sodium borohydride. The hydrogen released from this reaction, combines with the atmospheric oxygen in the sealed container to produce water. This reaction is catalyzed by the palladium in the container.

The Puget Sound Blood Center (PSBC) independently assessed the state of the platelets stored in anoxic conditions on days 0, 5 and 8 using a standardized panel of in vitro tests. Results indicated that platelets stored in anoxic conditions for up to 8 days perform as good, or better than, platelets stored under standard conditions. Ongoing studies are replicating this experiment, and extending the observation time to 13 days.

Those of skill in the art will be familiar with methods for assaying platelet function. For example, as described in U.S. Pat. No. 6,790,603, platelet function can be assayed by (1) internal protein expression on the cell membrane in response to challenge with an activation-inducing agonist; (2) ability to aggregate when challenged by an agonist; and (3) adenosine triphosphate secretion. Examples of agonist that can cause activation of platelet function include thrombin, epinephrine, ADP and collagen.

Internal protein expression may be measured by conjugation of a molecule with a fluorescent dye, followed by sorting in a fluorescent cell sorter. In general, it is preferable to use two monoclonal antibodies, one that binds a cell surface molecule that is constitutively expressed and a second that binds a cell surface molecule that is expressed only after activation. Each monoclonal antibody is conjugated to a different colored dye, that can be distinguished by spectrofluorometry. A non-limiting example of a constitutively expressed cell surface molecule is GPIIbIIIa; a non-limiting example of a cell surface molecule expressed after activation is P-selectin. It is well know in the art to make monoclonal antibodies to proteins. U.S. Pat. No. 5,470,738, is one example of a method of making monoclonal antibodies to GPIIIa. Another anti-platelet monoclonal antibody is that to GP IV, as disclosed by U.S. Pat. No. 5,231,025. Antibodies can also be purchased commercially from such companies as Becton-Dickinson (Philadelphia).

Another parameter of platelet function is the ability to aggregate when challenged by an agonist. The platelet suspension is dense and milky white. Aggregation and subsequent settling of the aggregates can be estimated visually, or measured with a densitometer.

Yet another measure of platelet function is the secretion of ATP. Platelets that are able to function well are able to secrete ATP while cells that have already been activated or have lost function in other ways cannot secrete ATP.

2. Cell Culture

The present invention can be extended to protecting cells in culture, which might otherwise die or be induced into apoptosis. In the context of the present invention, cells are exposed to an active compound prior to and/or while in culture. Cells that can be cultured according to the invention include those that can eventually be placed back into a physiological context, i.e., those for subsequent transplant. Such cells include, but are not limited to, bone marrow, skin cells and epithelial cells. Also, some transplantable cells would greatly benefit from expansion in culture, thereby increasing the amount of material that can be introduced into the host. Epithelial cells from the gastrointestinal tract are specifically contemplated as cells that can benefit from exposure to an active compound.

Furthermore, the invention extends to the culture of tumor cells. Culture of tumor cells is known to result in alteration of the phenotype, and in some cases death. This makes tissue culture experiments on tumor cells highly unpredictable.

General cell culture techniques are well known to those of skill in the art. Examples of this knowledge can be found in Shaw (1996) and Davis (1994), both of which are incorporated by reference herein. General information and modifications of traditional cell culture techniques is also found in U.S. Pat. No. 5,580,781, which is incorporated by reference. Furthermore, techniques for culturing skin cells are described in U.S. Pat. No. 6,057,148, which is incorporated by reference. It is contemplated that these techniques, as well as others known to those of skill in the art, will be supplemented with media containing one or more active compounds, or perfused with an active compound as liquids and/or gases.

E. Preservation of Cells, Tissue and Organs

In certain embodiments of the invention, it is desirable to preserve biological matter, so as to prevent as much as possible damage to the matter from perishing or decomposing. Though the first successful kidney transplant was performed in 1954 and the first heart and liver transplants were conducted in 1967, every year, thousands of people die in need of an organ transplant. Due to a variety of causes, they need hearts, lungs, kidneys, and livers. In addition, there are patients who could use a pancreas or a cornea. While there is a constant need for organ donors, another significant hurdle in providing those in need of an organ transplant with an organ is the limitations in current organ preservation techniques. For example, it is widely believed that a human heart must be transported within four hours for there to be any chance of the subsequent transplantation to be a success. Rager, 2004 (see table below).

Maximum cold ischemic time

| Organ | Preservation Time |
| --- | --- |
| Heart and Lungs | 4-6 hours |
| Liver | 12-24 hours |
| Kidney | 48-72 hours |
| Pancreas | 12-24 hours |
| Small Intestine | 12 hours |

Moreover, the primary cause of organ transplant failure for transplanted hearts in the first 30 days is ischemic-reperfusion injury.

Organ procurement and preservation, tissue matching, and immunosuppression are the principal ingredients for successful solid organ transplantation. The technical aspects of the organ procurement operation allow multiple teams to work together to procure all useful organs form a single donor. On average, 3.6 organs are procured from a single deceased donor.

Preserving solid organs depends on rapid intravascular cooling done in situ, followed by removal of the organs, storage of the organs in ice-cold preservation fluid and rapid transport to the recipients' hospitals. The cold ischemic time is the length of time the organs are on ice, without blood flow. The maximum cold ischemic time limits the amount of time that can pass between organ recovery and the organ transplant (Table 5). Between 2%-10% of matched and procured organs cannot be used due to extended ischemic time, depending on the type of organ. Similarly, approximately 10 to 20% of procured organs are not used due to poor organ function and/or infection (not including HIV/CMV/hepatitis).

Current preservation techniques involve the use of ice-cold solutions that include electrolytes, antioxidants, hydrogen ion buffers and sugars. Punch et al., 2001. Appropriate tissue matching depends on blood group matching (e.g., blood type, A, B or O) for all organs. Immunosuppresive regimens typically include three drugs: a glucocorticoid such as prednisone, an antimetabolite such as azathiprine or mycophenolate, and a calcineurin inhibitor such as cyclosporine or tacrolimus.

The two most frequently used methods for preserving/transporting hearts for transplantation are hypothermic storage and continuous perfusion. In the former method, the heart is arrested, removed from the donor, and then rapidly cooled and transported in cold storage. In the latter method, the following steps are typically employed: 1) pulsatile flow; 2) hypothermia; 3) membrane oxygenation, and 4) a perfusate containing both.

To improve the prospect of a successful transplant, techniques for better preserving an organ for transplantation have been developed. Two general areas of development have occurred, one in the area of preservation solutions and the other in the area of organ containers.

In certain contexts, such as transplant, adverse consequences of wound healing may impair or prevent proper engraftment of transplanted tissue. In the context of the present invention, it is envisioned that donated and recipient tissues will be treated pre-transplantation with an oxygen antagonist or other active compound, as discussed above with respect to wound healing, in an effort to inhibit biological processes such as inflammation, apoptosis and other wound healing/post-transplantation events that damage engrafted tissues.

F. Organisms

Such organisms could be used for research purposes, such as laboratory mice (mouse banking), or for consumption, such as fish. In these situation, it is contemplated that stasis can be maintained indefinitely. Moreover, stasis can be induced in plants or parts of plants, including fruit, flowers, leaves, stems, seeds, cuttings. Plants can be agricultural, medicinal, or decorative. Induction of stasis in plants may enhance the shelf life or pathogen resistance of the whole or part of the plant. Thus, in embodiments of the invention, an organism or part thereof can be exposed to an oxygen antagonist or other active compound for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein.

G. Preservation Agents

A variety of preservation solutions have been disclosed in which the organ is surrounded or perfused with the preservation solution while it is transported. One of the most commonly used solution is ViaSpan® (Belzer UW), which employed with cold storage. Other examples of such solutions or components of such solutions include the St. Thomas solution (Ledingham et al., J. Thorac. Cardiobasc. Surg. 93:240-246, 1987), Broussais solution, UW solution (Ledingham et al., Circulation 82 (Part 2)IV351-8, 1990), Celsior solution (Menasche et al., Eur. J. Cardio. Thorax. Surg. 8:207-213, 1994), Stanford University solution, and solution B20 (Bernard et al., J. Thorac. Cardiovasc. Surg. 90:235-242, 1985), as well as those described and/or claimed in U.S. Pat. Nos. 6,524,785; 6,492,103; 6,365,338; 6,054,261; 5,719,174; 5,693,462; 5,599,659; 5,552,267; 5,405,742; 5,370,989; 5,066,578; 4,938,961; and, 4,798,824.

In addition to solutions, other types of materials are also known for use in transporting organs and tissue. These include gelatinous or other semi-solid material, such as those described, for example, in U.S. Pat. No. 5,736,397.

Some of the systems and solutions for organ preservation specifically involve oxygen perfusion in the solution or system to expose the organ to oxygen because it is believed that maintaining the organ or tissue in an oxygenated environment improves viability. See Kuroda et al., (Transplantation 46(3): 457-460, 1988) and U.S. Pat. Nos. 6,490,880; 6,046,046; 5,476,763; 5,285,657; 3,995,444; 3,881,990; and, 3,777,507. Isolated hearts that are deprived of oxygen for more than four hours are believed to lose vigor and not be useful in the recipient because of ischemic/reperfusion injury. See U.S. Pat. No. 6,054,261.

Moreover, many, if not all, of the solutions and containers for organ preservation and transplantation involve hypothermia (temperature below room temperature, often near but not below 0° C.), which has been called the "bed rock of all useful methods of organ and tissue preservation." U.S. Pat. No. 6,492,103.

To improve the prospect of a successful transplant, techniques for better preserving an organ for transplantation have been developed. Two general areas of development have occurred, one in the area of preservation solutions and the other in the area of organ containers.

Moreover, many, if not all, of the solutions and containers for organ preservation and transplantation involve hypothermia (temperature below room temperature, often near but not below 0° C.), which has been called the "bed rock of all useful methods of organ and tissue preservation." U.S. Pat. No. 6,492,103.

In the field of organ transplantation, certain conditions are believed to be related to the condition of the organ and prognosis for a successful transplantation: 1) minimization of cell swelling and edema; 2) prevention of intracellular acidosis; 3) minimization of ischemic damage; and 4) provision of substrate for regeneration of high energy phosphate compounds and ATP during reperfusion. Ischemic/reperfusion injury in organ transplantation is especially problematic because the harvested organ is removed from the body, isolated from a blood source, and thereby deprived of oxygen and nutrients for an extended period of time (U.S. Pat. No. 5,912,019). In fact, one of the most critical problems in transplantation today is the relatively high incidence of delayed graft function (DGF) due to acute tubular necrosis (ATN) after surgery. Current methods still experience problems in these areas, which highlights the importance of the present invention.

Nonetheless, the present invention can be used in conjunction with other preservation compositions and methods. As discussed in U.S. Pat. Nos. 5,952,168, 5,217,860, 4,559,258 and 6,187,529 (incorporated specifically by reference), biological materials can be preserved, for example, for keeping transplantable or replaceable organs long-term.

Cells, tissue/organs, or cadavers can be given compounds that enhance or maintain the condition of organs for transplantation. Such methods and compositions include those described in U.S. Pat. Nos. 5,752,929 and 5,395,314.

Moreover, methods of the present invention can include exposing biological matter to preservation solutions, such as those discussed, in addition to exposure to an oxygen antagonist or other active compound.

It is contemplated that any agent or solution used with a biological sample that is living and that will be used as a living material will be pharmaceutically acceptable or pharmacologically acceptable. The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared either as liquid solutions or suspensions; solid forms suitable for solution in, or suspension in, liquid prior to use can also be prepared.

Organs for transplants may be monitored to assess their condition, particularly with respect to use as a transplant. Such methods are described in U.S. Pat. No. 5,699,793.

A number of drugs can be administered to a patient after receiving an organ transplant to assist in the recovery process. Such drugs include compounds and agents that reduce or inhibit an immune response against the donated organ.

Moreover, additional drugs are continually being researched and offered for use in organ transplants, such as those described in U.S. Pat. No. 6,552,083 (inhibitory agent comprising N-(3,4-dimethoxycinnamoyl)anthranililc acid) and U.S. Pat. No. 6,013,256 (antibodies that bind the IL-2 receptor, such as a humanized anti-Tax antibody).

H. Preservation Apparatuses and Applications

Systems or containers for transporting organs and tissues have also been developed through the years. Any of these embodiments may be combined with apparatuses of the invention, which allow for use with oxygen antagonists or other active compound.

Most involve cooling systems for implementation, for example, those described in U.S. Pat. Nos. 4,292,817, 4,473, 637, and 4,745,759, which employ active refrigeration with a cooling liquid that is pumped through the system. Several sophisticated devices have been designed involving multiple chambers or dual containers, such as is U.S. Pat. Nos. 5,434, 045 and 4,723,974.

Some constitute a system in which an apparatus is devised for perfusion of the organ or tissue in a preservation solution, as is described in U.S. Pat. Nos. 6,490,880; 6,100,082; 6,046, 046; 5,326,706; 5,285,657; 5,157,930; 4,951,482; 4,502,295; and, 4,186,565.

Some of the systems and solutions for organ preservation specifically involve oxygen perfusion in the solution or system to expose the organ to oxygen because it is believed that maintaining the organ or tissue in an oxygenated environment improves viability. See Kuroda et al., (Transplantation 46(3): 457-460, 1988) and U.S. Pat. Nos. 6,490,880; 6,046,046; 5,476,763; 5,285,657; 3,995,444; 3,881,990; and, 3,777,507. Isolated hearts that are deprived of oxygen for more than four hours are believed to lose vigor and not be useful in the recipient because of ischemic/reperfusion injury. See U.S. Pat. No. 6,054,261.

Moreover, in some embodiments of the invention, there are methods for preserving platelets, as mentioned above. Shortcomings of the prior art are reduced or eliminated using techniques of this disclosure. Embodiments concerning platelets and oxygen reduction find wide application including but not limited to any application that would benefit from longer-lasting storage of platelets.

In one embodiment, oxygen reduction techniques can be embodied in a kit. For example, the kit currently sold under product number 261215, available from Becton Dickinson, makes use of select techniques described here. That kit includes an anaerobic generator (e.g., a hydrogen gas generator), Palladium Catalysts, an anaerobic indicator, and a gas impermeable, sealable, "BioBag" into which the above components (together with platelets in a gas-permeable bag) are placed and sealed.

The anaerobic generator of this example kit is activated by the addition of water, which passes through a series of channels to a filter paper wick. The wick delays and regulates the introduction of water into the tablet chamber, providing a controlled release of hydrogen gas. The gas-generating tablet includes sodium borohydride. The hydrogen released from this reaction combines with the atmospheric oxygen in the sealed container to produce water. This reaction is catalyzed by the palladium in the container.

In a more general respect, techniques of this disclosure can be carried out using any number of sealed environments (e.g., a container such as a jar, impermeable bag, or chamber) in which oxygen tension can be reduced. In one embodiment, an oxygen level within the container and/or within platelets or an associated solution may be reduced to less than about 1% (about 10,000 parts per million). In another embodiment, the oxygen may be reduced to about a range of 10-100 parts per million, or less. In still other embodiments, the oxygen may be reduced to any percentage value that represents a decrease in oxygen within a container and/or within platelets or an associated solution. In preferred embodiments, the container is gas-impermeable, as well as sealable. As those having ordinary skill in the art will appreciate "gas impermeable" does not necessarily connote an absolute or 100% level of impermeability. Rather, "gas impermeable" should be interpreted as it is in the art to signify, e.g., able to hold an atmosphere that is less than 10 ppm (against a gradient of room air, typically 210,000 ppm) for at least 4 days. Typically, commercially available bags are impermeable for 6 weeks or longer.

A container may be sealed once pertinent oxygen reducing elements are placed inside. The reduction in atmospheric oxygen in this environment may be achieved by the generation of hydrogen gas, with or without a catalyst, to combine with the oxygen to produce water. Other reactions may be catalyzed to combine the oxygen with other compounds, such as carbon to produce carbon dioxide. Other reactions and combinations will be apparent to those having ordinary skill in the art. Also, oxygen may be replaced by exchanging gases in the chamber with gas containing any combination of gases that do not include oxygen. Additionally, oxygen may be removed by placing a container under a vacuum sufficient to remove gases and particularly sufficient to remove oxygen to a desired, reduced level. Alternatively, oxygen may be competed by using another gas or compound that competes for oxygen, such as CO. A combination of removal of oxygen and competition of remaining oxygen may be used.

In different embodiments, a device may be used to measure oxygen levels to ensure the appropriate anaerobic state has been achieved. An anaerobic indicator based on methylene blue that changes from blue color to colorless in the absence of oxygen may be used. Alternatively, a commercially available oxygen meter (e.g., a mechanical and/or electrical meter) or other oxygen measuring device may be used.

In different embodiments, platelets are contained in a sealed environment such that oxygen can be removed from the solution containing the platelets, as well as from the platelets themselves. For example, platelets in a gas-permeable bag may be placed inside a sealed environment. Other non-limiting examples may be to have an open container inside a sealed environment to hold platelets. Alternatively, one may contain platelets in an impermeable, sealed container (e.g., a bag) and have an oxygen removal mechanism incorporated.

In one embodiment, the invention involves a method in which platelets and a solution are introduced into a gas-impermeable container. The container is sealed. Oxygen is removed from the container or from the platelets and solution. It is contemplated that about, at least about, or at most about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein, of the oxygen in the gas permeable bag is removed.

This method may also include indicating a remaining oxygen level within the container following oxygen removal. Oxygen in the container may be reduced to a level of about 10,000 parts per million or less. Oxygen in the container may be reduced to a level between about 10 and about 100 parts per million. Introducing the platelets may involve inserting a gas-permeable container holding the platelets and solution into the gas-impermeable container. Introducing the platelets may involve inserting the platelets and solution into a sealable, flexible bag or a sealable, rigid chamber. Sealing the container, which can occur at any stage of a given process, can involve the use of an adhesive.

Removing oxygen may involve pumping oxygen from the container, and such pumping may involve pumping with a roughing and/or turbo pump. Removing oxygen may involve introducing hydrogen into the container, which combines with the oxygen to produce water. The hydrogen may be introduced through a chemical reaction. The chemical reaction may be catalyzed. Removing oxygen may involve introducing hydrogen into the container using a gas generating tablet. Water may be added to a gas generating tablet comprising sodium borohydride to generate hydrogen. Such water may be added in a delayed and regulated manner. For example, a filter paper wick may be used. Water may be introduced to the filter paper wick through one or more channels. Palladium may catalyze a chemical reaction that generates hydrogen. Removing oxygen may involve introducing one or more agents into the container that bond with the oxygen. CO may be introduced into the container, which bonds with the oxygen to form $CO_2$. Removing oxygen may involve displacing oxygen with one or more gases.

Indicating a remaining oxygen level may involve use of a methylene blue indicator that changes color in the absence of oxygen. Alternatively, an oxygen meter may be used. Indicating a remaining oxygen level within the container may involve indicating a remaining oxygen level within platelets or a solution.

In one embodiment, the invention involves a method in which platelets and a solution are introduced into a gas-impermeable container. The container is sealed. Hydrogen is generated through a chemical reaction by adding water to sodium borohydride. The chemical reaction removes oxygen from the platelets and solution through combination with the hydrogen to form water. A remaining oxygen level is indicated within the container following oxygen removal.

The chemical reaction may be catalyzed using palladium. The addition of water may involve use of a filter paper wick.

In one embodiment, the invention involves a system for removing oxygen from platelets and a solution. The system includes (a) a sealable, gas-impermeable container, (b) an oxygen-reducing generator, and (c) an oxygen indicator. The sealable, gas-impermeable container is configured and sized to receive the platelets and the solution. The oxygen-reducing generator is coupled to the container and is configured to remove oxygen from the platelets and the solution through pumping or chemical reaction. The oxygen indicator is coupled to the container and is configured to indicate an oxygen level within the container following oxygen removal.

The container may be a sealable, flexible bag. The oxygen reducing generator may include a hydrogen generator configured to generate hydrogen for combining with the oxygen to produce water. The hydrogen generator may include a gas generating substance that, when combined with an agent, generates the hydrogen. That gas generating substance may include a sodium borohydride tablet, and the agent may include water. A hydrogen generator may also include a palladium catalyst. The system may also include a member configured to delay or regulate a chemical reaction by controlling the introduction of one or more components of the chemical reaction. For example, the member can include a wick that delays and regulates a chemical reaction.

In one embodiment, the invention involves a kit including a hydrogen generator; a gas impermeable, sealable container; and an oxygen indicator.

The hydrogen generator may include a gas generating substance that, when combined with an agent, generates the hydrogen. That gas generating substance may include a sodium borohydride tablet, and the agent may include water. The kit may also include a palladium catalyst. The kit may also include a wick configured to delay or regulate a chemical reaction that generates the hydrogen.

As discussed above, methods of the invention can involve employing an apparatus or system that maintains the environment in which biological matter is placed or exposed to. The invention includes an apparatus in which an active compound, particularly as a gas, is supplied. In some embodiments, the apparatus includes a container with a sample chamber for holding the biological matter, wherein the container is connected to a supply of gas comprising the active compound(s). It is specifically contemplated that the container may be a solid container or it may flexible, such as a bag.

In some embodiments, the invention is an apparatus for preserving cell(s), the apparatus comprising: a container having a sample chamber with a volume of no greater than 775 liters; and a first gas supply in fluid communication with the sample chamber, the first gas supply including carbon monoxide. In further embodiments, the apparatus also includes a cooling unit that regulates the temperature inside the sample chamber and/or a gas regulator that regulates the amount of active compound in the chamber or the amount of active compound in a solution that is in the chamber.

It is contemplated that there may be a gas supply for a second or additional gas or a second or additional gas supply for the active compound. The second gas supply may be connected with the sample chamber or it may be connected with the first gas supply. The additional gas, as discussed above, may be a non-toxic and/or non-reactive gas.

A gas regulator is part of the apparatus in some embodiments of the invention. One, two, three, or more gas regulators may be employed. In some cases, the gas regulator regulates the gas supplied to the sample chamber from the first gas supply. Alternatively, it regulates the gas supplied to the sample chamber or first gas supply from the second gas supply, or there may be a regulator for both the first and second gas supplies. It is further contemplated that any gas regulator can be programmed to control the amount of gas supplied to the sample chamber and/or to another gas supply. The regulation may or may not be for a specified period of time. There may be a gas regulator, which may or may not be programmable, for any gas supply directly or indirectly connected to the sample chamber. In some cases, the gas regulator is electronically programmable.

In some cases, the pressure and/or the temperature inside the chamber can be regulated with either a pressure regulator or temperature regulator, respectively. As with the gas regulator, these regulators may be electronically programmable. The apparatus of the invention may also have a cooling and/or heating unit to achieve the temperatures discussed above. The unit may or may not be electronically programmable.

In additional embodiments, the apparatus includes a wheeled cart on which the container rests or it may have one or more handles.

It is specifically contemplated that the invention includes an apparatus for cell(s), in which the apparatus has: a container having a sample chamber; a first gas supply in fluid communication with the sample chamber, the first gas supply including the active compound(s); and an electronically-programmable gas regulator that regulates gas supplied to the sample chamber from the first gas supply.

In some embodiments, the apparatus also has a structure configured to provide a vacuum within the sample chamber.

Moreover, any oxygen antagonist described in this application is contemplated for use with apparatuses of the invention. In specific embodiments, carbon monoxide can be administered using this apparatus. In other cases, a chalcogenide compound can be administered or a compound having the reducing agent structure.

Figure 19:
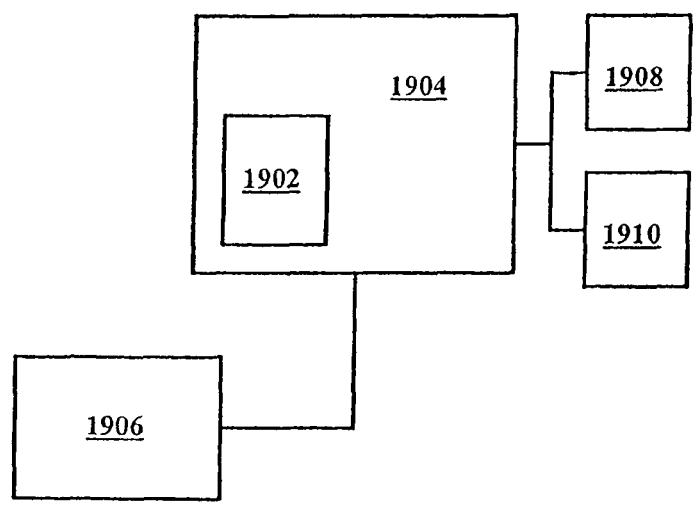
FIG. 19 is a schematic diagram of an example system for removing oxygen from platelets and a solution in accordance with embodiments of the present disclosure.

FIG. 19 is a schematic diagram of an example system for removing oxygen from platelets and a solution and embodies concepts discussed above. Gas permeable bag 1902 may be placed in sealable gas impermeable container 1904. Gas impermeable container 1904 may be coupled to oxygen reducing generator 1906. Oxygen reducing generator 1906, in one embodiment, may envelope sealable gas impermeable container 1904. In different embodiments, oxygen reducing generator 1906 may take different forms. For example, it may be a pump (e.g., a roughing or and/or turbo pump) or a hydrogen generator. Associated with oxygen reducing generator 1906 may be one or more components such as a wick or other delay mechanism. Coupled to sealable gas impermeable container 1904 are sensor 1908 and regulator 1910. Sensor 1908, in one embodiment, may be an oxygen meter, which may take various forms. In other embodiments, sensor 1908 may be a temperature or pressure meter. Of course, more than one sensor may be used. In one embodiment, regulator 1901 may be a temperature or pressure regulator. For example, regulator 1901 may be a heater or cooling device to regulate temperature inside sealable gas impermeable container 1904.

V. Diagnostic Applications

Sulfites are produced by all cells in the body during normal metabolism of sulfur containing amino acids. Sulfite oxidase, removes, and thus regulates the levels of sulfites. Differential activities of these enzymes would lead to different levels of sulfites evolved in tissue specific manner. In the example described above, for solid tumors in hypoxic conditions, sulfites may be produced at higher levels to provide local protective state to the tumor cells through the reduction of metabolic state as well as the inhibition of immune surveillance. Therefore, it would be beneficial to measure sulfite levels and incorporate this as part of diagnosis for several disease states such as solid tumors. Furthermore, since we propose using sulfites for various applications, it would be useful to follow this using some sort of imaging or other monitoring process.

It is possible to measure sulfite levels in serum to get a total sulfite level using current technology (e.g., HPLC). It is worth exploring the possibility of imaging sulfites. Alternatively, a proteomic approach may allow an understanding of how the regulation of the enzymes involved in sulfite metabolism may be altered in certain disease states, allowing for this approach to diagnostics.

VI. Screening Applications

In still further embodiments, the present invention provides methods for identifying oxygen antagonists and molecules that act in a like fashion with respect to inducing stasis and other active compounds. In some cases, the oxygen antagonist or active compounds being sought works like a chalcogenide compound in reducing core body temperature or preserving viability in hypoxic or anoxic environments that would otherwise kill the biological matter if it were not for the presence of the oxygen antagonist or other active compound. These assays may comprise random screening of large libraries of candidate substances; alternatively, the assays may be used to focus on particular classes of compounds selected with an eye towards attributes that are believed to make them more likely to act as oxygen antagonists or active compounds. providing a candidate active compound;
  (a) admixing the candidate active compound with a biological matter;
  (b) measuring one or more cellular responses characteristic of oxygen antagonist treatment; and
  (c) comparing the one or more responses with the biological matter in the absence of the candidate active compound.

Assays may be conducted with isolated cells, tissues/organs, or intact organisms.

It will, of course, be understood that all the screening methods of the present invention are useful in themselves notwithstanding the fact that effective candidates may not be found. The invention provides methods for screening for such candidates, not solely methods of finding them. However, it will also be understand that candidate active compound may be identified as an effective active compound according to one or more assays, meaning that the candidate active compound appears to have some ability to act as an active compound, such as by inducing stasis in a biological matter. Screening, in some embodiments, involves using an assay described in the Examples or elsewhere in the disclosure to identify a modulator. Moreover, in addition to or instead of the method described in this section, a candidate active compound may be tested for activity either as an oxygen antagonist or as another compound having a property of an active compound, such as protective metabolic agent or therapeutic substance. Some embodiments of screening methods are provided above.

An effective active compound may be further characterized or assayed. Moreover, the effective active compound may be used in an in vivo animal or animal model (as discussed below) or be used in further in vivo animals or animal models, which may involve the same species of animals or in different animal species.

Furthermore, it is contemplated that an active compound identified according to embodiments of the invention may also be manufactured after screening. Also, biological matter may be exposed to or contacted with an effective active compound according to methods of the invention, particularly with respect to therapeutic or preservation embodiments.

A. Active Compounds

As used herein the term "candidate active compound" refers to any molecule that may induce stasis in biological matter by, for example, altering core body temperature. The candidate active compound may be a protein or fragment thereof, a small molecule, or even a nucleic acid molecule. One may also acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate active compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate active compound identified by the present invention may be peptide, polypeptide, polynucleotide, small molecule inhibitors or any other compounds that may be designed through rational drug design starting from known inhibitors or stimulators.

Other suitable active compounds include antisense molecules, siRNAs, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the active compounds initially identified, the inventor also contemplates that other structurally similar compounds may be formulated to mimic the key portions of the structure of the active compounds. Such compounds, which may include peptidomimetics of peptide modulators, may be used in the same manner as the initial active compounds.

B. In Vivo Assays

In vivo assays involve the use of various animal models. Due to their size, ease of handling, and information on their physiology and genetic make-up, mice are a preferred embodiment. However, other animals are suitable as well, including rats, rabbits, hamsters, guinea pigs, gerbils, woodchucks, mice, cats, dogs, sheep, goats, pigs, cows, horses and monkeys (including chimps, gibbons and baboons). Fish are also contemplated for use with in vivo assays, as are nematodes. Assays for modulators may be conducted using an animal model derived from any of these species.

In such assays, one or more candidate substances are administered to an animal, and the ability of the candidate substance(s) to induce stasis, reduce core body temperature, or endow on the biological material the ability to survive hypoxic or anoxic environmental conditions, as compared to an inert vehicle (negative control) and $H_2S$ (positive control), identifies a modulator. Treatment of animals with test compounds will involve the administration of the compound, in an appropriate form, to the animal. Administration of the candidate compound (gas or liquid) will be by any route that could be utilized for clinical or non-clinical purposes, including but not limited to oral, nasal (inhalation or aerosol), buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

VII. Modes of Administration and Pharmaceutical Compositions

An effective amount of a pharmaceutical composition of a chalcogenide, oxygen antagonist, or other active compound, generally, is defined as that amount sufficient to detectably ameliorate, reduce, minimize or limit the extent of the condition of interest. More rigorous definitions may apply, including elimination, eradication or cure of disease.

A. Administration

The routes of administration of a chalcogenide or other active compound will vary, naturally, with the location and nature of the condition to be treated, and include, e.g., inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation. As detailed below, active compounds may be administered as medical gases by inhalation or intubation, as injectable liquids by intravascular, intravenous, intra-arterial, intracerobroventicular, intraperitoneal, subcutaneous administration, as topical liquids or gels, or in solid oral dosage forms.

Moreover, the amounts may vary depending on the type of biological matter (cell type, tissue type, organism genus and species, etc.) and/or its size (weight, surface area, etc.). It will generally be the case that the larger the organism, the larger the dose. Therefore, an effective amount for a mouse will generally be lower than an effective amount for a rat, which will generally be lower than an effective amount for a dog, which will generally be lower than an effective amount for a human. The effective concentration of hydrogen sulfide to achieve stasis in a human depends on the dosage form and route of administration. For inhalation, in some embodiments effective concentrations are in the range of 50 ppm to 500 ppm, delivered continuously. For intravenous administration, in some embodiments effective concentrations are in the range of 0.5 to 50 milligrams per kilogram of body weight delivered continuously.

Similarly, the length of time of administration may vary depending on the type of biological matter (cell type, tissue type, organism genus and species, etc.) and/or its size (weight, surface area, etc.) and will depend in part upon dosage form and route of administration. In particular embodiments, an active compound is provided for about or at least 30 seconds, 1 minute, 2 minutes, 3 minutes, 5 minutes, 10 minutes, 15 minutes, 30 minutes, 1 hour, 2 hours, 3 hours, four hours five hours, six hours, eight hours, twelve hours, twenty-four hours, or greater than twenty-four hours. An active compound may be administered in a single dos or multiple doses, with varying amounts of time between administered doses.

In the case of transplant, the present invention may be used pre- and or post-operatively to render host or graft materials quiescent. In a specific embodiment, a surgical site may be injected or perfused with a formulation comprising a chalcogenide. The perfusion may be continued post-surgery, for example, by leaving a catheter implanted at the site of the surgery.

B. Injectable Compositions and Formulations

The preferred methods for the delivery of oxygen antagonists or other active compound of the present invention are inhalation, intravenous injection, perfusion of a particular area, and oral administration. However, the pharmaceutical compositions disclosed herein may alternatively be administered parenterally, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Solutions of the active compounds may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Intravenous Formulations

In one embodiment, active compounds of the invention may be formulated for parenteral administration (e.g., intravenous, intra-arterial). In the cases where the active compound is a gas at room temperature, a solution containing a known and desired concentration of the gas molecule dissolved in a liquid or a solution for parenteral administration is contemplated. Preparation of the active compound solution may be achieved by, for example, contacting (e.g., bubbling or infusing) the gas with the solution to cause the gas molecules to dissolve in the solution. Those skilled in the art will recognize that the amount of gas that dissolves in the solution will depend on a number of variables including, but not limited to, the solubility of the gas in the liquid or solution, the chemical composition of the liquid or solution, its temperature, its pH, its ionic strength, as well as the concentration of the gas and the extent of contacting (e.g., rate of and duration of bubbling or infusing). The concentration of the active compound in the liquid or solution for parenteral administration can be determined using methods known to those skilled in the art. The stability of the active compound in the liquid or solution can be determined by measuring the concentration of the dissolved oxygen antagonist after varying intervals of time following preparation or manufacture of the oxygen antagonist solution, where a decrease in the concentration of the oxygen antagonist compared to the starting concentration is indicative of loss or chemical conversion of the active compound.

In some embodiments, there is a solution containing a chalcogenide compound is produced by dissolving a salt form of the chalcogenide into sterile water or saline (0.9% sodium chloride) to yield a pharmaceutically acceptable intravenous dosage form. The intravenous liquid dosage form may be buffered to a certain pH to enhance the solubility of the chalcogenide compound or to influence the ionization state of the chalcogenide compound. In the cases of hydrogen sulfide or hydrogen selenide, any of a number of salt forms known to those skilled in the art may suffice, including, but not limited to, sodium, calcium, barium, lithium, or potassium. In another preferred embodiment, sodium sulfide or sodium selenide is dissolved in sterile phosphate buffered saline and the pH is adjusted to 7.0 with hydrochloric acid to yield a solution of known concentration which can be administered to a subject intravenously or intraarterially.

It is contemplated that in some embodiments, a pharmaceutical composition of the invention is a saturated solution with respect to the active compound. The solution can be any pharmaceutically acceptable formulation, many of which are well known, such as Ringer's solution. In certain embodiments, the concentration of the active compound is about, at least about, or at most about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7.3.8, 3.9, 4.0, 4.1, 4.2, 4.3, 4.4, 4.5, 4.6, 4.7, 4.8, 4.9, 5.0 M or more, or any range derivable therein (at standard temperature and pressure (STP)). With $H_2S$, for example, in some embodiments, the concentration can be from about 0.01 to about 0.5 M (at STP). It is specifically contemplated the above concentrations may be applied with respect to carbon monoxide and carbon dioxide in a solution separately or together.

Furthermore, when administration is intravenous, it is contemplated that the following parameters may be applied. A flow rate of about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 gtts/min or µgtts/min, or any range derivable therein. In some embodiments, the amount of the solution is specified by volume, depending on the concentration of the solution. An amount of time may be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months, or any range derivable therein.

Volumes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mls or liters, or any range therein, may be administered overall or in a single session.

In some embodiments, the solution of the active compound for parenteral administration is prepared in a liquid or solution in which the oxygen has been removed prior to contacting the liquid or solution with the active compound. Certain oxygen antagonists, in particular certain chalcogenide compounds (e.g., hydrogen sulfide, hydrogen selenide), are not stable in the presence of oxygen due to their ability to react chemically with oxygen, leading to their oxidation and chemical transformation. Oxygen can be removed from liquids or solutions using methods known in the art, including, but not limited to, application of negative pressure (vacuum degasing) to the liquid or solution, or contacting the solution or liquid with a reagent which causes oxygen to be bound or "chelated", effectively removing it from solution.

In another embodiment, the solution of the oxygen antagonist or other active compound for parenteral administration may be stored in a gas-tight container. This is particularly desirable when the oxygen has previously been removed from the solution to limit or prevent oxidation of the oxygen antagonist or other active compound. Additionally, storage in a gas-tight container will inhibit the volatilization of the oxygen antagonist gas or other active compound from the liquid or solution, allowing a constant concentration of the dissolved oxygen antagonist to be maintained. Gas-tight containers are known to those skilled in the art and include, but are not limited to, "i.v. bags" comprising a gas impermeable construction material, or a sealed glass vial. To prevent exposure to air in the gas-tight storage container, an inert gas, such as nitrogen or argon, may be introduced into the container prior to closure.

D. Topical Formulations and Uses Thereof

Methods and compositions of the present invention are useful for inducing stasis in superficial layers of the skin and oral mucosa, including, but not limited to, hair follicle cells, capillary endothelial cells, and epithelial cells of the mouth and tongue. Radiation therapy and chemotherapy for the treatment of cancer damage normal cells in the hair follicles and oral mucosa, leading to the unintended, but debilitating side effects of cancer therapy, hair loss and oral mucositis, respectively. Induction of stasis in hair follicle cells and/or the vascular cells that supply blood to the hair follicles may slow, limit or prevent damage to hair follicle cells and the resultant hair loss that accompanies radiation therapy and chemotherapy, or other alopecia, male-pattern baldness, female-pattern baldness, or other absence of the hair from skin areas where it normally is present. Induction of stasis in oral epithelial and mesenchymal cells may slow, limit or prevent damage to cells lining the mouth, esophagus and tongue and the resultant painful condition of oral mucositis.

In certain embodiments the active compound is administered topically. This is achieved by formulating the active compound in a cream, gel, paste, or mouthwash and applying such formulation directly to the areas that require exposure to the active compound (e.g., scalp, mouth, tongue, throat).

The topical compositions of this invention can be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

E. Solid Dosage Forms

Pharmaceutical compositions include solid dosage forms in which the active compound is trapped, or sequestered, in a porous carrier framework that is capable of achieving a crystalline, solid state. Such solid dosage forms with the capacity for gas storage are known in the art and can be produced in pharmaceutically acceptable forms (e.g., Yaghi et al. 2003). A particular advantage of such a pharmaceutical composition pertains to chalcogenide compounds (e.g., hydrogen sulfide, carbon monoxide, hydrogen selenide), which can be toxic to certain mammals at certain concentrations in their free form. In certain embodiments, the compound may be formulated for oral administration.

F. Perfusion Systems

A perfusion system for cells may be used to expose a tissue or organ to an active compound in the form of a liquid or a semi-solid. Perfusion refers to continuous flow of a solution through or over a population of cells. It implies the retention of the cells within the culture unit as opposed to continuous-flow culture, which washes the cells out with the withdrawn media (e.g., chemostat). Perfusion allows for better control of the culture environment (pH, $pO_2$, nutrient levels, active compound levels, etc.) and is a means of significantly increasing the utilization of the surface area within a culture for cell attachment.

The technique of perfusion was developed to mimic the cells milieu in vivo where cells are continuously supplied with blood, lymph, or other body fluids. Without perfusion of a physiological nutrient solution, cells in culture go through alternating phases of being fed and starved, thus limiting full expression of their growth and metabolic potential. In the context of the present invention, a perfusion system may also be used to perfuse cells with an oxygen antagonist to induce stasis.

Those of skill in the art are familiar with perfusion systems, and there are a number of perfusion systems available commercially. Any of these perfusion systems may be employed in the present invention. One example of a perfusion system is a perfused packed-bed reactor using a bed matrix of a non-woven fabric (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 μm to 100 μm, providing for a high internal volume with pore volumes corresponding to 1 to 20 times the volumes of individual cells.

The perfused packed-bed reactor offers several advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium, which facilitates subsequent purification steps. This technology is explained in detail in WO 94/17178 (Aug. 4, 1994, Freedman et al.), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plates joined to create thin sealed laminar flow spaces between adjacent plates.

The Cellcube™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Other commercially available perfusion systems include, for example, CellPerf® (Laboratories MABIO International, Tourcoing, France) and the Stovall Flow Cell (Stovall Life Science, Inc., Greensboro, N.C.)

The timing and parameters of the production phase of cultures depends on the type and use of a particular cell line. Many cultures require a different media for production than is required for the growth phase of the culture. The transition from one phase to the other will likely require multiple washing steps in traditional cultures. However, one of the benefits of a perfusion system is the ability to provide a gentle transition between various operating phases. The perfusion system can also facilitate the transition from a growth phase to a static phase induced by an oxygen antagonist. Likewise, the perfusion system can facilitate the transition from a static phase to a growth phase by replacing the solution comprising an oxygen antagonist with, for example, a physiological nutrient media.

G. Catheters

In certain embodiments, a catheter is used to provide an active compound to an organism. Of particular interest is the administration of such an agent to the heart or vasculature system. Frequently, a catheter is used for this purpose. Yaffe et al., 2004 discusses catheters particularly in the context of suspended animation, though the use of catheters were generally known prior to this publication.

H. Delivery of Gases

1. Respiration System

Figure 9:
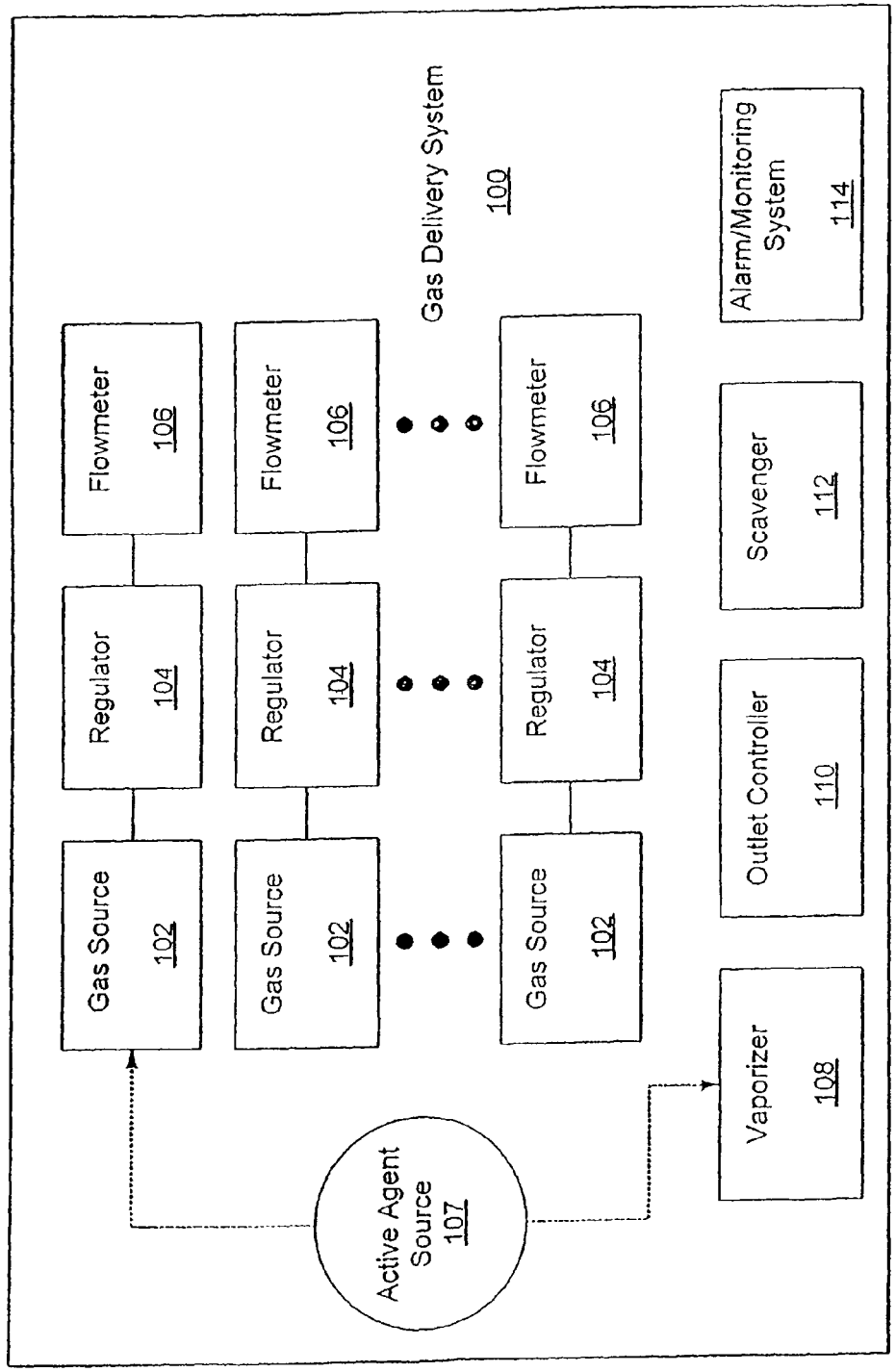
FIG. 9 is a block diagram illustrating a respiration gas delivery system according to embodiments of the present invention.

An exemplary gas delivery system 100 is illustrated in FIG. 9. The delivery system 100 is suited for delivering breathable gases, including an active agent, to the respiration system of a subject. The gas delivery system 100 includes one or more gas sources 102. Each of the gas sources 102 is connected to a regulator 104 and a flowmeter 106. The gas delivery system 100 also includes an active agent source 107, an optional vaporizer 108, an outlet controller 110, a scavenger 112, and an alarm/monitoring system 114.

The delivery system 100 may include certain elements generally used in an anesthesia delivery machine. For example, anesthesia delivery machines generally include a high pressure circuit, a low pressure circuit, a breathing circuit, and a scavenging circuit. As described in FIGS. 10-11, one or more of the gas sources 102, the vaporizer 108, the outlet controller 110, the scavenger 112, and/or the alarm/monitoring system 114 may be provided as part of a device having a high pressure, low pressure, breathing, and/or scavenging circuit, and these elements may be similar to those generally used in an anesthesia delivery machine. Anesthesia delivery machines are described, for example, in U.S. Pat. Nos. 4,034,753; 4,266,573; 4,442,856; and 5,568,910, the contents of which are hereby incorporated by reference in their entireties.

The gas sources 102 may be provided by tanks of compressed gas; however, it should be understood that the gas sources 102 can be either a gas or a liquid source that is converted to a gas. For example, the vaporizer 108 can be used to vaporize a liquid gas source. The regulators 104 include valves that reduce the pressure of each of the gas sources 102. The decompressed gas then passes through one of the flowmeters 106, which measures and controls the flow of gas from each of the respective gas sources 102.

The gas sources 102 may be carrier gases that are used to deliver the active agent 107. The carrier gases may be selected to provide a desired environment for a subject to which the active agent from the source 107 is delivered. For example, if the active agent is delivered to a patient as a breathable gas, the carrier gases can include oxygen, nitrous oxide, or air in sufficient quantities to satisfy the needs of the patient. Other inert or active gases may be used.

In some embodiments, one of the gas sources 102 includes the active agent source 107. The active agent from the source 107 may be a liquid gas source that is vaporized by the vaporizer 108 or the active agent may be a gaseous source, such as a compressed gas under high pressure. The active agent can be mixed with one or more of the gas sources 102. The outlet controller 110 controls the amount of the gas mixture that is provided to the subject.

The scavenger 112 is a device or system that scavenges and/or ventilates the gases that are provided to the subject. For example, if the active agent from the source 107 is provided as a breathable gas to a patient, the scavenger 112 can be used to remove the waste gases of the inhalant (such as the active agent), unused oxygen, and exhaled carbon dioxide.

The alarm/monitoring system 114 includes sensors that monitor the gas flow and/or gas content at one or more locations within the delivery system 100. For example, the flow or amount of oxygen may be monitored when the active agent from the source 107 is provided as a breathable gas to a patient to ensure that the carrier gases include sufficient oxygen for the patient. The alarm/monitoring system 114 also includes a user interface that is configured to provide an audio or visual alarm or monitoring information to a user of the delivery system 100, such as a visual display, a light, or audio alarm. The alarm/monitoring system 114 can be configured to notify the user when a predetermined condition is met and/or to provide information regarding gas levels.

Figure 10:
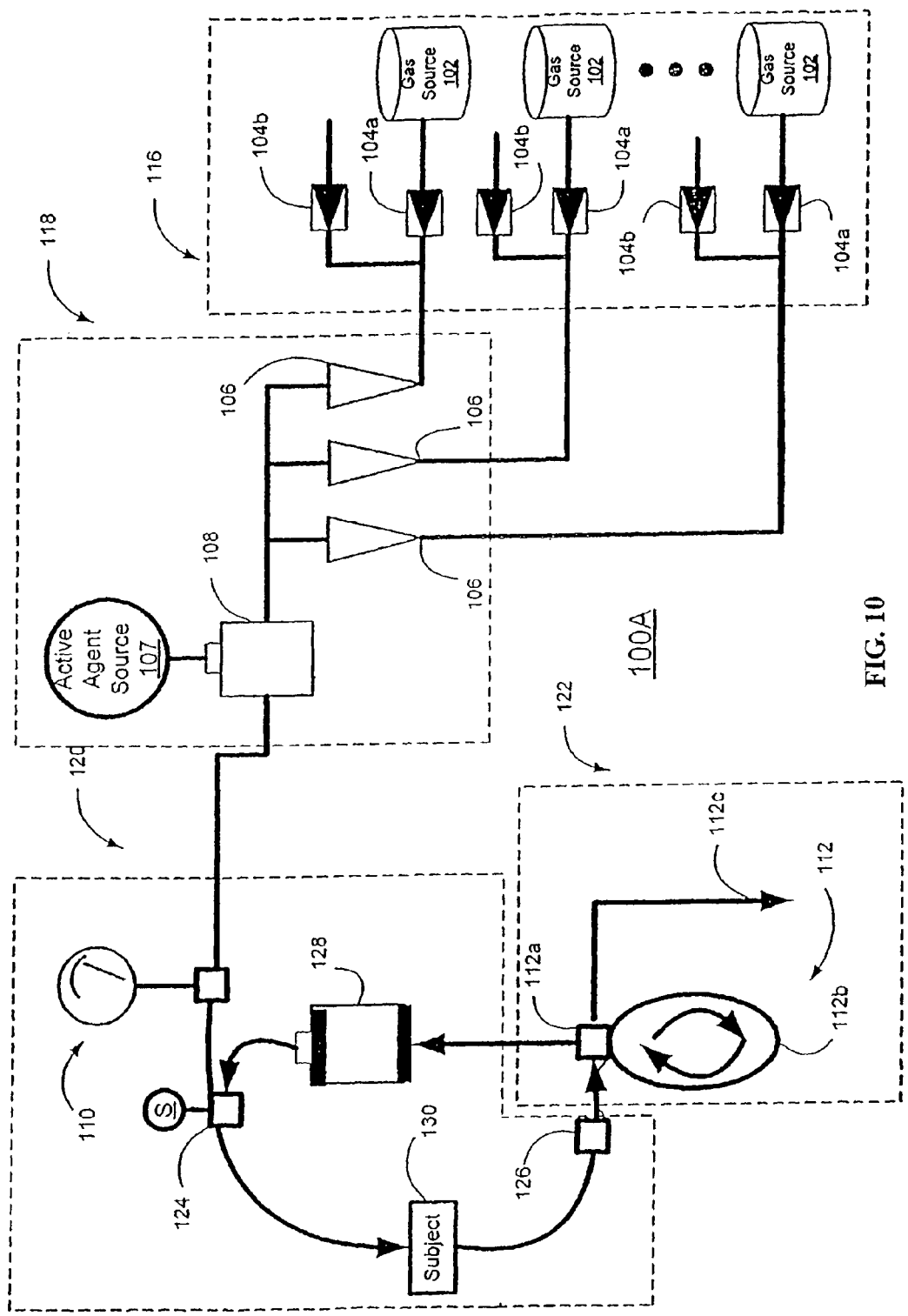
FIG. 10 is a schematic drawing illustrating a respiration gas delivery system according to embodiments of the present invention.

With reference to FIG. 10, a system 100A includes a high pressure circuit 116, a low pressure circuit 118, a breathing circuit 120, and a scavenging circuit 122.

The high pressure circuit 116 includes the compressed gas sources 102, which are connected to regulator valves 104b, 104a. The regulator valves 104a control the amount of gas that flows from each of the gas sources 102, and the regulator valves 104b may be opened to increase the pressure of the gas, for example, by providing an opening to the surrounding atmosphere.

The low pressure circuit 118 includes the flowmeters 106, the active agent source 107, and the vaporizer 108. A gas mixture from the gas sources 102 is provided by the flowmeters 106, which control the amount of each of the gases from the gas sources 102. As illustrated in FIG. 10, the active agent source 107 is a liquid. The active agent source 107 is vaporized by the vaporizer 108 and added to the gas mixture.

The breathing circuit 120 includes the outlet controller 110, two one-way valves 124, 126 and an absorber 128. The scavenger circuit 122 includes a valve 112a, a reservoir 112b, and an outlet 112c. A subject 130 receives the gas mixture from the outlet controller 110 and the resulting gas is ventilated by the scavenger circuit 122. More specifically, the outlet controller 110 controls the amount of the gas mixture that is delivered to the subject 130 via the one-way valve 124. Expired gases flow through the one-way valve 126 to the valve 112a and to the reservoir 112b. Excess gases exit through the outlet 112c of the scavenger 112. Some of the gases may be recycled and flow through the absorber 128 and into the breathing circuit 120. The absorber 128 may be a carbon dioxide absorbing canister for reducing carbon dioxide gases from exhaled gases. In this configuration, expired oxygen and/or active agent may be re-circulated and reused.

One or more sensors S may be added at various positions in the system 100A. The sensors S sense and/or monitor the gases in the system 100A. For example, if one of the gas sources 102 is oxygen, one of the sensors S may be an oxygen sensor configured and positioned to monitor the oxygen in the system 100A so that the patient receives a suitable amount of oxygen. The sensors S are in communication with the alarm/monitoring system 114 (see FIG. 9). If undesirable or dangerous gas levels are present in the system 100, the alarm/monitoring system 114 may alert a user of the system 100A so that appropriate action may be taken, such as increasing the oxygen levels given to the subject 130 or disconnecting the subject 130 from the delivery system 100A.

Figure 11:
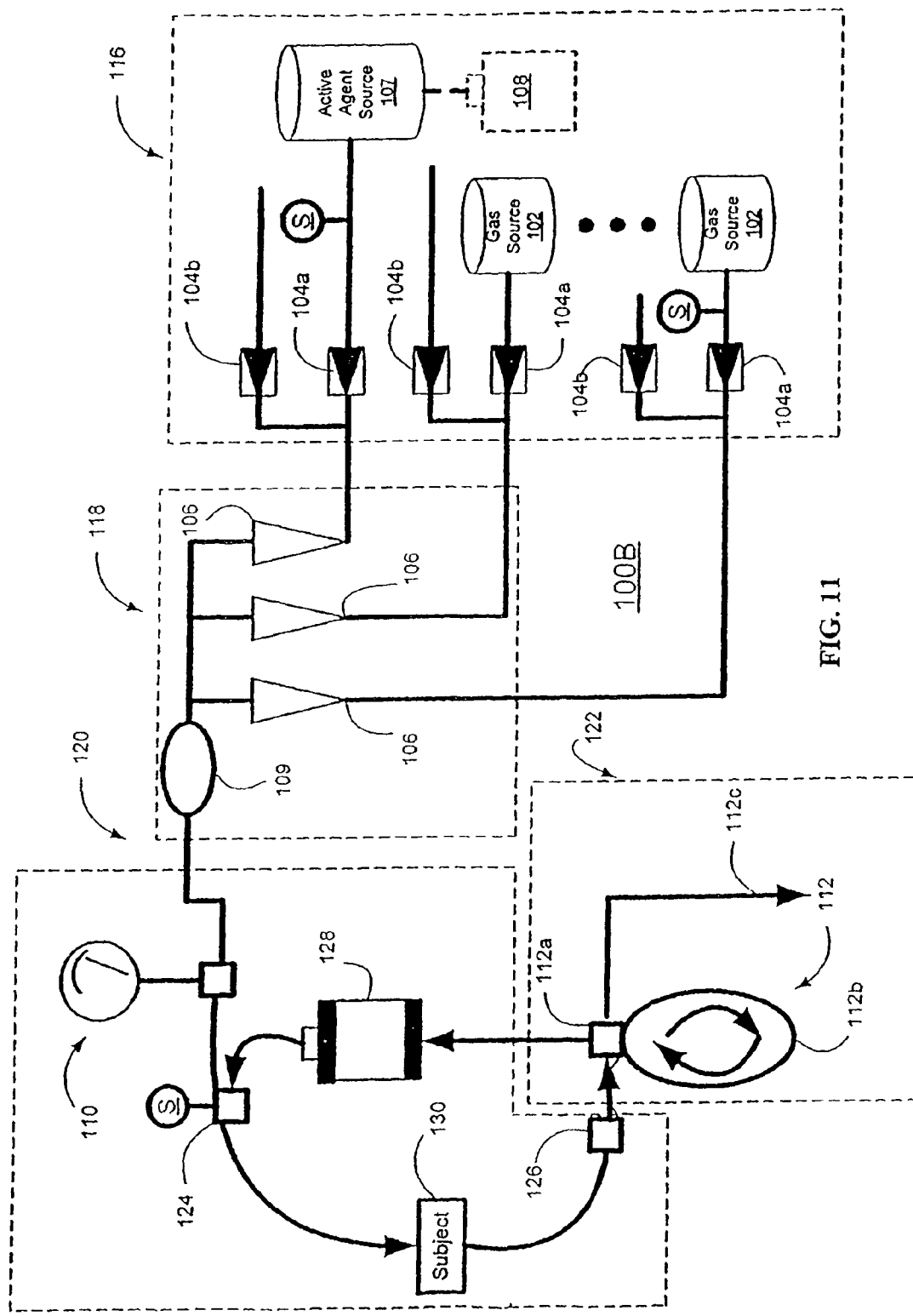
FIG. 11 is a schematic drawing illustrating a respiration gas delivery system according to further embodiments of the present invention.

With reference to FIG. 11, a system 100B is shown in which the active agent source 107 is connected to two of the regulator valves 104b, 104a. If the active agent source 107 is a liquid gas source, an optional vaporizer 108 is provided to vaporize the liquid gas source. If the active agent source 107 is gaseous (e.g., a high pressure gas), then the vaporizer 108 may be omitted. The active agent from the source 107 is mixed with the other gas sources 102 in the low pressure circuit 118 in amounts that are controlled by the flowmeters 106. The low pressure circuit 118 includes a gas reservoir 109 that contains any overflow of the gas mixture as it flows to the breathing circuit 120. It should be understood that the active agent source 107 and/or any of the gas sources 102 may be provided as a liquid gas source with a vaporizer. The elements of the system 100B illustrated in FIG. 11 are essentially the same as those described above with respect to FIG. 10 and will not be described further.

Figure 12:
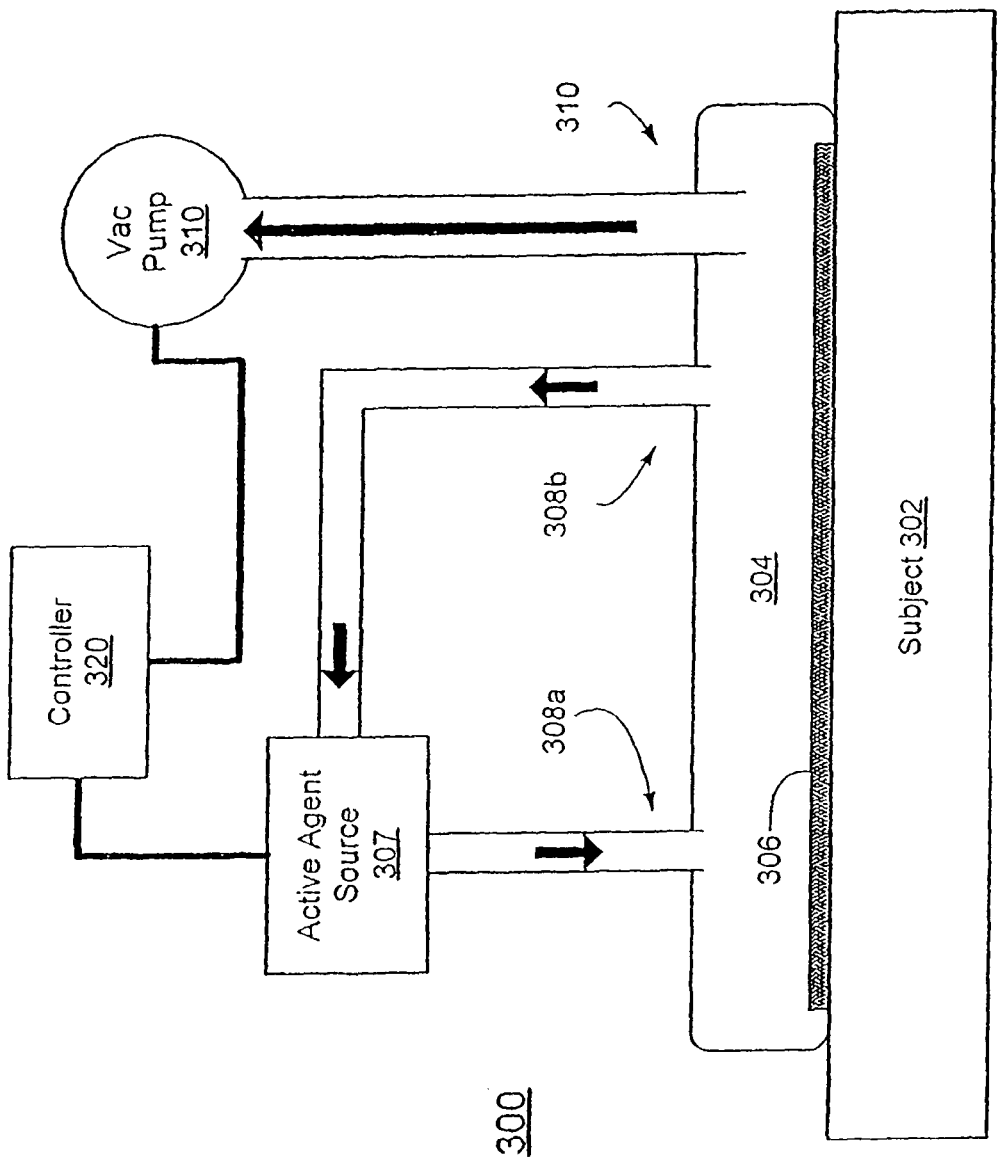
FIG. 12 is a flowchart illustrating operations according to embodiments of the present invention.

Methods according to embodiments of the present invention which may be carried out using the systems 100, 100A, 100B are illustrated in FIG. 12. A mixture of one or more breathable gas sources is provided (Block 202). The breathable gas sources may be obtained from the gas sources 102 as described with respect to FIGS. 9-11. A predetermined amount of the active agent is added to the gas mixture (Block 204), such as is shown with respect to the active agent source 107 in FIGS. 9-11. The gas mixture is administered to the subject 120 (Block 306). Exhaled gases are ventilated and/or recycled (Block 208), for example, by the scavenger 112. Although the methods of FIG. 12 are described with respect to the systems 100, 100A, 100B of FIG. 9-11, it should be understood that any suitable system or device may be used to carry out the steps in FIG. 12.

2. Reduced Pressure Delivery System

Figure 13:
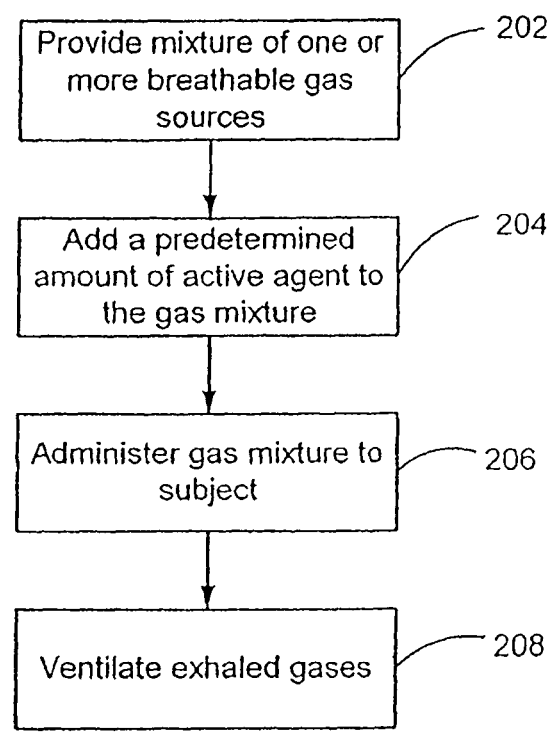
FIG. 13 is a schematic drawing illustrating a tissue treatment gas delivery system according to embodiments of the present invention.

Embodiments of a gas delivery system 300 are illustrated with respect to FIG. 13. The gas delivery system 300 is positioned on a subject 302. The gas delivery system 300 is particularly suited to deliver an active agent in a gas mixture to the tissue of a subject 302, for example, wound tissue.

The system 300 includes a reduced pressure chamber 304 having a screen 306 that covers the treatment area of the subject 302. The reduced pressure chamber 304 is connected to a vacuum pump 310 by a pump outlet 310a. The reduced pressure chamber 304 includes an inlet 308a and an outlet 308b, which are in turn connected to an active agent source 307. A controller 320 is connected to the active agent source 307 and the vacuum pump 310. Reduced pressure chambers and vacuum pump systems are discussed in U.S. Pat. Nos. 5,645,081 and 5,636,643, the contents of which are hereby incorporated by reference in their entireties.

The reduced pressure chamber 304 is configured to enclose an area of the subject 302 to provide a fluid-tight or gas-tight enclosure to effect treatment of the area with reduced or negative pressure and the active agent source 307. The pressure chamber 304 can be affixed to the subject 302 with a cover (not shown), such as a flexible, adhesive, fluid impermeable polymer sheet. The cover can have an adhesive backing that functions to cover the skin around the periphery of the area being treated and to provide a generally gas-tight or fluid-tight seal and to hold the chamber 304 in position.

The screen 306 is positioned over the treatment area of the subject 302. For example, if the treatment area of the subject 302 includes a wound, the screen 306 can be positioned over the wound to prevent its overgrowth. The size and configuration of the screen 306 can be adjusted to fit the individual treatment area, and may be formed from a variety of porous materials. The material should be sufficiently porous to allow oxygen any other gases, such as gases from the active agent source 307, to reach the treatment area. For example, the screen 306 can be in the form of an open-cell polymer foam, such as a polyurethane foam, which is sufficiently porous to allow gas flow to and/or from the treatment area. Foams may be used that vary in thickness and rigidity, although it may be desirable to use a spongy material for the patient's comfort if the patient must lie upon the appliance during treatment. The foam may also be perforated to enhance gas flow and to reduce the weight of the system 300. The screen 306 may be cut to an appropriate shape and size to fit within the treatment area, or alternatively, the screen 306 may be sufficiently large to overlap the surrounding skin.

The vacuum pump 310 provides a source of suction within the reduced pressure chamber 304. The active agent source 307 provides an amount of the active agent to the reduced pressure chamber 304. The controller 320 controls the amount of vacuum applied to the reduced pressure chamber 304 by the vacuum pump 310 and the amount of the active agent that is supplied to the chamber 304 by the active agent source 307.

It should be understood that the controller 320 can apply a vacuum and/or the active agent in a substantially constant manner, cyclically, or using various fluctuations or patterns or any combination thereof. In some embodiments, the active agent is supplied by the active agent source 307 alternatively with the vacuum pumping action of the vacuum pump 310. That is, the controller 320 alternatively activates the vacuum pump 310 while deactivating the active agent source 307 and then activates the active agent source 307 while deactivating the vacuum pump 310. The pressure in the reduced pressure chamber 304 is allowed to fluctuate. In other embodiments, a substantially constant pressure is maintained by the vacuum pump 310 and the active agent source 307 provides a substantially constant amount of active agent to the chamber 304 in the reduced pressure environment. In some embodiments, a substantially constant pressure is maintained by the vacuum pump 310 and the amount of the active agent varies in a cyclical manner. In other embodiments, the pressure in the reduced pressure chamber 304 is made to fluctuate by the vacuum pump 310, and the amount of active agent supplied by the source 307 also fluctuates. The fluctuations of either the vacuum pump 310 and the resulting pressure in the chamber 304 or the amount of active agent supplied by the source 307 may be cyclical or not cyclical.

Figure 14:
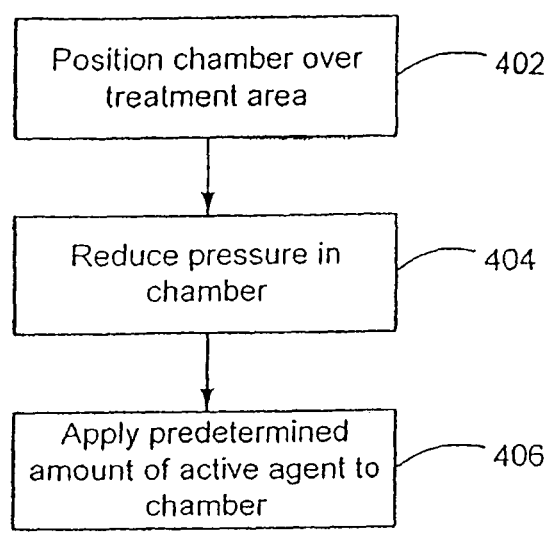
FIG. 14 is a flowchart illustrating operations according to embodiments of the present invention.

Methods according to embodiments of the present invention that may be carried out using the system 300 are illustrated in FIG. 14. The chamber 304 is positioned over the treatment area of the subject 302 (Block 402). Pressure is reduced in the chamber 304 by the vacuum pump 310 (Block 404). A predetermined amount of active agent from the active agent source 307 is applied to the chamber (Block 406). Although the methods of FIG. 14 are described with respect to the system 300 of FIG. 12, it should be understood that any suitable system or device may be used to carry out the steps in FIG. 14. For example, the outlet 308b may be omitted and the active agent may be supplied to the chamber 304 by the single inlet 308a. Other gases may also be added to the chamber 304, for example, using a single inlet or an inlet and an outlet, such as is illustrated with respect to the active agent source 307 and the inlet 308*a* and the outlet 308*b*. In some embodiments, the vacuum pump 310 is attached to an additional collection container between the pump 310 and the chamber 304 for collecting exudates from the treatment area, for example, as described in U.S. Pat. No. 5,636,643.

Figure 22A:
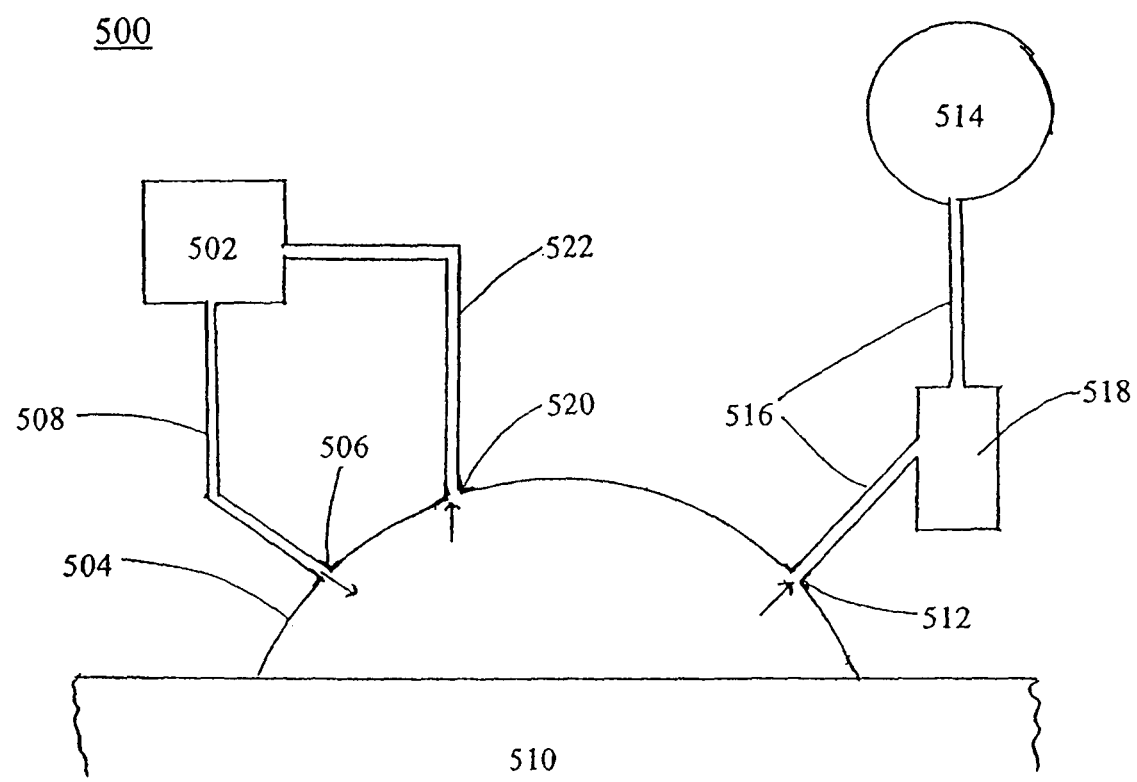
FIG. 22A-B show negative pressure devices that can be used to deliver or administer active compounds.

In some embodiments, the negative pressure gas delivery system 500, as depicted in FIG. 22A, comprises an active oxygen antagonist source in a container 502, connected to a drape 504, via an inlet 506, by a conduit 508. The drape forms a sealed envelope against a tissue site 510, which may a wound site. In some embodiments, the drape has an outlet 512 in communication with a negative pressure source 514, via a conduit 516. In some embodiments a waste canister 518, which may be a removable waste canister, is in communication between the outlet and the negative pressure source. In some embodiments, a return outlet 520 is connection with the container 502 via a conduit 522. In some embodiments, as shown in FIG. 22B, a vaporizer 524 is interposed in the communication between the container 502 and the drape 504.

The conduits may be flexible and may suitably be plastic of a like material hose. The negative pressure source 514, which may suitably be a vacuum pump, is in some embodiments in fluid communication with the outlet 512 via the conduit 516, for the promotion of fluid drainage, as is known in the art. In some embodiments, the waste canister 518 is placed under vacuum through fluid communication to collect drainage fluid. Preferably a filter (not shown), which may be a hydrophobic membrane filter, is interposed between the canister the negative pressure source to protect against contamination from drainage fluids sucked into the canister. In some embodiments, the drape 504 comprises an elastomeric material, which may therefore accommodate pressure changes over the tissue site area during intermittent operation of the negative pressure source. In some embodiments, the periphery of the drape is covered with a pressure sensitive adhesive, which may be acrylic adhesive, for sealing the drape over the tissue site.

Figure 22B:
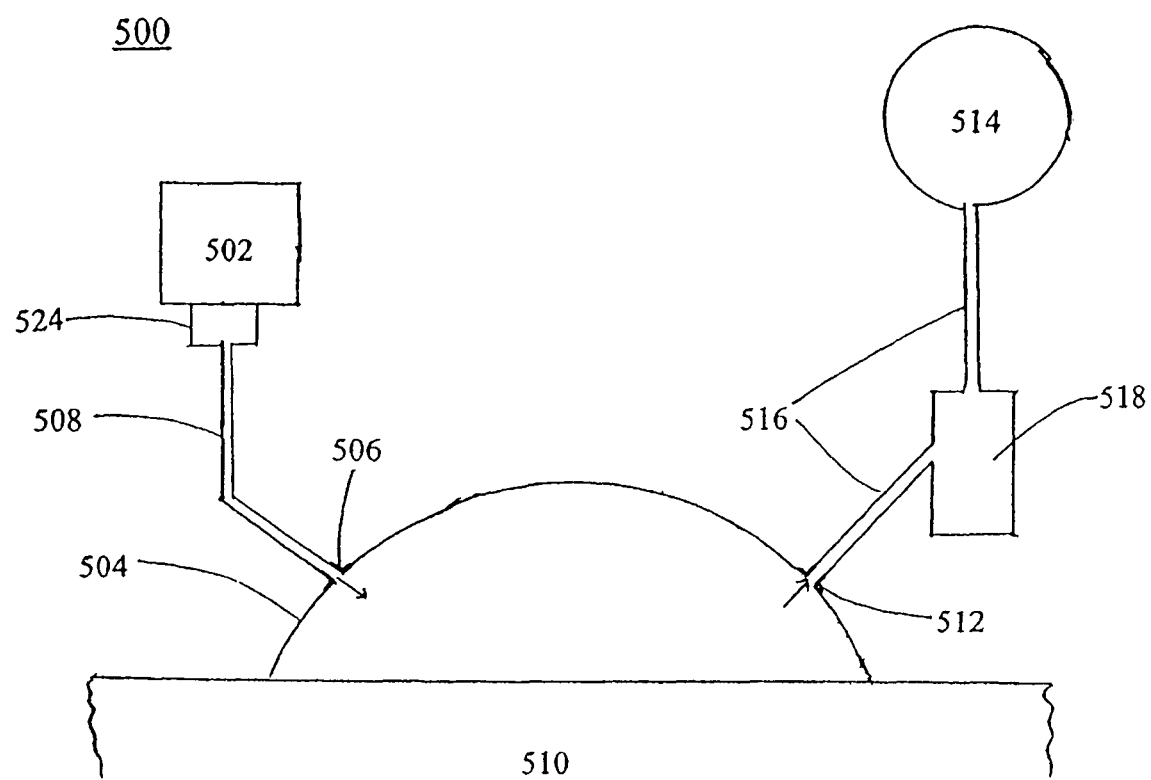

Negative pressure gas delivery systems 300 and 500 as illustrated in FIG. 12 and FIG. 22A-B are useful for treating a variety of areas for treatment, and, in particular, for treating wounds. Wounds that may be treated using the system 300 include infected open wounds, decubitus ulcers, dehisced incisions, partial thickness burns, and various lesions to which flaps or grafts have been attached. Treatment of a wound can be carried out by securing a gas delivery system to the treatment site as previously shown and described, maintaining a substantially continuous or cyclical reduced pressure within the reduced pressure chamber 304 and supplying the active agent to the chamber 304 in a substantially continuous or cyclical fashion until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex. The gas delivery system may be changed periodically, such as at 48 hrs intervals, during treatment, particularly when using a gas delivery system incorporating a screen on or in the wound. The method may be practiced using a negative or reduced pressure ranging from 0.01 to 0.99 atmospheres, or the method may be practiced using a negative or reduced pressure ranging between 0.5 to 0.8 atmospheres. The time period for use of the method on a wound may be at least 12 hrs, but can be, for example, extended for one or more days. There is no upper limit beyond which use of the method is no longer beneficial; the method can increase the rate of closure up to the time the wound actually closes. Satisfactory treatment of various types of wounds may be obtained via the use of reduced pressures equivalent to about 2 to 7 in. Hg below atmospheric pressure.

Supplying reduced pressure to the gas delivery system in an intermittent or cyclic manner, such as described above, may be useful for treating wounds in the presence of the active agent. Intermittent or cyclic supply of reduced pressure to a gas delivery system may be achieved by manual or automatic control of the vacuum system. A cycle ratio, the ratio of "on" time to "off" time, in such an intermittent reduced pressure treatment may be as low as 1:10 or as high as 10:1. A typical ratio is approximately 1:1 which is usually accomplished in alternating 5 minute intervals of reduced pressure supply and non-supply.

A suitable vacuum system includes any suction pump capable of providing at least 0.1 pounds of suction to the wound, or up to three pounds suction, or up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

Embodiments of the present invention also include methods of treating damaged tissue, which include the steps of applying negative pressure to a wound and the active agent for a selected time and at a selected magnitude sufficient to reduce bacterial density in the wound. Open wounds are almost always contaminated with harmful bacteria. Generally a bacterial density of $10^5$ bacterial organisms per gram of tissue is regarded as infected. It is generally accepted that at this level of infection, grafted tissue will not adhere to a wound. These bacteria must be killed, either through the wound host's natural immune response or through some external method, before a wound will close. The application of negative pressure and active agent to a wound may reduce the bacterial density of the wound. It is believed that this effect may be due to the bacteria's incompatibility with a negative pressure environment or the increased blood flow to the wound area in combination with exposure to the active agent, as blood brings with it cells and enzymes to destroy the bacteria. Methods according to embodiments of the present invention can be used to reduce bacterial density in a wound by at least half. In some embodiments, it can be used to reduce bacterial density by at least 1,000-fold or by at least 1,000,000-fold.

Embodiments of the present invention also include methods of treating a burn which include the steps of applying negative pressure and the active agent to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24-48 hrs into a full thickness burn, one in which all epidermal structures are destroyed. The application of negative pressure and an amount of the active agent to the wound may prevent the infection from becoming sufficiently severe to cause destruction of the underlying epidermal structures. The magnitude, pattern, and duration of pressure application can vary with the individual wound.

Embodiments of the present invention also include methods for enhancing the attachment of living tissue to a wound which comprises the steps of first joining the living tissue to the wound to form a wound-tissue complex, then applying a negative or reduced pressure of selected magnitude and an amount of the active agent to the wound-tissue complex over an area sufficient to promote migration of epithelia and subcutaneous tissue toward the complex, with the negative pressure and exposure to the active agent being maintained for a selected time period sufficient to facilitate closure of the wound. Attachment of living tissue to a wound is a common procedure that can take many forms. For example, one common technique is the use of a "flap," a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure and active agent to the wound-graft complex reduces bacterial density in the complex and improves blood flow to the wound, thereby improving the attachment of the grafted tissue.

I. Other Apparatuses

Within certain embodiments of the invention, it may be desirable to supplement the methods of the present invention for the treatment of patients who will be or have been subjected to trauma with the ability to externally manipulate the core body temperature of the patient. In this regard, the core body temperature of a patient may be, in combination with the methods of the present invention, manipulated by invasive or non-invasive routes. Invasive methods for the manipulation of core body temperature include, for example, the use of a heart-lung pump to heat or cool the patient's blood thus raising or cooling the patient's core body temperature. Non-invasive routes to manipulate core body temperature include systems and apparatuses that transfer heat into or out of the patient's body.

J. Further Delivery Devices or Apparatuses

In some embodiments it is contemplated that methods or compositions will involve a specific delivery device or apparatus. Any method discussed herein can be implemented with any device for delivery or administration including, but not limited, to those discussed herein.

For topical administration of active compounds of the invention may be formulated as solutions, gels, ointments, creams, suspensions, etc. as are well-known in the art. Systemic formulations may include those designed for administration by injection or infusion, e.g., subcutaneous, intravenous, intramuscular, intrathecal or intraperitoneal injection, as well as those designed for transdermal, transmucosal, oral or pulmonary administration.

For oral administration, the active compounds of the invention to be formulated as tablets, pills, dragees, capsules, liquids, gels, syrups, slurries, suspensions and the like, for oral ingestion by a patient to be treated or oral liquid preparations such as, for example, suspensions, elixirs and solutions.

For buccal administration, the compositions may take the form of tablets, lozenges, etc. formulated in conventional manner. Other intramucosal delivery might be by suppository or intranasally.

For administration directly to the lung by inhalation the compound of invention may be conveniently delivered to the lung by a number of different devices. For example, Metered-Dose Inhalers (MDIs): a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver the compound of invention directly to the lung. MDI devices are available from a number of suppliers such as 3M Corporation (e.g., on the world wide web at 3m.com/us/healthcare/manufacturers/dds/pdf/idd_valve_canister_brochure.pdf-), Nasacort from Aventis (e.g., world wide web at products.sanofi-aventis.us/Nasacort_HFA/nasacort_HFA.html-63k-), Boehringer Ingelheim, (e.g., world wide web at .boehringer-ingelheim.com/corporate/home/download/r_and_d2003.pdf) Aerobid from Forest Laboratories, (e.g., world wide web at .frx.com/products/aerobid.aspx) Glaxo-Wellcome, (for example, on the world wide web at .gsk.com/research/newmedicines/newmedicines_pharma.html) and Schering Plough, (world wide web at .schering-plough.com/schering_plough/pc/allergy_respiratory.jsp).

Dry Powder Inhalers (DPIs): DPI devices typically use a mechanism such as a burst of gas to create a cloud of dry powder inside a container, which may then be inhaled by the patient. DPI devices are also well known in the art and may be purchased from a number of vendors which include, for example, Foradil aerolizer from Schering Corporation, (e.g., world wide web .spfiles.com/piforadil.pdf) Advair Diskus from Glaxo-Wellcome. (e.g., world wide web at us.gsk.com/products/assets/us_advair.pdf-) A popular variation is the multiple dose DPI ("MDDPI") system, which allows for the delivery of more than one therapeutic dose. MDDPI devices are available from companies such as Plumicort Turbuhaler from AstraZeneca, (e.g., world wide web at .twistclickinhale.com/ GlaxoWellcome, (e.g., world wide web at us.gsk.com/products/assets/us_advair.pdf-) and Schering Plough, (e.g., world wide web at .schering-plough.com/schering_plough/pc/allergy_respiratory.jsp). It is further contemplated that such devices, or any other devices discussed herein, may be altered for single use.

Electrohydrodynamic (EHD) aerosol delivery: EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807. EHD aerosol devices may more efficiently deliver drugs to the lung than existing pulmonary delivery technologies.

Nebulizers: Nebulizers create aerosols from liquid drug formulations by using, for example, ultrasonic energy to form fine particles that may be readily inhaled Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974), Intal nebulizer solution by Aventis, (e.g., world wide web at .fda.gov/medwatch/SAFETY/2004/feb_PI/Intal_Nebulizer_PI.pdf).

For administration of a gas directly to the lungs by inhalation various delivery methods currently available in the market for delivering oxygen may be used. For example, a resuscitator such as an ambu-bag may be employed (see U.S. Pat. Nos. 5,988,162 and 4,790,327). An ambu-bag consists of a flexible squeeze bag attached to a face mask, which is used by the physician to introduce air/gas into the casualty's lungs.

A portable, handheld medicine delivery device capable producing atomized agents that are adapted to be inhaled through a nebulizer by a patient suffering from a respiratory condition. In addition, such delivery device provides a means wherein the dose of the inhaled agent can be remotely monitored and, if required altered, by a physician or doctor. See U.S. Pat. No. 7,013,894. Delivery of the compound of invention may be accomplished by a method for the delivery of supplemental gas to a person combined with the monitoring of the ventilation of the person with both being accomplished without the use of a sealed face mask such as described in U.S. Pat. No. 6,938,619. A pneumatic oxygen conserving device for efficiently dispensing oxygen or other gas used during respiratory therapy such that only the first part of the patient's breath contains the oxygen or other therapeutic gas. (See U.S. Pat. No. 6,484,721). A gas delivery device is used which is triggered when the patient begins to inhale. A tail of gas flow is delivered to the patient after the initial inhalation timed period to prevent pulsing of gas delivery to the patient. In this manner gas is only delivered to the patient during the first portion of inhalation preventing gas from being delivered which will only fill the air passageways to the patient's lungs. By efficiently using the oxygen, cylinder bottles of oxygen used when a patient is mobile will last longer and be smaller and easier to transport. By pneumatically delivering the gas to the patient no batteries or electronics are used.

All the devices described here may have an exhaust system to bind or neutralize the compound of invention.

Transdermal administration of the compound of the invention can be achieved by medicated device or patch which is affixed to the skin of a patient. The patch allows a medicinal compound contained within the patch to be absorbed through the skin layers and into the patient's blood stream. Such patches are commercially available as Nicoderm CQ patch from Glaxo Smithkline, (world wide web at nicodermcq-.com/NicodermCQ.aspx\) and as Ortho Evra from Ortho-McNeil Pharmaceuticals, (world wide web at .ortho-mcneil-pharmaceutical.com/healthinfo/womenshealth/products/orthoevra.html). Transdermal drug delivery reduces the pain associated with drug injections and intravenous drug administration, as well as the risk of infection associated with these techniques. Transdermal drug delivery also avoids gastrointestinal metabolism of administered drugs, reduces the elimination of drugs by the liver, and provides a sustained release of the administered drug. Transdermal drug delivery also enhances patient compliance with a drug regimen because of the relative ease of administration and the sustained release of the drug.

Other modifications of the patch include the Ultrasonic patch which is designed with materials to enable the transmission of ultrasound through the patch, effecting the delivery of medications stored within the patch, and to be used in conjunction with ultrasonic drug delivery processes (see U.S. Pat. No. 6,908,448). Patch in a bottle (U.S. Pat. No. 6,958,154) includes a fluid composition, e.g., an aerosol spray in some embodiments, that is applied onto a surface as a fluid, but subsequently dries to form a covering element, such as a patch, on a surface of a host. The covering element so formed has a tack free outer surface covering and an underlying tacky surface that helps adhere the patch to the substrate.

Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers. See U.S. Pat. No. 6,464,687.

PUMPS and Infusion Devices: An infusion pump or perfusor infuses fluids, medication or nutrients into a patient's circulatory system. Infusion pumps can administer fluids in very reliable and inexpensive ways. For example, they can administer as little as 0.1 mL per hour injections (too small for a drip), injections every minute, injections with repeated boluses requested by the patient, up to maximum number per hour (e.g. in patient-controlled analgesia), or fluids whose volumes vary by the time of day. Various types of infusion devices have been described in the following patent applications before the United States Patent and Trademark Office. These include but are not limited to U.S. Pat. No. 7,029,455 U.S. Pat. No. 6,805,693, U.S. Pat. No. 6,800,096, U.S. Pat. No. 6,764,472, U.S. Pat. No. 6,742,992, U.S. Pat. No. 6,589,229, U.S. Pat. No. 6,626,329, U.S. Pat. No. 6,355,019, U.S. Pat. No. 6,328,712, U.S. Pat. No. 6,213,738, U.S. Pat. No. 6,213,723, U.S. Pat. No. 6,195,887, U.S. Pat. No. 6,123,524 and U.S. Pat. No. 7,022,107. In addition, infusion pumps are also available from Baxter International Inc. (world wide web at .baxter.com/products/medication_management/infusion-_pumps/), Alaris Medical Systems (world wide web at alarismed.com/products/infusion.shtml) and from B Braun Medical Inc. (world wide web at bbraunusa.com/index.cfm?uuid=001AA837D0B759A1E34666434FF604ED).

Oxygen/Gas bolus delivery device: Such a device for delivering gas to Chronic Obstructive Pulmonary Disease (COPD) patients is a available from Tyco Healthcare (world wide web at .tycohealth-ece.com/files/d0004/ty_zt7ph2.pdf). It can also be used to deliver the compound of invention. The above device is cost-effective, lightweight, inconspicuous and portable.

"Patch in a bottle" (U.S. Pat. No. 6,958,154) includes a fluid composition, e.g., an aerosol spray in some embodiments, that is applied onto a surface as a fluid, but subsequently dries to form a covering element, such as a patch, on a surface of a host. The covering element so formed has a tack free outer surface covering and an underlying tacky surface that helps adhere the patch to the substrate.

Implantable Drug Delivery System: Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers. See U.S. Pat. No. 6,464,687.

The contents of each of the cited patents and web addresses discussed in this section are hereby incorporated by reference.

VIII. Combination Therapies

The compounds and methods of the present invention may be used in the context of a number of therapeutic and diagnostic applications. In order to increase the effectiveness of a treatment with the compositions of the present invention, such as oxygen antagonists or other active compounds, it may be desirable to combine these compositions with other agents effective in the treatment of those diseases and conditions (secondary therapy). For example, the treatment of stroke (antistroke treatment) typically involves an antiplatelet (aspirin, clopidogrel, dipyridamole, ticlopidine), an anticoagulant (heparin, warfarin), or a thrombolytic (tissue plasminogen activator).

Various combinations may be employed; for example, an active compound, such as $H_2S$, is "A" and the secondary therapy is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

-continued

B/B/A/A B/A/B/A B/A/A/B A/A/A/B B/A/A/A A/B/A/A

A/A/B/A

Administration of the oxygen antagonists and/or other active compounds of the Spresent invention to biological matter will follow general protocols for the administration of that particular secondary therapy, taking into account the toxicity, if any, of the oxygen antagonist (or other active compound) treatment. It is expected that the treatment cycles would be repeated as necessary. It also is contemplated that various standard therapies, as well as surgical intervention, may be applied in combination with the described therapies.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preservation of Nematodes in Carbon Monoxide

The atmosphere contains 210,000 ppm oxygen. Exposure to low levels of oxygen, or hypoxia, results in cellular damage and death in humans. In the nematode, C. elegans, oxygen concentrations between 100 ppm and 1000 ppm are also lethal. By critically studying the response of nematodes to a range of oxygen tensions, it was found that oxygen concentrations below 10 ppm and above 5000 ppm are not lethal. In 10 ppm oxygen balanced with nitrogen, nematodes enter into a state of reversible suspended animation in which all aspects of animation observable under the light microscope ceases (Padilla et al., 2002). In oxygen concentrations of 5000 ppm (balanced with nitrogen) and above, nematodes progress through their life cycle normally. In a search for drugs that protect nematodes against hypoxic damage, carbon monoxide was tested.

To achieve specific atmospheric conditions the following apparatus was used: a glass syringe barrel having a tip with a locking device such as a LUER-LOK with the large opening of the barrel sealed with a custom-machined steel and rubber fitting to make an airtight seal was locked to via locking device to the inlet port of an environmental chamber having an inlet and an outlet port each fitted with a locking devices such as a LUER-LOK fitting. A defined gas was humidified and provided to the environmental chamber by first venting the gas from a compressed tank (Byrne Specialty Gas, Seattle, Wash.) through a gas washing bottle (500 ml Kimex) filled with double distilled water. The gas washing bottle was connected to the environmental chamber past a gas-flow meter. A gas flow meter was used to provide a regulated 70 cc/min flow through the environmental chamber throughout the 24 hr incubation.

To test whether induced, reversible stasis could be achieved in C. elegans nematodes, 2-cell C. elegans embryos, L3 larvae or adult nematodes were collected and exposed to either an environment of effectively 100% CO, an environment of 100% $N_2$, an environment comprising 500 ppm oxygen balanced with carbon monoxide, or to environments comprising 100, 500 or 1000 ppm oxygen balanced with nitrogen at room temperature. Nematodes were visualized using differential interference contrast microscopy (also known as Nomarski optics). Images were collected and analyzed using NIH image and Adobe Photoshop 5.5. Embryos are approximately 50 µm in length.

Results of these experiments showed that 100% carbon monoxide was not lethal and induced reversible suspended animation. Nematodes did not survive 500 ppm oxygen balances with nitrogen, however, those treated with 500 ppm oxygen balanced with carbon monoxide entered into suspended animation and survived. See below:

Example 2

Preservation of Human Skin in Carbon Monoxide

Carbon monoxide is extraordinarily toxic to humans because it strongly competes with oxygen for binding to hemoglobin, the primary molecule that distributes oxygen to tissues. The fact that nematodes, which do not have hemoglobin, are resistant to carbon monoxide and even protected against hypoxic damage by this drug suggested the possibility that carbon monoxide would protect against hypoxic damage in human tissue in situations where blood is not present, such as in tissue transplant or blood free surgical fields. To tested this hypothesis using human skin.

Three human foreskins were obtained for this purpose. The foreskin tissue was preserved in keratinocyte growth medium (KGM) containing insulin, EGF (0.1 ng/ml), hydrocortisone (0.5 mg/ml) and bovine pituitary extract (approx. 50 micrograms/ml of protein). Foreskins were rinsed in PBS, and excess fatty tissue was removed. Each foreskin sample was divided into 2 equal pieces. Each piece was placed into a separate container containing a solution of PBS with 24 mg/ml of Dispase II (from Bacillus Polymyxa EC 3.4.24.4: Roche Diagnostics Corp., Indianapolis, Ind.). One container (containing a foreskin piece in PBS with Dispase II) was kept in a humid chamber in a fume hood. The other container (with the other half of the foreskin in PBS with Dispase II) was placed in the same fume hood in an environmental chamber perfused with humidified 100% CO. Both samples were maintained at room temperature for 24 hrs. Methods used to establish defined atmospheric conditions were identical to those used in Example 1.

Following the 24 hr exposure to normoxia or 100% CO, keratinocytes were isolated from the foreskins according to the method described by Boyce et al. (1983; 1985; each of which is incorporated herein by reference in its entirety). Briefly, the epidermis from each foreskin sample was removed to a fresh dish containing PBS. The epidermis was minced and homogenized prior to incubation in 3 ml of 0.05% Trypsin, 1 mM EDTA for 5 minutes, at room temperature, to separate basal cells from the epidermis. After incubation, 6 ml of 400 µg/ml (micrograms per ml) Soybean Trypsin Inhibitor, 1 mg/ml BSA was added and the samples were centrifuged at 900 RPM. The supernatant from each sample was discarded and the sample pellets were resuspended in 10 ml of KGM. Each sample was split into two 10 cm plates each of which contained 5 ml KGM and 100 µl of HEPES pH 7.3 (N-2-hydroxyethylpiperazine-N'-2-ethane sulfonic acid). The plates were incubated in a 37° C. incubator perfused with 95% room air, 5% carbon dioxide for five days.

Cells were inspected visually using an inverted phase contrast microscope. All three of the keratinocyte populations exposed to normoxia showed little or no growth. All three of the keratinocyte populations exposed to 100% CO showed significant growth. Quantitation of the number of viable keratinocytes as judged by colony formation was quantified for two of the three foreskins. See FIG. 1.

TABLE 1

Quantitation of Colony Formation

| Foreskin | Atmosphere | Total colonies |
|---|---|---|
| 1 | 100% CO | 542 colonies (many of which were very large) |
| 1 | Normoxia | 2 colonies (both small) |
| 2 | 100% CO | 780 colonies (many of which were very large) |
| 2 | Normoxia | 0 colonies |

Example 3

Further Preservation Experiments with Nematodes

The following example contains information that overlaps and extends the information disclosed in Example 1.

A. Materials and Methods

Environmental Chambers and Apparati.

Oxygen deprivation experiments were carried out using a custom atmospheric chamber designed by W. Van Voorhies (Van Voorhies et al., 2000). The chamber is a 30 mL glass syringe (Fisher #14-825-10B) fitted with a custom steel stopper that is lined with two viton o-rings to ensure a tight seal. The stopper is bored through and has a steel lure lock on the exterior face so that a hose carrying compressed gas can be attached. A defined gas mixture is delivered to the chamber at a constant pressure and flow rate from compressed tanks by passing first through a rotometer (Aalborg, flow-tube number 032-41ST) or mass flow controller (Sierra Instruments #810) to monitor flow rate and then through a 500 ml gas washing bottle (Fisher #K28220-5001) containing 250 ml water to hydrate the gas. ¼" OD nylon (Cole-Parmer #P-06489-06) or FEP (Cole-Parmer #A-06450-05) tubing was used and connections between tubing and the regulators and between the tubing and the rotometers were made with brass John-Guest-type fittings (Byrne Gas). All other connections were made with either microflow quick-connect fittings (Cole-Parmer #A-06363-57, #A-06363-52) or standard lure fittings (Cole-Parmer #A-06359-37, #A-06359-17).

Viability of Nematodes in Hypoxia.

Bristol strain N2 were continuously maintained at 20° C. with care taken to ensure the population did not starve. Log-phase, adult *C. elegans* were picked into a drop of sterile water containing 100 µg/ml ampicillin, 15 µg/ml tetracycline and 200 µg/ml streptomycin on a glass plate. Adults were chopped with a razor blade and 2-cell embryos were picked using a mouth pipet. 30-60 2-cell embryos were transferred to a small glass boat (custom made to fit atmospheric chambers, Avalon Glass Works, Seattle Wash.) filled with 3 ml of 1% agarose in M9. Boats were then placed into a humid chamber for 2 hours to allow the embryos to age and then placed into the environmental chamber. The environmental chambers were continuously perfused at room temperature with either pure $N_2$ (grade 4.5), 160 ppm $O_2/N_2$, 500 ppm $O_2/N_2$, 1000 ppm $O_2/N_2$, or 5000 ppm $O_2/N_2$ at 70 cc/min for 24 hrs. Following exposure, agarose chunks containing the embryos were cut out of the boat and placed with embryos facing up onto a medium-sized NGM plate seeded with *E. coli* (OP50). Embryos were scored for hatching 24 hours after exposure and hatched L1's were transferred to the surface of the NGM plate and followed to adulthood. Animals that could not be accounted for were dropped from the total. All gases were supplied by Byrne Gas (Seattle, Wash.). The pure $N_2$ was guaranteed to contain less than 10 ppm impurities and all $O_2/N_2$ mixtures were certified to ±2% of the oxygen content (e.g., 100 ppm $O_2/N_2$ was certified to contain between 98 ppm $O_2$ and 102 ppm $O_2$). Parts per million to kPa conversion was based on 1 million parts=101 kPa at 1 atmosphere.

Viability of Nematodes in Carbon Monoxide Based Atmospheres.

30-60 embryos were harvested from continuously maintained Bristol N2 and hif-2(ia04) strains as described above. Environmental chambers were continuously perfused at room temperature with pure CO (grade CP) or 500 ppm $O_2/CO$ at 70 cc/min for 24 hrs. To achieve 2500 ppm $O_2/CO$ or 2500 ppm $O_2/N_2$, 5000 ppm $O_2/N_2$ was mixed at a 1:1 ratio with either pure CO or pure $N_2$ using two mass flow controllers (Sierra Instruments 810) to precisely monitor flow. Each gas was delivered into a 3-way valve (Cole-Parmer #A-30600-23) at 50 cc/min and the resulting mixture was then passed through a gas washing bottle and into an environmental chamber throughout the 24 hour exposure. All gases were supplied by Byrne Gas (Seattle, Wash.). The 500 ppm $O_2/CO$ mixture was certified to 2% of the oxygen content and contained 7000 ppm $N_2$ to ensure a consistent $O_2/CO$ ratio throughout the use of the tank.

Cell Biological Analysis.

To determine the extent of developmental progression in nitrogen-based atmospheres (Table 2), 2-cell embryos were exposed to various degrees of hypoxia as described above and were either immediately photographed, or photographed following a 12 hr recovery period in a humid chamber. To determine whether embryos arrested in carbon monoxide-based atmospheres, 2-cell embryos were aged in room air for two hours and were either photographed immediately or put into 100% carbon monoxide or 0.05 kPa $O_2/CO$ for 24 hours and photographed immediately following the exposure. In all cases, DIC microscopy was done by placing embryos under a cover slip on a thin 1% agarose pad and viewing on a Zeiss axioscope. Photographs were taken using RS Image and Adobe Photoshop software.

B. Results

Figure 2:
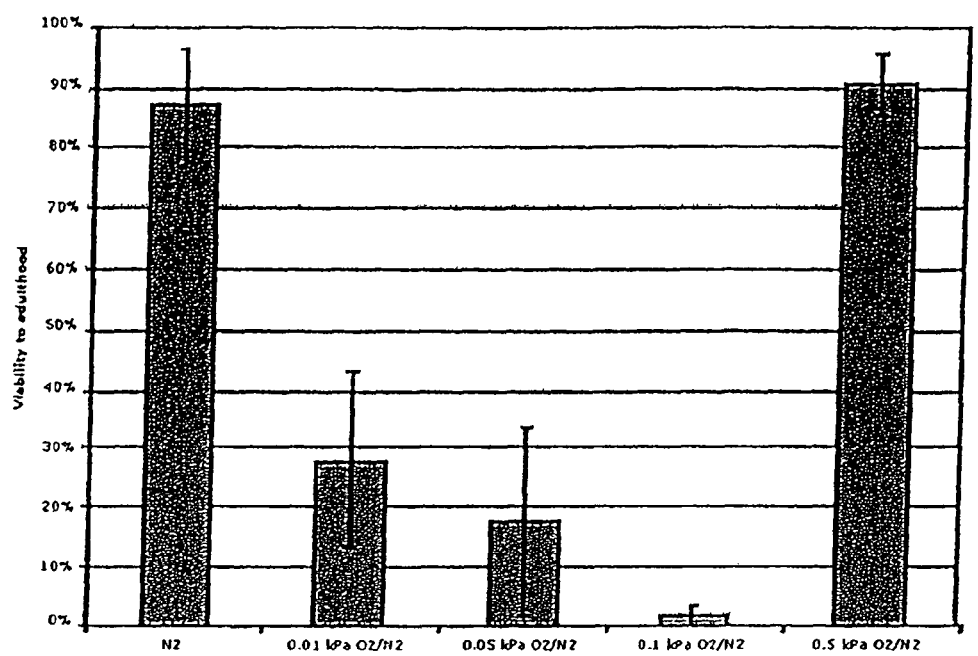
FIG. 2 Discontinuity of survivability in hypoxia. Viabilities to adulthood were assayed following exposure to 24 hours of anoxia (pure $N_2$), intermediate hypoxia (0.01 kPa $O_2$, 0.05 kPa $O_2$ or 0.1 kPa $O_2$) or mild hypoxia (0.5 kPa $O_2$) in wild-type embryos. All data points are the result of at least 3 independent experiments and worms that could not be accounted for were dropped from the total.

HIF-1 has been previously reported to be required in *C. elegans* in mild hypoxia (0.5 kPa $O_2$ (Padilla et al., 2002) and 1 kPa $O_2$ (Jiang et al., 2001)) and suspended animation is known to be possible in anoxia (>0.001 kPa $O_2$) (Padilla et al., 2002). To precisely define the ranges in which each of these responses are active, the viability of wild-type *C. elegans* embryos was determined following exposure to various oxygen tensions between mild hypoxia and anoxia for 24 hrs. Embryos exposed to anoxia entered suspended animation as previously reported, and thus survived the exposure with high viability. Embryos in 0.5 kPa $O_2$ remained animated throughout the exposure and also survived with high viability. However, embryos exposed to an intermediate range of oxygen tensions between mild hypoxia and anoxia (0.1 kPa $O_2$ to 0.01 kPa $O_2$) surprisingly did not survive (FIG. 2).

Embryos did not hatch during exposure to this intermediate range of hypoxia, indicating that they did not successfully execute the HIF-1 mediated response. To determine if they appeared suspended, it was examined whether embryos in this intermediate range arrested embryogenesis during the exposure. Embryos in lethal oxygen tensions did not arrest embryogenesis, and increased amounts of oxygen correlated with an increase in the extent of developmental progression in the embryo (Table 2). Upon reoxygenation, the majority of these embryos failed to hatch and many of those that did hatch arrested as abnormal L1s. These data show that this intermediate range of hypoxia is a unique stress in which oxygen levels are neither sufficiently high to facilitate continued animation nor sufficiently low to induce suspended animation.

Figure 3:
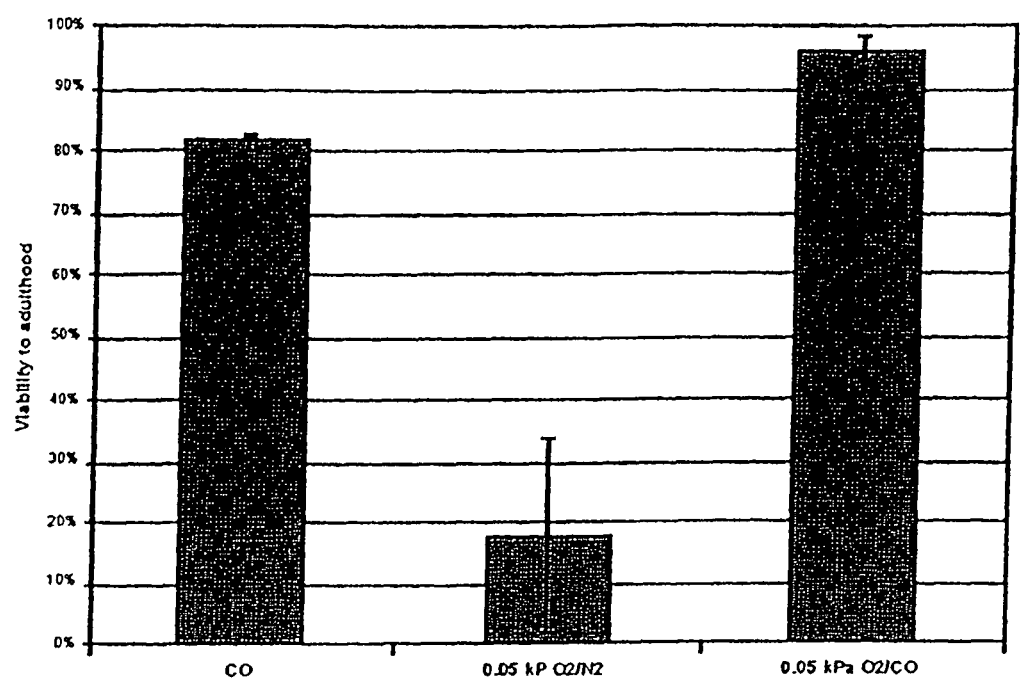
FIG. 3 Carbon monoxide protects against hypoxia. Viabilities to adulthood were assayed following exposure to 24 hours of pure carbon monoxide, 0.05 kPa $O_2/N_2$ or 0.05 kPa $O_2$/CO in wild-type embryos. All data points are the result of at least 3 independent experiments and worms that could not be accounted for were dropped from the total.

Based on these findings, it was hypothesized that if carbon monoxide, a competitive inhibitor of oxygen binding, could induce suspended animation in the presence of low levels of oxygen, it would provide protection against this lethal range of hypoxia. To examine this possibility, the viability of C. elegans embryos in various concentrations of carbon monoxide was first determined. Despite the toxic effects that high levels of carbon monoxide can have in some systems, C. elegans embryos was found to be remarkably tolerant to a wide range of carbon monoxide tensions. In fact, C. elegans embryos can withstand a continuous exposure to 101 kPa CO (100% CO) for 24 hrs with high viability (81.5% survival to adulthood, FIG. 3). Notably, in 101 kPa CO, embryos did not progress through embryogenesis during the exposure, indicating that they entered into suspended animation. To test whether carbon monoxide could protect embryos in the presence of lethal oxygen tensions, the viability of embryos exposed to 0.05 kPa $O_2$ balanced with carbon monoxide was determined. In contrast to embryos exposed to 0.05 kPa $O_2$ balanced with $N_2$ (most of which do not survive), these embryos recovered with 96.2% viability to adulthood (FIG. 3). Moreover, like embryos treated with 101 kPa CO, embryos in 0.05 kPa $O_2$ balanced with carbon monoxide arrested embryogenesis, indicating that they entered into suspended animation. Therefore, carbon monoxide can protect against hypoxic damage in the presence of lethal oxygen tensions by inducing suspended animation.

To further examine the range of oxygen tensions that can be protected by excess carbon monoxide, embryos lacking HIF-1 function (the hif-1(ia04) strain) were used to address whether protection against hypoxic damage was also possible in mild hypoxia. After testing various oxygen tensions between 0.1 kPa $O_2$ and 1 kPa $O_2$ balanced with nitrogen, it was found that the maximal requirement for HIF-1 was in 0.25 kPa $O_2$ balanced with nitrogen. In this atmosphere, wild-type embryos progress normally through development and exhibit high viability, but hif-1(ia04) embryos do not complete embryogenesis and exhibit 100% lethality (Table 3). Therefore, it was examined whether carbon monoxide could protect hif-1(ia04) embryos in 0.25 kPa $O_2$. In 0.25 kPa $O_2$ balanced with carbon monoxide, both wild-type and hif-1 (ia04) embryos entered into suspended animation and survived the exposure with high viabilities (78.7% and 84.0% survival to adulthood, respectively) (Table 3). Thus, the induction of suspended animation by carbon monoxide is possible at oxygen tensions as high as 0.25 kPa $O_2$, and carbon monoxide can protect against mild hypoxia, even in the absence of HIF-1 function.

TABLE 2

Quantitation of developmental progression in hypoxia

| Atmosphere | Percent of embryos within range | Range of embryogenesis (min post 2-cell stage) | N |
|---|---|---|---|
| >0.001 kPa $O_2/N_2$ | 100% ± 0.0 | 20-40 min | 35 |
| 0.01 kPa $O_2/N_2$ | 92.9% ± 6.0 | 40-80 min | 115 |
| 0.05 kPa $O_2/N_2$ | 97.7% ± 2.0 | 100-140 min | 108 |
| 0.1 kPa $O_2/N_2$ | 91.4% ± 1.3 | 300-340 min | 60 |

Wild-type 2-cell embryos were placed into various degrees of hypoxia for 24 hrs and scored for the extent to which they progressed through embryogenesis. Exposure to atmospheres containing increased amounts of oxygen resulted in increased progression through embryogenesis. The percent of embryos that arrested within a given 20-40 minute range of embryogenesis was determined. Data are the result of 3 independent experiments.

TABLE 3

Carbon monoxide protects hif-1 embryos against mild hypoxia

| | 0.25 kPa $O_2/N_2$ | n | 0.25 kPa $O_2$/CO | N |
|---|---|---|---|---|
| N2 | 94.2% ± 1.2 | 49 | 78.7% ± 21.9 | 109 |
| hif-1 (ia04) | 0.0% ± 0.0 | 68 | 83.9% ± 13.8 | 108 |

Viability of Nematodes in Response to Hypothermia.

Figure 15:
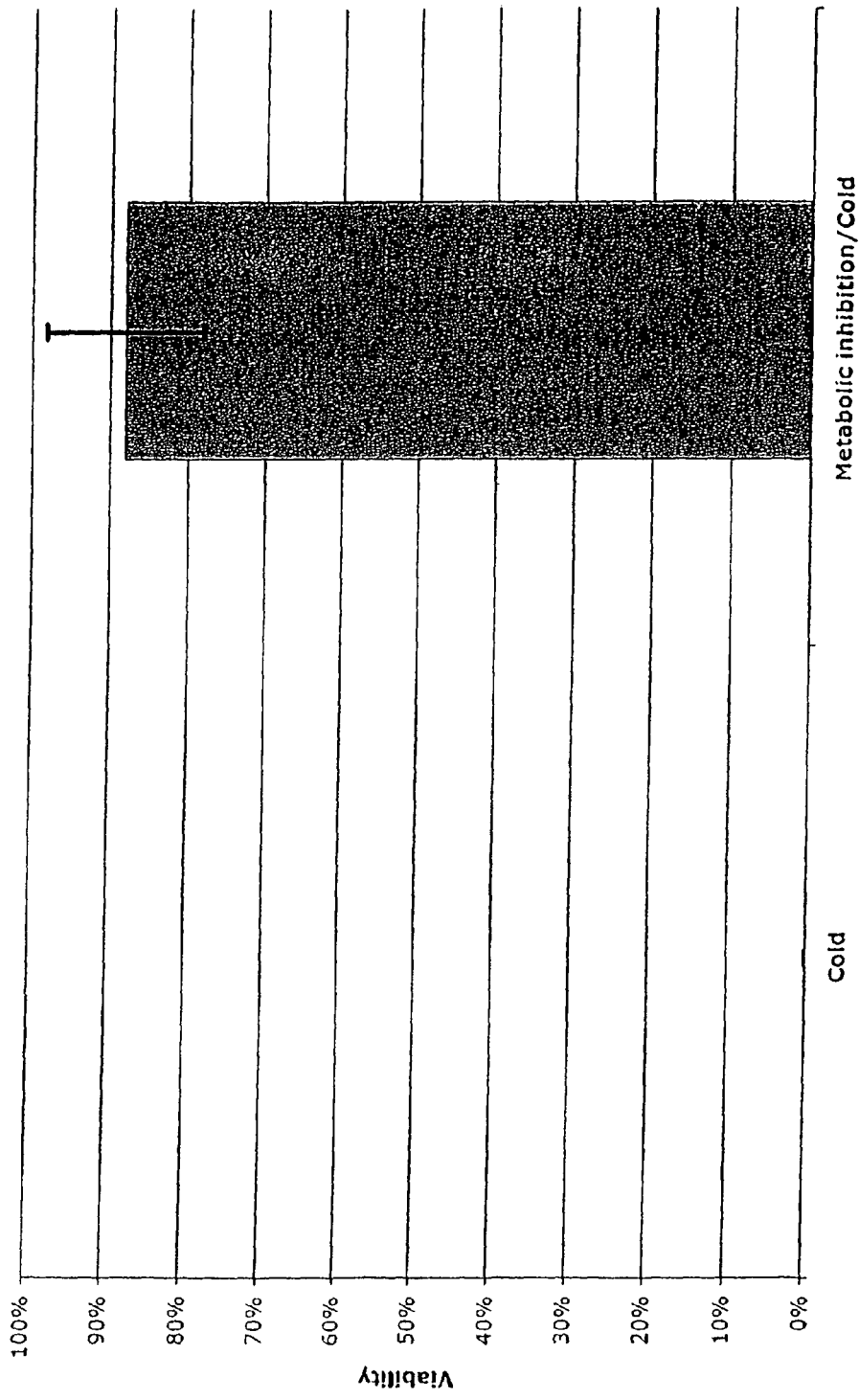
FIG. 15 Metabolic inhibition protects against hypothermia-induced death in Nematodes. Nematodes exposed to cold temperatures (4° C.) are unable to survive after 24 hours. However, if kept in anoxic conditions during the period of hypothermia (and for a 1 hour period before and after), a substantial proportion of the nematodes survive.

Viability of nematodes is also temperature sensitive, with 100% of a population being dead after a 24 hr exposure to cold temperature (4° C.; FIG. 15). However, if the nematodes are induced into stasis by equilibration into anoxic conditions (<10 ppm oxygen) for 1 hr prior to the temperature drop, a substantial proportion of them survive after a 24 hr exposure to 4° C. (FIG. 15). In this experiment, the nematodes were kept in stasis during the period of hypothermia, and for one hour after they have been returned to room temperature. Anoxic conditions (pure $N_2$), growth conditions, and viability measurements are described below.

Example 4

Reduction of Core Body Temperature and Respiration in Mice

A. Materials and Methods

Implantation of Telemetry Devices.

Female C57BL/6J mice (Jackson Laboratories—Bar Harbor, Me.) were implanted with telemetry devices (PDT-4000 HR E-Mitter—MiniMitter Inc.—Bend, Oreg.) according to standard protocol provided by the manufacturer. Mice were allowed to recover for several weeks to permit body temperature and heart rate signals to stabilize. Core body temperature, heart rate, and movement of the mice were continuously monitored via the telemetry devices and recorded using Vital-View software (provided by MiniMitter). Ambient temperature was monitored using a HOBO (Onset Computer Corp.—Pocasset, Mass.) and the data analyzed using BoxCar software (provided by Onset Computer Corp.).

Exposure of Mice to Regulated Atmosphere.

Each mouse was exposed to 1 L/min of either (a) an atmosphere containing 500 ppm $H_2S$ balanced nitrogen (Byrne Specialty Gas—Seattle, Wash.) mixed with room air (using a 3 channel gas proportioner meter from Aalborg—Orangeburg, N.Y.) to give a final concentration of 80 ppm $H_2S$ and 17% $O_2$, or (b) an atmosphere of nitrogen mixed with room air to give a final concentration of 17% $O_2$. $H_2S$ and $O_2$ measurements were taken using an Innova GasTech GT series portable gas monitor (Thermo Gas Tech—Newark, Calif.).

Prior to and during exposure to testing in regulated and unregulated atmospheres, the mice were placed in a gassing chamber comprising a glass cage (with drinking water and no food) fitted with import and export tubes of FEP tubing from Cole-Parmer (Vernon Hills, Ill.) for introduction and venting of the atmosphere. The cage was sealed with a lid using Dow Corning silicone vacuum grease (Sigma—St. Louis, Mo.). The gas from each cage was vented through the export tube into the chemical hood. To ensure that the system was gastight, a GasTech GT portable monitor was used to detect leaks.

Respirometry.

In some experiments, the consumption of oxygen was measured by use of a PA-10a $O_2$ analyzer (Sable Systems) which was used according to manufacturers instructions. Similarly, the carbon dioxide being produced by the animals was monitored using a LI-7000 $CO_2/H_2O$ analyzer (Li-Cor company) used according to the manufacturers instructions. These instruments were placed in line with the environmental chambers such that they sample the gas import and export tubing.

Regulation of Ambient Temperature.

Mice were housed in a Shel Lab low temperature diurnal illumination incubator (Sheldon Manufacturing Inc. —Cornelius, Oreg.) to regulate both temperature and light cycle (8 AM lights on, 8 PM lights off) for the mice. Mice were exposed to regulated atmosphere as described above. When the mice were exposed to the regulated atmosphere, the temperature inside the incubator was dropped to the desired temperature, for example, to 10° C. or 15° C. The mice were maintained in the regulated atmosphere and at the lowered temperature for six hours. The atmosphere in the gassing chamber was replaced with room air and the mice were returned to normal room temperature (22° C.) and allowed to recover.

B. Results

Baseline Data.

To determine the response of mice to sub-lethal doses of hydrogen sulfide, the inventor first established baselines of core temperature, heart rate and movement by recording data over a one-week period from four mice with implanted transceivers in the incubator held at ambient temperature and perfused with room air. The baseline data demonstrated that the mice have a circadian rhythm with peak of activity in the evening just after the lights are turned off, and in the early morning just before the lights are turned on. The core temperature varied from a high of 37° C. during their active periods to a low of 33.5° C. during their inactive periods. The heart rate varied from 750 bpm (beats per minute) during their active periods to 250 bpm during their inactive periods. Heart rate is likely to be correlated with core temperature (higher temp higher heart rate). Likewise gross motor movement was highest during the evening and just before dawn.

Exposure of Mice to Regulated Atmospheres at Room Temperature.

The first trial of the exposure of a mouse to hydrogen sulfide involved first placing the mouse into the gassing chamber held at 27° C. in the incubator for one hour. After the hour, the chamber was perfused with 80 ppm as generally described above and the temperature of the incubator was lowered to 18° C. for the duration of the experiment. While no immediate changes in heart rate and gross motor movement were detected, a dramatic decrease in core temperature was observed. The experiment was allowed to proceed for 90 min. during which time the core temperature dropped to 28.6° C.—five degrees below the lowest recording for any of the four mice in the baseline study described above. During recovery after the chamber was perfused with room air, the inventor noticed that the animal at first was relatively immobile (easy to catch); however within 60 min. it had returned to a normal range of core temperature and activity. A second mouse was exposed to the same protocol; however this time the gassing at 80 ppm was conducted for 3 hrs. During this time, the inventor noted that heart rate dropped significantly from 600 bpm to 250 bpm, gross motor movement showed almost no activity, and the core temperature dropped to 18.6° C.

Changes in Respiration Accompany the Drop in Core Temperature.

Figure 4A:
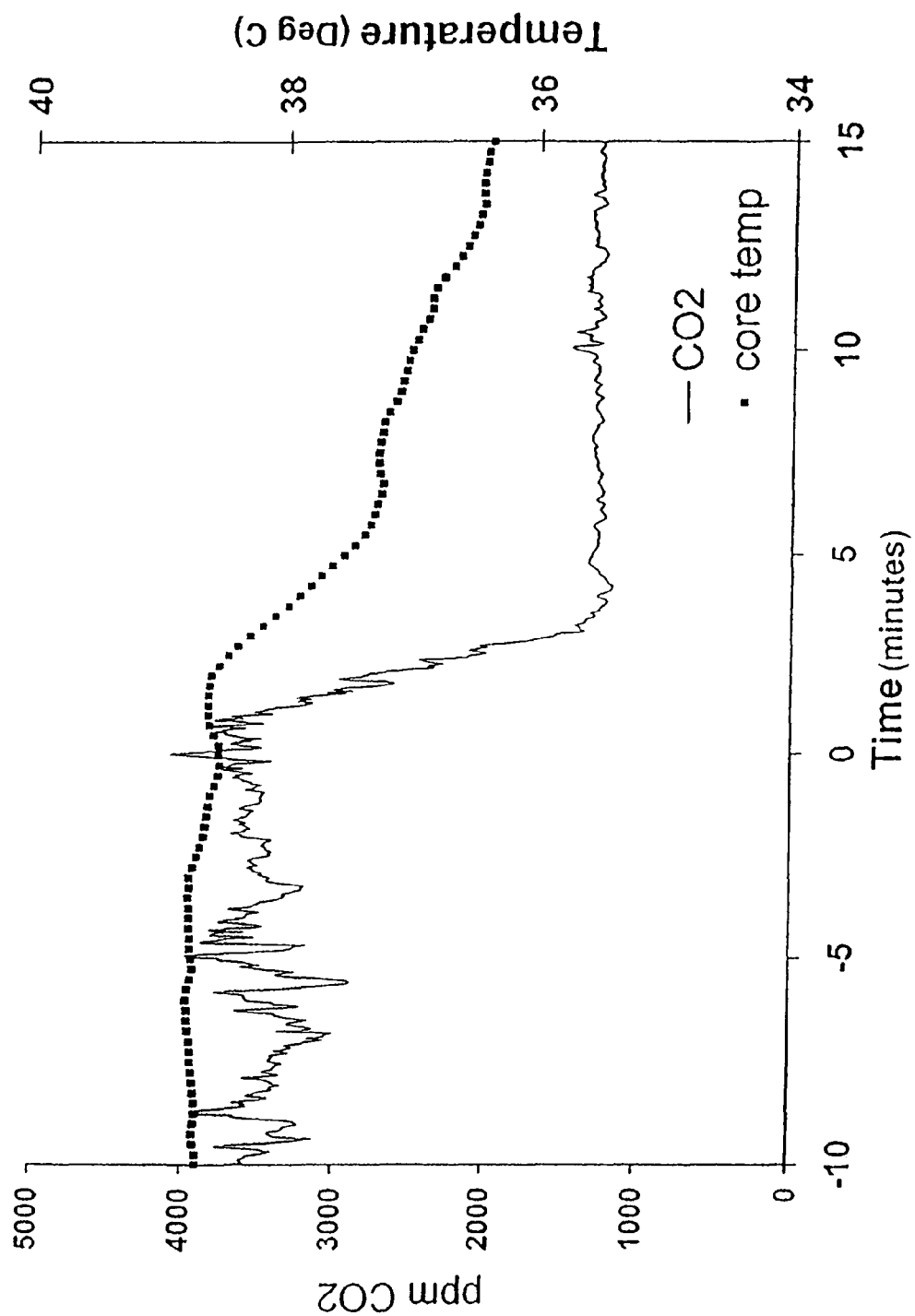
FIG. 4A Metabolic rate decreases before body core temperature when mice are exposed to hydrogen sulfide. Exposure of mice to 80 ppm (at 0 minutes on the X axis) results in an approximately 3-fold decrease in $CO_2$ production (black line) in less than five minutes. This precedes the drop in core temperature of the animal toward the ambient temperature (gray line).

Exposure of the mice to 80 ppm $H_2S$ results in decreased metabolic rate as well, as determined by measuring oxygen consumption and carbon dioxide production. For example, a mouse that had core temperature and carbon dioxide production measured simultaneously, demonstrated a rapid reduction in carbon dioxide production preceding the drop in core temperature of the animal (FIG. 4A). The approximately three-fold reduction in carbon dioxide production established a new baseline in approximately 5 minutes after the exposure to $H_2S$.

Table 4 shows results from an experiment with concurrent measurements of $O_2$ and $CO_2$ concentrations from mice exposed to room air that had had the $CO_2$ scrubbed (hence the 0 values for controls), with or without $H_2S$ (80 ppm). Measurements were over a period of 15 minutes, with the mice in a 0.5 L sealed environmental chamber with flow rates of 500 cc/min. Consumption of oxygen is obtained by subtracting the oxygen concentration when the mouse is present, from the control when the mouse is absent. Likewise, production of carbon dioxide is obtained by subtracting the carbon dioxide concentration when the mouse is present from the control when the mouse is absent. RQ stands for respiratory quotient, and is equal to the ratio of carbon dioxide produced to oxygen produced. This result demonstrates, a 2-3 fold drop in oxygen consumption in the presence of $H_2S$, as well as a 3-4 fold drop in carbon dioxide production. The change in the respiratory quotient reflects the disparity oxygen consumption and carbon dioxide production by the mice in the presence or absence of the $H_2S$.

TABLE 4

$H_2S$ exposure inhibits respiration in mice.

| Mouse present | $H_2S$ present | $[O_2]$ ppm | $[CO_2]$ ppm | RQ |
|---|---|---|---|---|
| − | − | 207,000 | 0 | |
| + | − | 203,600 | 2800 | |
| | Consumption, production | 3,400 | 2800 | 0.82 |
| − | + | 166,200 | 0 | |
| + | + | 164,900 | 750 | |
| | Consumption, production | 1300 | 750 | 0.58 |

The different parameters of stasis (reduction in oxygen consumption, decrease in carbon dioxide production or decrease in motility) can be assessed by a variety of assays and techniques. For example, probably the easiest way to measure the induction of stasis in mice administered $H_2S$ is through observation of their breathing. Indeed, this encompasses all three parameters in that it is indicative of decreased oxygen consumption, carbon dioxide production and motility. A normal mouse in room air at standard conditions will take approximately 200 breaths per minute. If $H_2S$ is administered to the mouse at 80 ppm, and the core temperature is dropped to 15° C., breathing is decreased at least an order of magnitude to somewhere between 1-10 breaths per minute. In fact, a mouse was observed under these conditions that did not take a breath for a period greater than an hour, indicating that deep levels of stasis are attainable. Thus, this represents at least about a 1-20-fold decrease in cellular respiration (i.e, oxygen consumption and carbon dioxide production).

Exposure of Mice to Regulated Atmospheres at Reduced Ambient Temperatures.

To begin to define the limits of the capacity for hydrogen sulfide to reduce the activity in mice, the inventor conducted several experiments in which a non-telemetry mouse was used, followed by exposure of a mouse bearing telemetry to acquire the data. The first experiment was to subject a non-telemetry mouse to a regulated atmosphere of $H_2S$ at 80 ppm in a reduced cabinet temperature of 10° C. essentially as described in Materials and Methods were as above except that the mouse was placed in the gassing chamber for one hour at 27° C. prior to exposure to the gas and reduction in ambient temperature. The non-telemetry mouse did well in this treatment, and recovered activity within approximately 90 min. after removal from the gassing chamber. The telemetry mouse was subjected to the same conditions also did well, and showed decreased core temperature to approximately 12.5° C. The inventor was unable to accurately determine this temperature because the electronics failed at 15.3° C. The temperature drop to 12.5° C. is therefore an estimation based on the slope of the drop prior to failure and the time the animal remained in the chamber after failure of the electronics.

Figure 4B:
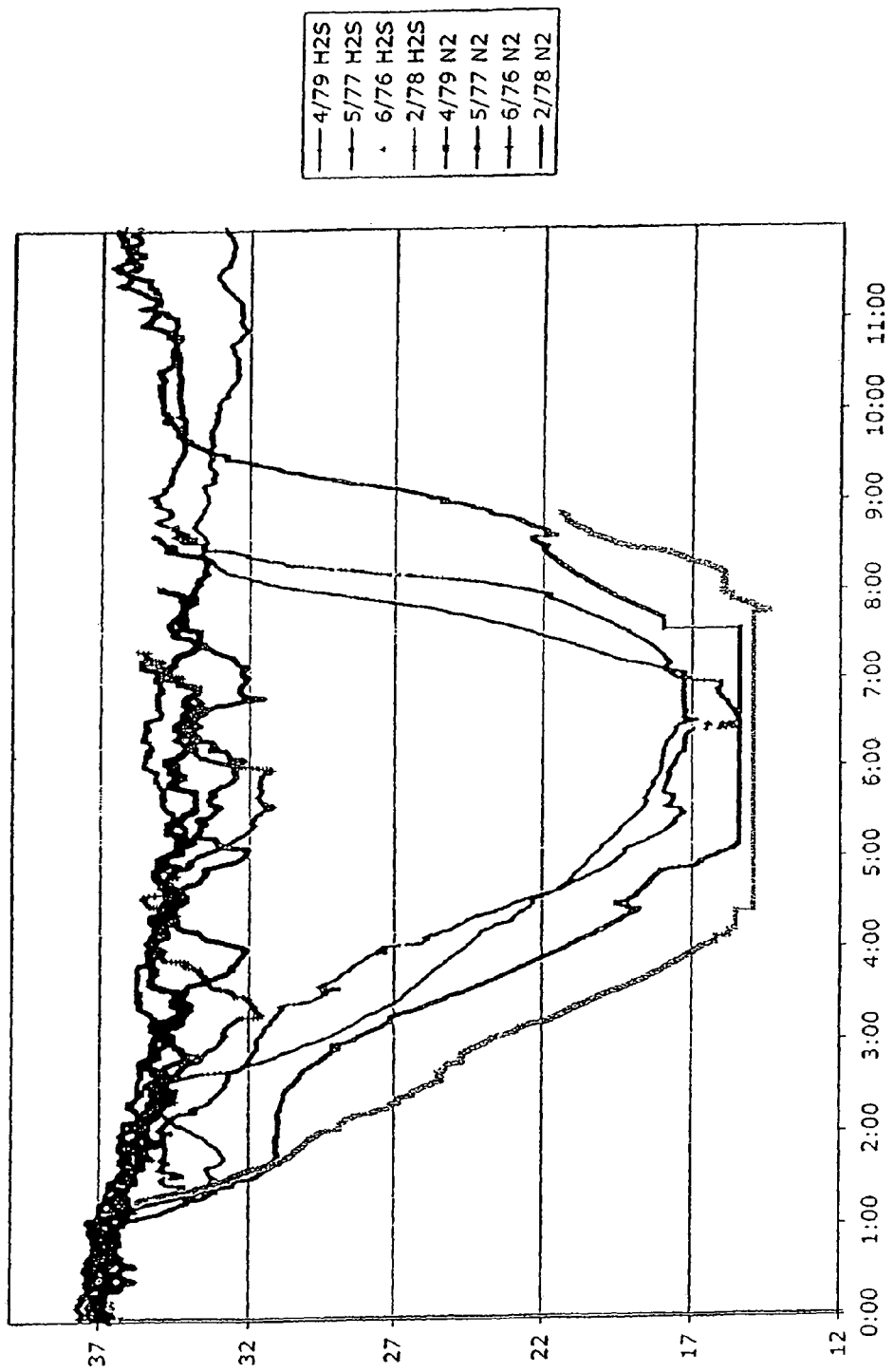
FIG. 4B Temperature of mice exposed to hydrogen sulfide. Each trace represents a continuous measurement of core body temperature in individual mouse exposed to either 80 ppm of $H_2S$, or to room air. Numbers on the vertical axis are temperature in °Celsius. On the horizontal axis, the numbers reflect time in hours. The experiments were carried out for 6 hours followed by recordings of the recovery. The beginning point is at 1:00, and the end of the 6 hr treatment is about 7:00.

Because of the limitation of the equipment, the inventor next tested each of the four telemetry mice for a 6 hr period in the gassing chamber with a regulated atmosphere containing approximately 80 ppm hydrogen sulfide or with room air essentially as described above. The temperature of the incubator was reduced at initiation of the experiment (exposure to the regulated atmosphere, or time 0 for the mice exposed to room air) to a constant 15° C. At the end of the six-hour period, the mice were returned to an atmosphere of room air and an ambient temperature of 22° C. as generally described above. There was a clear decrease in core body temperature in all four mice that was dependent on the use of 80 ppm hydrogen sulfide (FIG. 4B). There was also a marked drop in heart rate and gross motor movement associated with the decrease in temperature. The mice were maintained for 4 weeks with no apparent change in the behavior of the animals.

Example 5

Murine Studies on Reduction of Radiation Injury

A. Scientific Rationale

While aspects of the radiation injury model can and have been evaluated in cell culture, to test the ability of an experimental drug to affect the injury and healing process requires inclusion of all of the response systems that are affected. At this point in time, the only way to achieve that is in a whole animal. The inventor is proposing the use of mice for such studies as the most appropriate model. The C57BL/6 mice have been selected for study because this strain of mouse is readily susceptible to radiation lung injury, the level of radiation that is tolerated in this strain has been established, and the inventor has recently shown that $H_2S$ decreases the core temperature of this mouse strain.

Two identical experiments are planned under this protocol. Each experiment will investigate the efficacy of $H_2S$-induced hypothermia on the development of radiation induced lung injury. Ten mice per group will be exposed to one of four test conditions ($H_2S$/17.5 Gy thoracic irradiation, $H_2S$/no thoracic irradiation, no $H_2S$/17.5 Gy thoracic irradiation, or no $H_2S$/no thoracic irradiation), then followed for 13 weeks. Twelve animals per group will be similarly exposed and followed for 26 weeks (the increased n is required to compensate for the increased mortality that occurs late in the course of the disease).

For these experiments, analysis of variance (ANOVA) will be used as the statistical model for data analysis. A completely crossed and randomized two factor ANOVA with 4 groups (irradiated or non-irradiated mice receiving $H_2S$ or not receiving $H_2S$) and two time intervals (13 or 26 weeks) will be used to analyze temporal changes in bronchoalveolar lavage inflammatory cell number and total protein concentration and lung hydroxyproline levels. Assuming 80% power, 5% significance and a two-tailed test, five surviving mice per combination of injury group, intervention group and time point will allow a detectable difference among group means greater than or equal to 1.7 times the underlying within-group standard deviation. The within-group standard deviation is expected to be equal to about 25%. Thus, changes in inflammatory cell numbers or lung collagen content of 35-50% of control values should be discernable in these experiments.

$H_2S$ exposure and thoracic irradiation will be done in SLU AHR in a linear accelerator suite. Bronchoalveolar lavage and lung procurement at necropsy will be performed in the AHR mouse necropsy room. Bronchoalveolar lavage cell counts and protein concentrations and lung hydroxyproline content measurements will be performed in the another lab (D3-255). Wild genotype C57BL/6 mice will receive 17.5 Gy of thoracic irradiation. Mice will be anesthetized with intraperitoneal Avertin, placed into individual cloth mouse restrains and irradiated via the linear accelerator with 8.5 Gy at a dose rate of 3 Gy/min through two lateral fields collimated to target the thorax only (total thoracic dose 17.5 Gy).

B. Protocol

Anesthesia.

Wild genotype C57BL/6 mice will be anesthetized for intratracheal dosing with Isoflurane. The depth of anesthesia will be monitored by respiratory rate for response to tactile stimulation. Intraperitoneal injection of Avertin (0.4-0.7 ml/mouse i.p.) will be used to anesthetize animals for the thoracic irradiation procedure. The depth of anesthesia will be monitored by respiratory rate and response to tactile stimulation.

Exposure to Hydrogen Sulfide.

Mice will be placed into a closed plexiglass gassing chamber similar to the one used previously for mice (IR1606). The chamber will have two ports (import and export). A gas containing H2S (80 ppm) balanced with room air will be vented through the chamber at a rate of 1 liter per minute. The gas will be vented from the room using the house ventilation system with a hose that extends from the export vent to the exhaust vent for the room.

Hazardous Agent Administration.

Mice will be irradiated while they are in the gassing chamber with a total dose of 17.5 Gray using the linear accelerator. This radiation dose will induce an subacute pulmonary injury in the mice which progresses to fibrosis. The mice will not be radioactive or otherwise provide a hazard to personnel or other animals. No special monitoring, containment or disposal is required due to the irradiation.

Scheduled Euthanasia.

At approximately weeks 13 and 26 after thoracic irradiation, the animals will be euthanized by deep anesthesia (using avertin 0.4-0.7 ml i.p.) followed by exsanguination via inferior vena cava puncture. Bronchoalveolar lavage will be performed to determine inflammatory cell number, differential counts and lavage fluid protein concentrations. Lung and esophagus tissue will be removed for histologic evaluation and collagen content analysis.

Moribund Animals.

Thoracic radiation is associated with a finite mortality rate in mice, with 15% dying by week 10 and 50% by week 22 post irradiation. The investigators will monitor the animals daily for adverse effects (2-3 times per day initially, until they appear stable, then once daily until disease begins to progress, at which point the inventor will return to multiple daily observations). If an animal is losing weight, failing to groom, exhibiting severe respiratory distress, and/or awkward or significantly diminished movement, it will be euthanized with an avertin overdose. When practical, bronchoalveolar lavage and tissue collection for histology will be performed for these unscheduled euthanasias.

Thoracic irradiation should produce a lung injury which itself is not painful but may manifest itself (week 10) by increased respiratory rate, mild appetite loss, mild weight loss and/or failure to groom. The investigators and animal facility staff will monitor the animals daily for such adverse effects. If an animal does not seem to be eating, soft food and fluid support will be provided. If the animal is perceived to be in pain, analgesia with Butorphanol (0.2 mg/kg i.p.) or Buphrenorphine (1.0 mg/kg bid s.q.) will be administered as needed. If an animal appears to be suffering and palliative measures do not lead to improvement, it will be euthanized immediately. Lung and esophagus tissue will be collected for histopathologic evaluation and collagen content analysis at the scheduled necropsies.

Post-Irradiation Husbandry.

To minimize the risk of transmitting any pathogens to the rest of the facility, and to protect these animals while they are somewhat immunocompromised, all husbandry work on these animals will be done first thing each day (before any other animals in the facility) and will be done in a biosafety cabinet. To minimize the risk of adventitious infections, the mice will have autoclaved cages and bedding. In addition, they will be fed standard rodent food that has been irradiated to kill pathogens.

Wild genotype C57BL/6 mice will receive 17.5 Gy of thoracic irradiation. Mice will be anesthetized with intraperitoneal Avertin, placed into individual cloth mouse restraints and moved into a closed plexiglass gassing chamber similar to the one used previously for mice (IR1606). The chamber will have two ports (import and export). A gas containing $H_2S$ (80 ppm) balanced with room air will be vented through the chamber at a rate of 1 liter per minute. The gas will be vented from the room using the house ventilation system with a hose that extends from the export vent to the exhaust vent for the room. Once in the gassing chamber the mice will be irradiated via the linear accelerator with 8.5 Gy at a dose rate of 3 Gy/min through two lateral fields collimated to target the thorax only (total thoracic dose 17.5 Gy). After completion of thoracic irradiation the animals will be returned to their micro-isolater cages monitored until recovered from anesthesia.

Scheduled Necropsises.

One set of animals will be necropsied in week 13 post-irradiation to evaluate the inflammatory phase of the injury. The second set will be euthanized in week 26 to evaluate the fibrotic phase of the injury. Animals will be anesthetized with avertin, then exsanguinated. The lungs will be lavaged with 1000 µl PBS and the lavage fluid kept on ice for total and differential cell counts. The right lung will then be harvested for hydroxyproline content and the left lung will be infused with 10% NBF at 25-30 cm pressure through the trachea. The esophagus, trachea, left lung and heart will be immersed in 10% NBF and set to the FHCRC histology shared resource lab for processing and pathology evaluation.

Thoracic irradiation should produce a lung injury which itself is not painful but may manifest itself (week 10) by increased respiratory rate, mild appetite loss, mild weight loss and/or failure to groom. The investigators and animal facility staff will monitor the animals daily for such adverse effects. If an animal does not seem to be eating, soft food and fluid support will be provided. If the animal is perceived to be in pain, analgesia with Batorphanol (0.2 mg/kg i.p.) or Buphrenorphine (1.0 mg/kg bid s.q.) will be administered as needed. If an animal appears to be suffering and palliative measures do not lead to improvement, it will be euthanized immediately by $CO_2$ asphyxiation.

The primary problems are likely to be esophagitis (resulting in decreased food and water intake) and respiratory insufficiency (reducing oxygen uptake). The inventor will be checking these animals 2-3 times per day until they are convinced that they are stable and doing well, at which point the inventor may reduce the frequency of checks to once daily, until the disease begins to progress, at which point they return to multiple daily checks. Supportive care will be provided in several ways. If an animal is not eating or drinking well (evidenced by weight loss and grooming problems), the inventor will provide soft food and try fluid supplementation (Lactated Ringer's solution, 1-2 ml/mouse, sc using a small bore needle (>20 G), 1-2 times daily). If the animal is perceived to be in pain, analgesia with Batorphanol (0.2 mg/kg i.p.) or Buphrenorphine (1.0 mg/kg bid s.q.) will be administered as needed. If an animal appears to be suffering and palliative measures do not lead to improvement, it will be euthanized immediately by $CO_2$ asphyxiation. In the event that an animal experiences significant pain or distress at the time of thoracic irradiation, the animal will be euthanized by $CO_2$ asphyxiation.

A third experiment was to subject a telemetry mouse to a regulated atmosphere of $H_2S$ at 80 ppm in a reduced cabinet temperature of 10.5° C. essentially as described above. During the experiment, the mouse was visually observed and its movements were recorded by web camera, and telemetry measurements were recorded as described above. The mouse was exposed to a regulated atmosphere of 80 ppm $H_2S$, and the temperature of the cabinet was reduced to a constant 10.5° C. At the end of an approximately six-hour period, heat was applied to the cabinet by setting the cabinet temperature to 25° C. The mouse was allowed to warm up in the regulated $H_2S$ atmosphere until the core temperature of the mouse was between 17° C. and 18° C. after which time the regulated atmosphere was replaced with room air. There was a clear decrease in core body temperature of the mouse to 10.5° C. in the regulated atmosphere accompanied by a marked drop gross motor movement. The respiration rate dropped to an undetectable rate by visual observation for approximately one hour and fifteen minutes. After the cabinet was warmed, weak respiration was observed when the core body temperature of the mouse achieved 14° C. During the warming phase, when the core body temperature rose to between 17° C. and 18° C., and the mouse was exhibiting respiration and movement, the regulated atmosphere was replaced with room air. Normal movement and respiration were fully apparent when the core body temperature returned to 25° C. The mouse has exhibited no apparent change in the behavior compared to animals that were untreated.

Example 6

Cell and Mammal Studies

A. Canine Studies

Canine studies will be conducted with dogs surgically implanted with telemetry devices to monitor their core body temperature. The animals will be studied in the presence or absence of a sub-lethal dose of hydrogen sulfide for 10 hrs. During this time, they will be continuously monitored for vital signs by telemetry. The temperature of the environment will also be reduced to 15° C. for 30 min to determine whether this has any effect on the core body temperature of the animals.

The procedure will be conducted with 2 groups of 2 dogs (four total). Because of the expense of the telemetry equipment the inventor will do these experiments in succession. If the results from the first group indicate that the hypothesis is incorrect, the study will be repeated with the second group of two dogs. If the results from the second group do not support the hypothesis, the project will be discontinued.

Toxicology studies demonstrate that, while the level of $H_2S$ is above the OSHA limit for humans (10 ppm), it has been shown previously that exposure of both rats and mice to 80 ppm of $H_2S$ for 6 hrs per day, 5 days per week, for 90 days, showed no observed adverse effect. This included both gross and histopathological examination of the gut, lung, heart, liver, kidneys, or other organs conducted at the end of the treatment. To the inventor's knowledge, no information is available concerning exposure of dogs to hydrogen sulfide.

A critical issue in working with $H_2S$ is to not exceed the dose (80 ppm) described by others who have published studies on rodents exposed to hydrogen sulfide and not seen detrimental effects. There is considerable experience in gas sciences available, and the inventor is capable of delivering the gas to the mice at the prescribed dose. Many precautions are taken to ensure that both animals and investigators are not harmed. These precautions include constant monitoring of the gas mixture with alarm set to OSHA limits and sensitivity to 1 ppm, and a variety of equipment that is able to mix and deliver the gas according to specifications without leakage into or out of the system.

A time line for the protocol is given in Table 5.

TABLE 5

Study Time Line

| Day | Activity | Detail |
| --- | --- | --- |
| −1 | Pre-surgery | A CBC/Chemistry will be performed; dog will be fasted in p.m., but allowed free access to water. |
| 0 | Surgery | Fentanyl transdermal patch placed p.m. of day before surgery for preemptive analgesia. Preoperative placement of cephalic catheter; premedication with Acepromazine, Buprenorphine, Glycopyrrolate; induction with either Ketamine:Diazepam or Propofol to permit intubation; maintenance anesthesia by isoflurane and oxygen. Dog will be placed in dorsal recumbancy and the abdomen clipped/prepped and draped. Monitoring of pulse, respiration rates, end-tidal carbone dioxide, inhaled percentage of anesthetic agent, $SpO_2$ will be performed and recorded every 15 minutes or more frequently. Fluid support during and after surgery will occur. Once the dog is stable and appropriately prepared for the procedure, a ventral midline laparotomy, beginning caudal to the umbilicus and extending 5-10 cm caudally, will be performed. A sterile transmitter will be placed into the peritoneal cavity. Placement will be checked to insure that the transmitter is able to move freely; the momentum will be replaced, and closure of the peritoneal cavity will be performed in 3 layers. The dog will be monitored until it is extubated, is able to thermoregulate and is sternally recumbent. Daily monitoring of the dog's incision site, abdomen (via palpation and ultrasound, if indicated), appetite, temperature (for the first 3-5 post-operative days), weight and activity will be performed. |
| 7 | Establishment of Baselines | This date is flexible. Will only proceed with this step with approval. Four animals will be placed onto the receiver equipment (this does not involve removal of the animals from their cages and will occur in AHR) and baselines for the vital signs will be established for all four animals. |
| 8 | Exposure to $H_2S$ | Animals will be transferred to a room to be determined where they will be placed into caging with food and water that has an enclosed atmosphere. After establishing baselines two of the four animals will be subjected to $H_2S$ at a concentration of 80 ppm. Following a ten-hour exposure, the atmosphere will be returned to room air temperature and the animals will be returned to their cages. Exposure to $H_2S$ will repeated once per week to begin to determine whether any data set is reproducible. |

B. Human Platelets

To test the concept that using inhibitors of oxidative phosphorylation could be used for human benefit, the inventor induced a state of suspended animation in human tissues to protect them from lethal exposure to oxygen. In pilot experiments, the inventor placed human skin in an environment of 100% CO. The inventor observes that after 24 hrs skin cells survive 100-fold better in CO than those in room air. These results are very exciting; they provide evidence that inhibitors of oxidative phosphorylation can be effective in human tissues.

Another set of experiments demonstrates the protective effects of induced suspended animation on platelets. A unit of platelets was split in half. The first half was kept at standard storage conditions, which involves keeping the platelets at room temperature (22-25° C.) with constant shaking. The other half was placed inside an anoxic environment (<10 ppm oxygen) using standard methods to remove the oxygen. The two sets of platelets were compared on days 0, 5 and 8. The platelets kept in anoxic conditions performed as well or better than those kept at standard conditions over a panel of five different in vitro tests, including the ability to aggregate, cell morphology, Annexin-V staining (phosphatidyl-serine flipping to the outer membrane as an early apoptotic marker), and so on. This indicates that controlling metabolic activity, specifically oxidative phosphorylation, can be accomplished by the removal of oxygen and has a protective effect on cellular function over long periods of stasis.

Hydrogen sulfide is able to bind cytochrome C oxidase as well as CO and stop oxidative phosphorylation on demand. It is so potent at impeding oxidative phosphorylation, that should a person take a single breath in an atmosphere with 0.1% hydrogen sulfide, they will not take another. Instead, they immediately collapse to the floor—an event commonly referred to in industrial settings as a "knock down." It also appears to be reversible because, if rapidly removed to fresh air (and uninjured from the fall) these individuals can sometimes reanimate and go on to live without neurological problems. Here is an agent that is not only common in our world, indeed, is produced even in our own cells, but is also a potent reversible inhibitor of oxidative phosphorylation that does not effect oxygen delivery.

C. Murine Studies

Induction of a Hibernation-Like State Using $H_2S$.

Homeothermic animals, by definition, maintain a core body temperature 10-30° C. above the ambient temperature. For these animals to do this, they must generate heat from the energy produced by oxidative phosphorylation. The terminal enzyme complex in oxidative phosphorylation is cytochrome c oxidase. Since hydrogen sulfide inhibits this complex (Petersen, 1977; Khan et al., 1990), the inventor predicts that exposing a homeothermic animal to hydrogen sulfide will prevent such an animal from maintaining its core body temperature well above ambient temperatures.

To test this hypothesis, the inventor wanted to continuously monitor both the core body temperature and the activity levels of a homeothermic animal (a mouse). Telemetry devices, implanted into the peritonea of mice, can do both of these things and have the advantage of not introducing bias to the readings due to the handling of the mice (Briese, 1998). Additionally, they can remotely monitor the mice during the exposure to the hydrogen sulfide gas. A dose of 80 parts per million (ppm) hydrogen sulfide has been previously shown to be innocuous to mice for exposures lasting up to ten weeks (CIIT 1983; Hays, 1972). Therefore, for these experiments the inventor used a dose of 80 ppm hydrogen sulfide to test our hypothesis. Creating an atmosphere containing 80 ppm of hydrogen sulfide is not trivial. Over time, in the presence of oxygen, hydrogen sulfide will be oxidized to sulfate. For that reason, in order for the inventor to continuously expose a mouse to an atmosphere containing 80 ppm hydrogen sulfide, the inventor constantly mixes room air with a tank of 500 ppm hydrogen sulfide balanced nitrogen.

Characterization of Core Temperature Control

Figure 5:
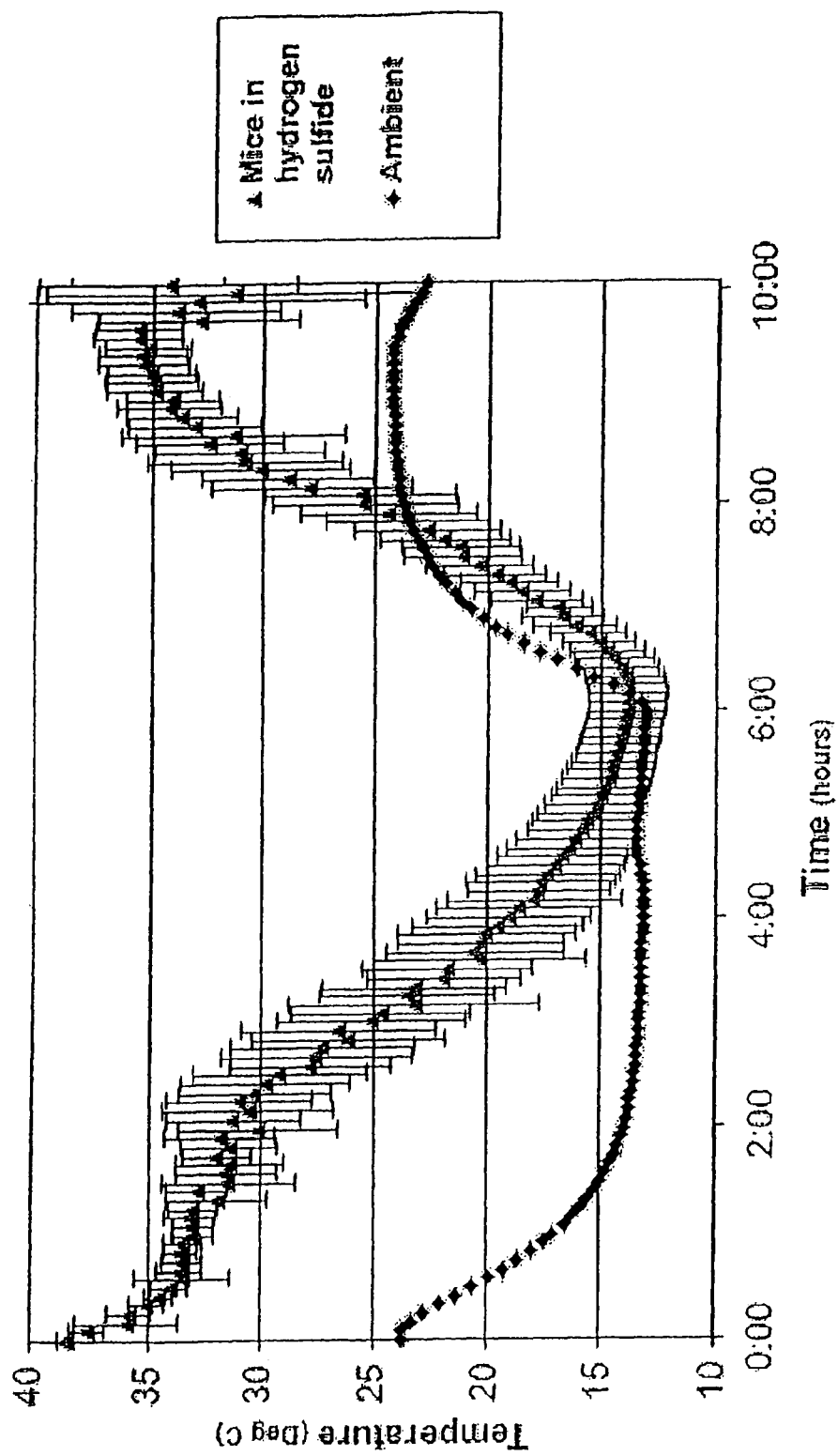
FIG. 5 Exposure to 80 ppm hydrogen sulfide causes the core body temperature of a mouse to approach ambient temperature. Gas was turned on and temperature decreased starting at time 0:00. Atmosphere switched back to room air at time 6:00. Triangles indicate the core body temperature of the mouse as determined by radiotelemetry. This was approximately 39° C. at time 0:00. Diamonds indicate the ambient temperature which was reduced from 23° C. to 13° C. in the first 3 hours of the experiment, and then increased again toward 23° C. from hour 6:00 stabilizing at around hour 9:00.

Exposing a mouse to 80 ppm $H_2S$ dropped its core temperature to approximately two degrees Celsius above ambient (FIG. 5). This effect was highly reproducible as the average core body temperature of seven mice exposed to 80 ppm of hydrogen sulfide for 6 hrs followed a similar pattern (FIG. 5). The lowest average core body temperature of these seven mice was 15° C. in an ambient temperature of 13° C. All of these mice successfully recovered after rewarming when the atmosphere was switched to one containing only room air. As a control, the inventor substituted nitrogen for the hydrogen sulfide and did not see the substantial drop in core body temperature.

Although these mice appear superficially normal despite temporary decrease in both core body temperature and breathing rate, the inventor conducted a battery of behavior tests to rule out the possibility that neurological damage was incurred by either the exposure to hydrogen sulfide gas, the extreme reduction in core body temperature, the reduction in breathing rate, or the combination of these effects. All of the tests were performed on the mice both before and after exposure to hydrogen sulfide. These behavior tests were selected from the SHIRPA protocol developed by the Mouse Models for Human Disease consortium (Rogers et al., 1997). There were no detectable behavioral differences in the mice after gas exposure. From this, the inventor concluded that entry into a hibernation-like state is not detrimental.

Preliminary Optimization of $H_2S$ Dose.

Figure 6:
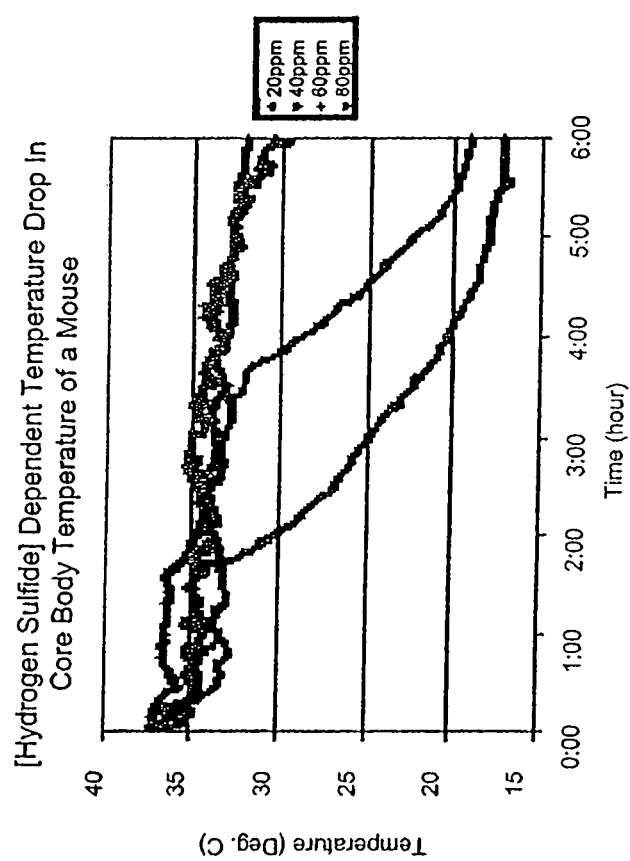
FIG. 6 The rate of body core temperature drop is dependent upon the concentration of hydrogen sulfide given to the mice. All lines represent core body temperature of a single mouse as determined by radiotelemetry. Mice subjected to 20 ppm and 40 ppm $H_2S$ exhibit minor drops in core temperature. Exposure to 60 ppm induced a substantial drop in temperature beginning at approximately hour 4:00. The mouse exposed to 80 ppm exhibited a substantial drop in temperature beginning at approximately hour 2:00.

The above experiments describe the effect of 80 ppm of hydrogen sulfide on the core body temperature of a mouse. In order to determine the concentration of hydrogen sulfide sufficient for the loss of thermoregulation, the inventor exposed mice to a range of hydrogen sulfide concentrations (20 ppm, 40 ppm, 60 ppm, and 80 ppm), (FIG. 6). While 20 ppm and 40 ppm of hydrogen sulfide were sufficient to cause a drop in the core body temperature of a mouse, this was minor compared to the drop seen with 60 ppm and 80 ppm of hydrogen sulfide. From this experiment, the inventor concluded that the loss of thermogenesis is directly dependent upon the concentration of hydrogen sulfide given to the mice. This preliminary study on the dose range and pharmacokinetics of hydrogen sulfide emphasizes the need for a more comprehensive analysis.

Preliminary Definition of Low Core Temperature Limit.

Figure 7:
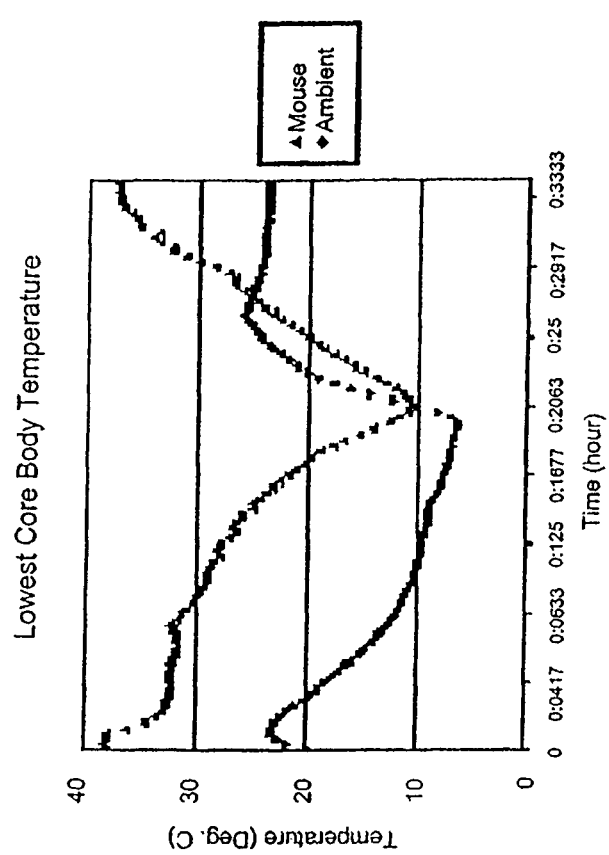
FIG. 7 Lowest core body temperature. The lowest core body temperature recorded for a mouse exposed to 80 ppm hydrogen sulfide was 10.7° C. Triangles indicate the core body temperature of the mouse as determined by radiotelemetry which started at approximately 39° C. at time 0. Diamonds indicate the ambient temperature which began at approximately 23° C. and was dropped to less than 10° C. by the mid-point of the experiment, after which it was then increased again toward room temperature.

The inventor is also interested in establishing a more complete understanding of the tolerance of both the range of core body temperatures and the length of time allowed in this state for mice. The experiments above show that the inventor can repeatedly lower the core body temperature of a mouse to 13-15° C. on demand. Furthermore, the mice seem to tolerate the treatment for many hours. Using the same protocol, while lowering the ambient temperature, the inventor has successfully brought the core body temperature of a mouse to 10.7° C. (FIG. 7). Further attempts to push core body temperatures even lower, and for longer periods of time, will be performed in the future. Although preliminary, these results demonstrate that there is a significant range of core body temperatures allowed by mouse biology and that this range can be explored through the loss of thermoregulation due to hydrogen sulfide exposure.

Modulation of Endogenous $H_2S$ Levels.

It is well known that mammalian cells make hydrogen sulfide endogenously (Wang 2002). Since this chemical is dynamically produced in the cell, it is crucial to understand the basal levels under different conditions as this could dramatically affect the pharmacokinetics of exogenously administered hydrogen sulfide. To address this essential aspect of our research, the inventor has begun to assay endogenous hydrogen sulfide levels in the mouse. The inventor uses an extractive alkylation technique coupled with gas chromatography and mass specific detection to quantify hydrogen sulfide (Hyspler et al., 2002). Using this method, the inventor looked at the levels of hydrogen sulfide in unperturbed mice.

Figure 8:
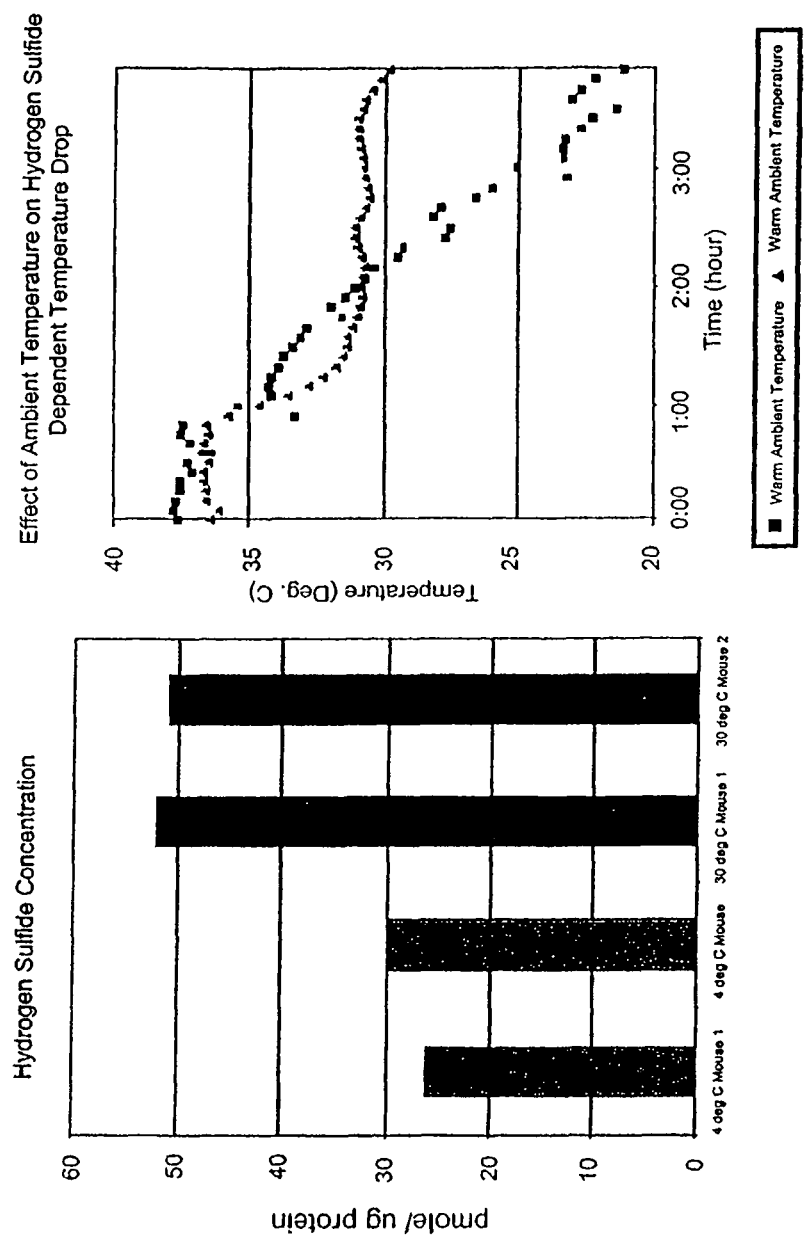
FIG. 8A Endogenous levels of hydrogen sulfide are increased in mice acclimated to warm temperatures. Gray bars (two left bars) indicate endogenous $H_2S$ concentrations of two individual mice acclimated to 4° C.; black bars (two right bars) indicate the endogenous $H_2S$ concentrations of two individual mice acclimated to 30° C. Hydrogen sulfide concentration determined by GC/MS.
FIG. 8B Effects of Ambient Temperature on Hydrogen Sulfide Dependent Temperature Drop. The rate of core temperature (expressed in degrees Centigrade) drop due to hydrogen sulfide exposure is dependent on the acclimation temperature. The mice were exposed to the gas at 1:00. Triangles indicate the core body temperature of the mouse, acclimated to 12° C., as determined by radiotelemetry. Squares indicate the core body temperature of the animal acclimated to 30° C.

FIG. 8A shows that there is a significant amount of hydrogen sulfide within the mouse. Additionally, the levels of hydrogen sulfide appear to be dependent upon the ambient temperature of the mouse. Specifically, when mice are in the cold, they have reduced endogenous sulfide levels and, when mice are at warm ambient temperatures, they have increased endogenous sulfide levels. From this, the inventor concludes that mice regulate their sulfide levels in response to the ambient temperature.

Changes in Endogenous Levels Affect the Efficacy of $H_2S$.

Since the ambient temperature changes the endogenous levels of sulfide in mice, the inventors hypothesized that the ambient temperature might impact the changes in core body temperature upon exposure to exogenous hydrogen sulfide. Acclimatizing a mouse to cold temperatures, ~12° C., creates a longlasting plateau that the inventor sees after the initial drop in core body temperature (FIG. 8B). Therefore it appears that this acclimatization to the cold made the mouse more resistant to core body cooling by the action of hydrogen sulfide gas. However, allowing the mouse to acclimatize to a warm thermoneutral temperature prior to gas exposure eliminates this plateau. In fact, the normothermic mouse cooled much more quickly when exposed to hydrogen sulfide than the cold-acclimated mouse (FIG. 8B). These data suggest that endogenous levels of hydrogen sulfide in the mouse have a direct impact upon the efficacy of the exogenous hydrogen sulfide.

$H_2S$ Protects Mice from Hypoxia.

Normal room air contains approximately 21% oxygen. In a preliminary experiment exploring the protective effects of stasis on hypoxia in the mouse model, a mouse exposed to 80 ppm of hydrogen sulfide survived 11 minutes of 5.2% oxygen and 3 weeks later, it was still doing well. Previously published work shows that 90% of these animals (C57Bl) exposed in this way without hydrogen sulfide do not survive (Zhang et al., 2004). This experiment involved pre-equilibrating the mouse to 80 ppm $H_2S$ for 3 hours, then dropping the oxygen tension in the chamber as described in experiments above. The same flow rates were used as described above (i.e., 500 cc/mL in a 0.5 L chamber). It is well established in those familiar with the field that if a group of mice are exposed to 4% oxygen, 100% will be dead within 15 minutes. However, mice in which $H_2S$ is administered during periods when the oxygen tension is reduced to 4%, remain viable, even for extended periods (up to an hour) in these hypoxic conditions. The mice appear to be unaffected by these conditions after recovery, and are viable and normally responsive when tested 24 hours later. This experiment differs from the one above in that the mice were retained in the $H_2S$ at the end of the hypoxic exposure until the oxygen tensions were returned to normal levels (21% $O_2$).

Example 7

Additional Animal Studies

A. Protection from Adverse Conditions

Experiments were conducted to test the ability of a mouse in a 'hibernation-like' state to survive in conditions where it would normally die. The adverse condition was hypoxia, which the literature states that mice (C57BL6/J males) can live in for a maximum of 20 minutes at 5% Oxygen. (Zhang et al. 2004).

As shown in Table 6, the experiment involved exposing the mouse to 80 ppm (unless otherwise noted) $H_2S$ for the time indicated, followed by the decrease in oxygen tension in the chamber, while still under $H_2S$. The hypoxic exposure was timed (indicated below) and viability of the mice was determined.

Short exposures of the mice to $H_2S$ (at least at 80 ppm) was less successful at protecting the mouse from hypoxia, although there was at least one that did survive a 50-minute hypoxic exposure after just 8 minutes in $H_2S$. Furthermore, it was observed that a mouse exposed to 90 ppm $H_2S$ for just 10 minutes did survive much longer in the 5% Oxygen condition, although it did eventually expire.

Exposing the mice to 80 ppm $H_2S$ for longer periods of time had a strong effect on protecting them from hypoxia for up to an hour.

TABLE 6

| Ambient Temp | Time in H2S Prior to hypoxic exposure | Oxygen % | Time in Hypoxia | Result |
|---|---|---|---|---|
| 20° C. | 5 hrs | 5.20% | 11 minutes | life |
| 20° C. | 5.5 hrs | 5.00% | 25 minutes | life |
| 20° C. | 5 hrs | 5.00% | 60 minutes | life |
| 20° C. | 5 hrs | 4% | 28 minutes | life |
| 24° C. | no H2S | 5% | 14 minutes | dead |
| 24° C. | simultaneous | 5.10% | 10 minutes | dead |
| 24° C. | 8 minutes | 5% | 20 minutes | dead |
| 24° C. | 8 minutes | 4.00% | 8 minutes | dead |
| 24° C. | 8 minutes | 4.50% | 23 minutes | dead |
| 30° C. | 8 minutes | 4.50% | 6 minutes | dead |
| 24° C. | 10 minutes (90 ppm) | 5% | 56 minutes | dead |
| 24° C. | 8 minutes | 5.00% | 50 minutes | life |

B. Enhancing Anoxia Tolerance

1. Background

The use of carbon dioxide ($CO_2$) and hydrogen sulfide ($H_2S$) to enhance the survival of a complex metazoan, *Drosophila melanogaster*, in anoxia was investigated. These experiments indicated that these agents, especially $H_2S$, can increase the anoxia tolerance of adult *D. melanogaster*.

*C. elegans* embryos survive in anoxia (<10 ppm $O_2$) by entering into suspended animation, and development can proceed in 0.5% $O_2$. However, there is a 10-fold range (0.01-0.1% $O_2$) of lethal oxygen concentrations. Moreover, preventing oxygen utilization with carbon monoxide can prevent hypoxic damage in embryos. Thus, if there is not enough oxygen available for efficient biological activity, then it is better to not have (or use) any oxygen.

In more complex metazoans, the cellular oxygen concentration is not necessarily the same as the environmental oxygen levels. In *C. elegans*, oxygen is delivered to the tissue by diffusion. However, in higher organisms there are proteins that bind oxygen in order to transport it to the tissues, such as hemoglobin. Therefore, when environmental oxygen levels drop, there may be residual oxygen at the cells.

Most organisms are not able to survive exposure to environmental anoxia. One possibility is that the residual oxygen at the cellular level is toxic, corresponding to the lethal oxygen range observed in *C. elegans* embryos. In this scenario, survival of anoxia would be enhanced if the residual oxygen was removed or made un-utilizable. $CO_2$ promotes the release of $O_2$ from hemoglobin and $H_2S$ is a potent inhibitor of oxidative phosphorylation.

2. Materials and Methods

Basic Experimental Setup.

Adult flies were introduced into 35 mL tubes made of glass with a gas-tight rubber stopper (Balsh tubes). This was usually accomplished by anesthetizing flies with $CO_2$, moving groups of flies to vials with food to recover for at least 2 hours, and then transferring them into the Balsh tube. To exchange the gaseous environment in the Balsh tube, two 18 gauge needles were inserted into the rubber stopper, and gas is blown into one of the needles at 100 mL/min. To prevent dessication, gasses were humidified by bubbling through 10 mL of water before passing it through the Balsch tube. The water in the bubbler is equilibrated with the gas for at least 20 minutes before starting the experiment.

For "stopped-flow" experiments, gas exchange proceeded for 60 minutes before sealing the tube. For "low-flow" experiments, gas flow continued throughout the experiment. $CO_2$ was from the house source (100%), and anoxic environments were established by flushing out room air with 100% nitrogen ($N_2$). Care was taken to prevent introduction of room air into the system while switching the atmosphere from $CO_2$ to $N_2$.

After anoxic treatment, oxygen was reintroduced into the Balsh tube by flushing with house air for 20 minutes. The rubber stopper was then removed and a food vial is inverted over the top of the Balsh tubes with Parafilm. Flies were scored as alive if they resume movement. Viability was scored at least 18 hours after the end of anoxic treatment. After two weeks, if the food vials contained larvae and/or pupae the flies were considered to be fertile.

3. Results

Treatment with $CO_2$ Prior to Anoxic Exposure.

Adult flies exhibited a higher rate of anoxic survival if they are first pretreated with $CO_2$. After a 19 h anoxic exposure in a stopped-flow experiment, adult flies pretreated with $CO_2$ for 30 or 90 minutes exhibited 54% or 28% survival, respectively. No survival was observed in controls exposed to anoxia without $CO_2$ pretreatment or $CO_2$ without subsequent anoxic exposure. Furthermore, no flies survived anoxic exposure with $CO_2$ pretreatment if they were also exposed to $CO_2$ immediately following anoxic exposure for 20 minutes.

Figure 16:
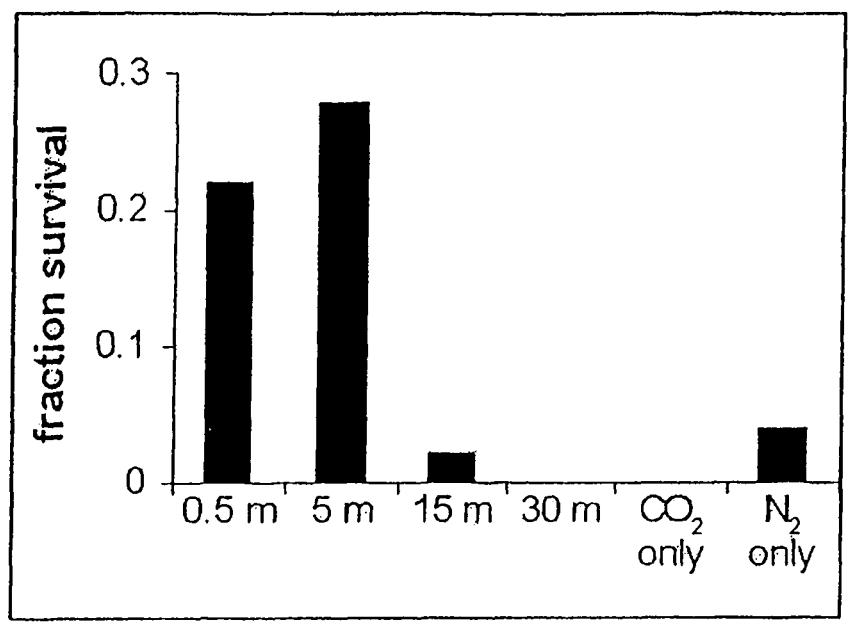
FIG. 16 Short $CO_2$ pretreatment leads to greatest extension of anoxic survival. Adult flies were exposed to 100% $CO_2$ for the indicated time, the atmosphere was made anoxic by flushing with $N_2$, and then the tube was sealed. After 22 h, the tubes were opened to room air. The flies were allowed to recover for 24 h before scoring viability.

A short exposure to $CO_2$ was sufficient for enhanced survival of anoxia. In stopped-flow experiments with 22 h anoxic exposure, the fraction of flies that survive was highest if $CO_2$ was administered for 0.5-5 minutes before switching to the nitrogen atmosphere (FIG. 16). Thus, for subsequent experiments, the standard protocol was to treat with $CO_2$ for 10 minutes before anoxic exposure. In a low-flow experiment using this protocol, 6% of adult flies survived a 20 h anoxic exposure, and this survival required the $CO_2$ pretreatment.

Experiments suggested that it is important to prevent reintroduction of $O_2$ between the $CO_2$ treatment and establishing the $N_2$ environment. When the water in the bubbler used to humidify the air was not equilibrated with $N_2$ before flushing out the $CO_2$, no flies survived a 13 h anoxic exposure in these experiments, whether the $N_2$ was introduced at 10, 50, or 100 mL/min. Under these conditions, the $CO_2$ atmosphere was flushed out with a $N_2/O_2$ mix resulting from the $O_2$ dissolved in the water.

Figure 17:
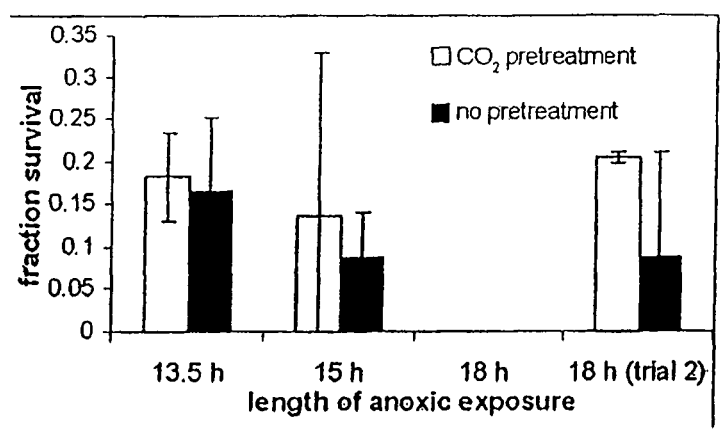
FIG. 17 $CO_2$ variably enhances anoxic survival. Adult flies were made anoxic in low-flow experiment, either directly from room air (no pretreatment) or after being exposed to 100% $CO_2$ for 10 min. After the indicated time, the tubes were opened to room air. The flies were allowed to recover for 24 h before scoring viability.

A series of low-flow experiments were conducted to determine the time of anoxic exposure that can be tolerated with $CO_2$ exposure compared to no pretreatment, testing each condition in duplicate (FIG. 17). In these data, the trend is that $CO_2$ pretreatment results in greater survival. An important caveat is that these experiments deviated from the standard protocol in that the flies were anesthetized with $CO_2$ and transferred to the Balsh tubes and allowed to recover for only 10-20 minutes before initiating the $CO_2$ treatment (except for Trial 2 of the 18 h timepoint).

Several other experiments were performed that were not informative to whether pretreatment with $CO_2$ was beneficial. For instance, in one experiment no survival was observed after 17, 22, and 24 h of anoxia in a low-flow experiment with a 10 min $CO_2$ pretreatment period. However, in other experiments, many flies survived after 17 h. This may indicate that in certain cases other factors affect the outcome, such as age of the adults, circadian rhythms or variations in room temperature. In another experiment to compare the stopped-flow setup to the low-flow setup, no flies survived a 17 or 19.5 h anoxic exposure; however, in this instance mold contamination may have contributed to the demise of the flies.

Treatment with $H_2S$ Prior to Anoxic Exposure.

Figure 18:
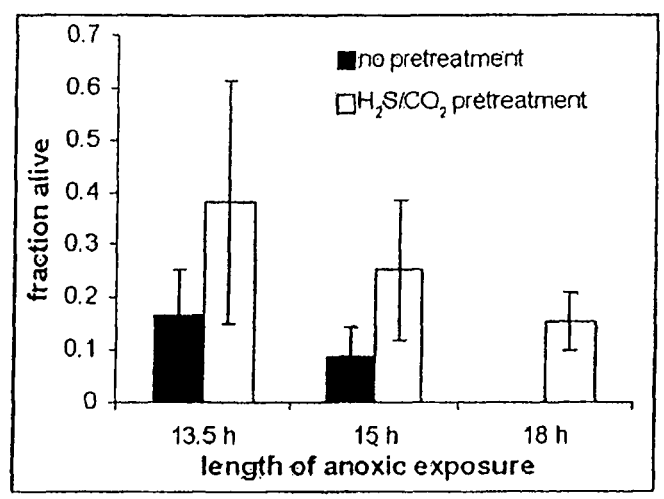

Including $H_2S$ in the pretreatment protocol more dramatically enhanced the ability of adult flies to survive anoxia. In a series of experiments analogous to those shown in FIG. 17, adding 50 ppm $H_2S$ to the $CO_2$ pretreatment ($H_2S/CO_2$) increased the fraction of flies that survived treatment (FIG. 18). These flies seem healthy, and produced progeny after exposure. However, in a similar experiment no flies survived 18, 20, 25, or 30 h in anoxia after 10 minutes in $H_2S/CO_2$. The cause of this discrepancy is unclear. Consistent with a beneficial influence of $H_2S$ treatment, after a 15 h anoxic exposure 50% of flies pretreated with $H_2S$ survived, whereas there was no recovery of control flies that were not exposed to $H_2S$. In this experiment, the flies were treated with $CO_2$ for 10 min, then $H_2S/CO_2$ for 10 min, then $N_2/H_2S$ for 10 min, and finally with $N_2$ for the duration of the low-flow experiment.

$CO_2$ treatment is not required for the $H_2S$-dependent increase in survival of anoxia. 25% of flies treated with 50 ppm $H_2S$ in room air prior to being made anoxic for 18.5 h survived. The fraction of flies surviving was unaffected if a 10 min exposure to $H_2S/CO_2$ was added before establishing the anoxic environment. In a control experiment where flies were treated only with CO for 10 min before the anoxic exposure, only 11% of the flies recovered.

The time at which $H_2S$ is administered appears important for enhancing anoxic survival. If $H_2S$ is present throughout the anoxic exposure (20 h) no flies recover, whether $H_2S$ was present during the $CO_2$ pretreatment or not. However, 35% of flies survive if 50 ppm $H_2S$ is present in the $CO_2$ pretreatment and then is removed as the anoxic environment is established. In parallel experiments, 6% of flies exposed to anoxia after 10 min pretreatment with $CO_2$ (no $H_2S$) survived.

Preliminary Experiments with Larvae and Embryos.

The enhanced survival of anoxia after treatment with CO and CO with HS is also observed in embryos and larvae. After exposure to anoxia for 24 h, 7 pupae were formed from a pool of 0-19 h old embryos. However, 20 pupae were observed from a matched pool that was pretreated with $CO_2$ for 10 min. Similarly, larvae exposed to 24.5 h anoxia can resume movement upon reoxygenation only if they were pretreated with $CO_2$ or $H_2S/CO_2$. 0-24 h old embryos survive 18.5 h anoxic exposure and develop to adulthood whether pretreated with $CO_2$ or $H_2S/CO_2$.

Cold Treatment During Anoxia

Decreasing the environmental temperature may extend the length of time that adult flies can survive anoxic exposure. At room temperature, no flies survived a 15.5 h anoxic exposure in a stopped-flow setup, but 20% of those kept at 4° C. while anoxic recovered. Similarly, no flies survived being transitioned to anoxia at 4° C. and then moved to room temperature for 16.5 h. However, after 16.5 and even 40 h flies that were kept at 4° C. during the entire exposure recovered and were fertile. Pretreating with $CO_2$ before establishing anoxic environment did not have a noticeable difference in these experiments.

Example 8

Drop in Core Body Temperature

Figure 20A:
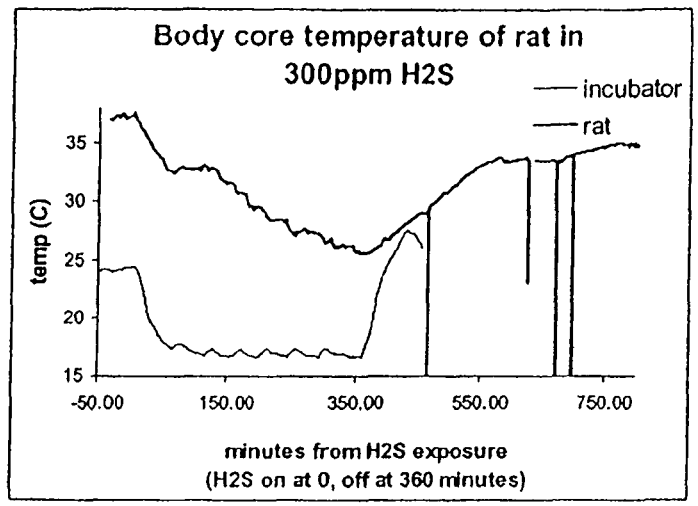
FIG. 20A-B show the change in core temperature of rats exposed to hydrogen sulfide (A) and mice exposed to carbon dioxide (B).
Figure 20B:
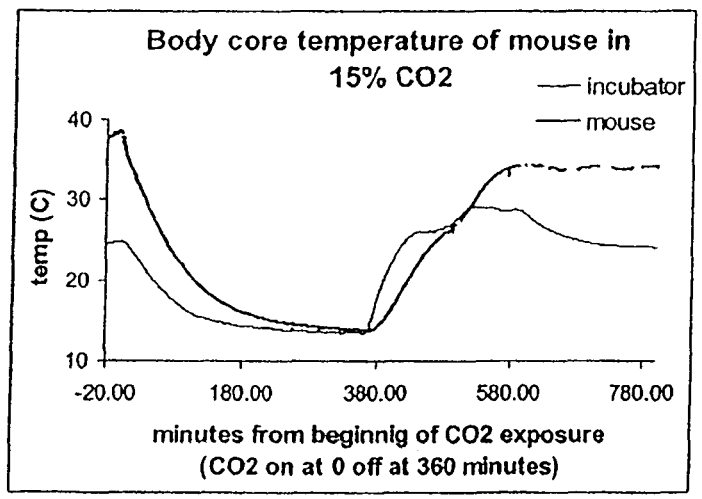

In both rats and mice, it was shown that using $H_2S$ and $CO_2$, metabolic output can be reduced, shown as reduced body core temperature. FIG. 20A-B show that at time 0 when $H_2S$ or $CO_2$ are first applied, the body core temperature of the animals begins to drop. Six hours later, when the $H_2S$ or $CO_2$ are removed, the temperature begins to return to normal. It is clear that larger mammals require more $H_2S$ to affect metabolism.

Prophetic Example 9

Gas Matrix

In order to determine the concentration of each component gas in a custom mixed atmosphere that provides the greatest capacity to control metabolic flexibility in mammals, the following experiments can be performed. The gases include oxygen ($O_2$), nitrogen ($N_2$), carbon dioxide ($CO_2$), hydrogen sulfide ($H_2S$), and helium (He). While $H_2S$ probably reduces oxygen demand in mitochondria, $CO_2$ may further reduced oxygen demand. In addition, it has been found that reduced body core temperature is essential for reduced metabolism. Therefore, helium gas, with its high heat capacity, may provide a simple and noninvasive cooling method. Furthermore, using 100% $O_2$, a normoxic 20.95% oxygen can be maintained in any gas mix in which the other constituents make up less than 79.05% of the total. And finally, nitrogen is used to balance the mix to 100%.

Figure 21:
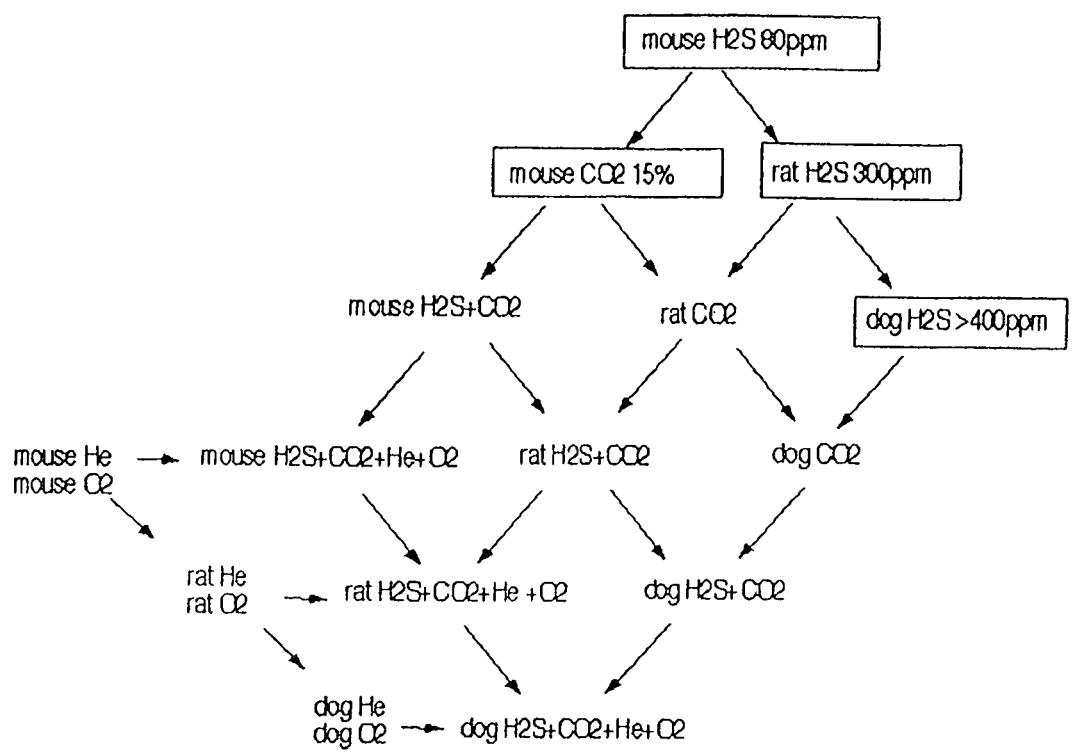
FIG. 21 Gas Matrix showing stepwise experimental plan to determine concentration of active compounds.

These experiments describe a progressive approach to assay the gases singly and in combination first in mouse then rat, then dog. It is the goal with this gas matrix to develop a foundation on which to work with multiple variables in a logical order. The experimental design is depicted in FIG. 21.

One of the features of the gas matrix is that it makes clear that experiments will only be performed if previous experiments (linked by arrows) are complete. Mixing experiments will not be performed in any animal model without first optimizing the component gases. Furthermore, a gas or gas mix will not be used in a rat without first optimizing the dose in mouse nor in a dog without first optimizing in rat. Thus, it shows the progression of experiments using single gases to multiple gas mixes (reading top-right to bottom-left) and mice to rats to dogs (reading top-left to bottom-right). Mice will always be used first to determine the concentration of component gases that provide the best control of metabolic flexibility. Once the most effective dose of a gas is determined using mice, the same experiments will be performed in rat. At the same time, the next gas or gas mix will be assayed using mice. Once the concentration is determined in rat, the gas will be tested in dogs. The following table provides a slightly different way to view the gas matrix and defines the order of experiments:

| sequential order | mouse | rat | dog |
|---|---|---|---|
| 1 | $H_2S + CO_2$ | $CO_2$ | |
| 2 | $He/O2$ | $H_2S + CO_2$ | $CO_2$ |
| 3 | $H_2S + CO_2 + He$ | $He/O2$ | $H_2S + CO_2$ |
| 4 | | $H_2S + CO_2 + He$ | $He/O2$ |
| 5 | | | $H_2S + CO_2 + He$ |

Procedure 1. Carbon Dioxide ($CO_2$)

Mice: It was found that 15% $CO_2$ affords control of metabolic flexibility in mice. However, given the limitations of our mixing abilities, we were unable to test higher concentrations. This is no longer true, and we can test $CO_2$ concentrations up to 80%. Therefore, we will begin at 15% $CO_2$ and increase in 5% increments to 40% then 10% increments to 80%. Animals will be exposed for 6 hours. Mice will be exposed using a 375 ml glass chamber in which the animals will be supplied with water and into which a premixed gas atmosphere will be flowed at a rate of 500 milliliter per minute. These chambers will be contained in an incubator so that ambient temperature can be controlled. This table provides a framework for our high-concentration $CO_2$ experiments but additional experiments may be required to better understand the effects. Mice can be used in multiple experiments but we will not use an animal more frequently than once per week. Furthermore, animals can function as their own controls in subsequent experiments.

| % $CO_2$ | 15 | 20 | 25 | 30 | 35 | 40 | 50 | 60 | 70 | 79 |
|---|---|---|---|---|---|---|---|---|---|---|
| % $O_2$ | 21 | 21 | 21 | 21 | 21 | 21 | 21 | 21 | 21 | 21 |
| % N2 | 64 | 59 | 54 | 49 | 44 | 39 | 29 | 19 | 9 | 0 |

Metabolism ($O_2$ consumption and body core temperature) and activity will be monitored. At 15% $CO_2$, tidal volume increases but respiration rate remains unchanged. The mice do not appear to "gasp". Increasing $CO_2$ concentrations should increase the narcotic effect.

These experiments will be performed in an incubator so that we can then reduce ambient temperature to 110° C. to assay the relationship between body core temperature and metabolic output.

Rats: Experiments in rats will begin using a 3% $CO_2$ and 21% $O_2$ balanced nitrogen environment. This is regarded as normocapnia as it is the exhaled concentration of $CO_2$. From 3% we will increase in 2% increments to 15%. This increase can be performed in a single baseline experiment where we increase the $CO_2$ concentration until we see a change in metabolism. Metabolism will be monitored by measuring $O_2$ consumption and body core temperature. A single rat in one experiment can be used to determine this minimal $CO_2$ dose. In subsequent experiments, where the effects of 6 hours of $CO_2$ exposure will be assayed, a single rat will be used for a single $CO_2$ dose (i.e., the level will not change during the experiment). Rats can be used in multiple experiments; they will be used no more than one time in a week. Rats will be exposed using a 2800 ml glass container in which the animals will be supplied with water and into which premixed gases will be flowed at a rate of 3 liters per minute. This table shows the structure of the first $CO_2$ experiments using rats but others may be required to fully explore the effects.

| % CO2 | 3 | 5 | 7 | 9 | 11 | 13 | 15 |
|---|---|---|---|---|---|---|---|
| % $O_2$ | 21 | 21 | 21 | 21 | 21 | 21 | 21 |
| % $N_2$ | 76 | 74 | 72 | 70 | 68 | 66 | 64 |

From 15% to 80% experiments will progress as was done using mice (5% increments from 15%-40%, 10% increments from 40%-80%). Metabolism and behavior will be monitored. Once the effective dose of $CO_2$ for the rats is determined, the ambient temperature will be reduced to learn if metabolism is further reduced by reduced body core temperature as it is using $H_2S$. These experiments will be performed in an incubator that will provide the cooling at the beginning of and during the experiment as well as the heat at the end of the experiment.

After completion of the rat $CO_2$ studies, it will be known if rats require more $CO_2$ than mice to reduce their metabolism (as is true for $H_2S$), the same, or less. Understanding of this key allometric trend will provide a better hypothesis for the active $CO_2$ dose in dogs.

The stopping points for these procedures in mice and rats will be a drop in $O_2$ consumption by 99% or a drop in $CO_2$ production by 99%.

Dogs: The experimental design for the dogs will be the same as that used for rats and mice (using a flow rate of 10 liters/minute). Experiments will begin using 3% $CO_2$ and increase until a physiological response is seen. Dogs will be exposed to mixed gases using an anesthesia mask to which they have been preconditioned before exposure. $O_2$ consumption and body core temperature will be monitored. The same one or two dogs can be used for these experiments.

Procedure 2. Hydrogen Sulfide and Carbon Dioxide ($H_2S+CO_2$)

By mixing $H_2S$ and $CO_2$ we will look for synergistic effects of the two gases. That is, can $H_2S$ and $CO_2$ be used together to reduce metabolism as profoundly as higher concentrations of single gases. In the first experiments, using mice, $H_2S$ at 20 ppm and titrated in $CO_2$ to 15% (or other concentration to be determined in procedure 1) will be used. A single animal can be used to vary the concentration of $CO_2$ while holding $H_2S$ constant. Second, we will use 40 ppm $H_2S$ and add $CO_2$ to 15%. Third, we will use 80 ppm $H_2S$ and bring $CO_2$ to 15%. A single animal can be used in each of these experiments. $O_2$ consumption, body core temperature, and behavior will be monitored. The experiments listed in the table(s) provide a foundation for exploring the effects of the $H_2S+CO_2$ mix and other experiments will be necessary to understand effects.

| exp | $O_2$ % | $H_2S$ ppm | $CO_2$ % |
| --- | --- | --- | --- |
| 1 | 21 | 20 | 5-10-15 |
| 2 | 21 | 40 | 5-10-15 |
| 3 | 21 | 80 | 5-10-15 |

Once an effective mix is determined, ambient temperature will be lowered to learn if the optimized gas mix synergizes with lower body core temperature to further lower metabolic rate. In these temperature dependent experiments, the concentrations of the gases in the mix will not change. Once again, one animal can be used in multiple experiments with no more than one experimental procedure per animal per week.

The experiments using rats and dogs will be performed using the same methodology. The $CO_2$ concentrations for rat and dog will be optimized in procedure 1 but it is hypothesized that they will be between 5% and 15%. For dogs, the high $H_2S$ concentration is greater than 400 ppm but has not yet been determined.

Procedure 3 Helium (He)

Helium is an effective heat dissipator; its thermal conductance is six times greater than nitrogen. It has been used in many mammals including rats, dogs, and humans to promote cooling. It is non toxic, inexpensive, and easy to handle. It is desirable to use helium as others have in an 80%/20% mixture with oxygen (He—$O_2$) to enhance thermal conductivity via respiration. Five preliminary experiments are proposed to analyze the effect of He—$O_2$ on metabolism and behavior. The standard 80%-20% mix that is widely used will be employed. A mix containing 60% He will also be tested to better reflect the minimum He—$O_2$ mix we will use in protocol 5 where we mix $H_2S$, $CO_2$ and He.

| exp. | animal | temp | He—$O_2$—N2 |
| --- | --- | --- | --- |
| 1 | mouse | 23° C. | 80-20-0 |
| 2 | mouse | 10° C. | 80-20-0 |
| 3 | mouse | 23° C. | 60-20-20 |
| 4 | mouse | 10° C. | 60-20-20 |
| 5 | rat | 23° C. | 80-20-0 |
| 6 | rat | 10° C. | 80-20-0 |
| 7 | rat | 23° C. | 60-20-20 |
| 8 | rat | 10° C. | 60-20-20 |
| 9 | dog | 23° C. | 80-20-0 |
| 10 | dog | 23° C. | 60-20-20 |

Oxygen consumption, carbon dioxide production, body core temperature, and behavior will be monitored to learn if the same effects that others have using He—$O_2$ can be induced.

Procedure 4: Oxygen (O2)

That reduced oxygen concentration can reduce body core temperature was shown by Gellhorn and Janus in 1936 using Guinea pigs. It is desired to reproduce these experiments first in mice, then in rats, and finally in dogs to learn if decreased $O_2$ concentration decreases metabolism.

Mice: Experiments are proposed in which mice will be exposed to decreasing concentrations of $O_2$ down to 6%. Experiments will progress in 5% increments. $O_2$ consumption, $CO_2$ production, body core temperature, and behavior will be assayed. If convulsive behavior indicative of extreme hypoxia is observed, $O_2$ will be returned to 21%. The table below provides a general outline of the $O_2$ experiments. Exposure time is six hours in a controlled chamber (with water) into which premixed gas is flowed. Since there is evidence of hypoxic preconditioning, four separate animals for these four experiments.

| exp. | % O2 | % N2 |
| --- | --- | --- |
| 1 | 21 | 79 |
| 2 | 16 | 84 |
| 3 | 11 | 89 |
| 4 | 6 | 94 |

Once the relationship between $O_2$ tension and metabolism has been determined, it may be important to repeat the experiments in a cold environment. These experiments will be performed exactly as the previous experiments except the temperature of the incubator will be lowered to 10° C.

Rats: It is desirable to conduct the same experiments using rats that were performed previously with mice. If convulsive behavior indicative of extreme hypoxia is observed, $O_2$ concentration will be returned to 21%.

Dogs: If a positive correlation between reduced oxygen tension and reduced metabolic rate is observed in mice and/or rats, it will be desirable to perform the same series of experiments using dogs.

Procedure 5: Hydrogen Sulfide, Carbon Dioxide, Helium, and Oxygen ($H_2S+CO_2+He+O_2$)

These experiments are the goal of the gas matrix; to determine mix of $O_2$, $CO_2$, $H_2S$, and He combined with optimized ambient temperature that affords the most robust and reversible control of metabolism. Therefore, using the concentrations of the individual gases that were determined in the previous procedures as a foundation, mixes of the four gases will be assayed to find the one which affords the best control of metabolic flexibility. $O_2$, $CO_2$, and $H_2S$ will be varied relative to one another while helium will be used to balance the mix. In the mouse experiments shown below, $CO_2$ will be varied while $O_2$ and $H_2S$ will be held constant; helium will be changed to maintain constant flow. We will use the same metabolic assays including oxygen consumption and body core temperature. A single animal can be used in multiple experiments. Mice will be exposed for six hours. These experiments will then be repeated using lower ambient temperature to learn how much reduced body core temperature affects metabolism using the gas mix.

| | Mouse: | | | |
|---|---|---|---|---|
| exp. | $O_2$ conc. % | $H_2S$ conc. ppm | $CO_2$ conc. % | He balance |
| 1 | 21 | 20 | 5-10-15 | |
| 2 | 21 | 40 | 5-10-15 | |
| 3 | 21 | 80 | 5-10-15 | |
| 4 | 16 | 20 | 5-10-15 | |
| 5 | 16 | 40 | 5-10-15 | |
| 6 | 16 | 80 | 5-10-15 | |
| 7 | 11 | 20 | 5-10-15 | |
| 8 | 11 | 40 | 5-10-15 | |
| 9 | 11 | 80 | 5-10-15 | |
| 10 | 9 | 20 | 5-10-15 | |
| 11 | 9 | 40 | 5-10-15 | |
| 12 | 9 | 80 | 5-10-15 | |
| 13 | 6 | 20 | 5-10-15 | |
| 14 | 6 | 40 | 5-10-15 | |
| 15 | 6 | 80 | 5-10-15 | |

Rats: After it is learned what the optimal gas mixture is for mice, experiments using rats will be done identical to those performed using mice except the $H_2S$ concentrations are 100, 200, and 300 ppm. Rats will be treated for 6 hours.

Dogs: Experiments using dogs will be identical to those using mice and rats. The concentrations will begin at 300 ppm and go to a to-be-determined concentration. Single animal can be used for multiple experiments but not more than once per week. Mice and rats will be treated for 6 hours, dogs will be treated for two hours.

Prophetic Example 10

Hydrogen Sulfide Dose Selection in Humans

Hydrogen sulfide can be administered to an animal or human to induce stasis by any of a number of dosage forms and routes of administration, including, but not limited to, inhalation of the gaseous form or intravenous administration of a solution of hydrogen sulfide. A method to determine the dosage form and route of administration of hydrogen sulfide sufficient to induce stasis in a whole organism in need of stasis is described. A test organism (e.g., a rat, dog, pig, monkey) is exposed to increasing concentrations of hydrogen sulfide administered either as bolus doses, intermittently, or continuously, and the physiological state, including but not limited to, core body temperature, oxygen consumption, carbon dioxide production, heart rate, blood pressure, breathing rate, blood pH, movement, and wakefulness are monitored while at various timepoints blood samples (0.5 mL) are removed. Concentrations of hydrogen sulfide that are present in the test animals' blood-derived plasma are measured using methods known in the art, including, but not limited to X derivatization, Y extraction, and quantitation using gas chromatography and mass spectrometry.

Correlation of the steady state plasma levels of hydrogen sulfide engendered by a particular dosing regimen in the test animal with the achievement of stasis, to varying degrees, in the test animal, defines an effective dose of hydrogen sulfide sufficient to induce stasis in the test animal. The effective dose for inducing stasis in a human in need of stasis is determined by identifying the dose, route of administration, and dosing regimen of hydrogen sulfide that achieves the same steady state plasma concentrations of hydrogen sulfide in the humans as are achieved in the test animals under conditions where stasis is induced. The effective concentration of hydrogen sulfide to achieve stasis in a human depends on the dosage form and route of administration. For inhalation, in some embodiments effective concentrations are in the range of 50 ppm to 500 ppm, delivered continuously. For intravenous administration, in some embodiments effective concentrations are in the range of 0.5 to 50 milligrams per kilogram of body weight delivered continuously.

The range in each case is characterized by increasing degrees of stasis achieved with increasing dose of the hydrogen sulfide. A dose of hydrogen sulfide sufficient to cause a sustained, 12-24 hour drop of three to five degrees Celsius to 32-34 degrees Celsius in the core body temperature of a human who has suffered out-of-hospital cardiac arrest and who is unconscious upon resuscitation and resumption of a heartbeat is predicted to have a significant survival advantage over a similar human not exposed to hydrogen sulfide, as described in Bernard et al. 2002.

Example 11

Animal Pre-Treatment Studies

The studies shown in Example 7 demonstrated that prior and continuous treatment of male C57Bl/6 mice with $H_2S$ can enhance their ability to survive under hypoxic conditions of 5% oxygen or 4% oxygen.

Figure 23:
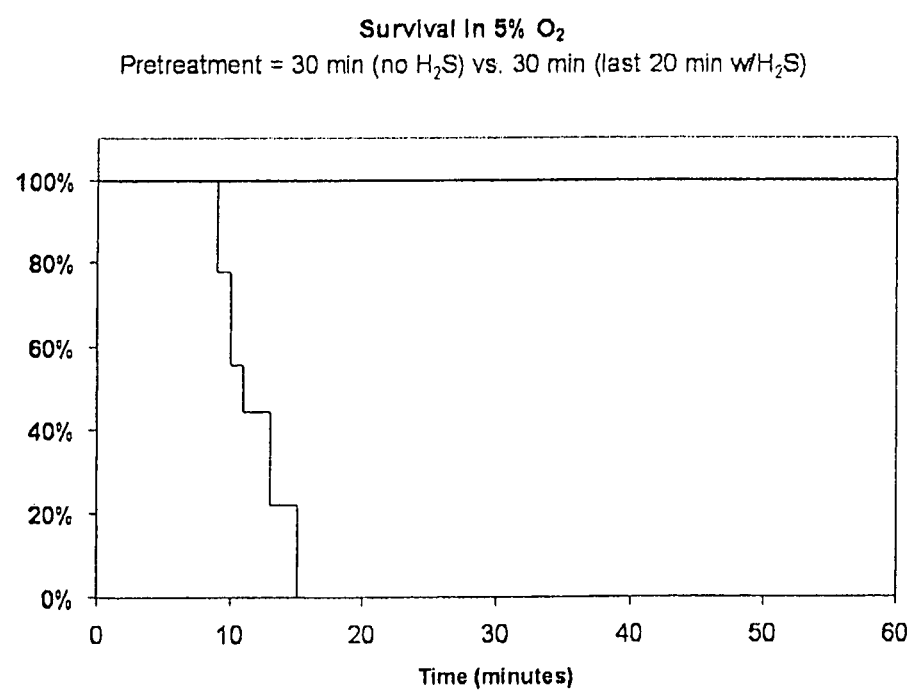
FIG. 23 Survival of Mice in 5% Oxygen. Mice were exposed to either 30 minutes of room air before exposure to 5% $O_2$ (control; black line; n=9) or 10 minutes of room air followed by 20 minutes of 150 ppm $H_2S$ before exposure to 5% $O_2$ (experimental; red line; n=20) and their length of survival measured. Experiments were stopped at 60 minutes and if the animals were still alive (all of the experimental, none of the controls) they were returned to their cage.

To determine the effect of $H_2S$ pre-treatment alone on survivability under hypoxic conditions (without continuous $H_2S$ exposure during hypoxia), mice were exposed to either 30 minutes of room air (No PT) or 10 minutes of room air followed by 20 minutes of 150 ppm $H_2S$ in room air (PT) before exposure to 5% $O_2$ (5%), 4% $O_2$ (4%), 1 hr 5% $O_2$ followed by 4% $O_2$ (4%+1 hr 5%), or 1 hr 5% $O_2$ followed by 3% $O_2$ (3%+1 hr 5%), and their survival time determined. Experiments were stopped at 60 minutes, and animals still alive were returned to their cage. As shown in FIG. 23, all of the mice in a cohort of animals pre-exposed to 150 ppm $H_2S$ in room air for 20 minutes survived subsequent exposure to 5% $O_2$, while all of the control animals exposed to room air alone had died within 15 minutes of exposure to 5% $O_2$. Thus, pre-exposure of mice to $H_2S$ establishes a physiological state in the mice that allows prolonged survival to otherwise lethal hypoxia. The protection observed in $H_2S$ pre-treated mice far exceeds the known protective effect of whole body hypoxia preconditioning that has been reported in the literature, in which survivability in 5% $O_2$ was extended only twofold (Zhang et al. 2004). Although not shown in FIG. 23, some $H_2S$ pre-treated mice were able to survive for more than four hours in 5% $O_2$ and were able to recover with no noticeable motor or behavioral deficits.

Figure 24:
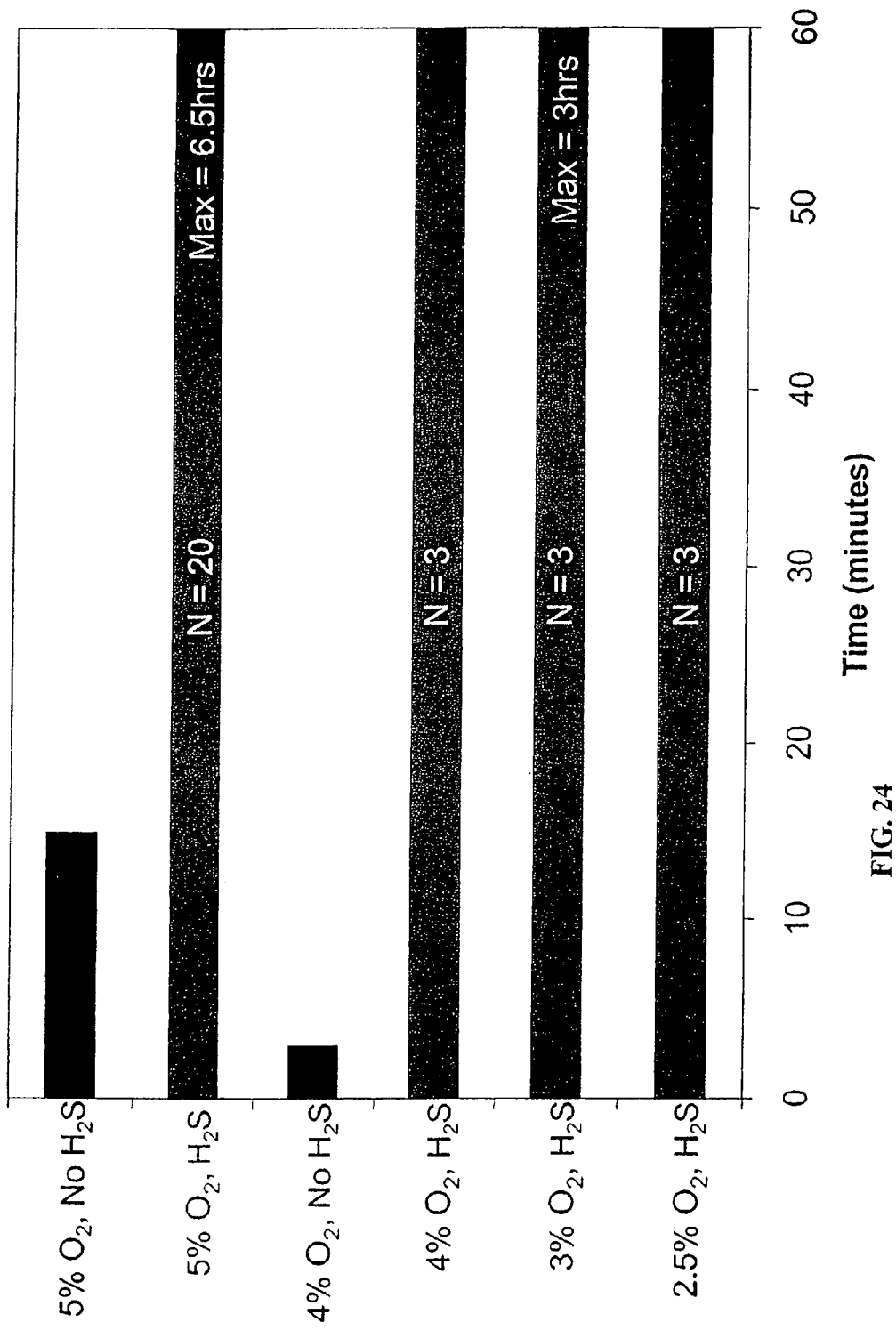
FIG. 24 $H_2S$ Increases Survival at Lethal Oxygen Tensions. Chart showing results of experiment described in FIG. 23. The x-axis shows the time in minutes that the mice survived in the lower oxygen tensions. The dark bars show when $H_2S$ is absent while the lighter bars show when $H_2S$ is present. In the latter groups, mice were exposed to 150 ppm $H_2S$ prior to the oxygen tension being reduced to between 5% and 2.5%. Survival times were measured and was at least 60 minutes in all the $H_2S$ treated groups.
Figure 28:
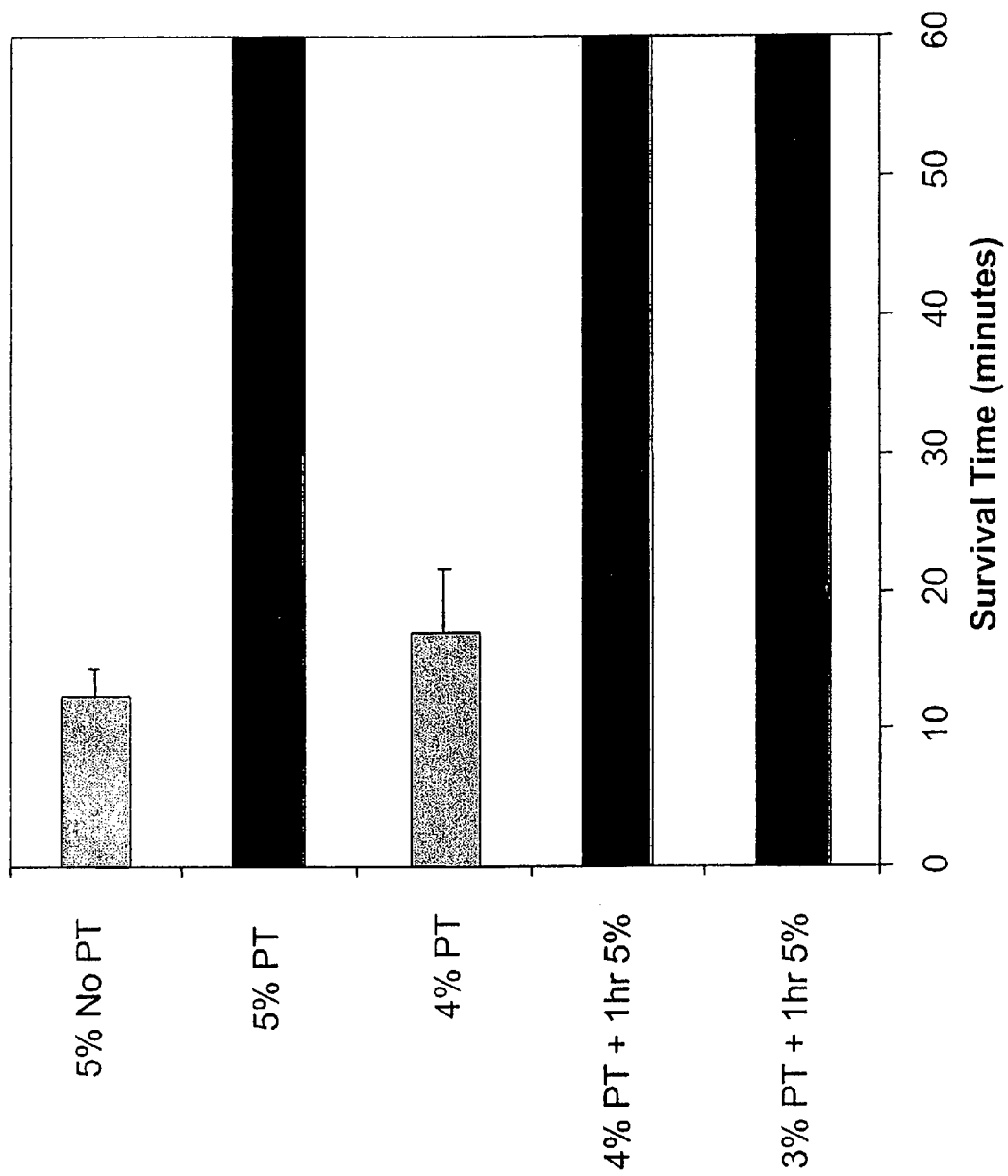
FIG. 28 $H_2S$ Pre-treatment Enhances Survival of Mice Under Hypoxic Conditions. Mice were exposed to either 30 minutes of room air (No PT) or 10 minutes of room air followed by 20 minutes of 150 ppm $H_2S$ (PT) before exposure to 5% $O_2$ (5%), 4% $O_2$ (4%), 5% $O_2$ for 1 hr followed by 4% $O_2$ (4%+1 hr 5%), or 5% $O_2$ for 1 hr followed by 3% $O_2$ (3%+1 hr 5%), and their length of survival measured. Experiments were stopped at 60 minutes and if the animals still alive were returned to their cage.

To determine if $H_2S$ pre-treatment enhances survivability to even lower oxygen tensions, mice were exposed to lower $O_2$ concentrations. As shown in FIG. 24, $H_2S$ pre-treatment greatly enhances survival in the presence of 5% $O_2$. In contrast, $H_2S$ pre-treatment provided only a small increase in survival in the presence of 4% $O_2$. However, if $H_2S$ pre-treated mice were exposed to a step-wise reduction in $O_2$ levels, such that they were first pre-treated and then exposed for 1 hour to 5% $O_2$ and then exposed to either 4% $O_2$ or 3% $O_2$, their survival time was enhanced to the same level as that observed when they were exposed to 5% $O_2$ following $H_2S$ pre-treatment (FIG. 28). Thus, pre-exposure to $H_2S$ establishes a physiological state in which mice can survive a graded reduction in oxygen tensions exceeding 80% (21% normoxia reduced to 3% $O_2$). Furthermore, in some experiments, graded reduction of oxygen tension following $H_2S$ pre-treatment showed the mice can survive for an hour in oxygen tensions as low as 2.5%.

These data and those described in Example 7 demonstrate that exposure to $H_2S$ has a pharmacological effect in which survival in otherwise lethal hypoxia is greatly enhanced. In this context, the pharmacological effects of $H_2S$ depend on dose levels and duration of exposure to $H_2S$, parameters that one skilled in the art can vary to achieve optimum survivability to lethal hypoxia. One skilled in the art will appreciate that the route of administration (e.g., inhaled versus parenteral administration) can also be varied to achieve the desired effect of lethal hypoxia tolerance in a mammal. In addition, the pharmacological effect can be observed either when $H_2S$ exposure is limited to pre-treatment or is extended into the period of hypoxia. Likewise, the timing of exposure to $H_2S$ relative to the onset of lethal hypoxia can be varied to maximize the enhanced survivability. These data are consistent with the hypothesis that reduction in oxygen demand resulting from pretreatment with an active compound, such as an oxygen antagonist, allows survival in reduced oxygen supply that is otherwise lethal to the animal.

Figure 25:
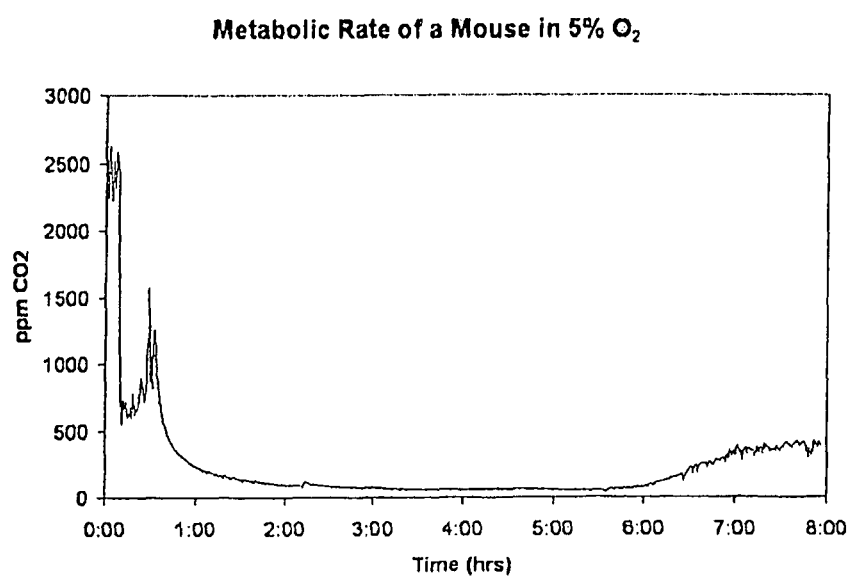
FIG. 25 Metabolic Rate of a Mouse in 5% Oxygen. A mouse was exposed to 10 minutes of room air followed by 20 minutes of 150 ppm $H_2S$ prior to exposure to 5% $O_2$-Metabolic rate measured by $CO_2$ output. Pre-exposure $CO_2$ output was approximately 2500 ppm, after 20 minutes of $H_2S$ then metabolic rate was down approximately 2-fold and after several hours of exposure to 5% $O_2$ the $CO_2$ output had dropped approximately 50-fold from pre-exposure levels to approximately 50 ppm. At hour 6 the mouse was returned to room air and allowed to recover. This data is from one of the mice included in FIG. 23 (experimental group).
Figure 29:
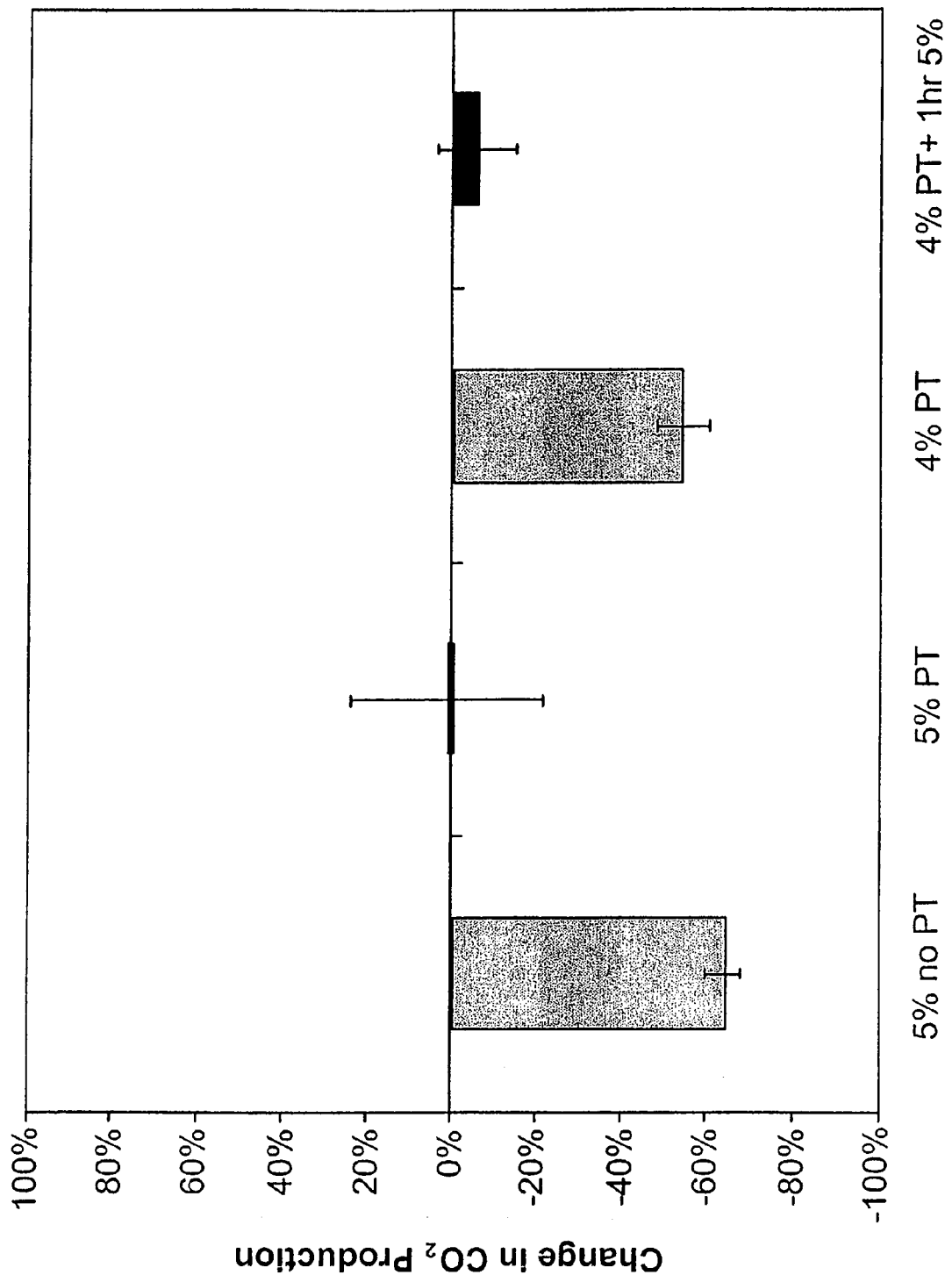
FIG. 29 $CO_2$ Production During Transition to Lethal Hypoxia. Changes in $CO_2$ production upon transition to either 5% $O_2$ or 4% $O_2$ were measured in mice exposed to either room air for 30 minutes (No PT) or room air for 10 minutes followed by 150 ppm $H_2S$ for 20 minutes (PT). In addition, the change in $CO_2$ production upon step-wise transition to 5% $O_2$ for 1 hr followed by 4% $O_2$ was measured. The percent change in $CO_2$ production is plotted with standard error indicated.

To characterize the changes in metabolism that occur in the setting of enhanced survivability to lethal hypoxia afforded by $H_2S$ treatment, $CO_2$ production by the mice was measured during exposure to $H_2S$ and thereafter following termination of $H_2S$ treatment and subsequent exposure to 5% $O_2$. The change in $CO_2$ production is shown in FIG. 25. Changes in $CO_2$ production upon transition to either 5% $O_2$ or 4% $O_2$ were measured in mice exposed to either room air for 30 minutes (No PT) or room air for 10 minutes followed by 150 ppm $H_2S$ for 20 minutes (PT). In addition, the change in $CO_2$ production upon step-wise transition to 5% $O_2$ for 1 hr followed by 4% $O_2$ was measured. The results of these experiments are provided in FIG. 29.

$CO_2$ production was reduced approximately two to three-fold in the first five to ten minutes of $H_2S$ pre-treatment, suggesting that stasis is induced in the mice during the 20 minute pre-treatment with 150 ppm $H_2S$ in room air. However, $O_2$ consumption and core body temperature of the animals did not change significantly during the $H_2S$ pre-treatment (data not shown), suggesting that a physiological state other than stasis may be established in the mice during exposure to $H_2S$ that allows enhanced survivability to lethal hypoxia. Such a state might be characterized by a reduction in metabolism within the biological material of a magnitude that is less than that defined as stasis. In order to achieve stasis using an active compound, the biological matter necessarily must transition through a graded hypometabolic state in which oxygen consumption and $CO_2$ production are reduced less than twofold in the biological matter. Such a continuum, in which metabolism or cellular respiration is reduced by an active compound to a degree less than twofold, is described as a state of "pre-stasis." Continued monitoring of $CO_2$ production following termination of $H_2S$ pre-treatment and induction of lethal hypoxia shown in FIG. 25 demonstrates an approximately 50-fold reduction in $CO_2$ production, indicating that stasis is achieved during the exposure to lethal hypoxia. A concomitant decrease in $O_2$ consumption and strong attenuation of motility in the mice during exposure to lethal hypoxia further supports the observation that stasis is subsequently achieved during exposure to lethal hypoxia.

Changes in $CO_2$ production associated with transition to hypoxic conditions of either 5% $O_2$ or 4% $O_2$ after $H_2S$ pre-treatment or no pre-treatment were measured. As shown in FIG. 28, mice exposed to either 5% $O_2$ in the absence of $H_2S$ pre-treatment or exposed to 4% $O_2$ in the presence of $H_2S$ pretreatment displayed a substantial decrease in $CO_2$ production. In contrast, $H_2S$ pre-treated mice that were subsequently exposed to either 5% $O_2$ or 5% $O_2$ followed by 4% $O_2$ did not show any significant changes in $CO_2$ production as compared to the new baseline level following $H_2S$ pre-treatment. These results demonstrate a correlation between reduced metabolic activity and death associated with exposure to 5% $O_2$ in the absence of $H_2S$ pre-treatment or exposure to 4% $O_2$ with $H_2S$ pre-treatment. In addition, these data demonstrate that exposure to 5% $O_2$ or a step-wise reduction from 5% $O_2$ to 4% $O_2$ following $H_2S$ pre-treatment does not result in an additional reduction in metabolic activity. To summarize these results, decreases in $CO_2$ evolution that occur upon transition form normoxia to lethal hypoxia were blunted in mice that were pre-treated with $H_2S$. Transition from normoxia to lethal hypoxia caused a 40% reduction in $CO_2$ evolution, but pre-treatment with $H_2S$, while itself causing a 50-60% reduction in $CO_2$ evolution to a new, lower baseline, prevented any further decrease in $CO_2$ evolution on transition to lethal hypoxia. These data demonstrate that $H_2S$ pretreatment alone prevents additional reductions in metabolic activity typically associated with a transition to lethal hypoxia, thereby enhancing survival under hypoxic conditions. In addition, these data support a model wherein pre-exposure of biological matter to active compounds is sufficient to enhance survivability and/or reduce damage from injuries or disease insults.

Example 12

Hydrogen Selenide Reduces Core Body Temperature in Mice at Reduced Concentrations It had been previously reported in the literature that greater than 1 ppm of $H_2Se$ was lethal to animals. Experiments were conducted according to the Materials and Methods discussed in Example 4, except that $H_2Se$ was used at even lower concentrations than with $H_2S$. The $H_2Se$ used had an initial concentration from the source tank of 20 ppm in nitrogen, which was then diluted with room air to approximately 10 or 100 parts per billion (ppb). Animals were then exposed to this mixture.

Figure 26:
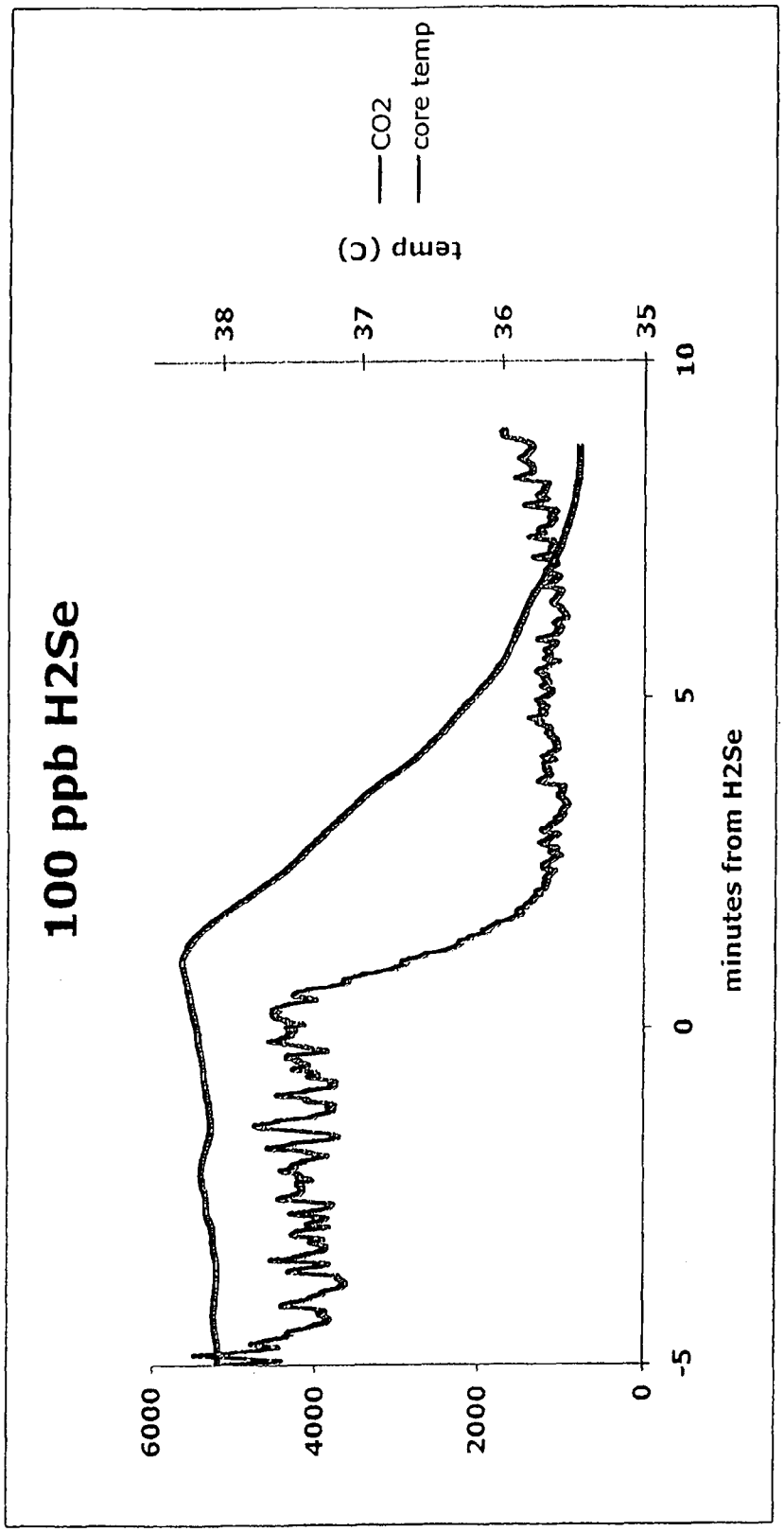
FIG. 26 Mouse Exposed to 100 ppb $H_2Se$. Chart shows exposure to $H_2Se$ in minutes (x-axis) with drop in core body temperature (temperature in celsius shown on right plotted with line showing gradual decrease) and with decrease in respiration (ppm $CO_2$ shown on left plotted with jagged line showing decrease).

Two mice were exposed to 100 ppb $H_2Se$ for less than 10 minutes. FIG. 26 shows the drop in core body temperature and 3-fold reduction in metabolic activity as evidenced by respiration in one mouse.

Figure 27:
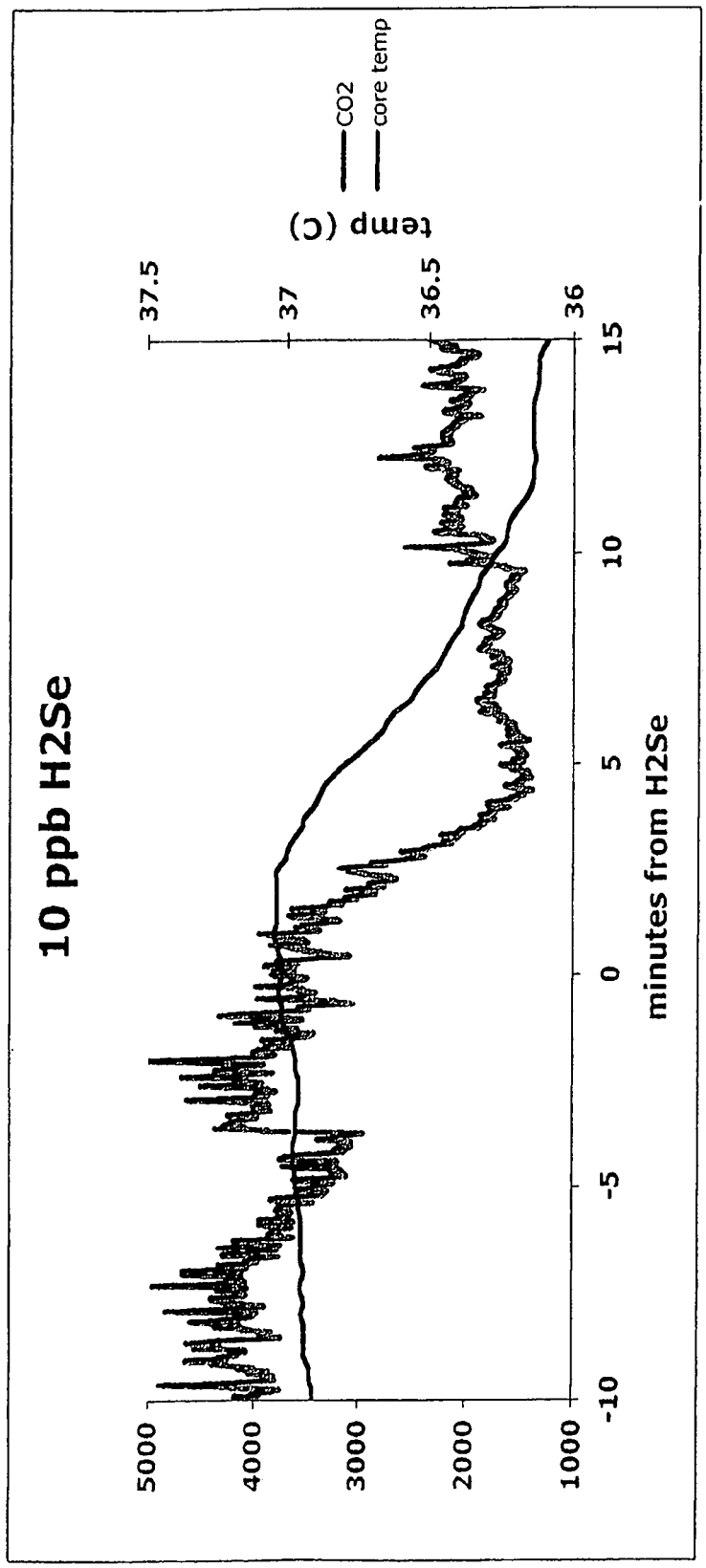
FIG. 27 Mouse Exposed to 10 ppb $H_2Se$. Chart shows exposure to $H_2Se$ in minutes (x-axis) with drop in core body temperature (temperature in celsius shown on right plotted with line showing gradual decrease) and with decrease in respiration (ppm $CO_2$ shown on left plotted with jagged line showing decrease with lowest point at five minute exposure).

The concentration of $H_2Se$ was reduced even further to 10 ppb. A mouse exposed to 10 ppb of $H_2Se$ also experienced a reduction in core body temperature and respiration (FIG. 27).

Moreover, the effects of $H_2Se$ appear fully reversible based on tests used to evaluate reversibility with $H_2S$ (Blackstone et al., 2005, which is hereby incorporated by reference).

Example 13

Hydrogen Sulfide Protects Against Lethal Hemorrhage

The studies shown in Examples 7 and 11 demonstrated that treatment of mice with hydrogen sulfide ($H_2S$) enhances their ability to survive under hypoxic conditions of 5% oxygen or 4% oxygen. To determine whether $H_2S$ treatment could also be used to reduce morbidity and/or tissue damage associated with a more clinically relevant acute injury model of ischemic hypoxia, rats were treated with $H_2S$ during controlled lethal hemorrhage, which reduces oxygen supply to tissues and results in death (Blackstone et al., 2005). In this study, rats treated with $H_2S$ survived lethal blood loss and fully recovered.

Rats were treated with $H_2S$ during controlled lethal hemorrhage (60% blood loss). After surgical implantation of catheters and recovery, blood was removed from conscious animals in 40 minutes. A small amount (300 ppm) of $H_2S$ mixed with room air was administered to treated animals twenty minutes after the beginning of the bleed (i.e., after 30% blood loss). Animals were returned to room air without $H_2S$ at the end of the bleed. Three hours after the end of the bleed, surviving animals were given one shed-blood volume of lactated ringers solution intravenously.

Most (6/7) of the $H_2S$ treated rats survived hemorrhage and 3 hour shock period and recovered completely (Table 7). None of these surviving rats exhibited behavioral or functional defects after recovery. One $H_2S$ treated animal died 174 minutes after the end of the bleed. All of the untreated animals died within 82 minutes after the end of the bleed; average survival time of untreated animals was 35+/−26 minutes. Using a two-tailed Fishers exact T-test, the p value is 0.0047.

In the first twenty minutes of bleeding (before 30% blood loss) rats increased respiration rate and tidal volume to compensate for decreased oxygen carrying capacity due to blood loss. This increase in ventilation resulted in a decreased respiratory carbon dioxide production ($V_{CO2}$) (Table 7). After 60% blood loss, both $H_2S$ treated and untreated animals exhibited decreased $V_{CO2}$. Arterial blood lactate increased while $pCO_2$, bicarbonate ($[HCO_3^-]$), pH, and base excess decreased (Table 7). Thus hemorrhage resulted in metabolic acidosis with respiratory compensation. However, in $H_2S$ treated rats, these changes were smaller in magnitude representing a decrease in metabolic acidosis. Furthermore, in $H_2S$ treated animals, $V_{CO2}$ did not continue to decrease after hemorrhage. In untreated animals, $V_{CO2}$ decreased steadily until the animals stopped breathing. $H_2S$ administration appears to prevent the shock response from progressing to death.

TABLE 7

Survival and physiology of a rat hemorrage model using $H_2S$

| | $H_2S$ Treated | Untreated |
|---|---|---|
| Survival | | |
| Complete recovery | 85.7% (6/7) | 0% (0/7) |
| Time to death of non-survivors (min) | 174 (1/7) | 35 +/− 26 |
| $CO_2$ production ($V_{CO2}$) in ml/kg/min: | | |
| Pre-bleed | 25 +/− 4 | 26 +/− 6 |
| Mid-bleed | 20 +/− 2 | 21 +/− 3 |
| End of bleed | 16 +/− 2 | 11 +/− 3 |
| 15 minutes post bleed | 17 +/− 3 | 7 +/− 5 |
| Blood $CO_2$ content ($pCO_2$) in mmHg | | |
| Pre-bleed | 45 +/− 6 | 44 +/− 3 |
| End of bleed | 35 +/− 6 | 21 +/− 3 |
| Blood bicarbonate content ($[HCO_3]$) in mmol/L | | |
| Pre-bleed | 32 +/− 3 | 30 +/− 1 |
| End of bleed | 21 +/− 3 | 12 +/− 3 |
| Blood pH | | |
| Pre-bleed | 7.46 +/− 0.03 | 7.45 +/− 0.02 |
| End of bleed | 7.41 +/− 0.02 | 7.35 +/− 0.06 |

TABLE 7-continued

Survival and physiology of a rat hemorrage model using $H_2S$

| | $H_2S$ Treated | Untreated |
|---|---|---|
| Blood base excess in mmol/L | | |
| Pre-bleed | 8 +/− 2 | 6 +/− 1 |
| End of bleed | −5 +/− 4 | −14 +/− 3 |
| Blood Lactate in mmol/L | | |
| Pre-bleed | 1.4 +/− 0.5 | 1.2 +/− 0.2 |
| End of bleed | 6.6 +/− 1 | 11 +/− 3 |

Example 14

Benefit of Short-Term Exposure to Hydrogen Sulfide During Hemorrhage

Male Sprague Dawley rats weighing 275-350 grams were purchased from Charles River Laboratories one week before each experiment and allowed to acclimate. On the day of the experiment, catheters were surgically implanted into the right femoral artery and vein. Catheters exited behind scapulae. Rats were administered buprenorphine post-surgically and allowed to recover.

The anti-coagulant drug heparin (80-100 units) was administered intravenously as a bolus to decrease the clotting ability of the blood and enhance hemorrhage. Following heparin administration, conscious unrestrained rats were placed individually in a 2.75 liter crystallization dish with a glass lid. Catheters, temperature probe, and gas sampling tube were passed through a hole drilled in the middle of the lid. Temperature was maintained at approximately isothermal temperature (27+/−2° C.).

The hemorrhage model was defined by the removal of 60% of total body blood over the course of a 40 minute bleed. Blood was removed using a peristaltic pump. To determine the amount of blood that constitutes 60% of total body blood, rats were weighed and the volume of blood to was calculated using the following equation (0.06×body mass)+0.77 (Lee et al., 1985).

Treatment groups received exposure to either room air with hydrogen sulfide (test animals), or room air containing nitrogen (control animals) at a rate of 3 liters per minute administered by a thermal mass flow controller (Sierra Instruments).

Hydrogen sulfide ($H_2S$) (20,000 ppm balanced with nitrogen) (Byrne Specialty Gas) was diluted into room air to a concentration of 2000 ppm for treatment. Blood was removed at the calculated rate via the femoral catheter artery. Blood was weighed as it was removed. After twenty minutes (or at 50% of the 40 minute bleed) the test animals were exposed to room air containing 2000 ppm hydrogen sulfide. The exposure was terminated when animals exhibited apnea and dystonia. The average length of exposure to hydrogen sulfide ($H_2S$) was generally between 1 and 2 minutes. The maximum concentration of $H_2S$ in the chamber was estimated to be between 1000 and 1500 ppm. When the apnea and dystonia were observed, the animals received exposure to room air. Test animals resumed regular breathing patterns within 20 to 30 seconds upon exposure. Control animals were bled at the same rate as the test animals, but did not receive treatment with hydrogen sulfide. Control animals did not exhibit apnea or dystonia during the course of the experiment.

Metabolic rate was determined by measuring $CO_2$ production (Licor Li7000). Temperature and $CO_2$ data were collected (ADI PowerLab). Arterial blood values were measured (I-Stat blood chemistry analyzer). Following the bleed, animals were placed in a cage for three hours and observed. At the end of three hours, surviving rats were given lactated ringers ad libitum. For non-surviving animals, time of death was declared when animals stopped breathing and $CO_2$ production ceased. After resuscitation, rats were transferred to clean cages with food and water and housed at 30° C. for approximately 16 hours. Catheters were surgically removed and animals were allowed to recover for several hours at 30° C. before transfer back to the colony. Behavior and function tests were selected from a battery of tests described in the SHIRPA protocol (Rogers et al., 1997).

In these experiments, 7 out of 8 (88%) of the animals treated with hydrogen sulfide (H2S) during the course of the hemorrhage survived the hemorrhage. Two control animals who did not receive treatment died during the three hour observation period.

Example 15

Additional Results from Example 2

Figure 30:
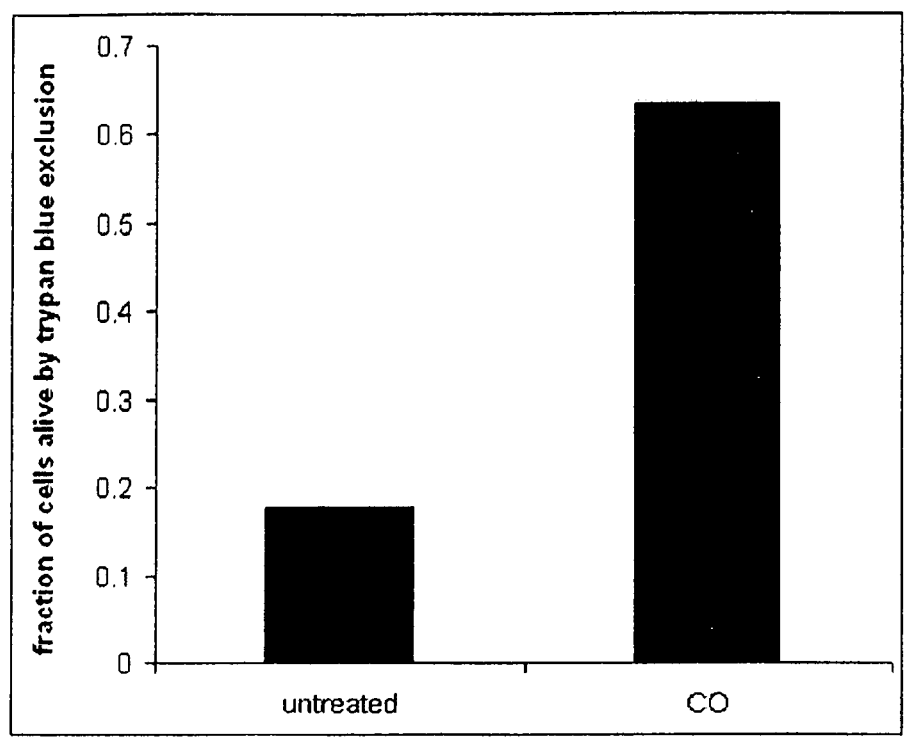
FIG. 30 Human keratinocytes survive exposure to 100% carbon monoxide (CO). Cells were inspected visually using an inverted phase contrast microscope. Quantitation of the number of viable keratinocytes as judged by trypan blue staining, which is an indicator of cell death.

As discussed in Example 2 above, human foreskins were used to evaluated the preservation of cells and tissue in carbon monoxide. A total of eight human foreskins were ultimately evaluated (Example 2 reports on three). The number of viable keratinocytes was evaluated using trypan blue (Table 8 and FIG. 30). This showed that carbon monoxide exposure increased the number of viable cells.

TABLE 8

Viability of keratinocytes isolated from Foreskins exposed to either room air (RA) or CO for 24 hours were tested for viability using trypan blue (tb) staining.

| | RA | | | CO | | |
|---|---|---|---|---|---|---|
| | live (tb−) | dead (tb+) | fraction alive | live (tb−) | dead (tb+) | fraction alive |
| | 0 | 3 | 0.00 | 10 | 1 | 0.91 |
| | 1 | 1 | 0.50 | 4 | 4 | 0.50 |
| | 0 | 0 | | 10 | 3 | 0.77 |
| | 0 | 0 | | 5 | 1 | 0.83 |
| | 7 | 34 | 0.17 | 49 | 42 | 0.54 |
| | 0 | 1 | 0.00 | 24 | 6 | 0.80 |
| | 1 | 2 | 0.33 | 3 | 3 | 0.50 |
| | 0 | 1 | 0.00 | 1 | 1 | 0.50 |
| SUM | 9 | 42 | 0.18 | 106 | 61 | 0.63 |

| | # cells recovered | fraction alive | | | |
|---|---|---|---|---|---|
| untreated | 51 | 0.18 | ttest | 0.000883884 | |
| CO | 167 | 0.63 | | | |

Example 16

Low Level Chronic $H_2S$ Exposure Increases Survivability

Using methods and apparatus described in Example 1, *C. elegans* nematodes were exposed to low levels of $H_2S$ (<100 ppm). Nematodes adapted to this treatment exhibit increased lifespan and resistance to thermal stress, however, there is no discernable decrease in metabolic activity as with induction of stasis.

In nematodes, the inability to perform aerobic metabolism (by reducing ambient oxygen concentration or addition of CO) results in the induction of suspended animation, or stasis (see Example 1). However, suspended animation was not induced by exposing them to <100 ppm $H_2S$ in house air. At doses above 100 ppm, $H_2S$ can result in considerable lethality of the population of nematodes exposed. Interestingly, even in conditions where the majority of worms are killed by $H_2S$, those that survive appear normal and are not obviously harmed by the agent. The worms growing in approximately 50 ppm $H_2S$ complete embryogenesis, develop to sexual maturity and produce progeny at the same rate as siblings raised in environments without $H_2S$. In contrast, in concentrations of oxygen where metabolic rate is reduced (less than 3.5% $O_2$), all of these processes are slowed. Moreover, worms raised in $H_2S$ produce the same number of progeny as controls in house air, suggesting that there are no deleterious effects from these conditions. These data indicate that $H_2S$ does not reduce metabolic activity under these conditions in *C. elegans*.

Figure 31:
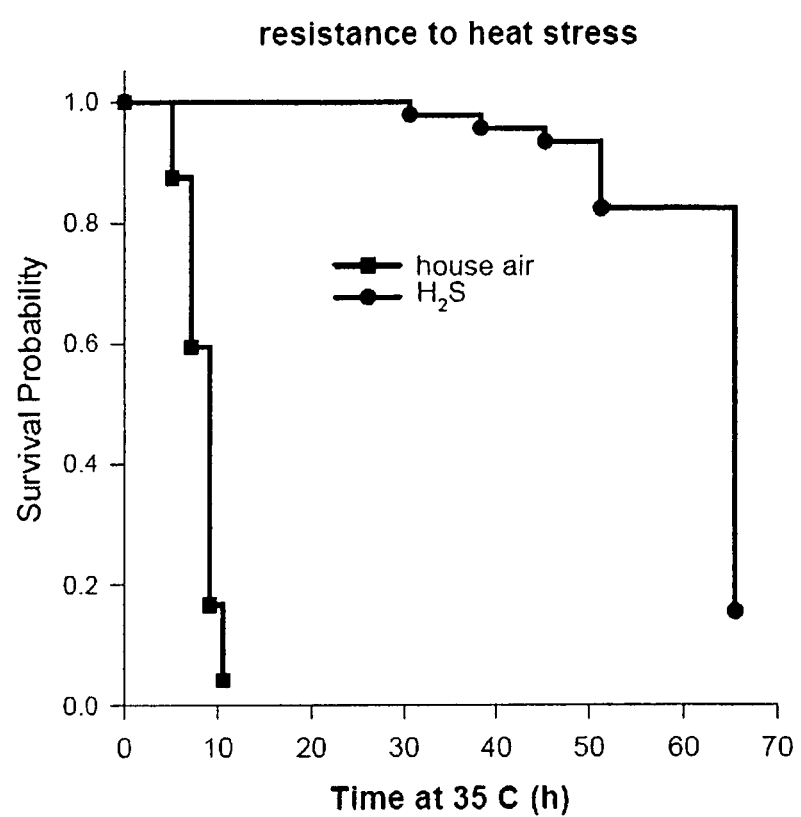
FIG. 31 Chronic exposure to low levels of $H_2S$ leads to heat resistance in C. elegans. Nematodes adapted to environments containing approximately 50 ppm $H_2S$ in house air, were significantly more resistant to lethal effects of elevating the ambient temperature to 35 degrees C. compared to siblings raised in house air alone.

Nematodes grown in $H_2S$ are more resistant to heat stress than age-matched controls in house air alone (FIG. 31). In this assay, worms raised in 50 ppm $H_2S$ were exposed to high temperature in $H_2S$ and worms raised in house air were exposed in house air. Thus, $H_2S$-induced resistance to stress is not correlated with decreased metabolic activity. However, this resistance to heat-stress requires that the nematodes be adapted to the $H_2S$ environment. Worms raised in house air and exposed to heat-stress in $H_2S$ die more rapidly than if they were exposed in house air. The adaptation to $H_2S$ is persistent, insofar as worms raised in $H_2S$ and exposed to heat stress in house air survive better than controls raised in house air. In addition, worms adapted to a non-toxic low concentration of $H_2S$ (e.g., 50 ppm) were resistant to higher concentrations of $H_2S$ that are lethal to unadapted worms.

These data are consistent with data that flies transiently exposed to $H_2S$ are subsequently able to survive anoxia better than untreated controls (e.g., Example 7 and Example 11). The protection against heat stress (in worms) and anoxic stress (in flies) suggests that $H_2S$ may be able to increase survivability in a variety of adverse or stressful states that may be encountered clinically.

Figure 32:
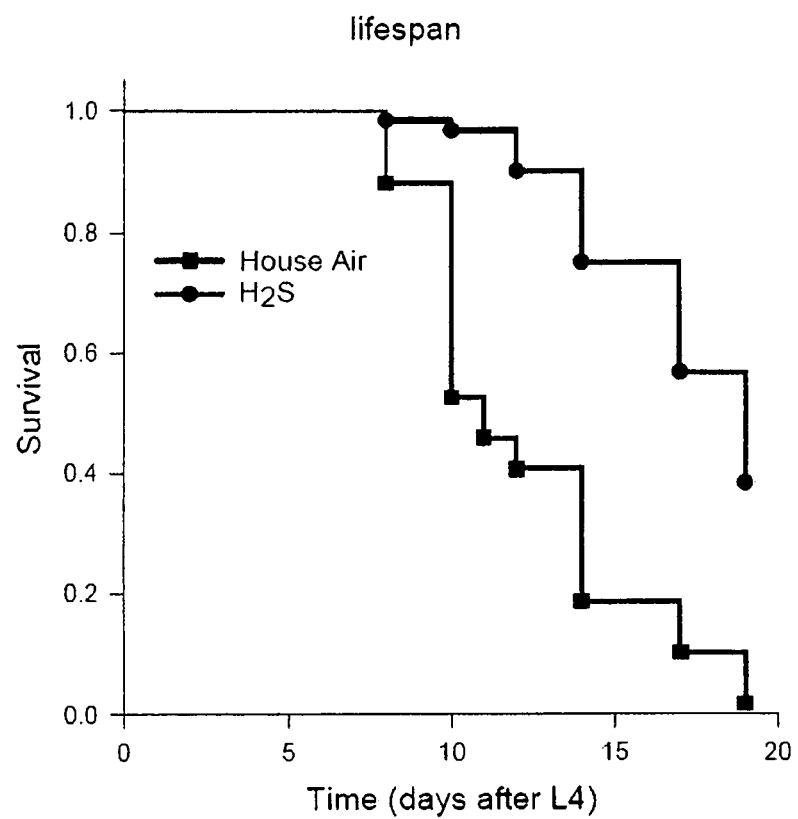
FIG. 32 Chronic exposure to low levels of $H_2S$ increases lifespan in C. elegans. Nematodes that were adapted to environments containing approximately 50 ppm $H_2S$ in house air had longer lifespan compared to untreated controls.

Worms adapted to 50 ppm $H_2S$ also have increased lifespan compared to isogenic untreated controls (FIG. 32). This is consistent with the idea that they are in a state that is generally more resistant to various stresses associated with aging. In fact, old worms grown in $H_2S$ seem more vigorous and healthy than those of similar age not treated with $H_2S$. Moreover, this is also true when comparing worms from each population at the midpoint of lifespan (i.e., the house air controls and $H_2S$-treated worms are not chronologically age matched, but the point where 50% of each population has died). Thus, adaptation to $H_2S$ may slow chronic cellular damage associated with aging in *C. elegans*.

Example 17

Implementation of Gas Matrix Experiments

Metabolic flexibility was evaluated in mice rats and dogs using altered gas environments. Three parameters were used to define this reduction in metabolism including changes in carbon dioxide production, oxygen consumption measured by respirometry, and core temperature as measured using telemetry. In experiments with mice and rats the animals were placed into sealed chambers with one gas import and one gas export. For dogs a mask was placed over the snout of the animal with two hoses (import and export) attached to the mask. The flow rate of gas for each of the animals mice—500 cc per minute, rats—2 liters per minute, and dogs 40 liters per minute. Each atmosphere was constructed from compressed gas by dilution into room air unless otherwise noted. For rat and mouse experiments the ambient temperature was 7 to 10° C. during exposure to the test gases. For dogs ambient temperature was room temperature (22° C.).

TABLE 9

Description of gas environments constructed to test for metabolic flexibility in mice rats and dogs.

|  | Mouse | Rat | Dog |
|---|---|---|---|
| Hydrogen sulfide | Yes 0.01% | Yes 0.03% | No 0.85% |
| Hydrogen selenide | Yes 0.0001% | Yes 0.003% | N/D |
| Phosphine | No 0.016% | N/D | N/D |
| Carbon dioxide | Yes 15% | Yes 15% | No 9% |
| $H_2S + CO_2$ | Yes 0.01% + 15% | N/D | N/D |
| $CO_2$ + low $O_2$ | Yes 15% + 8% | Yes 15% + 8% | N/D |
| $CO_2$ + low $O_2$ + He | Yes 15% + 8% + 77% | Yes 15% + 8% + 77% | Yes 9% + 15% + 77% |

Table 9 shows the amount of each gas, which is given as a percentage of the room air atmosphere unless otherwise noted. Evidence of depression in metabolic rate of greater than 5-fold as judged by carbon dioxide production or oxygen consumption during a 6-hour treatment is described by "Yes"; "No" (reduction or less than a 5-fold reduction in these values is described as such; "N/D" denotes experiments not done. The temperature drop in the dog experiment (Carbon dioxide+low oxygen+Helium) was approximately 1.5° C. over the course of 30 minutes of exposure. This drop in temperature was considered significant because the dog was 12 kg and no such temperature drop was seen during extensive baseline recording of the animal in room air.

Figure 33:
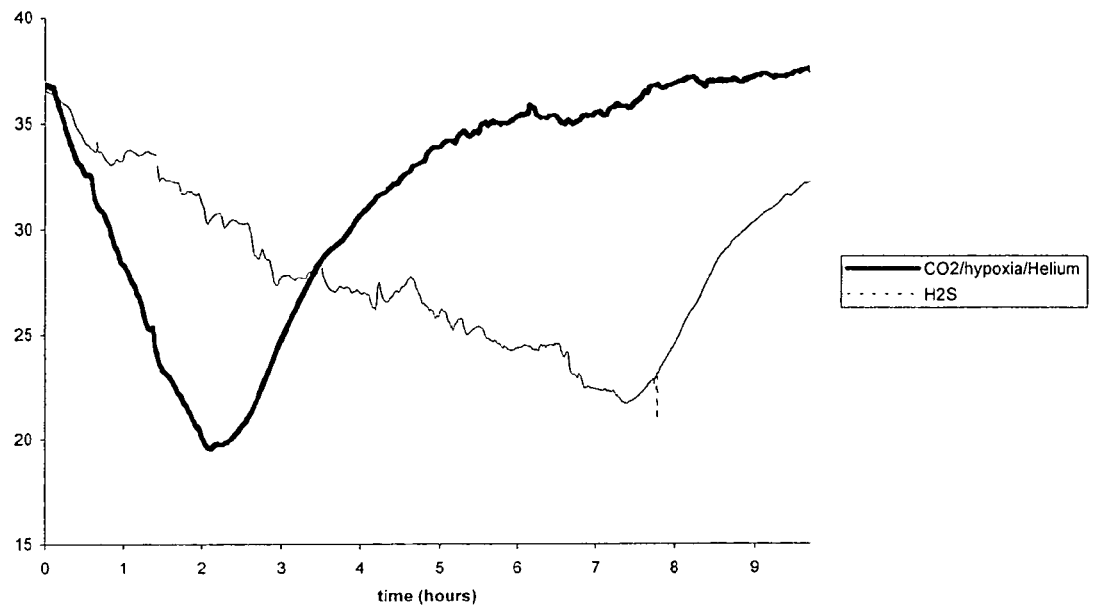
FIG. 33 Examples of transient core temperature drop in Sprague-Dawley rats. Core temperature measurements from rats exposed to 0.03% hydrogen sulfide mixed with room air (gray/dotted line) or 15% carbon dioxide/8% oxygen/77% helium (dark/solid line). In this experiment the temperature of the environmental chamber was 10° C. during the treatment phase. The temperature of the environmental chamber was restored to room temperature (22° C.) when the gas was returned to room air. In each case this was the point (approximately 2 hours for the dark/solid line and approximately 7.4 hours for the gray/dotted line) where the core temperature began to rise.
Figure 34:
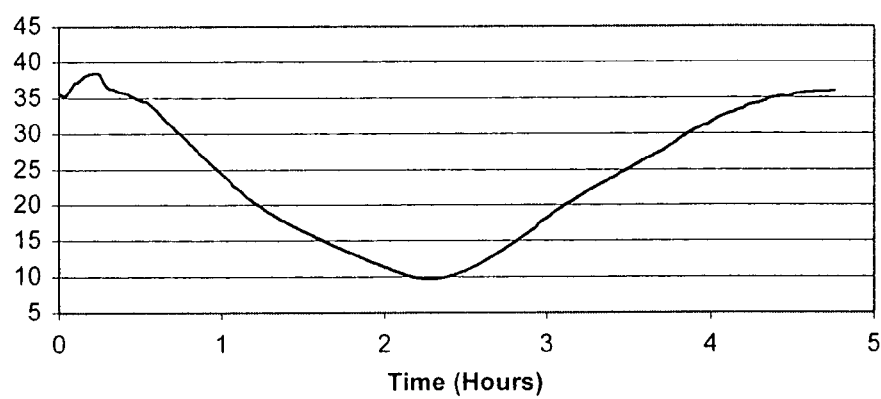
FIG. 34 Mouse core body temperature during exposure to 1.2 ppm of hydrogen selenide for 2 hours and 10 minutes in room air at 5° C. ambient temperature.
Figure 35:
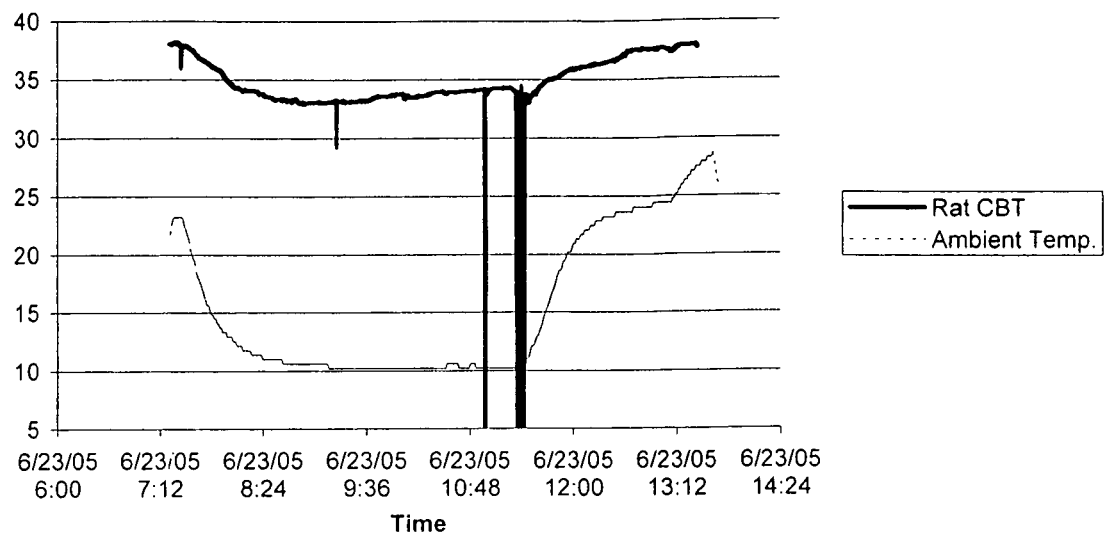
FIG. 35 Rat core body temperature during exposure to room air in an environmental chamber at an ambient temperature of 10° C. Dark line describes the core temperature of the rat. The gray line describes the ambient temperature.
Figure 36:
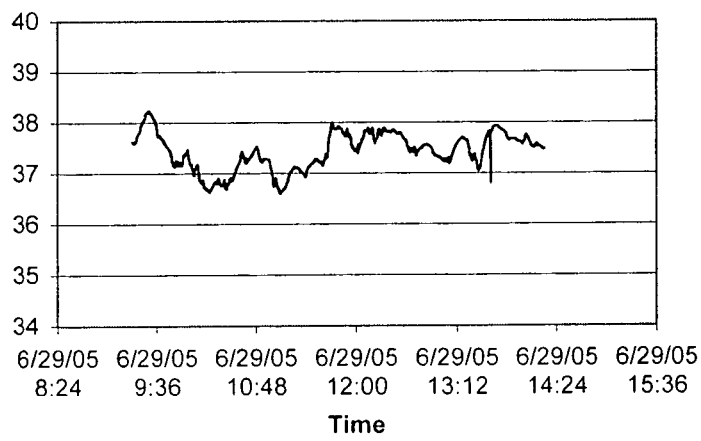
FIG. 36 Core body temperature of a rat exposed to 80% helium 20% oxygen at an ambient temperature of 7° C. Time is described on the X axis in hours. The total time of exposure was approximately 5 hours (from 9:15 AM to 2:15 PM). No significant drop in core body temperature was seen.
Figure 37:
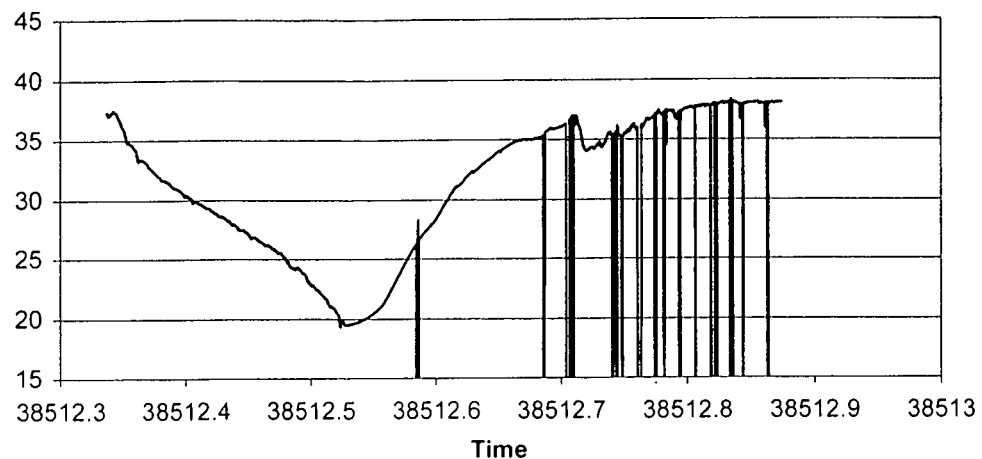
FIG. 37 Core body temperature of a rat during exposure to 15% carbon dioxide, 20% oxygen, and 75% Helium at an ambient temperature of 7° C. The time of exposure was approximately 2 hours. The rat was exposed to room air beginning at the point where the temperature begins to rise (shortly after the point labeled 38512.6). During the period when the rat was exposed to room air the temperature of the environment was restored to room temperature.
Figure 38:
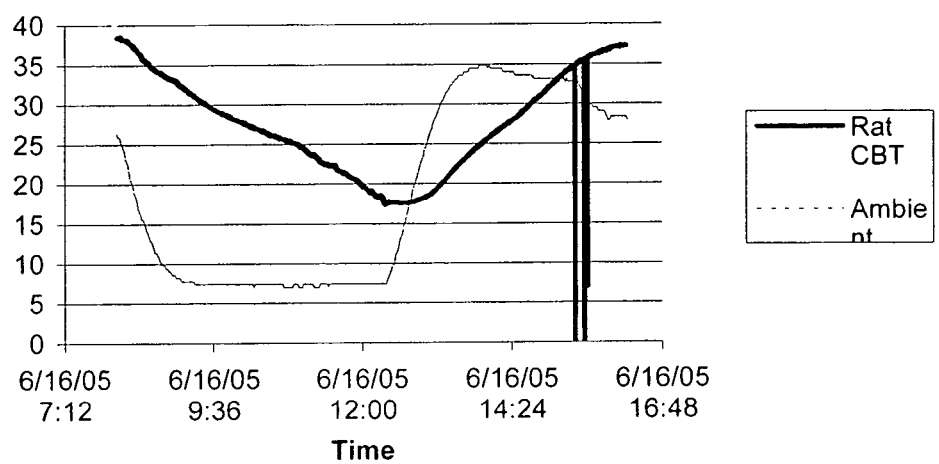
FIG. 38. Core temperature of a rat exposed to 15% carbon dioxide, 8% oxygen, and 77% Helium at an ambient temperature of 7° C. The exposure time was approximately 4 hours. The gray line describes the ambient temperature. The dark line describes the core temperature. At the point where the ambient and cores temperatures rise is the point where the gas was switched to room air.
Figure 39:
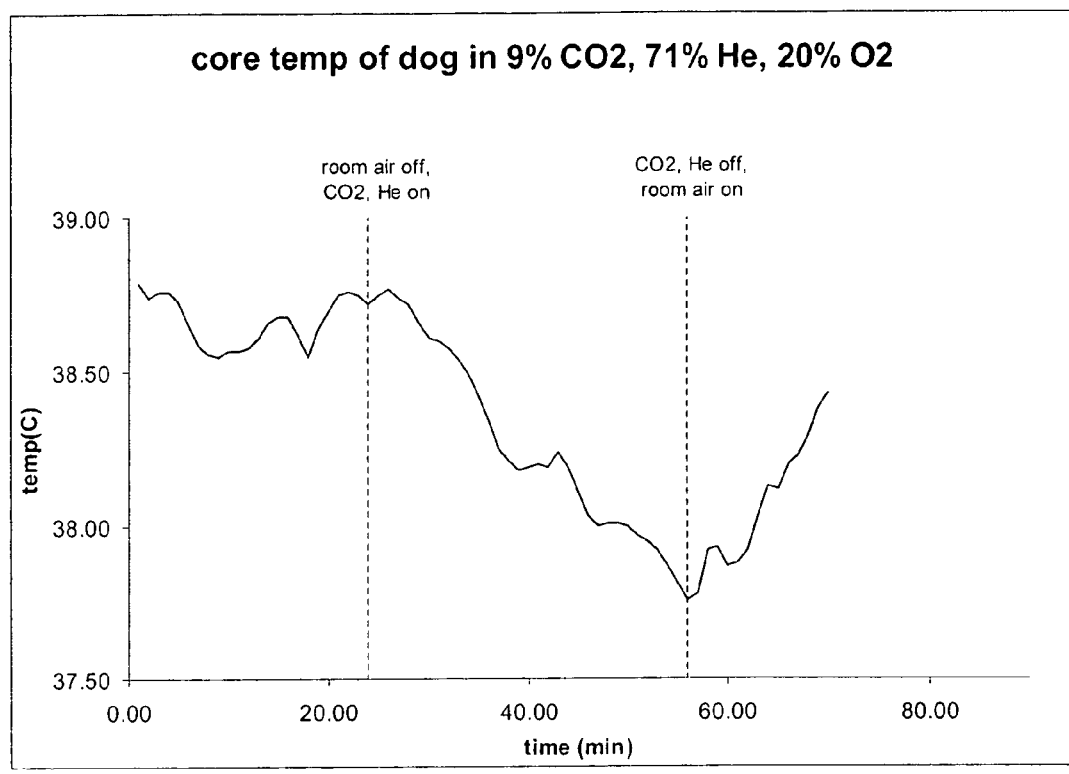
FIG. 39. Core temperature of a dog exposed to carbon dioxide/helium/oxygen. Dotted lines are when the gas went on (approximately 24 minutes) and off (approximately 55 minutes).
Figure 40:
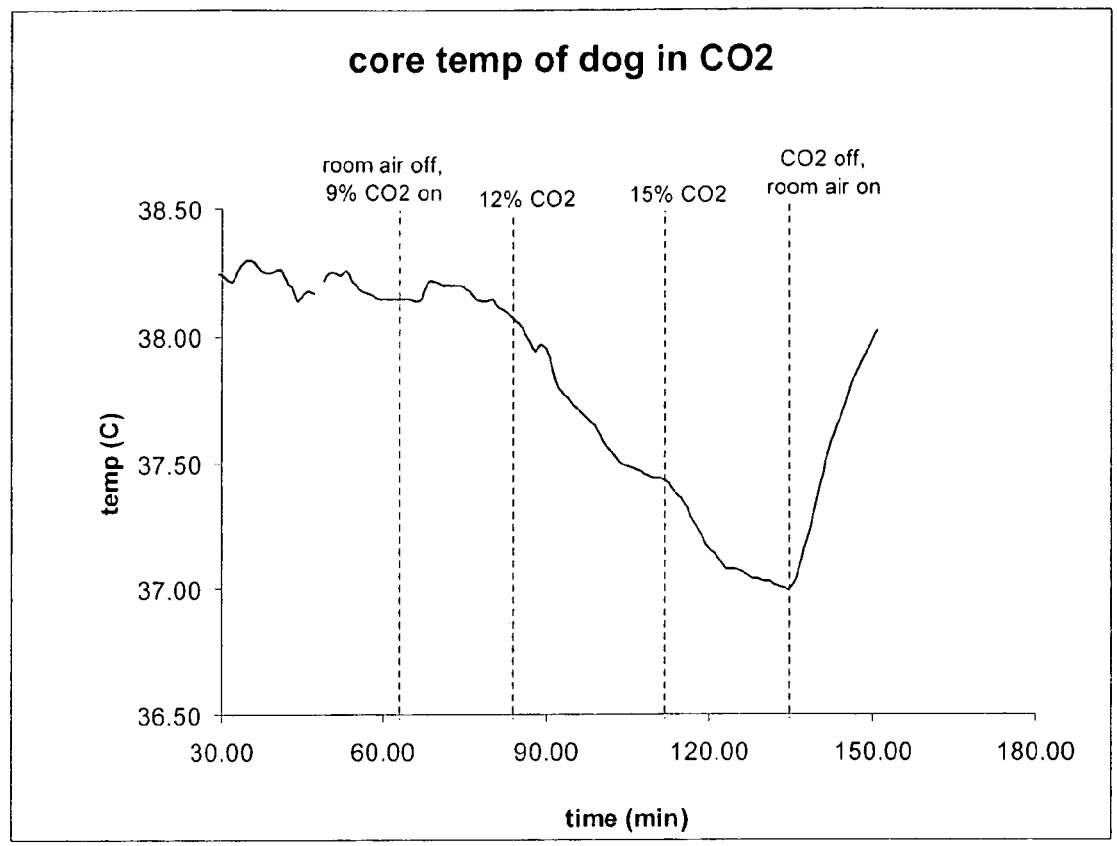
FIG. 40. Core temperature of a dog exposured to increasing concentrations of carbon dioxide. Dotted lines indicate when changes in the gas were made. At approximately 63 minutes the gas was changed from room air to 9% carbon dioxide in room air. At approximately 85 minutes the atmosphere was changed from 9% carbon dioxide in room air to 12% carbon dioxide in room air. At approximately 115 minutes the atmosphere was changed from 12% carbon dioxide in room air to 15% carbon dioxide in room air. The experiment ended at approximately 135 minutes.
Figure 41:
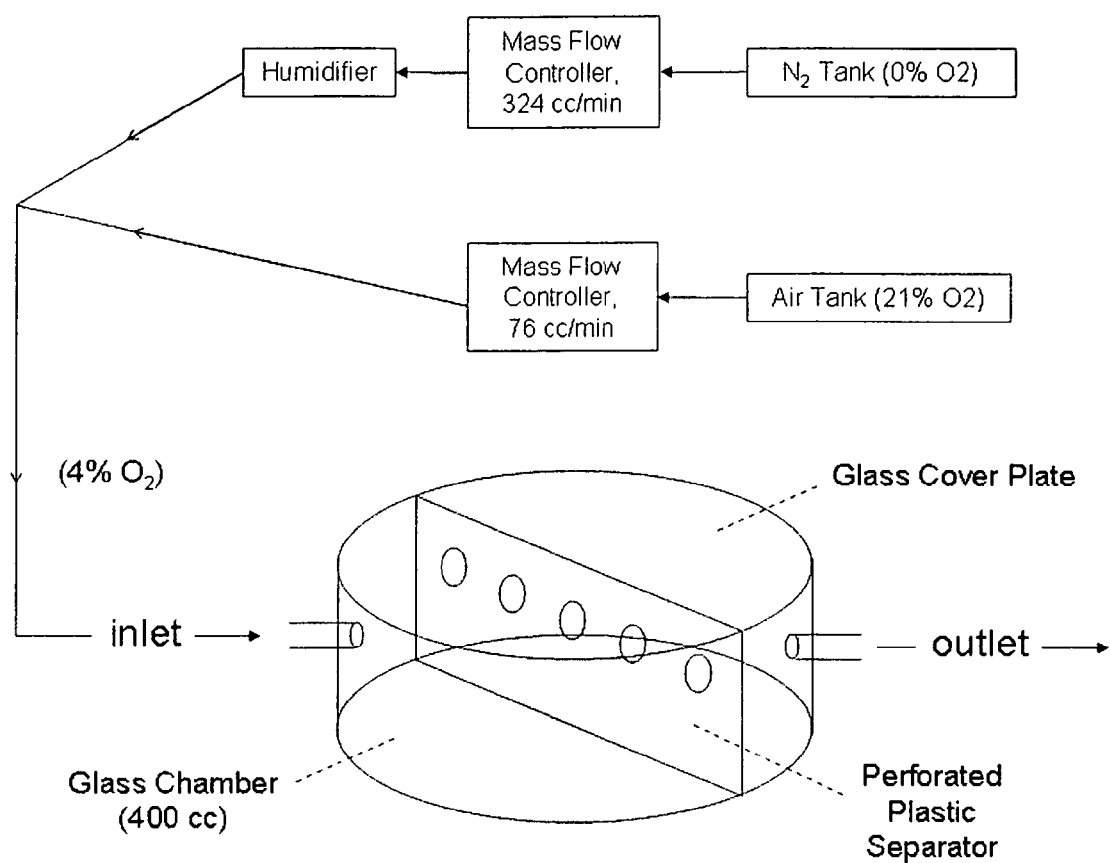
FIG. 41 Apparatus employed in screening methods.

Animals exposed to various constructed atmospheres exhibited metabolic flexibility as demonstrated by changes in core body temperature (CBT) that approach ambient temperature (FIGS. 33-40). FIG. 33 demonstrates a rat exposed to an atmosphere containing 15% $CO_2$, 8% $O_2$, and 77% He has a metabolic depression that is accelerated compared to a rat exposed to 300 ppm $H_2S$ under similar conditions. FIG. 34 demonstrates a significant drop in CBT of a mouse exposed to 1.2 ppm of $H_2Se$. Rats exposed to room air at an ambient temperature of 10° C. do not show significant drop in CBT (FIG. 35), nor do rats exposed to 80% He, 20% $O_2$ at 7° C. (FIG. 36). Rats exposed to an atmosphere of 15% $CO_2$, 20% $O_2$, 65% He at an ambient temperature of 7° C. show significant drop in CBT (FIG. 37). Similarly, FIG. 38 shows a significant CBT drop in a rat exposed to an atmosphere of 15% $CO_2$, 8% $O_2$, 77% He at 7° C. A significant drop in CBT was also demonstrated in a dog exposed to an atmosphere of 9% $CO_2$, 20% $O_2$, 71% He (FIG. 39). The magnitude of the drop is lower, presumably because of the larger size of the animal and the limitations of thermal diffusion. A similar drop is seen in a dog exposed to different concentrations of $CO_2$.

Example 18

Screening of Compounds

A compound screen was performed to identify test compounds capable of causing a reversible drop in subcutaneous temperature in a mouse. Identified test compounds were then tested for their ability to provide protection against lethal hypoxia (measured at 4% $O_2$ as opposed to a typical environment of 21% $O_2$ balanced nitrogen environment). The entire screening procedure involved three steps:

1) a primary (1°) screen to determine the minimum effective dose of a test compound that would produce a measurable drop in a test mouse's subcutaneous temperature;

2) a secondary (2°) screen to determine the reversibility of the temperature drop, as defined by the test mouse having normal behavior 24 hours after treatment and having returned to normal subcutaneous temperature in 24 hours or less; and 3) a tertiary (3°) screen to assess the ability of the test mouse to survive lethal hypoxia (4% $O_2$) as compared to an untreated control subject under identical hypoxic conditions.

The mice used in these studies were male C57BL/6 jugular vein catheterized (JVC) mice, 5-6 weeks old (Taconic), which were implanted dorsally with a subcutaneous RFID temperature sensor (IPTT-300, Bio Medic Data Systems, Inc. (BMDS)) and allowed to recover for at least 24 hours. The mice were dosed through the in-dwelling catheter with the infusion of test compound using 1 or 5 ml Luer-Lok syringes (Becton Dickinson) and an infusion pump (Harvard Apparatus). A DAS-6008 data acquisition module from BMDS recorded subcutaneous temperature of the mouse via the transponder, and this data was input into a computer spreadsheet and plotted against time.

Primary (1°) Screen:

For the primary screen, the infusion of test compound was made up at a concentration that was considered to be the maximum optimized concentration. The pH was adjusted with NaOH or HCl to 6-8, the osmolarity was adjusted with sodium chloride to 250-350 mOsm and the total dose of test compound to be administered (in mg) divided by the test subject's weight (in kg) did not exceed 400% of its published mg/kg LD50 in a mouse.

Mice were placed into a tall glass-bottom jar with opaque walls and infused via the jugular vein. The test compound was infused using a step protocol with increased infusion rates over 2 hours (Table 10).

TABLE 10

Test Compound Infusion Step Protocol

| time (min) | infusion rate µL/min | microliters infused | microliters infused total |
|---|---|---|---|
| 0-20 | 0.8 | 15.875 | 15.875 |
| 20-40 | 1.6 | 31.75 | 47.625 |
| 40-60 | 3.2 | 63.5 | 111.125 |
| 60-80 | 6.3 | 127 | 238.125 |
| 80-100 | 12.7 | 254 | 492.125 |
| 100-120 | 25.4 | 508 | 1000.125 |

During the infusion, the mouse subcutaneous temperature was read every 3-5 minutes, and any changes in the mouse behavior were recorded. The results of the primary screen revealed whether the test compound had the ability to lower subcutaneous temperature to 33° C. or lower, and indicated the effective dose required to lower subcutaneous temperature as measured by the infusion rate of the test compound at which a steady temperature drop was first observed.

Secondary (2°) Screen:

Test compounds that produced a decrease in mouse subcutaneous temperature to 33° C. or below were tested in the secondary screen. In the secondary screen, the mouse was infused with test compound for 60 minutes at a rate of 50% of the effective infusion rate determined in the primary screen. During the infusion, the mouse subcutaneous temperature was monitored by taking measurements every 3-5 minutes. If the subcutaneous temperature did not decrease in the first 60 minutes, the infusion rate was doubled and continued for another 60 minutes. When the mouse subcutaneous temperature decreased to 33° C. or below, the infusion was immediately stopped, and the mouse recovery was assessed by measuring subcutaneous temperature and observing the mouse behavior. The mouse temperature and behavior were observed and recorded 24 hours after treatment. The result of the secondary screen determined if the test compound caused a reversible drop in subcutaneous temperature without lethality.

Tertiary/lethal hypoxia (3°) screen: In the tertiary screen, the mouse was infused with test compound at the rate determined in the secondary screen. The mouse subcutaneous temperature was measured every 3-5 minutes until it decreased to 33° C., as in the secondary screen. The infusion was stopped and the mouse was immediately transferred to a hypoxic chamber (4% $O_2$), together with a control mouse, either infused with vehicle (salt solution, 148 mM, osmolarity=300), or untreated. The closed glass chamber was perfused with air and nitrogen at a continuous flow to achieve the desired hypoxic atmosphere of 4% $O_2$. If the mouse survived 60 minutes in the hypoxic atmosphere, it was transferred back to room air, and its recovery was monitored for 24 hours by recording the subcutaneous temperature and by behavioral observation.

The control mouse typically died within 6-15 minutes.

Mice infused with either sodium sulfide (effective dose 0.79 mmol/kg), sodium thiomethoxide (effective dose 4.61 mmol/kg), or sodium thiocyanate (effective dose 4.67 mmol/kg) survived exposure to lethal hypoxia for 60 minutes. A mouse infused with cysteamine (effective dose 7.58 mmol/kg) survived in lethal hypoxia for 45 minutes; a mouse infused with cysteamine-5-phosphate sodium salt survived in lethal hypoxia for 31 minutes; and a mouse infused with tetrahydrothiopyran-4-ol survived in lethal hypoxia for 15 minutes. These survival rates are compared to the survival rate of a control mouse, which typically died within 6-15 minutes in the hypoxic environment.

In comparison, certain other test compounds identified in the primary screen as having the ability to lower body temperature did not protect from lethal hypoxia. Thioacetic acid, selenourea, and phosphorothioic acid S-(2-((3-aminopropyl)amino)ethyl) ester all reduced body temperature, but did not enhance survival in hypoxia. 2-mercapto-ethanol, thioglycolic acid, and 2-mercaptoethyl ether all reduced body temperature but were toxic at the effective temperature reducing dose. Thiourea, dimethyl sulfide, sodium selenide, sodium methane sulfinate, N-acetyl-L-cysteine did not reduce subcutaneous temperature at the highest doses given in this study. Dimethylsulfoxide was excluded because the effective dose (10% DMSO) was too high to be considered for pharmaceutical purposes.

These studies establish that the screening procedures developed may be successfully used to identify compounds capable of protecting animals subjected to lethal hypoxia. In addition, the results of this studies indicate that the identified compounds, as well as other compounds to be identified using this procedure, may be used to protect patients from injury resulting from hypoxic and ischemic injury.

Example 19

Daily Exposure to Active Compound

The ability to adapt physiologically to extended treatment with hydrogen sulfide ($H_2S$) and the time required for adaptation was tested in a mouse. Adaptation was defined as a failure to exhibit a decrease in core body temperature (greater than 4° C.) when an animal was exposed to 80 ppm of hydrogen sulfide in room air for an extended treatment. Extended treatment was defined as exposure to 80 ppm of hydrogen sulfide in room air for four hours per day, four days per week for six weeks.

The mice used in these studies were male C57BL/6 mice or male C129 mice, 5-6 weeks old. Telemetry devices were implanted into the coelomic cavity of the mice prior to the experiments to record core temperature.

Mice (eight per treatment) were exposed to hydrogen sulfide in a single plexiglass box with separate chambers for each mouse at a flow rate was 10 liters per minute. Detection of carbon dioxide production and oxygen consumption animals in 500 cc glass bowls had flow rate of 0.5 liters per minute.

Figure 42:
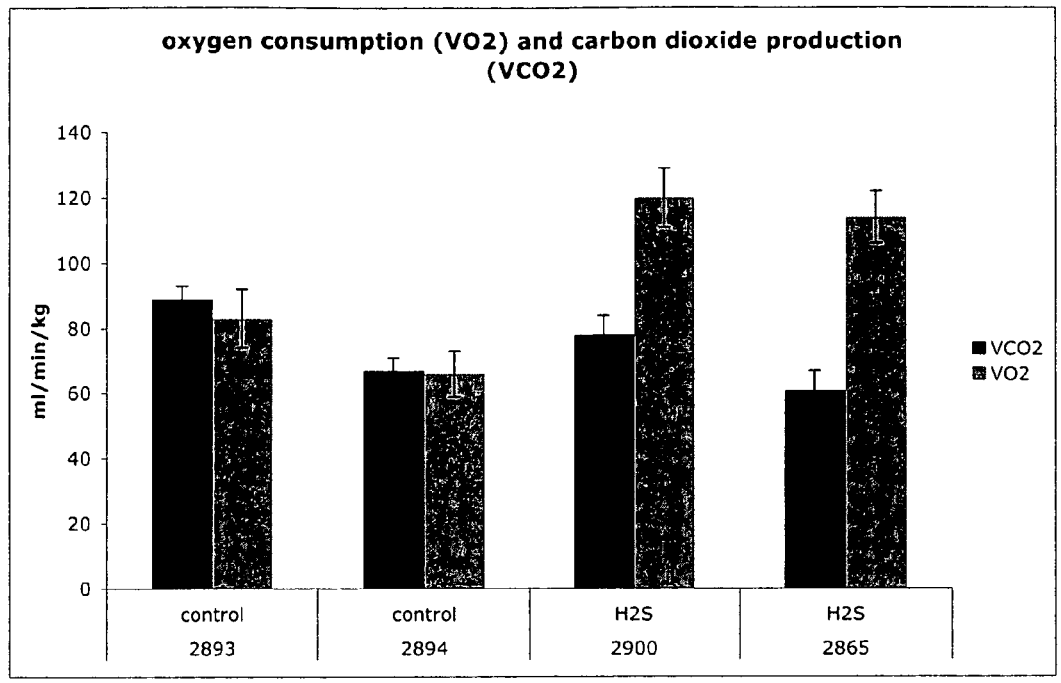
FIG. 42 Oxygen consumption (gray bars) and carbon dioxide production (black bars) of animals exposed to hydrogen sulfide for 4 hours per day for at least 1 week and for control animals that were exposed to the same conditions lacking hydrogen sulfide.
Figure 43:
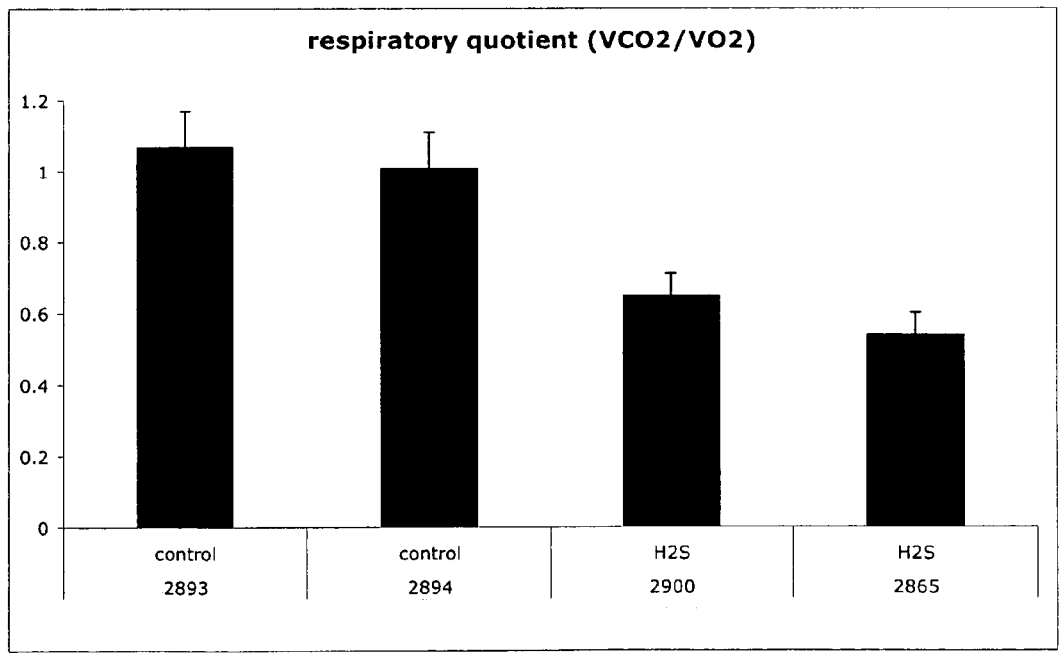
FIG. 43 Respiratory quotient for animals exposed to hydrogen sulfide for 4 hours per day for at least 1 week ($H_2S$ 2900 and $H_2S$ 2865) and for control animals (2893 and 2894) that were exposed to the same conditions lacking hydrogen sulfide.

Mice adapted to hydrogen sulfide exposure on average, in a one week period. Adaptation was defined by a failure to exhibit a decrease (greater than 4° C.) in core temperature when animals were exposed to 80 ppm of hydrogen sulfide in room air for 4 hours. Mice that did not exhibit a drop in core temperature were deemed to have a physiological adaptation to hydrogen sulfide. Mice treated with hydrogen sulfide that developed an adaptation showed an increase in oxygen consumption (vO2) compared to carbon dioxide production (vCO2) when compared to untreated control mice (FIG. 42). Mice with an adaptation to $H_2S$ showed a lower Respiratory Quotient (RQ ratio), defined as the ratio of vCO2/vO2 or a comparison of produced carbon dioxide to consumed oxygen (FIG. 43).

Example 20

Applications for Thalassemia

Based on the current results in other model systems presented here, it expected the red blood cells of animals with the hematological disorder, thalassemia, will have an increased ability to withstand oxidative damage, leading to prolonged red cell survival when they are treated with sulfides. The following experiments will be performed to confirm that treatment with active compounds can protect animals with thalassemia from oxidate damage.

In a first series of experiments, animals with thalssemia will be treated by chronic exposure to an active compound. After initial tests to establish baselines, treatment will be initiated following the protocol summarized below. If erythropoiesis or red cell survival are improved, an effect may be observed in as early as 1-2 weeks, since the half-life of thalassemic red cells is estimated at 4-7 days. We will review a smear and obtain a reticulocyte count at two weeks, and initiate more extensive studies after an additional two weeks. If an improvement in the red blood cells is determined in mice, as identified by an improved reticulocyte count and blood smear, the study will continue until a plateau is observed in the metrics used in the monthly studies. This study has a projected final end point of one year. At one year, red cell survival studies will be completed, and the animals will be sacrificed. If no improvement is observed, exposure will continue for up to one additional year, when survival studies will be accomplished and the animals sacrificed.

Protocol 1:
1) Animals will undergo initial studies.
2) Within one week after initial studies, animals will be housed identically and either:
  A) exposed to 80 ppm $H_2S$ for 8 hours/day;
  B) no exposure; or
  C) given water with 0.25% dimethyl sulfide (DMSO) and allowed to drink ad lib (estimates from prior studies suggest mice will consume 5-10 cc/day/mouse with 2.5-25 microgram/day DMSO content. Using an average weight of 18 g per mouse, consumption is estimated to be 700-1,400 ug/kg/day).

In a second series of experiments, the effect of in utero treatment with an active compound will be determined, following the protocol summarized below.

Protocol 2:
1) Plugged dams will be treated in one of the following groups three days post conception:
  A) exposed to 80 ppm $H_2S$ for 8 hours/day;
  B) no exposure; or
  C) Given water with 0.25% dimethyl sulfide (DMSO) and allowed to drink ad lib (estimates from prior studies suggest mice will consume 5-10 cc/day/mouse with 2.5-25 microgram/day DMSO content. Using an average weight of 18 g per mouse, consumption is estimated to be 700-1,400 ug/kg/day).
2) Plugged dams will be allowed to give birth naturally, and pups will be genotyped and sacrificed for detailed analysis soon after birth.

The test animals will be monitored throughout these studies as indicated below.

Monitoring:
1) Initial studies:
  1. reticulocyte count;
  2. blood smear
  3. Computed Tomography (CT scan) of spleen and bones;
  4. $O_2$ consumption and $CO_2$ production;
  5. weight;
  6. sulfide metabolites and
  7. hematocrit (60 µl blood total).
2) At two weeks: reticulocyte count and blood smear (5 µl blood).
3) Monthly studies:
  1. reticulocyte count;
  2. CT of spleen and bones;
  3. $O_2$ consumption and $CO_2$ production;
  4. weight; and
  5. sulfide metabolites (blood draw will be less than 30 µl).
4) One month prior to sacrifice: red cell survival studies.
5) Sacrifice and detailed in vitro analysis.

Example 21

Applications for Sickle Cell Anemia

To test this hypothesis, a mouse model of sickle cell disease (SCD) will be used in which the strain was engineered so that it no longer expresses mouse Hba and Hbb, but does express human HBA and HBB (Patsy, et al, 1997). It mimics the genetic, hematologic and histopathologic features that are found in humans afflicted with sickle cell anemia, including irreversibly sickled red blood cells, anemia and multiorgan pathology. A significant percentage of sickle cell mice do not survive to adulthood.

Using this mouse model, various agents and sulfide containing compounds will be tested for efficacy against SCD. Exposures will be acute and chronic, and animals will be exposed either at birth or in utero. Viability to birth for pups exposed in utero or to adulthood will be one endpoint to measure efficacy. Phenotypic effects will be evaluated through reticulocyte count, hematocrit and red blood cell (RBC) half-life measurements (which are normally 20 fold less for SCD compared to wild type controls).

Example 21

Cyanide Exposure Experiment

This example shows that when mice are exposed to 80 ppm of cyanide in room air they gradually reduce their core temperature to about 34° C.

One goal of these metabolic flexibility studies has been the identification of compounds that can reduce oxygen consumption and protect animals from hypoxic injury. Previously, it was demonstrated that Hydrogen Sulfide ($H_2S$), a potent inhibitor of oxygen consumption, can reduce metabolism and protect mice and rats from hypoxic injuries. Hydrogen Cyanide (HCN) is similar to $H_2S$ in many ways and we would like to use our assays of metabolic output to learn if it can be used to regulate metabolism. Like $H_2S$, HCN is widely used in industrial chemical syntheses and it is found in many biological systems including humans. It is not known if HCN is merely a byproduct of carbon-nitrogen metabolism or if it possesses specific biological activities. Like H2S, HCN is thought to act by reacting with transition metal containing proteins such as oxidases and dehydrogenases. HCN is not strongly reactive with components of hemoglobin.

In humans, the NIOSH IDLH (immediately dangerous to life and health) value is 50 ppm. The OSHA PEL (permissible exposure limit) TWA (time weighted average for 8 hours) is 10 ppm. The LC50 for rat is 143 ppm for 60 minutes.

To measure metabolic effects of HCN, mice were exposed to increasing concentrations of HCN starting at 1 ppm. Oxygen ($O_2$) consumption, carbon dioxide (CO2) production, body core temperature (BCT) and behavior were measured or evaluated. The concentration of HCN was raised by 10 ppm increments until an effect on metabolism was observed or when the animals appeared to show signs of distress. A metabolic effect is defined as a 10% change in less than 10 minutes in any of the assay values described above.

It was found that when mice were exposed to 80 ppm of cyanide in room air at room temperature they gradually reduced their core temperature to about 34° C. This is distinct from the decrease seen with 80 ppm hydrogen sulfide where the core temperature drops to approximately 28 degrees C. In addition, there was a very slow recovery of the core temperature in mice exposed to cyanide (approximately 14 hours) compared to hydrogen sulfide (approximately 2 hours).

The hypothesis was tested that the slow recovery, as judged by core temperature, in cyanide could be rescued by brief exposure to 80 ppm hydrogen sulfide. This was based on the idea that, a conserved enzyme, rhodanese (and other similar enzymes), might use hydrogen sulfide and cyanide to produce the relatively less toxic agent, thiocyanate. Already it has been shown that rhodanese can use cyanide and thiosulfate to produce thiocyanate. (Chen 1933) Furthermore, intravenous administration of thiosulfate is the standard of care for treating cyanide intoxication in the US. It was found that the time to recover the core temperature following exposure to cyanide was reduced by brief treatment with hydrogen sulfide. This result suggests that hydrogen sulfide exposure might be used to treat conditions in which patients suffer from cyanide intoxication.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,777,507
U.S. Pat. No. 3,881,990
U.S. Pat. No. 3,989,816
U.S. Pat. No. 3,995,444
U.S. Pat. No. 4,034,753
U.S. Pat. No. 4,186,565
U.S. Pat. No. 4,266,573
U.S. Pat. No. 4,292,817
U.S. Pat. No. 4,442,856
U.S. Pat. No. 4,444,762
U.S. Pat. No. 4,447,415
U.S. Pat. No. 4,473,637
U.S. Pat. No. 4,502,295
U.S. Pat. No. 4,559,258
U.S. Pat. No. 4,723,974
U.S. Pat. No. 4,745,759
U.S. Pat. No. 4,798,824
U.S. Pat. No. 4,828,976
U.S. Pat. No. 4,938,961
U.S. Pat. No. 4,951,482
U.S. Pat. No. 5,066,578
U.S. Pat. No. 5,157,930
U.S. Pat. No. 5,217,860
U.S. Pat. No. 5,231,025
U.S. Pat. No. 5,285,657
U.S. Pat. No. 5,326,706
U.S. Pat. No. 5,370,989
U.S. Pat. No. 5,395,314
U.S. Pat. No. 5,399,363
U.S. Pat. No. 5,405,742
U.S. Pat. No. 5,434,045
U.S. Pat. No. 5,466,468
U.S. Pat. No. 5,470,738
U.S. Pat. No. 5,476,763
U.S. Pat. No. 5,543,158
U.S. Pat. No. 5,552,267
U.S. Pat. No. 5,568,910
U.S. Pat. No. 5,569,579
U.S. Pat. No. 5,580,781
U.S. Pat. No. 5,599,659
U.S. Pat. No. 5,636,643
U.S. Pat. No. 5,641,515
U.S. Pat. No. 5,645,081
U.S. Pat. No. 5,693,462
U.S. Pat. No. 5,699,793
U.S. Pat. No. 5,719,174
U.S. Pat. No. 5,736,397
U.S. Pat. No. 5,739,169
U.S. Pat. No. 5,752,929
U.S. Pat. No. 5,801,005
U.S. Pat. No. 5,830,880
U.S. Pat. No. 5,846,945
U.S. Pat. No. 5,912,019
U.S. Pat. No. 5,952,168
U.S. Pat. No. 6,013,256
U.S. Pat. No. 6,046,046
U.S. Pat. No. 6,054,261
U.S. Pat. No. 6,057,148
U.S. Pat. No. 6,100,082
U.S. Pat. No. 6,187,529
U.S. Pat. No. 6,365,338
U.S. Pat. No. 6,490,880
U.S. Pat. No. 6,492,103
U.S. Pat. No. 6,524,785
U.S. Pat. No. 6,552,083
U.S. Pat. No. 6,602,277
U.S. Pat. No. 6,790,603
U.S. patent application Ser. No. 10/971,575,
U.S. patent application Ser. No. 10/971,576
U.S. patent application Ser. No. 10/972,063
U.S. Prov. Appln. 60/513,458
U.S. Prov. Appln. 60/548,150
U.S. Prov. Appln. 60/557,942
Alam, *Antioxid Redox Signal*, 4(4):559-62, 2002.
Amersi et al., *Hepatology*, 35(4):815-823, 2002.
Austin-Ward and Villaseca, *Revista Medica de Chile*, 126(7): 838-845, 1998.
Barton & Ollis, Oxford, UK, Jones (Ed.), Pergamon Press, 3:373-487, 1979.
Baskin and Wang, *Tetrahedron Lett.*, 43:8479-8483, 2002.
Baskin et al., *Org. Lett.*, 4:4423, 2002.
Beauchamp et al., *Crit. Rev. Toxicol.* 13, 25, 1984.
Beck et al., *Proc. Soc. Exp. Biol. Med.* 86, 823, 1954.
Behringer et al., *Crit. Care Med.*, 31(5):1523-1531, 2003.
Bellamy et al., *Crit. Care Med.*, 24(2 Suppl):S24-47, 1996.
Bernard et al., *J. Thorac. Cardiovasc. Surg.* 90:235-242, 1985.
Bernard et al., *N. Engl. J. Med.*, 346(8):557-563, 2002.
Blackstone et al., *Science*, 308:518, 2005.
Boyce and Ham, *J. Invest. Dermatol.*, 81:335-405, 1983.
Boyce and Ham, *J. Tissue Culture Methods*, 9:83-93, 1985.
Briese, *Neurosci. Biobehav. Rev.*, 22(3):427-436, 1998.
Brizel, *Seminars Radiation Oncol.*, 8(4Suppl):17-20, 1998.
Brouard et al., *J. Biol. Chem.*, 277(20):17950-17961, 2002.
Bukowski et al., *Clinical Cancer Res.*, 4(10):2337-2347, 1998.
Burns & Murphey, *Arch. Biochem. Biophys.*, 339:33-39, 1997.1997
Burns et al., *Arch. Biochem. Bipophys*, 10:60-68, 1995.
Cairns et al., *J. Am. Chem. Soc.*, 74:3982, 1952.

Chapter IV; Chapter VI; Chapter VII; Chapter VIII; Chapter IX of Klayman, D. L.; Gunther, W. H. H. Eds, Wiley Interscience, New York, 1973.
Chasteen and Bentley, *Chem. Rev.,* 103(1):1-25, 2003.
Christodoulides et al., *Microbiology,* 144(Pt 11):3027-3037, 1998.
CIIT (Chemical Industry Institute of Toxicology), In: *90 day vapor inhalation toxicity study of hydrogen sulfide,* Toxigenics, 420-0710, 1983.
Clive et al., *J. Org. Chem.,* 47:1641, 1982.
Cloarec & Charette, *Org. Lett.,* 6:4731, 2004.
Cohen et al., *Ann. Thorac. Surg.,* 67(5):1489-1491, 1999.
Curran, *Seminars Radiation Oncol.,* 8(4Suppl):2-4, 1998.
Davidson et al., *J. Immunother.,* 21(5):389-398, 1998.
Davis (1994)
Demuynck and Vialle, *Bulletin de la Societe Chimique de France,* 4:1213-1218, 1967
Demuynck et al., *Bulletin de la Societe Chimique de France,* 3366-3367, 1966.
Demuynck et al., *Bulletin de la Societe Chimique de France,* 8:2748-2754, 1967.
Dhanasekaran et al., *J. Biol. Chem.,* 279:37575-37587, 2004.
Dillman, Cancer Biother. Radiopharm., 14(1):5-10, 1999.
Dittmer and Hoey, In: *The Chemistry of Sulphinic Acids, Esters, and Their Derivatives,* Wiley: Chichester, U.K., 239-273, 1990.
Dorman et al. Neurotoxicol. Teratol., 22(1):71-84, 2000.
Dulak et al., *Antioxid. Redox Signal,* 4(2):229-240, 2002.
Duus, In *Comprehensive Organic Chemistry: The Synthesis and Reactions of Organic Compounds,* $1^{st}$ Ed., 1994.
Eto et al., *Biochem. Biphys. Res. Commun.,* 293:1483-1488, 2002.
Ganther, *Carcinogenesis* 20(9):1657-66 (1999)
Gilbert et al., *LANCET,* 355:375-376, 2000.
Gladysz et al., *J. Org. Chem.,* 43:1204, 1987.
Glass, *Phosph. Sulfur Silicon Rel. Elem.,* 136, 137, 138:159-174, 1998.
Gorman et al., *Toxicology,* 187(1):25-38, 2003.
Guillemin et al., *Cell,* 89(1):9-12, 1997.
Hanibuchi et al., *Intl. J. Cancer,* 78(4):480-45, 1998.
Hannan et al., *JAMA,* 290(6):773-780, 2003.
Harris, *J. Org. Chem.,* 25:225, 1960.
Harris, *J. Org. Chem.,* 30:2190, 1965.
Hays, In: *Studies of the Effects of Atmospheric Hydrogen Sulfide in Animals,* thesis dissertation, University of Missouri-Columbia, 1972.
Hellstrand et al., *Acta Oncologica,* 37(4):347-353, 1998.
Higuchi and Fukamachi, *Folia Pharmacologica Japonica,* 73(3):307-319, 1977.
Hobert et al., *Organometallics,* 20:1370, 2001.
Hochachka et al., *Comp. Biochem. Physiol. B Biochem. Mol. Biol.,* 130(4):435-459, 2001.
Hochachka et al., *Proc. Natl. Acad. Sci. USA,* 93(18):9493-94938, 1996.
Hui and Hashimoto, *Infection Immun.,* 66(11):5329-5336, 1998.
Hwang & Greenberg, *Biochemistry,* 38:14248, 1999.
Hyspler et al., *J. Chromatography,* 770:255-259, 2002.
Innicenti et al., *Bioorg. Med. Chem. Lett.* 14, 5769 (2004).
Jiang et al., *Am. J. Physiol. Cell Physiol.,* 280:1140-1150, 2001.
Ju et al., *J. Neuropathol. Exp. Neurol.,* 59(3):241-50, 2000.
Kamoun, *Amino Acids* 26, 243, 2004.
Kelso et al., *J. Biol. Chem.,* 276:4588-4596, 2001.
Khan et al., *Toxicol. Applied Pharmacol.,* 103:482-490, 1990.
Kilburn and Warshaw, *Toxicology Indust. Health,* 11(2):185-197, 1995.
Kilburn, *Environ. Health,* 54(3):150, 1999
Kilburn, *Environ. Res.,* 81(2):92-99, 1999.
Knapp and Darout, *Org. Lett.,* 7:203, 2005.
Kontou et al., *J. Agricultureal and Food Chem.,* 52:1212, 2004.
Kuroda et al., *Transplantation,* 46(3):457-460, 1988.
Kuroda et al., *Transplantation,* 46(3):457-460, 1988.
Lai et al., *Biochemistry,* 40:4904-4910, 2001.
Langer et al., *Biochemistry* 33:14034, 1994.
Langer et al., *Biochemistry,* 33:10867, 1997.
Ledingham et al., *Circulation,* 82(2):IV351-358, 1990.
Ledingham et al., *J. Thorac. Cardiobasc. Surg.,* 93:240-246, 1987.
Lee et al., *J. Nuc. Med.* 26:72, 1985.
Liu et al., *J. Org. Chem.,* 67:9267, 2002.
Lundgren-Eriksson et al., Anticancer Res. 2001 September-October; 21(5):3269-74
Mehlhom et al., *Cardiovasc Surg.,* 9(5):482-486, 2001.
Menasche et al., *Eur. J. Cardio. Thorax. Surg.,* 8:207-213, 1994.
Michaels et al., *Circulation,* 106(23):e187-190, 2002.
Mugesh et al., *Chem. Rev.,* 101:2125, 2001.
Murai and Kato, In: *Organoselenium Chemistry: Modern Developments in Organic Synthesis,* Wirth (Ed.), Springer, N.Y., Vo. 28, 2000.
Murai, et al., *J. Org. Chem.,* 66:8101, 2001.
Netherton & Fu, *Org. Lett.,* 3:4295, 2001.
Noguchi et al., *Biochemistry,* 42:11642, 2003.
Nogueira et al., *Chem. Rev.,* 104:6255, 2004.
Nystul et al., *Science,* 302(5647):1038-1041, 2003.
O'Sullivan et al., *J. Am. Chem. Soc.,* 126:2194, 2004.
Olojo et al., *J. Phys. Chem. A,* 108:1018, 2004.
Otterbein et al., *Am. J. Physiol. Lung Cell Mol. Physiol.,* 279(6):L1029-L1037, 2000.
Otterbein et al., *Trends Immunol.,* 24(8):449-455, 2003.
Padilla et al., *Molec. Biology of the Cell,* 13:1473-1483, 2002.
Padilla et al., *Proc. Natl. Acad. Sci. USA,* 98(13):7331-7335, 2001.
Partlo et al., *Neurotoxicology,* 22(2):177-189, 2001.
PCT Appln. WO 94/17178
Petersen, *Biochemica et Biophysica Acta,* 460:299-307, 1977.
Pietras et al., *Oncogene,* 17(17):2235-2249, 1998.
Punch et al., 2001
Qin et al., *Proc. Natl. Acad. Sci. USA,* 95(24):14411-14416, 1998.
Quirante et al., *J. Org. Chem.,* 67:2323, 2002.
Rager et al., *NC Med. J.,* 65(1):18-25, 2004.
Reigan et al. *J. Med. Chem.,* 48:392, 2005.
Remington's Pharmaceutical Sciences, $15^{th}$ ed., pages 1035-1038 and 1570-1580, Mack Publishing Company, Easton, Pa., 1980.
Rogers et al., *Mamm. Genome,* 8:711-713, 1997.
Ryter and Otterbein, *BioEssays,* 26:270-280, 2004.
Seburg and Squires, *Intl. J. Mass Spectrometry Ion Proc.,* 167/168:541, 1997.
Semenza, *Cell,* 98(3):281-284, 1999.
Semenza, *Trends Mol. Med.,* 7(8):345-350, 2001.
Shaw (1996)
Shawali et al., *J. Org. Chem.,* 61:4055, 2001.
Shen et al., *J. Agric. Food Chem.,* 50:2644, 2002.
Smith et al., *Eur. J. Biochem.,* 263:709-716, 1999.
Soledad et al., *Org. Lett.,* 3:1213, 2001.
Steudel, *Chem. Rev.,* 102:3905, 2002.
Struve et al., *Neurotoxicology,* 22(3):375-385, 2001.
Sundarrajan et al., *Macromolecules,* 35:3331, 2002.
Supuran et al., *Med. Res. Rev.,* 23(2):146-189, 2003.

Sweeney, In: *A Survey of Compounds from the Antiradiation Drug Development Program of the US. Army Medical Research and Development Command.* Walter Reed Army Institute of Research, Washington D.C., 1979.
Teodoro and OFarrell, *EMBO J.,* 22(3):580-587, 2003.
The Hypothermia After Cardiac Arrest Study Group et al., 2002.
Tisherman, *Crit. Care Med.,* 32(2):S46-S50, 2004.
Van Voorhies et al., *J. Exp. Biol.,* 203(Pt 16):2467-2478, 2000.
Wang et al., 1992
Wang et al., 1993
Wang et al., 1994
Wang, *FASEB J.,* 16(13):1792-1798, 2002.
Yaffe et al., Crit. Care Med., 32(2):S51-55, 2004.
Yaghi et al., *Nature,* 423(6941):705-714, 2003.
Yang et al., *J. Agric. Food Chem.,* 52:7051, 2004.
Yoshikawa et al., *J. Biochem. (Tokyo),* 71:859-872, 1972.
Zhang et al., *J. Appl. Physiol.* 96(1):392-397, 2004.
Zhang et al., *J. Org. Chem.* 63:5314, 1998.
Ziegler, *Ann. Rev. Biochem.* 54, 305, 1985.

What is claimed is:

1. A method for treating hemorrhagic shock comprising administering to a subject in need thereof an effective amount of a $H_2S$ intravenously or by inhalation.

2. The method of claim 1, wherein the effective amount of the $H_2S$ is administered intravenously.

3. The method of claim 1, wherein the effective amount of the $H_2S$ is administered by inhalation.

\* \* \* \* \*